(12) United States Patent
Robbins et al.

(10) Patent No.: US 8,455,455 B1
(45) Date of Patent: Jun. 4, 2013

(54) COMPOSITIONS AND METHODS FOR SILENCING GENES INVOLVED IN HEMORRHAGIC FEVER

(75) Inventors: Marjorie Robbins, Vancouver (CA); Susan de Jong, Vancouver (CA); Vandana Sood, Vancouver (CA); Lisa E. Hensley, Frederick, MD (US); Ian MacLachlan, Mission (CA)

(73) Assignees: Protiva Biotherapeutics, Inc., Burnaby, BC (CA); The United States Army Medical Research and Materiel Command, Washington, DC (US)

( * ) Notice: Subject to any disclaimer, the term of this patent is extended or adjusted under 35 U.S.C. 154(b) by 78 days.

(21) Appl. No.: 13/077,856

(22) Filed: Mar. 31, 2011

Related U.S. Application Data

(60) Provisional application No. 61/319,855, filed on Mar. 31, 2010.

(51) Int. Cl.
*C07H 21/02* (2006.01)
*C07H 21/04* (2006.01)
*A61K 31/70* (2006.01)
*C12Q 1/68* (2006.01)
*C12N 5/00* (2006.01)

(52) U.S. Cl.
USPC ....... 514/44 A; 536/23.1; 536/24.1; 536/24.5; 435/6.1; 435/375; 435/377

(58) Field of Classification Search
None
See application file for complete search history.

(56) References Cited

U.S. PATENT DOCUMENTS

| | | | |
|---|---|---|---|
| 5,334,761 A | 8/1994 | Gebeyehu et al. |
| 5,578,475 A | 11/1996 | Jessee |
| 5,627,159 A | 5/1997 | Shih et al. |
| 5,674,908 A | 10/1997 | Haces et al. |
| 5,736,392 A | 4/1998 | Hawley-Nelson et al. |
| 5,877,220 A | 3/1999 | Schwartz et al. |
| 5,958,901 A | 9/1999 | Dwyer et al. |
| 6,020,202 A | 2/2000 | Jessee |
| 6,020,526 A | 2/2000 | Schwartz et al. |
| 6,034,135 A | 3/2000 | Schwartz et al. |
| 6,051,429 A | 4/2000 | Hawley-Nelson et al. |
| 6,075,012 A | 6/2000 | Gebeyehu et al. |
| 6,172,049 B1 | 1/2001 | Dwyer et al. |
| 6,251,939 B1 | 6/2001 | Schwartz et al. |
| 6,339,173 B1 | 1/2002 | Schwartz et al. |
| 6,376,248 B1 | 4/2002 | Hawley-Nelson et al. |
| 6,638,529 B2 | 10/2003 | Schwartz et al. |
| 6,671,393 B2 | 12/2003 | Hays et al. |
| 7,166,745 B1 | 1/2007 | Chu et al. |
| 7,479,573 B2 | 1/2009 | Chu et al. |
| 7,601,872 B2 | 10/2009 | Chu et al. |
| 7,687,070 B2 | 3/2010 | Gebeyehu et al. |
| 7,915,450 B2 | 3/2011 | Chu et al. |
| 8,058,068 B2 | 11/2011 | Hawley-Nelson et al. |
| 8,158,827 B2 | 4/2012 | Chu et al. |
| 2003/0069173 A1 | 4/2003 | Hawley-Nelson et al. |
| 2003/0143732 A1 | 7/2003 | Fosnaugh et al. |
| 2004/0259247 A1 | 12/2004 | Tuschl et al. |
| 2005/0260757 A1 | 11/2005 | Gebeyehu et al. |
| 2005/0282188 A1 | 12/2005 | Haeberli et al. |
| 2006/0147514 A1 | 7/2006 | Gebeyehu et al. |
| 2006/0228406 A1 | 10/2006 | Chiou et al. |
| 2007/0202598 A1 | 8/2007 | Chu et al. |
| 2007/0202600 A1 | 8/2007 | Chu et al. |
| 2009/0143583 A1 | 6/2009 | Chu et al. |
| 2010/0159593 A1 | 6/2010 | Chu et al. |
| 2012/0136073 A1 | 5/2012 | Yang et al. |
| 2012/0238747 A1 | 9/2012 | Chu et al. |

FOREIGN PATENT DOCUMENTS

| | | |
|---|---|---|
| WO | WO 2005/007196 A2 | 1/2005 |
| WO | WO 2006/074546 A1 | 7/2006 |
| WO | WO 2007/051303 A1 | 5/2007 |

OTHER PUBLICATIONS

Reynolds, A. et al., "Rational siRNA design for RNA interference," Nature Biotech., 2004, vol. 22, pp. 326-330.

Müller, Stefanie et al., "Broad-Spectrum Antiviral Activity of Small Interfering RNA Targeting the Conserved RNA Termini of Lassa Virus," Antimicrobial Agents and Chemotherapy, Jun. 2007, vol. 51, No. 6, pp. 2215-2218.

*Primary Examiner* — Sean McGarry
(74) *Attorney, Agent, or Firm* — Kilpatrick Townsend & Stockton LLP

(57) ABSTRACT

The present invention provides compositions comprising therapeutic nucleic acids such as interfering RNA (e.g., dsRNA such as siRNA) that target Lassa virus (LASV) or tissue factor (TF) gene expression, lipid particles comprising one or more (e.g., a cocktail) of the therapeutic nucleic acids, methods of making the lipid particles, and methods of delivering and/or administering the lipid particles (e.g., for treating hemorraghic fever).

30 Claims, 10 Drawing Sheets

FIG. 3

SEQUENCE LISTING

<160> NUMBER OF SEQ ID NOS: 115

<210> SEQ ID NO 1
<211> LENGTH: 2351
<212> TYPE: DNA
<213> ORGANISM: Homo sapiens
<220> FEATURE:
<223> OTHER INFORMATION: human tissue factor (TF), coagulation factor
      III (F3), thromboplastin, CD142 cDNA

<400> SEQUENCE: 1
gaggcgcggg agagcgcgcc gccggccctt tatagcgcgc ggggcaccgg ctccccaaga      60

```
ctgcgagctc cccgcacccc ctcgcactcc ctctggccgg cccagggcgc cttcagccca    120
acctccccag ccccacgggc gccacggaac ccgctcgatc tcgccgccaa ctggtagaca    180
tggagacccc tgcctggccc cgggtcccgc gccccgagac cgccgtcgct cggacgctcc    240
tgctcggctg ggtcttcgcc caggtggccg gcgcttcagg cactacaaat actgtggcag    300
catataattt aacttggaaa tcaactaatt tcaagacaat tttggagtgg gaacccaaac    360
ccgtcaatca agtctacact gttcaaataa gcactaagtc aggagattgg aaaagcaaat    420
gcttttacac aacagacaca gagtgtgacc tcaccgacga gattgtgaag gatgtgaagc    480
agacgtactt ggcacgggtc ttctcctacc cggcagggaa tgtggagagc accggttctg    540
ctggggagcc tctgtatgag aactccccag agttcacacc ttacctggag acaaacctcg    600
gacagccaac aattcagagt tttgaacagg tgggaacaaa agtgaatgtg accgtagaag    660
atgaacggac tttagtcaga aggaacaaca cttttcctaag cctccgggat gttttttggca    720 aggacttaat ttatacactt tattattgga aatcttcaag ttcaggaaag aaaacagcca    780
aaacaaacac taatgagttt ttgattgatg tggataaagg agaaaactac tgtttcagtg    840
ttcaagcagt gattccctcc cgaacagtta accggaagag tacagacagc ccggtagagt    900
gtatgggcca ggagaaaggg gaattcagag aaatattcta catcattgga gctgtggtat    960
ttgtggtcat catccttgtc atcatcctgg ctatatctct acacaagtgt agaaaggcag    1020
gagtggggca gagctggaag gagaactccc cactgaatgt ttcataaagg aagcactgtt    1080
ggagctactg caaatgctat attgcactgt gaccgagaac ttttaagagg atagaataca    1140
tggaaacgca aatgagtatt tcggagcatg aagaccctgg agttcaaaaa actcttgata    1200
tgacctgtta ttaccattag cattctggtt ttgacatcag cattagtcac tttgaaatgt    1260
aacgaatggt actacaacca attccaagtt ttaattttta acaccatggc accttttgca    1320
cataacatgc tttagattat atattccgca ctcaaggagt aaccaggtcg tccaagcaaa    1380
aacaaatggg aaaatgtctt aaaaaatcct gggtggactt ttgaaaagct tttttttttt    1440
tttttttttt tttgagacgg agtcttgctc tgttgcccag gctggagtgc agtagcacga    1500
tctcggctca ctgcacccctc cgtctctcgg gttcaagcaa ttgtctgcct cagcctcccg    1560
agtagctggg attacaggtg cgcactacca cgccaagcta attttttgtat tttttagtag    1620 agatgggggtt tcaccatctt ggccaggctg gtcttgaatt cctgacctca ggtgatccac    1680
ccaccttggc ctcccaaagt gctagtatta tgggcgtgaa ccaccatgcc cagccgaaaa    1740
gcttttgagg ggctgacttc aatccatgta ggaaagtaaa atggaaggaa attgggtgca    1800
tttctaggac ttttctaaca tatgtctata atatagtgtt taggttcttt tttttttcag    1860
gaatacattt ggaaattcaa acaattggc aaactttgta ttaatgtgtt aagtgcagga    1920
gacattggta ttctgggcac cttcctaata tgctttacaa tctgcacttt aactgactta    1980
agtggcatta acatttgag agctaactat atttttataa gactactata caaactacag    2040
agtttatgat ttaaggtact taaagcttct atggttgaca ttgtatatat aattttttaa    2100
aaaggttttc tatatgggga tttctatttt atgtaggtaa tattgttcta tttgtatata    2160
ttgagataat ttatttaata tactttaaat aaaggtgact gggaattgtt actgttgtac    2220
ttattctatc ttccatttat tatttatgta caatttggtg tttgtattag ctctactaca    2280
gtaaatgact gtaaaattgt cagtggctta caacaacgta tcttttttcgc ttataataca    2340 ttttggtgac t                                                         2351
```

-continued

```
<210> SEQ ID NO 2
<211> LENGTH: 3402
<212> TYPE: DNA
<213> ORGANISM: Lassa virus
<220> FEATURE:
<223> OTHER INFORMATION: Lassa virus Joshiah strain, segment S genomic
      sequence, S strand ambisense

<400> SEQUENCE: 2
cgcacagtgg atcctaggct attggattgc gctttgcttt tgtcattttg gcagatagtc      60
tcagttcttt gttgcgtgca tacaacacaa caatctggcg atgagtgcct caaggaaat      120 aaaatccttt ttgtggacac aatctttgag gagggaatta tctggttact gctccaacat      180
caaactacag gtggtgaaag atgcccaggc tcttttacat ggacttgact tctccgaagt      240
cagtaatgtt caacggttga tgcgcaagga gagaagggat gacaatgatt tgaaacggtt      300
gagggaccta aatcaagcgg tcaacaatct tgttgaatta aaatcaactc aacaaaagag      360
tatactgaga gttgggactc taacctcaga tgacttatta atcttagccg ctgatctaga      420
gaagttaaag tcaaggtga tcagaacaga aaggccatta agtgcaggtg tctatatggg      480
caacctaagc tcacagcaac ttgaccaaag aagagctctc ctgaatatga taggaatgag      540
tggtggtaat caaggggctc gggctgggag agatggagtg gtgagagttt gggatgtgaa      600
aaatgcagag ttgctcaata atcagttcgg gaccatgcca agtctgacac tggcatgtct      660
gacaaaacag gggcaggttg acttgaatga tgcagtacaa gcattgacag atttgggttt      720
gatctacaca gcaaagtatc ccaacacttc agacttagac aggctgactc aaagtcatcc      780
catcctaaat atgattgaca ccaagaaaag ctctttgaat atctcaggtt ataattttag      840
cttgggtgca gctgtgaagg caggagcttg catgctggat ggtggcaata tgttggagac      900
aatcaaggtg tcacctcaga caatggatgg tatcctcaaa tccattttaa aggtcaagaa      960
ggctcttgga atgttcattt cagacacccc tggtgaaagg aatccttatg aaaacatact     1020
ctacaagatt tgtttgtcag gagatggatg ccatatatt gcatcaagaa cctcaataac     1080
aggaagggcc tgggaaaaca ctgtcgttga tctggaatca gatgggaagc cacagaaagc     1140
tgacagcaac aattccagta aatccctgca gtcggcaggg tttaccgctg gcttaccta     1200 ttctcagctg atgaccctca aggatgcaat gctgcaactt gacccaaatg ctaagacctg     1260
gatggacatt gaaggaagac tgaagatcc agtggaaatt gccctctatc aaccaagttc     1320
aggctgctac atacacttct tccgtgaacc tactgattta aagcagttca gcaggatgc     1380 taagtactca catgggattg atgtcacaga cctcttcgct acacaaccgg gcttgaccag     1440
tgctgtcatt gatgcactcc cccggaatat ggtcattacc tgtcagggt ccgatgacat     1500 aaggaaactc cttgaatcac aaggaagaaa agacattaaa ctaattgata ttgccctcag     1560
caaaactgat tccaggaagt atgaaaatgc agtctgggac cagtataaag acttatgcca     1620
catgcacaca ggtgtcgttg ttgaaaagaa gaaaagaggc ggtaaagagg aaataacccc     1680
tcactgtgca ctaatggact gcatcatgtt tgatgcagca gtgtcaggag gactgaacac     1740
atcggttttg agagcagtgc tgcccagaga tatggtgttc agaacatcga cacctagagt     1800
cgttctgtaa atggacgccc ccgtgaccca ccgccaatag gcggtgggtc acggggcgcc     1860
tgacaagggt ctcatctctt ccatttcaca ggcacaccag gctgtttgta gagtccacag     1920
gaacaaatgc ccatatgatt caatctgtga ggtttgggac acgacttgcc tacaatatgc     1980
ctatgagttg gtattttgac taggtgaagg aagatgctaa taagatagaa acttgtactg     2040
aacacaaaga ggtcaactag acccaatggt gtcttcccct gcctctccat atactccttc     2100
```

```
tgtaacatct cagtgatcat attgtcagct tgttgttcaa tatcatcaga aaagtgggtc      2160
tcgttcaagt atgaaccatt tgatacaagc caacatttgg gcagtgatgt tctcccagta      2220
gttgtgtggt tgaggtacca atacttgctg taattacagt atggaattcc catgatgtcc      2280
cgtagatggt tcttcattat aagttggtca tttatcaaag catttactgc tttgttgatc      2340
aactgaatgc tcatttgtgc ttcagctttc aacctttgaa tggcttgttt gttgaagtca      2400
aacagcctca gcatgtcaca aaattcctca tcatgcttct cattacattt tgccacagct      2460
gtgttcccga agcattttag ttcagcctca attagcatcc acctggtcag acaatatccc      2520
cctggtgtgt ctttaccttc agaatctgac agtgtccatg tgaatgtgcc tagcaatctt      2580
ctactaatat aaatatctct agtcctttgt gagaggagcc cgagataacc gatgggagat      2640
ggtctcgaga attggcagtg atcttcccag gttgtatttt ggattatcag atattgataa      2700
ctagtcataa tacagtccca gttgccacgg cctgagtcaa gagcaatgta gctcccaccc      2760
caagccatcc tcataaaagt ctgtaacaca ccatttgcaa cagtaccaca atggttggct      2820
gcatccccag catagctgtg actcaggttg tactgcacac taatctttcc cccattaaaa      2880
tcgcagctca ttgcctcata ctgattgaag ttggggatgg acaagtggaa agttgagatt      2940
atgctcataa gagcgtggtc atagaggttc tttttgtggg catcagacag attgcaaaat      3000
ttgtgattaa taatgctcgt gttggtcaag gtcagttcta gtcctgtctc attgcccacc      3060
attatataat gatgactgtt gttctttgtg caggagagag gcatggtcat attgagtgtc      3120
tccatgttta gttccagagt ctgaagctca taaaccccctt tataaagact ggttgtgcaa      3180
gacctaccac acaacaggag gaaagtgacc aaaccaacaa ggccacacgt tgcaaaattg      3240
tacagacctt tcagcactgc tagtacagac agtgcaatga aacaatgtt catcacctct      3300 tctattacat gaggcacttc ctggaagaat gtcactattt gtcccatttt aaataggaca      3360
cttgaattgc gcaaccaaaa atgcctagga tccccggtgc gc                        3402
```

<210> SEQ ID NO 3
<211> LENGTH: 7279
<212> TYPE: DNA
<213> ORGANISM: Lassa virus
<220> FEATURE:
<223> OTHER INFORMATION: Lassa virus Joshiah strain, segment L genomic sequence, L strand negative sense

<400> SEQUENCE: 3

```
cgcaccgggg atcctaggca atttggttgt cttttttga ggccttgtgc gctgtacttc        60
tccaaatggg aaacaagcaa gccaaagccc cagaatcaaa agacagtccg agagccagcc      120
tgatcccaga tgccacacat ctagggccac agttctgtaa gagctgctgg ttcgaaaaca      180
agggcctggt tgagtgcaac aaccactatc tgtgtctcaa ctgcctcacc ttacttctaa      240
gtgtcagcaa caggtgtccc atttgcaaga tgcctctccc cacaaaactg agaccatcag      300
ccgctccaac agcacctcca accggagcag cggacagcat cagacccccca ccctacagtc      360 cctgaatctc ccaccgaccc ccaccactcc catcctcccc ccgacacccc cggggggac       420 ccccgccgg gggcccccc ggggagcca accatcacca aaaaactact caatgtcttc         480
gatgcattca tccttcctag tcagctcctc acatgttctg cccttcaatc tcaatttacc      540
accacttgat tgtaccatca ccttccccct tgacttacta taacagagag cataacccttt     600 gaactccacc cagttgtcca ctgcctcaag aaccgcactc aagatccctt cacaactcgg      660
cgctgcagcc ctaagtgtgg agacaatgtc caccctgac cactgcatcc ttaacccag        720 cctgtctatc atcatatcac tcaatgcccc aatcagcagg tcagacgaag tgtccccaac      780
```

```
ctctctcaca aatatctcaa gatcctggtc ttgtataaca ggtgtaaagg atgccaattt    840 cttttccacat tcccacaagc ctcccctatg cacaaccagg ggggttggtt cagtgcaagg    900
acccaccaat acaaagtcat actccgtaaa ctgcaacctt tccatatcaa caacaatctc    960 aacagggtc acatgcccta gttgatttgt gtcaattaaa aactcattaa tgatctcggt   1020
gtcaacatac catgctgatt tgcccttgaa agtaggtcct gacaaaacca gtctccaaca   1080
gtctgacaag acacacggac tcactgcacc tgagtacata acggttacat catgtactag   1140
atacttggcc tgttgattca ttgagccagt atactcaagg tggatggcaa agctttcctt   1200
aaaactagca tcttgacttt taacacggaa cctcactgtc tgactcagtt ttgcagaccc   1260
tggaggtagt gaagctacgg catcaaagaa atcctccaat gagtcaaact taggatcaac   1320
taaacctgat gcgatcaatt gattttgatt gaatctagct ggctcaatat caaagtctat   1380
ccaagcataa cccatcatca gatcatgctt aaacattggc ctttcaacac ctttgtgaat   1440
aactttctct acaaatgaag aaaatggacc cattctatgc aacccttcac cctctggaac   1500
tgatgtcttg tgtggaaacc acgtgaagga ccccaatgtt cttgtagtcg caacaaatgg   1560
tctcacgtaa gactcaaaat aaatttgcct catgaaattg tcaacagcat cactagtgct   1620
cactactctt tcttccacca tgggttcatg tgtcctactg tgagacaacc tcaattcaga   1680
tgataacaca atgtaatgtt cctctctttt ccatttttact atgtgtgaga caagagacaa   1740
ggcttcacag ttaacatcca acgctacaca gagatctaga aattttattc tgggtgacca   1800
cttcattttg gttgacgcta gatcgctcat gaatggtaat atgtgtttct caaacactga   1860
tgggtacagc cttcttaaag aatgaatgat gtgattcaaa ccaaccctat cctccaatag   1920
ttttgatgca gttggcttta agggaaaata gtcacaaggg ttatgtttga aaaaatcaaa   1980
caccttaact gtcttaggtt cccctaagac ccatgcaccc agttctattg cagttgataa   2040
ggagatgcac atataatccc ataacaaggg tctgaaataa ctgaccacac tttcacctcc   2100
acttccattt ctaagttcta gcggaacttg ccaatattga atgccattag aatttgtcaa   2160
caatttgatt cccttgacat cagaaatcag agactgaatg gacttaatat acagattctc   2220
tttatttggt ccccgaacac atttgctacc caatgttctg cacaatccta caaagccaga   2280
tgcaatggaa ctttggaatg cagatttgtt gatagcttca gacagcaatt tttgcgcacc   2340
tcgagtgaaa gtggaagaca acttattttg gattgttttg acaatggtag gaatcttctc   2400
atcatctagg ttcacagcac ctgaatatat tatcttttgt ctcaacacca ttcttaaagg   2460
atgatgcgca gccaagttta gccaagaata ctcaaggtca gactcagatg ggggctcaac   2520
atccaacagc tcacaaagat tcttagtga tgagaggtgc tcactagaca aatagtttgt   2580
tgtgaactct tcatggagtt gcccagtctt caacctattg tacagttttc ttaacataga   2640
tctaatcttg ctgcaagcat taggaatcaa tccctctatt tgcctcataa tcctataact   2700
acggttgcca tctacccagt ctctaacatc tgtctcgcaa ttcaataaga atgggtcaat   2760
agggtatctt gcatattgca aaggatttaa ggttctttc tgtattagat tacataagtg   2820
aacagggaca ccattcgcaa ccgactgatc aatgattgtg tcaattgttt ctgccagttg   2880
gtgtggctct ttacacttta tattgtgaag agctgctgca acgaactttg tcaataatgg   2940
cacttcatct ccccaaacaa aaaatctaga tttaaactct gcaacaaacc tgccaatgac   3000
acttttaggg ctcacaaaact tattgagttg atcactcata taatagtgga actctattag   3060
agtcctaaat tcttctgggt ctcttttgcaa aagctctgtg agagattgat caaagagaga   3120
aatctgatca tcactagagg tataagcatc tatcgtacca ccgcatatac aactgatagc   3180
```

```
ataattaatg aacctctctg aaatgagggc ataaaaatct gatgtgttgt gtaatattcc    3240
ttgacccatg tcaagtattg aactgatgtg agaaggcact acaccagctt ggaaattaga    3300
gtaaaagaaa tcttctgtta ttgactgttt agttttcttc cttaacccta gttgggcttt    3360
aatgaaagac ttcatcatgg ctgtcaccac attaaaaggt atttccacca ttttgtgcat    3420
atgccacata agtagggttg agagatagtc cctcccttt atgtcagctt gcaagtcctt    3480
tgagaggaaa attaaattct gtaagacagt caagaacaaa aatggacaca tcattgggcc    3540
ccacttacta tgatccatgc tataagacac atgtgccaat gaaacattca atttcatgga    3600
aaggatagca ttttcaaatt ccttctcgtt gttcaggcaa ctccctgata actgtaggct    3660
tatagcttca aagtaatctt ctataagtct agtaaacatc tttgttctaa gatcaccaat    3720
atataattct ctgttaccac ccacttgttc tttatatgac aaagaaaact taagccttcc    3780
tgtatcaggt cccactgagt cataagattg tggcgactct tggctataaa aacacaaatt    3840
ctttaacatt gctgtggtac agtttgtcag tgacagagcc ttactaagtg cctctgaatt    3900
gctctccctt tcactaattc ttacatcatc agagagttta cccatatcaa acttgaaatt    3960
aaggttcctt gacttataat gagtgtacct ccccataagt gtattcgcat tcatgatcaa    4020
gagtatggac ttaaaacact gaaagtattc atggttaaag tatgtccttg ttgacactgc    4080
ctttgtcaac tctccaatag acactgtga catatgtcca cagtaaaaat acttctgctt    4140
caatctacta ttctcataga cagcattaca gaattcttca taaaatttac ctggtaagat    4200
atcatgatca aactcctcaa ccatgtgatt ggataattca cccttgatca acctaatgta    4260
aaacttattt gagacaatct catctagatc atttattgat ggttggccat caccattagg    4320
gcctgagcct agcttgacag gttccctata ctgatcaaca atttttcaa cagtctcctt    4380
tagctgatca aaataatcgc ttgcacctcc atcgagcaaa atttcgtcta ggtcagcccc    4440
atcagcatca cttttgagct gcccagatcc tagaaccaaa ttgctcattg cctgctgaac    4500
tttgtactca tagtcctgct tgttgagaag gtactttcct ttccttgaga agacttcagt    4560
gagctgcgac acggccagtg ctgtgagctt attgaagtca tagtttaata ttctagaacc    4620
atctgtgtat ttattaacaa caacactttt cttgctggct aaatccaagg ctgcactgcc    4680
actggtgatg agaggatctt tgatttccct ttttacttcc ctctccttaa atagtgaacc    4740
attgttaaaa gaggatgtaa gaagagataa atacttcttt gaaacaccag gccttttata    4800
atctggtccc tcgatagttg tgcatccatc tttacttaaa aacttttttg cattgtagac    4860
catgtcatcc aattcttcct cagtggctgt gtctgcagga ttagtgctca catgaccaaa    4920
tctcaccttt ggttccagaa acttctcaaa acatttttatc tgatctgtca atctatctgg    4980
tgtttctttc gtaatgaagt ggcacatgta ggaaacattc aaaatgaact tgaacctatt    5040
agtcatcatg ctcttcacat cctcagataa aaccagattc attaatgtcc ttattaacct    5100
atagagcagg aactcaacat cagtgattaa ttcttccctt attttgtcaa tgaggtcctt    5160
atgatgataa tctgatagat aagccattac aaagtaccta agattttgga ggagcttttg    5220
agaacgttta ctggggtgag ctaaaattaa accaggatc atctttgtca gagacctgat    5280
attgttcaac tgcccttcca gctcattgca atcttctatc caagaaatca tagtgcttat    5340
tgttgtttgt aaaacctcag ctgaaaatat tgctggaaaa tatcttttag gatcagcata    5400
aaatgagcac acctcaccaa ctttgttatc attaatagca tagcacttcg agcactcccc    5460
tgtcttttga taaatcagtt gtaattcagt gttacccaat gaaaactctt gacaatatgc    5520
ttctttgcat ctgaccactt gataccttgc gggtccaaat tcattctgtc tcagctttac    5580
```

-continued

```
ggtagaagaa gttttcatag agttcaccaa agcgaggctc aatgaggaaa gtctctctaa    5640
gtcagtggtt cccagtagtt ccacatcccc catcacataa gggaatgttt cttcctctgt    5700
tctctgataa ctgattgttg ggacaactcc ggagacatca aagtccataa tcaaatcata    5760
gctgttaagg cagatcacct ccatatcaat tttatagtgg tccacactga tcccaacatc    5820 cttaaagca gtggtggcct tcaaaatggt tttctggaat attgaattga ggatttgatt     5880
cttactcaaa cactgggagg actgtgtgat tctagatctt agcctgttgc ctcgctctcc    5940
ccatttctcg agatccctct tgttgcctc caaagaaact agtctatctt taactcttaa     6000
gaagcaagac cccaaccacc cttttaaaca cttttgtttc atcaggtcat gcttacttgc    6060
aaggagaatt agtgcatcaa aaattaatag aagtttcctc cttgtgttca atatcctcaa    6120 agatttact ttatttagga atgatctcca gcattgaacc tgacattctc caatagtttg     6180 gtttccctt ttttcattcc cctcatcaac atttgcatac aaaaatctca atattggtga     6240
tgctctcttg aactggtaaa ttaagtgttc gatattgtct tctgcaacta ccttatcagc    6300
gtacaaattg ttaagctcat taagtaactg gctcttatca accttaaaa actgaccttc     6360 tatctctcct ttcctcaatc tgttcctaaa cacttgatac tcctcttcga tctgcagctt    6420
tacctcatga gctgttaatt tattattgat gccctggtgg catgaggcaa tcacttcctc    6480
ataatgatta gagcgattgt ccatcagaac atttaaactc tccaccctg ataatctacc     6540 cgaagtcatg aataaagatt cacagagtct gctatactct gactcttcaa aaagtgaatt    6600
actctcctgt gcatacttta aaagtgagaa gagcgtatcc ctcaacttat cattgaccca    6660
gtcaggtatt tgttcattgt agaatgatgt tctcccgtct ataagtggta ttaaattgat    6720
gtcgacactc ttcaggtctt cttttcagctg ctctaatttt ttgaagtcct caatgtactt   6780
ctgctcaaag ttagcaggag atgatctaac aaaacactcc agcagtatta gaacattgcc    6840
cgtcagtttg taaccgtccg ggtaccacaa acatagtgaa ggtgtcaaga ttccatggtc    6900
atggagaatt cttttccacag atttgtcctc actgttatgc tcgcaaccat ttgcgttgca   6960
agaatcaacc tcaatacaga gggacaagag tttcaaccct tccattaata gcatcctagg    7020
ctctgtctgc acaagaaatg ctaacttctg tcttgacaat ctctcgttgt ccactaggta    7080
ttttgatact aagtctttga cacaggctat gtcttcctcc atgtttagct gcaggtatga    7140
tgttcagaac cctcagaaca tgtggtctgc tagagcaaca gttcgctatg ggatagggtc    7200
ccgtaggggc acagaagaca caagaggcaa ttaaagacaa ttaaataaga tagccttaat    7260
gcctaggatc ctcggtgcg                                                 7279
```

<210> SEQ ID NO 4
<211> LENGTH: 19
<212> TYPE: RNA
<213> ORGANISM: Artificial Sequence
<220> FEATURE:
<223> OTHER INFORMATION: synthetic human tissue factor (TF) hTF292 siRNA
       target or sense strand

<400> SEQUENCE: 4
guggcagcau auaauuuaa                                                   19

<210> SEQ ID NO 5
<211> LENGTH: 19
<212> TYPE: RNA
<213> ORGANISM: Artificial Sequence
<220> FEATURE:
<223> OTHER INFORMATION: synthetic human tissue factor (TF) hTF292 siRNA
       antisense strand

<400> SEQUENCE: 5
uuaaauuaua ugcugccac                                             19

<210> SEQ ID NO 6
<211> LENGTH: 19
<212> TYPE: RNA
<213> ORGANISM: Artificial Sequence
<220> FEATURE:
<223> OTHER INFORMATION: synthetic human tissue factor (TF) hTF271 siRNA
      target or sense strand

<400> SEQUENCE: 6
gcgcuucagg cacuacaaa                                             19

<210> SEQ ID NO 7
<211> LENGTH: 19
<212> TYPE: RNA
<213> ORGANISM: Artificial Sequence
<220> FEATURE:
<223> OTHER INFORMATION: synthetic human tissue factor (TF) hTF271 siRNA
      antisense strand

<400> SEQUENCE: 7
uuuguagugc cugaagcgc                                             19

<210> SEQ ID NO 8
<211> LENGTH: 19
<212> TYPE: RNA
<213> ORGANISM: Artificial Sequence
<220> FEATURE:
<223> OTHER INFORMATION: synthetic human tissue factor (TF) hTF1238
      siRNA target or sense strand

<400> SEQUENCE: 8
gcauuaguca cuuugaaau                                             19

<210> SEQ ID NO 9
<211> LENGTH: 19
<212> TYPE: RNA
<213> ORGANISM: Artificial Sequence
<220> FEATURE:
<223> OTHER INFORMATION: synthetic human tissue factor (TF) hTF1238
      siRNA antisense strand

<400> SEQUENCE: 9
auuucaaagu gacuaaugc                                             19

<210> SEQ ID NO 10
<211> LENGTH: 19
<212> TYPE: RNA
<213> ORGANISM: Artificial Sequence
<220> FEATURE:
<223> OTHER INFORMATION: synthetic human tissue factor (TF) hTF369 siRNA
      target or sense strand

<400> SEQUENCE: 10
agucuacacu guucaaaua                                             19

<210> SEQ ID NO 11
<211> LENGTH: 19
<212> TYPE: RNA
<213> ORGANISM: Artificial Sequence
<220> FEATURE:
<223> OTHER INFORMATION: synthetic human tissue factor (TF) hTF369 siRNA
      antisense strand

<400> SEQUENCE: 11
uauuugaaca guguagacu                                    19

<210> SEQ ID NO 12
<211> LENGTH: 19
<212> TYPE: RNA
<213> ORGANISM: Artificial Sequence
<220> FEATURE:
<223> OTHER INFORMATION: synthetic human tissue factor (TF) hTF290 siRNA
      target or sense strand

<400> SEQUENCE: 12
cuguggcagc auauaauuu                                    19

<210> SEQ ID NO 13
<211> LENGTH: 19
<212> TYPE: RNA
<213> ORGANISM: Artificial Sequence
<220> FEATURE:
<223> OTHER INFORMATION: synthetic human tissue factor (TF) hTF290 siRNA
      antisense strand

<400> SEQUENCE: 13
aaauuauaug cugccacag                                    19

<210> SEQ ID NO 14
<211> LENGTH: 19
<212> TYPE: RNA
<213> ORGANISM: Artificial Sequence
<220> FEATURE:
<223> OTHER INFORMATION: synthetic human tissue factor (TF) hTF288 siRNA
      target or sense strand

<400> SEQUENCE: 14
uacuguggca gcauauaau                                    19

<210> SEQ ID NO 15
<211> LENGTH: 19
<212> TYPE: RNA
<213> ORGANISM: Artificial Sequence
<220> FEATURE:
<223> OTHER INFORMATION: synthetic human tissue factor (TF) hTF288 siRNA
      antisense strand

<400> SEQUENCE: 15
auuauaugcu gccacagua                                    19

<210> SEQ ID NO 16
<211> LENGTH: 19
<212> TYPE: RNA
<213> ORGANISM: Artificial Sequence
<220> FEATURE:
<223> OTHER INFORMATION: synthetic Lassa virus (LASV) L-polymerase
      (L-pol) LS-L-844 siRNA target or sense strand

<400> SEQUENCE: 16
gacaauaucg aacacuuaa                                    19

<210> SEQ ID NO 17
<211> LENGTH: 19
<212> TYPE: RNA
<213> ORGANISM: Artificial Sequence
<220> FEATURE:
<223> OTHER INFORMATION: synthetic Lassa virus (LASV) L-polymerase
      (L-pol) LS-L-844 siRNA antisense strand

<400> SEQUENCE: 17
uuaaguguuc gauauuguc                                    19

```
<210> SEQ ID NO 18
<211> LENGTH: 19
<212> TYPE: RNA
<213> ORGANISM: Artificial Sequence
<220> FEATURE:
<223> OTHER INFORMATION: synthetic Lassa virus (LASV) L-polymerase
      (L-pol) LS-L-1022 siRNA target or sense strand

<400> SEQUENCE: 18
ggaggaaacu ucuauuaau                                                19

<210> SEQ ID NO 19
<211> LENGTH: 19
<212> TYPE: RNA
<213> ORGANISM: Artificial Sequence
<220> FEATURE:
<223> OTHER INFORMATION: synthetic Lassa virus (LASV) L-polymerase
      (L-pol) LS-L-1022 siRNA antisense strand

<400> SEQUENCE: 19
auuaauagaa guuuccucc                                                19

<210> SEQ ID NO 20
<211> LENGTH: 19
<212> TYPE: RNA
<213> ORGANISM: Artificial Sequence
<220> FEATURE:
<223> OTHER INFORMATION: synthetic Lassa virus (LASV) L-polymerase
      (L-pol) LS-L-1778 siRNA target or sense strand

<400> SEQUENCE: 20
caacaauaag cacuaugau                                                19

<210> SEQ ID NO 21
<211> LENGTH: 19
<212> TYPE: RNA
<213> ORGANISM: Artificial Sequence
<220> FEATURE:
<223> OTHER INFORMATION: synthetic Lassa virus (LASV) L-polymerase
      (L-pol) LS-L-1778 siRNA antisense strand

<400> SEQUENCE: 21
aucauagugc uuauuguug                                                19

<210> SEQ ID NO 22
<211> LENGTH: 19
<212> TYPE: RNA
<213> ORGANISM: Artificial Sequence
<220> FEATURE:
<223> OTHER INFORMATION: synthetic Lassa virus (LASV) L-polymerase
      (L-pol) LS-L-3513 siRNA target or sense strand

<400> SEQUENCE: 22
ugcuauccuu uccaugaaa                                                19

<210> SEQ ID NO 23
<211> LENGTH: 19
<212> TYPE: RNA
<213> ORGANISM: Artificial Sequence
<220> FEATURE:
<223> OTHER INFORMATION: synthetic Lassa virus (LASV) L-polymerase
      (L-pol) LS-L-3513 siRNA antisense strand

<400> SEQUENCE: 23
uuucauggaa aggauagca                                                19
```

```
<210> SEQ ID NO 24
<211> LENGTH: 19
<212> TYPE: RNA
<213> ORGANISM: Artificial Sequence
<220> FEATURE:
<223> OTHER INFORMATION: synthetic Lassa virus (LASV) L-polymerase
      (L-pol) LS-L-6313 siRNA target or sense strand

<400> SEQUENCE: 24
gaccaggauc uugagauau                                                    19

<210> SEQ ID NO 25
<211> LENGTH: 19
<212> TYPE: RNA
<213> ORGANISM: Artificial Sequence
<220> FEATURE:
<223> OTHER INFORMATION: synthetic Lassa virus (LASV) L-polymerase
      (L-pol) LS-L-6313 siRNA antisense strand

<400> SEQUENCE: 25
auaucucaag auccugguc                                                    19

<210> SEQ ID NO 26
<211> LENGTH: 19
<212> TYPE: RNA
<213> ORGANISM: Artificial Sequence
<220> FEATURE:
<223> OTHER INFORMATION: synthetic Lassa virus (LASV) nucleoprotein (NP)
      LS-NP-548 siRNA target or sense strand

<400> SEQUENCE: 26
cacuggcaug ucugacaaa                                                    19

<210> SEQ ID NO 27
<211> LENGTH: 19
<212> TYPE: RNA
<213> ORGANISM: Artificial Sequence
<220> FEATURE:
<223> OTHER INFORMATION: synthetic Lassa virus (LASV) nucleoprotein (NP)
      LS-NP-548 siRNA antisense strand

<400> SEQUENCE: 27
uuugucagac augccagug                                                    19

<210> SEQ ID NO 28
<211> LENGTH: 19
<212> TYPE: RNA
<213> ORGANISM: Artificial Sequence
<220> FEATURE:
<223> OTHER INFORMATION: synthetic Lassa virus (LASV) nucleoprotein (NP)
      LS-NP-672 siRNA target or sense strand

<400> SEQUENCE: 28
aagucauccc auccuaaau                                                    19

<210> SEQ ID NO 29
<211> LENGTH: 19
<212> TYPE: RNA
<213> ORGANISM: Artificial Sequence
<220> FEATURE:
<223> OTHER INFORMATION: synthetic Lassa virus (LASV) nucleoprotein (NP)
      LS-NP-672 siRNA antisense strand

<400> SEQUENCE: 29
auuuaggaug ggaugacuu                                                    19

<210> SEQ ID NO 30
<211> LENGTH: 19
```

```
<212> TYPE: RNA
<213> ORGANISM: Artificial Sequence
<220> FEATURE:
<223> OTHER INFORMATION: synthetic Lassa virus (LASV) nucleoprotein (NP)
      LS-NP-943 siRNA target or sense strand

<400> SEQUENCE: 30
gauggauggc cauauauug                                                19

<210> SEQ ID NO 31
<211> LENGTH: 19
<212> TYPE: RNA
<213> ORGANISM: Artificial Sequence
<220> FEATURE:
<223> OTHER INFORMATION: synthetic Lassa virus (LASV) nucleoprotein (NP)
      LS-NP-943 siRNA antisense strand

<400> SEQUENCE: 31
caauauaugg ccauccauc                                                19

<210> SEQ ID NO 32
<211> LENGTH: 19
<212> TYPE: RNA
<213> ORGANISM: Artificial Sequence
<220> FEATURE:
<223> OTHER INFORMATION: synthetic Lassa virus (LASV) nucleoprotein (NP)
      LS-NP-1222 siRNA target or sense strand

<400> SEQUENCE: 32
ggcugcuaca uacacuucu                                                19

<210> SEQ ID NO 33
<211> LENGTH: 19
<212> TYPE: RNA
<213> ORGANISM: Artificial Sequence
<220> FEATURE:
<223> OTHER INFORMATION: synthetic Lassa virus (LASV) nucleoprotein (NP)
      LS-NP-1222 siRNA antisense strand

<400> SEQUENCE: 33
agaaguguau guagcagcc                                                19

<210> SEQ ID NO 34
<211> LENGTH: 19
<212> TYPE: RNA
<213> ORGANISM: Artificial Sequence
<220> FEATURE:
<223> OTHER INFORMATION: synthetic Lassa virus (LASV) nucleoprotein (NP)
      LS-NP-1284 siRNA target or sense strand

<400> SEQUENCE: 34
guacucacau gggauugau                                                19

<210> SEQ ID NO 35
<211> LENGTH: 19
<212> TYPE: RNA
<213> ORGANISM: Artificial Sequence
<220> FEATURE:
<223> OTHER INFORMATION: synthetic Lassa virus (LASV) nucleoprotein (NP)
      LS-NP-1284 siRNA antisense strand

<400> SEQUENCE: 35
aucaauccca ugugaguac                                                19

<210> SEQ ID NO 36
<211> LENGTH: 19
<212> TYPE: RNA
<213> ORGANISM: Artificial Sequence
```

```
<220> FEATURE:
<223> OTHER INFORMATION: synthetic human tissue factor (TF) S-1
      2'OMe-modified siRNA sense strand
<220> FEATURE:
<221> NAME/KEY: modified_base
<222> LOCATION: (2)...(16)
<223> OTHER INFORMATION: n = um

<400> SEQUENCE: 36
gnggcagcau auaaunuaa                                                    19

<210> SEQ ID NO 37
<211> LENGTH: 19
<212> TYPE: RNA
<213> ORGANISM: Artificial Sequence
<220> FEATURE:
<223> OTHER INFORMATION: synthetic human tissue factor (TF) AS-1
      2'OMe-modified siRNA antisense strand
<220> FEATURE:
<221> NAME/KEY: modified_base
<222> LOCATION: (12)...(12)
<223> OTHER INFORMATION: n = gm

<400> SEQUENCE: 37
uuaaauuaua uncugccac                                                    19

<210> SEQ ID NO 38
<211> LENGTH: 19
<212> TYPE: RNA
<213> ORGANISM: Artificial Sequence
<220> FEATURE:
<223> OTHER INFORMATION: synthetic human tissue factor (TF) S-2
      2'OMe-modified siRNA sense strand
<220> FEATURE:
<221> NAME/KEY: modified_base
<222> LOCATION: (2)...(17)
<223> OTHER INFORMATION: n = um

<400> SEQUENCE: 38
gnggcagcan anaannnaa                                                    19

<210> SEQ ID NO 39
<211> LENGTH: 19
<212> TYPE: RNA
<213> ORGANISM: Artificial Sequence
<220> FEATURE:
<223> OTHER INFORMATION: synthetic human tissue factor (TF) AS-2
      2'OMe-modified siRNA antisense strand
<220> FEATURE:
<221> NAME/KEY: modified_base
<222> LOCATION: (12)...(15)
<223> OTHER INFORMATION: n = gm

<400> SEQUENCE: 39
uuaaauuaua uncunccac                                                    19

<210> SEQ ID NO 40
<211> LENGTH: 19
<212> TYPE: RNA
<213> ORGANISM: Artificial Sequence
<220> FEATURE:
<223> OTHER INFORMATION: synthetic human tissue factor (TF) S-3
      2'OMe-modified siRNA sense strand
<220> FEATURE:
<221> NAME/KEY: modified_base
<222> LOCATION: (2)...(17)
<223> OTHER INFORMATION: n = um

<400> SEQUENCE: 40
gnggcagcau anaanunaa                                                    19
```

```
<210> SEQ ID NO 41
<211> LENGTH: 19
<212> TYPE: RNA
<213> ORGANISM: Artificial Sequence
<220> FEATURE:
<223> OTHER INFORMATION: synthetic human tissue factor (TF) AS-4
      2'OMe-modified siRNA antisense strand
<220> FEATURE:
<221> NAME/KEY: modified_base
<222> LOCATION: (6)...(6)
<223> OTHER INFORMATION: n = um
<220> FEATURE:
<221> NAME/KEY: modified_base
<222> LOCATION: (12)...(12)
<223> OTHER INFORMATION: n = gm

<400> SEQUENCE: 41
uuaaanuaua uncugccac                                              19

<210> SEQ ID NO 42
<211> LENGTH: 19
<212> TYPE: RNA
<213> ORGANISM: Artificial Sequence
<220> FEATURE:
<223> OTHER INFORMATION: synthetic human tissue factor (TF) AS-5b
      2'OMe-modified siRNA antisense strand
<220> FEATURE:
<221> NAME/KEY: modified_base
<222> LOCATION: (6)...(6)
<223> OTHER INFORMATION: n = um
<220> FEATURE:
<221> NAME/KEY: modified_base
<222> LOCATION: (12)...(15)
<223> OTHER INFORMATION: n = gm

<400> SEQUENCE: 42
uuaaanuaua uncunccac                                              19

<210> SEQ ID NO 43
<211> LENGTH: 19
<212> TYPE: RNA
<213> ORGANISM: Artificial Sequence
<220> FEATURE:
<223> OTHER INFORMATION: synthetic human tissue factor (TF) AS-6
      2'OMe-modified siRNA antisense strand
<220> FEATURE:
<221> NAME/KEY: modified_base
<222> LOCATION: (2)...(6)
<223> OTHER INFORMATION: n = um
<220> FEATURE:
<221> NAME/KEY: modified_base
<222> LOCATION: (12)...(15)
<223> OTHER INFORMATION: n = gm

<400> SEQUENCE: 43
unaaanuaua uncunccac                                              19

<210> SEQ ID NO 44
<211> LENGTH: 19
<212> TYPE: RNA
<213> ORGANISM: Artificial Sequence
<220> FEATURE:
<223> OTHER INFORMATION: synthetic Lassa virus (LASV) L-polymerase
      (L-pol) or nucleoprotein (NP) S-1 2'OMe-modified siRNA
      sense strand
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (12)...(12)
<223> OTHER INFORMATION: n = gm
```

```
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (17)...(17)
<223> OTHER INFORMATION: n = gm

<400> SEQUENCE: 44
gnacucacau gnganunau                                              19

<210> SEQ ID NO 45
<211> LENGTH: 19
<212> TYPE: RNA
<213> ORGANISM: Artificial Sequence
<220> FEATURE:
<223> OTHER INFORMATION: synthetic Lassa virus (LASV) L-polymerase
     (L-pol) or nucleoprotein (NP) AS-1 2'OMe-modified siRNA
     antisense strand
<220> FEATURE:
<221> NAME/KEY: modified_base
<222> LOCATION: (13)...(17)
<223> OTHER INFORMATION: n = um

<400> SEQUENCE: 45
aucaauccca ugngagnac                                              19

<210> SEQ ID NO 46
<211> LENGTH: 19
<212> TYPE: RNA
<213> ORGANISM: Artificial Sequence
<220> FEATURE:
<223> OTHER INFORMATION: synthetic Lassa virus (LASV) L-polymerase
     (L-pol) or nucleoprotein (NP) S-2 2'OMe-modified siRNA
     sense strand
<220> FEATURE:
<221> NAME/KEY: modified_base
<222> LOCATION: (2)...(5)
<223> OTHER INFORMATION: n = um
<220> FEATURE:
<221> NAME/KEY: modified_base
<222> LOCATION: (12)...(12)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (17)...(17)
<223> OTHER INFORMATION: n = gm

<400> SEQUENCE: 46
gnacncacau gnganunau                                              19

<210> SEQ ID NO 47
<211> LENGTH: 19
<212> TYPE: RNA
<213> ORGANISM: Artificial Sequence
<220> FEATURE:
<223> OTHER INFORMATION: synthetic Lassa virus (LASV) L-polymerase
     (L-pol) or nucleoprotein (NP) AS-2 2'OMe-modified siRNA
     antisense strand
<220> FEATURE:
<221> NAME/KEY: modified_base
<222> LOCATION: (13)...(17)
<223> OTHER INFORMATION: n = um

<400> SEQUENCE: 47
aucaauccca ugngagnac                                              19
```

```
<210> SEQ ID NO 48
<211> LENGTH: 19
<212> TYPE: RNA
<213> ORGANISM: Artificial Sequence
<220> FEATURE:
<223> OTHER INFORMATION: synthetic Lassa virus (LASV) L-polymerase
      (L-pol) or nucleoprotein (NP) AS-3 2'OMe-modified siRNA
      antisense strand
<220> FEATURE:
<221> NAME/KEY: modified_base
<222> LOCATION: (6)...(17)
<223> OTHER INFORMATION: n = um

<400> SEQUENCE: 48
aucaanccca ugngagnac                                                 19

<210> SEQ ID NO 49
<211> LENGTH: 19
<212> TYPE: RNA
<213> ORGANISM: Artificial Sequence
<220> FEATURE:
<223> OTHER INFORMATION: synthetic Lassa virus (LASV) L-polymerase
      (L-pol) or nucleoprotein (NP) AS-4 2'OMe-modified siRNA
      antisense strand
<220> FEATURE:
<221> NAME/KEY: modified_base
<222> LOCATION: (2)...(17)
<223> OTHER INFORMATION: n = um

<400> SEQUENCE: 49
ancaauccca ugngagnac                                                 19

<210> SEQ ID NO 50
<211> LENGTH: 21
<212> TYPE: DNA
<213> ORGANISM: Artificial Sequence
<220> FEATURE:
<223> OTHER INFORMATION: synthetic Lassa virus (LASV) L-polymerase
      (L-pol) LS-L-844 siRNA sense strand

<400> SEQUENCE: 50
gacaauaucg aacacuuaat t                                              21

<210> SEQ ID NO 51
<211> LENGTH: 21
<212> TYPE: DNA
<213> ORGANISM: Artificial Sequence
<220> FEATURE:
<223> OTHER INFORMATION: synthetic Lassa virus (LASV) L-polymerase
      (L-pol) LS-L-844 siRNA antisense strand

<400> SEQUENCE: 51
uuaaguguuc gauauugct t                                               21

<210> SEQ ID NO 52
<211> LENGTH: 21
<212> TYPE: DNA
<213> ORGANISM: Artificial Sequence
<220> FEATURE:
<223> OTHER INFORMATION: synthetic Lassa virus (LASV) L-polymerase
      (L-pol) LS-L-1022 siRNA sense strand

<400> SEQUENCE: 52
ggaggaaacu ucuauuaaut t                                              21

<210> SEQ ID NO 53
<211> LENGTH: 21
<212> TYPE: DNA
<213> ORGANISM: Artificial Sequence
<220> FEATURE:
```

```
<223> OTHER INFORMATION: synthetic Lassa virus (LASV) L-polymerase
      (L-pol) LS-L-1022 siRNA antisense strand

<400> SEQUENCE: 53
auuaauagaa guuccucct t                                               21

<210> SEQ ID NO 54
<211> LENGTH: 21
<212> TYPE: DNA
<213> ORGANISM: Artificial Sequence
<220> FEATURE:
<223> OTHER INFORMATION: synthetic Lassa virus (LASV) L-polymerase
      (L-pol) LS-L-1778 siRNA sense strand

<400> SEQUENCE: 54
caacaauaag cacuaugaut t                                              21

<210> SEQ ID NO 55
<211> LENGTH: 21
<212> TYPE: DNA
<213> ORGANISM: Artificial Sequence
<220> FEATURE:
<223> OTHER INFORMATION: synthetic Lassa virus (LASV) L-polymerase
      (L-pol) LS-L-1778 siRNA antisense strand

<400> SEQUENCE: 55
aucauagugc uuauuguugt t                                              21

<210> SEQ ID NO 56
<211> LENGTH: 21
<212> TYPE: DNA
<213> ORGANISM: Artificial Sequence
<220> FEATURE:
<223> OTHER INFORMATION: synthetic Lassa virus (LASV) L-polymerase
      (L-pol) LS-L-3513 siRNA sense strand

<400> SEQUENCE: 56
ugcuauccuu uccaugaaat t                                              21

<210> SEQ ID NO 57
<211> LENGTH: 21
<212> TYPE: DNA
<213> ORGANISM: Artificial Sequence
<220> FEATURE:
<223> OTHER INFORMATION: synthetic Lassa virus (LASV) L-polymerase
      (L-pol) LS-L-3513 siRNA antisense strand

<400> SEQUENCE: 57
uuucauggaa aggauagcat t                                              21

<210> SEQ ID NO 58
<211> LENGTH: 21
<212> TYPE: DNA
<213> ORGANISM: Artificial Sequence
<220> FEATURE:
<223> OTHER INFORMATION: synthetic Lassa virus (LASV) L-polymerase
      (L-pol) LS-L-6313 siRNA sense strand

<400> SEQUENCE: 58
gaccaggauc uugagauaut t                                              21

<210> SEQ ID NO 59
<211> LENGTH: 21
<212> TYPE: DNA
<213> ORGANISM: Artificial Sequence
<220> FEATURE:
<223> OTHER INFORMATION: synthetic Lassa virus (LASV) L-polymerase
      (L-pol) LS-L-6313 siRNA antisense strand
```

-continued

```
<400> SEQUENCE: 59
auaucucaag auccugguct t                                              21

<210> SEQ ID NO 60
<211> LENGTH: 21
<212> TYPE: DNA
<213> ORGANISM: Artificial Sequence
<220> FEATURE:
<223> OTHER INFORMATION: synthetic Lassa virus (LASV) nucleoprotein (NP)
      LS-NP-548 siRNA sense strand

<400> SEQUENCE: 60
cacuggcaug ucugacaaat t                                              21

<210> SEQ ID NO 61
<211> LENGTH: 21
<212> TYPE: DNA
<213> ORGANISM: Artificial Sequence
<220> FEATURE:
<223> OTHER INFORMATION: synthetic Lassa virus (LASV) nucleoprotein (NP)
      LS-NP-548 siRNA antisense strand

<400> SEQUENCE: 61
uuugucagac augccagugt t                                              21

<210> SEQ ID NO 62
<211> LENGTH: 21
<212> TYPE: DNA
<213> ORGANISM: Artificial Sequence
<220> FEATURE:
<223> OTHER INFORMATION: synthetic Lassa virus (LASV) nucleoprotein (NP)
      LS-NP-672 siRNA sense strand

<400> SEQUENCE: 62
aagucauccc auccuaaaut t                                              21

<210> SEQ ID NO 63
<211> LENGTH: 21
<212> TYPE: DNA
<213> ORGANISM: Artificial Sequence
<220> FEATURE:
<223> OTHER INFORMATION: synthetic Lassa virus (LASV) nucleoprotein (NP)
      LS-NP-672 siRNA antisense strand

<400> SEQUENCE: 63
auuuaggaug ggaugacuut t                                              21

<210> SEQ ID NO 64
<211> LENGTH: 21
<212> TYPE: DNA
<213> ORGANISM: Artificial Sequence
<220> FEATURE:
<223> OTHER INFORMATION: synthetic Lassa virus (LASV) nucleoprotein (NP)
      LS-NP-943 siRNA sense strand

<400> SEQUENCE: 64
gauggauggc cauauauugt t                                              21

<210> SEQ ID NO 65
<211> LENGTH: 21
<212> TYPE: DNA
<213> ORGANISM: Artificial Sequence
<220> FEATURE:
<223> OTHER INFORMATION: synthetic Lassa virus (LASV) nucleoprotein (NP)
      LS-NP-943 siRNA antisense strand

<400> SEQUENCE: 65
```

```
caauauaugg ccauccauct t                                          21
```

<210> SEQ ID NO 66
<211> LENGTH: 21
<212> TYPE: DNA
<213> ORGANISM: Artificial Sequence
<220> FEATURE:
<223> OTHER INFORMATION: synthetic Lassa virus (LASV) nucleoprotein (NP)
      LS-NP-1222 siRNA sense strand

<400> SEQUENCE: 66

```
ggcugcuaca uacacuucut t                                          21
```

<210> SEQ ID NO 67
<211> LENGTH: 21
<212> TYPE: DNA
<213> ORGANISM: Artificial Sequence
<220> FEATURE:
<223> OTHER INFORMATION: synthetic Lassa virus (LASV) nucleoprotein (NP)
      LS-NP-1222 siRNA antisense strand

<400> SEQUENCE: 67

```
agaaguguau guagcagcct t                                          21
```

<210> SEQ ID NO 68
<211> LENGTH: 21
<212> TYPE: DNA
<213> ORGANISM: Artificial Sequence
<220> FEATURE:
<223> OTHER INFORMATION: synthetic Lassa virus (LASV) nucleoprotein (NP)
      LS-NP-1284 siRNA sense strand

<400> SEQUENCE: 68

```
guacucacau gggauugaut t                                          21
```

<210> SEQ ID NO 69
<211> LENGTH: 21
<212> TYPE: DNA
<213> ORGANISM: Artificial Sequence
<220> FEATURE:
<223> OTHER INFORMATION: synthetic Lassa virus (LASV) nucleoprotein (NP)
      LS-NP-1284 siRNA antisense strand

<400> SEQUENCE: 69

```
aucaauccca ugugaguact t                                          21
```

<210> SEQ ID NO 70
<211> LENGTH: 21
<212> TYPE: RNA
<213> ORGANISM: Artificial Sequence
<220> FEATURE:
<223> OTHER INFORMATION: synthetic control anti-Luc siRNA sense strand

<400> SEQUENCE: 70

```
gauuaugucc gguuauguau u                                          21
```

<210> SEQ ID NO 71
<211> LENGTH: 21
<212> TYPE: RNA
<213> ORGANISM: Artificial Sequence
<220> FEATURE:
<223> OTHER INFORMATION: synthetic control anti-Luc siRNA antisense
      strand

<400> SEQUENCE: 71

```
uacauaaccg gacauaaucu u                                          21
```

```
<210> SEQ ID NO 72
<211> LENGTH: 21
<212> TYPE: DNA
<213> ORGANISM: Artificial Sequence
<220> FEATURE:
<223> OTHER INFORMATION: synthetic control Luc U/U v2 siRNA sense strand
<220> FEATURE:
<221> NAME/KEY: modified_base
<222> LOCATION: (3)...(18)
<223> OTHER INFORMATION: n = um

<400> SEQUENCE: 72
gannangncc ggnnangnat t                                               21

<210> SEQ ID NO 73
<211> LENGTH: 21
<212> TYPE: DNA
<213> ORGANISM: Artificial Sequence
<220> FEATURE:
<223> OTHER INFORMATION: synthetic control Luc U/U v2 siRNA antisense
      strand
<220> FEATURE:
<221> NAME/KEY: modified_base
<222> LOCATION: (5)...(18)
<223> OTHER INFORMATION: n = um

<400> SEQUENCE: 73
uacanaaccg gacanaanct t                                               21

<210> SEQ ID NO 74
<211> LENGTH: 21
<212> TYPE: RNA
<213> ORGANISM: Artificial Sequence
<220> FEATURE:
<223> OTHER INFORMATION: synthetic control Luc U/U v3 siRNA sense strand
<220> FEATURE:
<221> NAME/KEY: modified_base
<222> LOCATION: (3)...(18)
<223> OTHER INFORMATION: n = um

<400> SEQUENCE: 74
gannangncc ggnnangnaa a                                               21

<210> SEQ ID NO 75
<211> LENGTH: 21
<212> TYPE: RNA
<213> ORGANISM: Artificial Sequence
<220> FEATURE:
<223> OTHER INFORMATION: synthetic control Luc U/U v3 siRNA antisense
      strand
<220> FEATURE:
<221> NAME/KEY: modified_base
<222> LOCATION: (5)...(18)
<223> OTHER INFORMATION: n = um

<400> SEQUENCE: 75
uacanaaccg gacanaanca u                                               21

<210> SEQ ID NO 76
<211> LENGTH: 21
<212> TYPE: RNA
<213> ORGANISM: Artificial Sequence
<220> FEATURE:
<223> OTHER INFORMATION: synthetic Lassa virus (LASV) L-polymerase
      (L-pol) LASV-Lpol3513-mod 2'OMe-modified siRNA sense
      strand
<220> FEATURE:
<221> NAME/KEY: modified_base
<222> LOCATION: (2)...(2)
<223> OTHER INFORMATION: n = gm
<220> FEATURE:
```

```
<221> NAME/KEY: modified_base
<222> LOCATION: (6)...(15)
<223> OTHER INFORMATION: n = um

<400> SEQUENCE: 76
uncuanccuu uccangaaau u                                              21

<210> SEQ ID NO 77
<211> LENGTH: 21
<212> TYPE: RNA
<213> ORGANISM: Artificial Sequence
<220> FEATURE:
<223> OTHER INFORMATION: synthetic Lassa virus (LASV) L-polymerase
      (L-pol) LASV-Lpol3513-mod 2'OMe-modified siRNA antisense
      strand
<220> FEATURE:
<221> NAME/KEY: modified_base
<222> LOCATION: (3)...(3)
<223> OTHER INFORMATION: n = um
<220> FEATURE:
<221> NAME/KEY: modified_base
<222> LOCATION: (7)...(13)
<223> OTHER INFORMATION: n = gm

<400> SEQUENCE: 77
uuncaungaa agnauagcau u                                              21

<210> SEQ ID NO 78
<211> LENGTH: 21
<212> TYPE: RNA
<213> ORGANISM: Artificial Sequence
<220> FEATURE:
<223> OTHER INFORMATION: synthetic Lassa virus (LASV) L-polymerase
      (L-pol) LASV-Lpol6313-mod 2'OMe-modified siRNA sense
      strand
<220> FEATURE:
<221> NAME/KEY: modified_base
<222> LOCATION: (6)...(6)
<223> OTHER INFORMATION: n = gm
<220> FEATURE:
<221> NAME/KEY: modified_base
<222> LOCATION: (12)...(17)
<223> OTHER INFORMATION: n = um

<400> SEQUENCE: 78
gaccangauc ungaganauu u                                              21

<210> SEQ ID NO 79
<211> LENGTH: 21
<212> TYPE: RNA
<213> ORGANISM: Artificial Sequence
<220> FEATURE:
<223> OTHER INFORMATION: synthetic Lassa virus (LASV) L-polymerase
      (L-pol) LASV-Lpol6313-mod 2'OMe-modified siRNA antisense
      strand
<220> FEATURE:
<221> NAME/KEY: modified_base
<222> LOCATION: (6)...(6)
<223> OTHER INFORMATION: n = um
<220> FEATURE:
<221> NAME/KEY: modified_base
<222> LOCATION: (16)...(16)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 79
auaucncaag auccungncu u                                              21

<210> SEQ ID NO 80
```

```
<211> LENGTH: 21
<212> TYPE: RNA
<213> ORGANISM: Artificial Sequence
<220> FEATURE:
<223> OTHER INFORMATION: synthetic Lassa virus (LASV) nucleoprotein (NP)
      LASV-NP1222-mod 2'OMe-modified siRNA sense strand
<220> FEATURE:
<221> NAME/KEY: modified_base
<222> LOCATION: (1)...(1)
<223> OTHER INFORMATION: n = gm
<220> FEATURE:
<221> NAME/KEY: modified_base
<222> LOCATION: (4)...(16)
<223> OTHER INFORMATION: n = um

<400> SEQUENCE: 80
ngcngcuaca uacacnucuu c                                               21

<210> SEQ ID NO 81
<211> LENGTH: 21
<212> TYPE: RNA
<213> ORGANISM: Artificial Sequence
<220> FEATURE:
<223> OTHER INFORMATION: synthetic Lassa virus (LASV) nucleoprotein (NP)
      LASV-NP1222-mod 2'OMe-modified siRNA antisense
      strand
<220> FEATURE:
<221> NAME/KEY: modified_base
<222> LOCATION: (6)...(8)
<223> OTHER INFORMATION: n = um
<220> FEATURE:
<221> NAME/KEY: modified_base
<222> LOCATION: (14)...(14)
<223> OTHER INFORMATION: n = gm

<400> SEQUENCE: 81
agaagngnau guancagccu g                                               21

<210> SEQ ID NO 82
<211> LENGTH: 21
<212> TYPE: RNA
<213> ORGANISM: Artificial Sequence
<220> FEATURE:
<223> OTHER INFORMATION: synthetic Lassa virus (LASV) nucleoprotein (NP)
      LASV-NP1284-mod 2'OMe-modified siRNA sense strand
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (12)...(12)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (17)...(17)
<223> OTHER INFORMATION: n = gm

<400> SEQUENCE: 82
gnacucacau nganunaug u                                                21

<210> SEQ ID NO 83
<211> LENGTH: 21
<212> TYPE: RNA
<213> ORGANISM: Artificial Sequence
<220> FEATURE:
<223> OTHER INFORMATION: synthetic Lassa virus (LASV) nucleoprotein (NP)
      LASV-NP1284-mod 2'OMe-modified siRNA antisense
      strand
<220> FEATURE:
```

```
<221> NAME/KEY: modified_base
<222> LOCATION: (13)...(17)
<223> OTHER INFORMATION: n = um

<400> SEQUENCE: 83
aucaauccca ugngagnacu u                                             21

<210> SEQ ID NO 84
<211> LENGTH: 21
<212> TYPE: RNA
<213> ORGANISM: Artificial Sequence
<220> FEATURE:
<223> OTHER INFORMATION: synthetic human/non-human primate tissue factor
      (TF) siRNA hTF292-5' antisense strand

<400> SEQUENCE: 84
uuaaauuaua ugcugccaca g                                             21

<210> SEQ ID NO 85
<211> LENGTH: 21
<212> TYPE: RNA
<213> ORGANISM: Artificial Sequence
<220> FEATURE:
<223> OTHER INFORMATION: synthetic human/non-human primate tissue factor
      (TF) siRNA hTF292-5' sense strand

<400> SEQUENCE: 85
guggcagcau auaauuuaac u                                             21

<210> SEQ ID NO 86
<211> LENGTH: 21
<212> TYPE: RNA
<213> ORGANISM: Artificial Sequence
<220> FEATURE:
<223> OTHER INFORMATION: synthetic human/non-human primate tissue factor
      (TF) siRNA hTF271-5' antisense strand

<400> SEQUENCE: 86
uuuguagugc cugaagcgcc g                                             21

<210> SEQ ID NO 87
<211> LENGTH: 21
<212> TYPE: RNA
<213> ORGANISM: Artificial Sequence
<220> FEATURE:
<223> OTHER INFORMATION: synthetic human/non-human primate tissue factor
      (TF) siRNA hTF271-5' sense strand

<400> SEQUENCE: 87
gcgcuucagg cacuacaaau a                                             21

<210> SEQ ID NO 88
<211> LENGTH: 21
<212> TYPE: RNA
<213> ORGANISM: Artificial Sequence
<220> FEATURE:
<223> OTHER INFORMATION: synthetic human/non-human primate tissue factor
      (TF) siRNA hTF1238-5' antisense strand

<400> SEQUENCE: 88
auuucaaagu gacuaaugcu g                                             21

<210> SEQ ID NO 89
<211> LENGTH: 21
<212> TYPE: RNA
<213> ORGANISM: Artificial Sequence
<220> FEATURE:
<223> OTHER INFORMATION: synthetic human/non-human primate tissue factor
```

(TF) siRNA hTF1238-5' sense strand

<400> SEQUENCE: 89
gcauuaguca cuuugaaaug u                                              21

<210> SEQ ID NO 90
<211> LENGTH: 21
<212> TYPE: RNA
<213> ORGANISM: Artificial Sequence
<220> FEATURE:
<223> OTHER INFORMATION: synthetic human/non-human primate tissue factor
      (TF) siRNA hTF369-5' antisense strand

<400> SEQUENCE: 90
uauuugaaca guguagacuu g                                              21

<210> SEQ ID NO 91
<211> LENGTH: 21
<212> TYPE: RNA
<213> ORGANISM: Artificial Sequence
<220> FEATURE:
<223> OTHER INFORMATION: synthetic human/non-human primate tissue factor
      (TF) siRNA hTF369-5' sense strand

<400> SEQUENCE: 91
agucuacacu guucaaauaa g                                              21

<210> SEQ ID NO 92
<211> LENGTH: 21
<212> TYPE: RNA
<213> ORGANISM: Artificial Sequence
<220> FEATURE:
<223> OTHER INFORMATION: synthetic human/non-human primate tissue factor
      (TF) siRNA hTF290-5' antisense strand

<400> SEQUENCE: 92
aaauuauaug cugccacagu a                                              21

<210> SEQ ID NO 93
<211> LENGTH: 21
<212> TYPE: RNA
<213> ORGANISM: Artificial Sequence
<220> FEATURE:
<223> OTHER INFORMATION: synthetic human/non-human primate tissue factor
      (TF) siRNA hTF290-5' sense strand

<400> SEQUENCE: 93
cuguggcagc auauaauuua a                                              21

<210> SEQ ID NO 94
<211> LENGTH: 21
<212> TYPE: RNA
<213> ORGANISM: Artificial Sequence
<220> FEATURE:
<223> OTHER INFORMATION: synthetic human/non-human primate tissue factor
      (TF) siRNA hTF288-5' sense strand

<400> SEQUENCE: 94
uacuguggca gcauauaauu u                                              21

<210> SEQ ID NO 95
<211> LENGTH: 21
<212> TYPE: RNA
<213> ORGANISM: Artificial Sequence
<220> FEATURE:
<223> OTHER INFORMATION: synthetic human/non-human primate tissue factor
      (TF) siRNA hTF288-5' antisense strand

```
<400> SEQUENCE: 95
auuauaugcu gccacaguau u                                              21

<210> SEQ ID NO 96
<211> LENGTH: 21
<212> TYPE: RNA
<213> ORGANISM: Artificial Sequence
<220> FEATURE:
<223> OTHER INFORMATION: synthetic human/non-human primate tissue factor
      (TF) 2'OMe-modified siRNA hTF292-S1 sense strand
<220> FEATURE:
<221> NAME/KEY: modified_base
<222> LOCATION: (2)...(21)
<223> OTHER INFORMATION: n = um

<400> SEQUENCE: 96
gnggcagcau auaaunuaac n                                              21

<210> SEQ ID NO 97
<211> LENGTH: 21
<212> TYPE: RNA
<213> ORGANISM: Artificial Sequence
<220> FEATURE:
<223> OTHER INFORMATION: synthetic human/non-human primate tissue factor
      (TF) 2'OMe-modified siRNA hTF292-AS1 antisense
      strand
<220> FEATURE:
<221> NAME/KEY: modified_base
<222> LOCATION: (12)...(21)
<223> OTHER INFORMATION: n = gm

<400> SEQUENCE: 97
uuaaauuaua uncugccaca n                                              21

<210> SEQ ID NO 98
<211> LENGTH: 21
<212> TYPE: RNA
<213> ORGANISM: Artificial Sequence
<220> FEATURE:
<223> OTHER INFORMATION: synthetic human/non-human primate tissue factor
      (TF) 2'OMe-modified siRNA hTF369-S1 sense strand
<220> FEATURE:
<221> NAME/KEY: modified_base
<222> LOCATION: (2)...(2)
<223> OTHER INFORMATION: n = gm
<220> FEATURE:
<221> NAME/KEY: modified_base
<222> LOCATION: (12)...(12)
<223> OTHER INFORMATION: n = um
<220> FEATURE:
<221> NAME/KEY: modified_base
<222> LOCATION: (21)...(21)
<223> OTHER INFORMATION: n = gm

<400> SEQUENCE: 98
anucuacacu gnucaaauaa n                                              21

<210> SEQ ID NO 99
<211> LENGTH: 21
<212> TYPE: RNA
<213> ORGANISM: Artificial Sequence
<220> FEATURE:
<223> OTHER INFORMATION: synthetic human/non-human primate tissue factor
      (TF) 2'OMe-modified siRNA hTF369-AS1 antisense
      strand
<220> FEATURE:
<221> NAME/KEY: modified_base
<222> LOCATION: (12)...(20)
<223> OTHER INFORMATION: n = um

<400> SEQUENCE: 99
```
uauuugaaca gnguagacun g     21

<210> SEQ ID NO 100
<211> LENGTH: 21
<212> TYPE: RNA
<213> ORGANISM: Artificial Sequence
<220> FEATURE:
<223> OTHER INFORMATION: synthetic human tissue factor (TF)
      2'OMe-modified siRNA hF3 292 S-1 sense strand
<220> FEATURE:
<221> NAME/KEY: modified_base
<222> LOCATION: (2)...(21)
<223> OTHER INFORMATION: n = um

<400> SEQUENCE: 100
gnggcagcau auaaunuaac n     21

<210> SEQ ID NO 101
<211> LENGTH: 21
<212> TYPE: RNA
<213> ORGANISM: Artificial Sequence
<220> FEATURE:
<223> OTHER INFORMATION: synthetic human tissue factor (TF)
      2'OMe-modified siRNA hF3 292 AS-1 antisense strand
<220> FEATURE:
<221> NAME/KEY: modified_base
<222> LOCATION: (12)...(21)
<223> OTHER INFORMATION: n = gm

<400> SEQUENCE: 101
uuaaauuaua uncugccaca n     21

<210> SEQ ID NO 102
<211> LENGTH: 21
<212> TYPE: RNA
<213> ORGANISM: Artificial Sequence
<220> FEATURE:
<223> OTHER INFORMATION: synthetic human tissue factor (TF)
      2'OMe-modified siRNA hF3 292 AS-2 antisense strand
<220> FEATURE:
<221> NAME/KEY: modified_base
<222> LOCATION: (12)...(21)
<223> OTHER INFORMATION: n = gm

<400> SEQUENCE: 102
uuaaauuaua uncunccaca n     21

<210> SEQ ID NO 103
<211> LENGTH: 21
<212> TYPE: RNA
<213> ORGANISM: Artificial Sequence
<220> FEATURE:
<223> OTHER INFORMATION: synthetic human tissue factor (TF)
      2'OMe-modified siRNA hF3 292 AS-3 antisense strand
<220> FEATURE:
<221> NAME/KEY: modified_base
<222> LOCATION: (7)...(7)
<223> OTHER INFORMATION: n = um
<220> FEATURE:
<221> NAME/KEY: modified_base
<222> LOCATION: (12)...(12)
<223> OTHER INFORMATION: n = gm
<220> FEATURE:
<221> NAME/KEY: modified_base
<222> LOCATION: (14)...(14)
<223> OTHER INFORMATION: n = um
<220> FEATURE:
<221> NAME/KEY: modified_base
<222> LOCATION: (21)...(21)
<223> OTHER INFORMATION: n = gm

<400> SEQUENCE: 103
uuaaaunaua uncngccaca n                                          21

<210> SEQ ID NO 104
<211> LENGTH: 21
<212> TYPE: RNA
<213> ORGANISM: Artificial Sequence
<220> FEATURE:
<223> OTHER INFORMATION: synthetic human tissue factor (TF)
      2'OMe-modified siRNA hF3 292 AS-4 antisense strand
<220> FEATURE:
<221> NAME/KEY: modified_base
<222> LOCATION: (6)...(6)
<223> OTHER INFORMATION: n = um
<220> FEATURE:
<221> NAME/KEY: modified_base
<222> LOCATION: (12)...(21)
<223> OTHER INFORMATION: n = gm

<400> SEQUENCE: 104
uuaaanuaua uncugccaca n                                          21

<210> SEQ ID NO 105
<211> LENGTH: 21
<212> TYPE: RNA
<213> ORGANISM: Artificial Sequence
<220> FEATURE:
<223> OTHER INFORMATION: synthetic human tissue factor (TF)
      2'OMe-modified siRNA hF3 292 AS-5 antisense strand
<220> FEATURE:
<221> NAME/KEY: modified_base
<222> LOCATION: (2)...(7)
<223> OTHER INFORMATION: n = um
<220> FEATURE:
<221> NAME/KEY: modified_base
<222> LOCATION: (12)...(12)
<223> OTHER INFORMATION: n = gm
<220> FEATURE:
<221> NAME/KEY: modified_base
<222> LOCATION: (14)...(14)
<223> OTHER INFORMATION: n = um
<220> FEATURE:
<221> NAME/KEY: modified_base
<222> LOCATION: (21)...(21)
<223> OTHER INFORMATION: n = gm

<400> SEQUENCE: 105
unaaaunaua uncngccaca n                                          21

<210> SEQ ID NO 106
<211> LENGTH: 21
<212> TYPE: RNA
<213> ORGANISM: Artificial Sequence
<220> FEATURE:
<223> OTHER INFORMATION: synthetic human tissue factor (TF)
      2'OMe-modified siRNA hF3 292 AS-5b antisense strand
<220> FEATURE:
<221> NAME/KEY: modified_base
<222> LOCATION: (6)...(6)
<223> OTHER INFORMATION: n = um
<220> FEATURE:
<221> NAME/KEY: modified_base
<222> LOCATION: (12)...(21)
<223> OTHER INFORMATION: n = gm

<400> SEQUENCE: 106
uuaaanuaua uncunccaca n                                          21

<210> SEQ ID NO 107
<211> LENGTH: 21
<212> TYPE: RNA
<213> ORGANISM: Artificial Sequence
<220> FEATURE:
<223> OTHER INFORMATION: synthetic human tissue factor (TF)

```
      2'OMe-modified siRNA hF3 292 AS-6 antisense strand
<220> FEATURE:
<221> NAME/KEY: modified_base
<222> LOCATION: (2)...(6)
<223> OTHER INFORMATION: n = um
<220> FEATURE:
<221> NAME/KEY: modified_base
<222> LOCATION: (12)...(21)
<223> OTHER INFORMATION: n = gm

<400> SEQUENCE: 107
unaaanuaua uncunccaca n                                          21

<210> SEQ ID NO 108
<211> LENGTH: 21
<212> TYPE: RNA
<213> ORGANISM: Artificial Sequence
<220> FEATURE:
<223> OTHER INFORMATION: synthetic human tissue factor (TF)
      2'OMe-modified siRNA hF3 292 S-2 sense strand
<220> FEATURE:
<221> NAME/KEY: modified_base
<222> LOCATION: (2)...(21)
<223> OTHER INFORMATION: n = um

<400> SEQUENCE: 108
gnggcagcan anaannnaac n                                          21

<210> SEQ ID NO 109
<211> LENGTH: 21
<212> TYPE: RNA
<213> ORGANISM: Artificial Sequence
<220> FEATURE:
<223> OTHER INFORMATION: synthetic human tissue factor (TF)
      2'OMe-modified siRNA hF3 292 S-3 sense strand
<220> FEATURE:
<221> NAME/KEY: modified_base
<222> LOCATION: (2)...(21)
<223> OTHER INFORMATION: n = um

<400> SEQUENCE: 109
gnggcagcau anaanunaac n                                          21

<210> SEQ ID NO 110
<211> LENGTH: 21
<212> TYPE: RNA
<213> ORGANISM: Artificial Sequence
<220> FEATURE:
<223> OTHER INFORMATION: synthetic Lassa virus (LASV) nucleoprotein (NP)
      LASV NP1284 S-1 2'OMe-modified siRNA sense strand
<220> FEATURE:
<221> NAME/KEY: modified_base
<222> LOCATION: (2)...(2)
<223> OTHER INFORMATION: n = um
<220> FEATURE:
<221> NAME/KEY: modified_base
<222> LOCATION: (12)...(12)
<223> OTHER INFORMATION: n = gm
<220> FEATURE:
<221> NAME/KEY: modified_base
<222> LOCATION: (15)...(15)
<223> OTHER INFORMATION: n = gm
<220> FEATURE:
<221> NAME/KEY: modified_base
<222> LOCATION: (17)...(17)
<223> OTHER INFORMATION: n = gm

<400> SEQUENCE: 110
gnacucacau gnganunaug u                                          21

<210> SEQ ID NO 111
<211> LENGTH: 21
```

```
<212> TYPE: RNA
<213> ORGANISM: Artificial Sequence
<220> FEATURE:
<223> OTHER INFORMATION: synthetic Lassa virus (LASV) nucleoprotein (NP)
      LASV NP1284 AS-1 2'OMe-modified siRNA antisense
      strand
<220> FEATURE:
<221> NAME/KEY: modified_base
<222> LOCATION: (13)...(17)
<223> OTHER INFORMATION: n = um

<400> SEQUENCE: 111
aucaauccca ugngagnacu u                                            21

<210> SEQ ID NO 112
<211> LENGTH: 21
<212> TYPE: RNA
<213> ORGANISM: Artificial Sequence
<220> FEATURE:
<223> OTHER INFORMATION: synthetic Lassa virus (LASV) nucleoprotein (NP)
      LASV NP1284 AS-2 2'OMe-modified siRNA antisense
      strand
<220> FEATURE:
<221> NAME/KEY: modified_base
<222> LOCATION: (13)...(21)
<223> OTHER INFORMATION: n = um

<400> SEQUENCE: 112
aucaauccca ugngagnacn n                                            21

<210> SEQ ID NO 113
<211> LENGTH: 21
<212> TYPE: RNA
<213> ORGANISM: Artificial Sequence
<220> FEATURE:
<223> OTHER INFORMATION: synthetic Lassa virus (LASV) nucleoprotein (NP)
      LASV NP1284 AS-3 2'OMe-modified siRNA antisense
      strand
<220> FEATURE:
<221> NAME/KEY: modified_base
<222> LOCATION: (6)...(21)
<223> OTHER INFORMATION: n = um

<400> SEQUENCE: 113
aucaanccca ugngagnacn n                                            21

<210> SEQ ID NO 114
<211> LENGTH: 21
<212> TYPE: RNA
<213> ORGANISM: Artificial Sequence
<220> FEATURE:
<223> OTHER INFORMATION: synthetic Lassa virus (LASV) nucleoprotein (NP)
      LASV NP1284 AS-4 2'OMe-modified siRNA antisense
      strand
<220> FEATURE:
<221> NAME/KEY: modified_base
<222> LOCATION: (2)...(21)
<223> OTHER INFORMATION: n = um

<400> SEQUENCE: 114
ancaauccca ugngagnacn n                                            21

<210> SEQ ID NO 115
<211> LENGTH: 21
<212> TYPE: RNA
<213> ORGANISM: Artificial Sequence
<220> FEATURE:
<223> OTHER INFORMATION: synthetic Lassa virus (LASV) nucleoprotein (NP)
      LASV NP1284 S-2 2'OMe-modified siRNA sense strand
<220> FEATURE:
<221> NAME/KEY: modified_base
<222> LOCATION: (2)...(5)
```

```
<223> OTHER INFORMATION: n = um
<220> FEATURE:
<221> NAME/KEY: modified_base
<222> LOCATION: (12)...(12)
<223> OTHER INFORMATION: n = gm
<220> FEATURE:
<221> NAME/KEY: modified_base
<222> LOCATION: (15)...(15)
<223> OTHER INFORMATION: n = um
<220> FEATURE:
<221> NAME/KEY: modified_base
<222> LOCATION: (17)...(20)
<223> OTHER INFORMATION: n = gm
<220> FEATURE:
<221> NAME/KEY: modified_base
<222> LOCATION: (21)...(21)
<223> OTHER INFORMATION: n = um

<400> SEQUENCE: 115
gnacncacau ngnganunaun n                                     21
```

COMPOSITIONS AND METHODS FOR SILENCING GENES INVOLVED IN HEMORRHAGIC FEVER

CROSS-REFERENCE TO RELATED APPLICATION

The present application claims priority to U.S. Provisional Application No. 61/319,855, filed Mar. 31, 2010, the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant No. W81XWH-07-2-0016, awarded by the Transformational Medical Technologies Initiative. The Government has certain rights in this invention.

BACKGROUND OF THE INVENTION

Arenaviruses and filoviruses are among the most lethal and destructive viruses. They cause severe, often fatal viral hemorraghic fevers in humans and nonhuman primates (e.g., monkeys, gorillas, and chimpanzees). Both genera of viruses are of particular concern as possible biological weapons since they have the potential for aerosol dissemination and weaponization.

The incubation period for Filovirus infection ranges from 2 to 21 days. The onset of illness is abrupt and is characterized by high fever, headaches, joint and muscle aches, sore throat, fatigue, diarrhea, vomiting, and stomach pain. A rash, red eyes, hiccups and internal and external bleeding may be seen in some patients. Within one week of becoming infected with the virus, most patients experience chest pains and multiple organ failure, go into shock, and die. Some patients also experience blindness and extensive bleeding before dying.

Filoviridae are a family of RNA viruses. Two members of the Filoviridae family have been identified: Ebola virus (EBOV) and Marburg virus (MARV). There is one identified strain of MARV and four identified subtypes (i.e., strains) of EBOV: Ebola-Zaire, Ebola-Sudan, Ebola-Ivory Coast (i.e., Ebola-Tai), and Ebola-Reston. The exact origin, locations, and natural habitat of Filoviridae are unknown. However, on the basis of available evidence and the nature of similar viruses, it is postulated that Filoviridae are zoonotic (i.e., animal-borne) and are normally maintained in an animal host that is native to the African continent.

For more than 30 years, EBOV has been associated with periodic episodes of hemorrhagic fever in Central Africa that produce severe disease in infected patients. Mortality rates in outbreaks have ranged from 50% for the Sudan species of EBOV (SEBOV) to up to 90% for the Zaire species of EBOV (ZEBOV) (Sanchez et al., Filoviridae: Marburg and Ebola Viruses, in *Fields Virology* (eds. Knipe, D. M. & Howley, P. M.) 1409-1448 (Lippincott Williams & Wilkins, Philadelphia)). An outbreak late in 2007 caused by an apparently new species of EBOV in Uganda resulted in a fatality rate of about 25% (Towner et al., *PLoS Pathog.*, 4:e1000212 (2008)). ZEBOV has also decimated populations of wild apes in this same region of Africa (Walsh et al., *Nature*, 422:611-614 (2003)).

Arenaviridae are also a family of RNA viruses. Arenaviruses can be divided into two serogroups, which differ genetically and by geographical distribution: the lymphocytic choriomeningitis virus (LCMV)-Lassa virus (Old World) complex and the Tacaribe virus (New World) complex. Lassa virus (LASV) causes lassa fever, which is an acute viral hemorrhagic fever first described in 1969 in the town of Lassa, in Borno State, Nigeria. The infection is endemic in West African countries, and causes 300,000-500,000 cases annually, with approximately 5,000 deaths. Outbreaks of the disease have been observed in Nigeria, Liberia, Sierra Leone, Guinea, and the Central African Republic, but it is believed that human infections also exist in Democratic Republic of the Congo, Mali, and Senegal.

Prevention and treatment of viral infections responsible for causing hemorraghic fevers presents many challenges. In fact, there are no vaccines or postexposure treatment modalities available for preventing or managing such infections. Patients instead receive supportive therapy, i.e., electrolyte and fluid balancing, oxygen, blood pressure maintenance, and treatment for any secondary infections.

Thus, there is a need for compositions and methods for treating and preventing viral infections, e.g., by specifically modulating viral or host genes involved in hemorraghic fever. The present invention addresses these and other needs.

BRIEF SUMMARY OF THE INVENTION

The present invention provides compositions comprising therapeutic nucleic acids such as interfering RNA (e.g., dsRNA such as siRNA) that target Lassa virus (LASV) or tissue factor (TF) gene expression and methods of using such compositions to silence target gene expression. More particularly, the invention provides unmodified and chemically modified interfering RNA (e.g., siRNA) which silence LASV (e.g., one or more of the NP, GP, L, and/or Z genes) or TF gene expression and methods of use thereof, e.g., for preventing or treating infections caused by one or more strains or subtypes of filoviruses (e.g., EBOV) and/or arenaviruses (e.g., LASV). The invention also provides serum-stable nucleic acid-lipid particles (e.g., SNALP) comprising one or more (e.g., a cocktail) therapeutic nucleic acids (e.g., interfering RNA such as siRNA) described herein, a cationic lipid, and a non-cationic lipid, which can further comprise a conjugated lipid that inhibits aggregation of particles. Methods of silencing LASV or TF expression by administering interfering RNA (e.g., siRNA) to a mammalian subject are also provided, e.g., for treating hemorraghic fever or any disease indication associated with TF expression or overexpression.

In one aspect, the present invention provides interfering RNA molecules such as siRNA that target tissue factor (TF) gene expression. In certain embodiments, the present invention provides compositions comprising a combination (e.g., a cocktail) of at least about 2, 3, 4, 5, 6, 7, 8, 9, 10, or more interfering RNA molecules that target the same and/or different regions of the TF gene. The interfering RNA (e.g., siRNA) molecules of the invention are capable of silencing TF gene expression in vitro or in vivo, inactivating hemorraghic fever viruses such as LASV, EBOV, and/or MARV in vitro or in vivo, inhibiting the replication of hemorraghic fever viruses such as LASV EBOV, and/or MARV in vitro or in vivo, preventing or treating filovirus (e.g., EBOV, MARV) and/or arenavirus (e.g., LASV) infections, and/or preventing or treating diseases or disorders associated with TF expression or overexpression.

A non-limiting example of a TF target sequence is set forth in Genbank Accession No. NM_001993 (SEQ ID NO:1). Those of skill in the art will appreciate that TF is also known as F3, coagulation factor III, thromboplastin, and CD142.

In another aspect, the present invention provides interfering RNA molecules such as siRNA that target LASV gene expression. In certain embodiments, the invention provides compositions comprising a combination (e.g., a cocktail) of at least about 2, 3, 4, 5, 6, 7, 8, 9, 10, or more interfering RNA molecules that target the same and/or different regions of the LASV genome. The interfering RNA (e.g., siRNA) molecules of the present invention are capable of silencing LASV gene expression in vitro or in vivo, inactivating LASV in vitro or in vivo, inhibiting the replication of LASV in vitro or in vivo, and/or preventing or treating LASV infections.

Non-limiting examples of LASV genome sequences are set forth in Genbank Accession Nos. NC_004296 (LASV segment S) (SEQ ID NO:2) and NC_004297 (LASV segment L) (SEQ ID NO:3). Exemplary regions of the LASV genome that can be targeted include, but are not limited to, nucleoprotein (NP), glycoprotein (GP), L-polymerase (L), and/or Z protein (Z) sequences.

Each of the interfering RNA sequences present in the compositions of the invention may independently comprise at least one, two, three, four, five, six, seven, eight, nine, ten, or more modified nucleotides such as 2'OMe nucleotides, e.g., in the sense and/or antisense strand of the double-stranded region. Preferably, uridine and/or guanosine nucleotides are modified with 2'OMe nucleotides. In particular embodiments, each of the interfering RNA sequences present in the compositions of the invention comprises at least one 2'OMe-uridine nucleotide and at least one 2'OMe-guanosine nucleotide in the sense and/or antisense strands.

In some embodiments, each of the interfering RNA (e.g., siRNA) sequences present in the compositions of the invention may independently comprise a 3' overhang of at least 1, 2, 3, or 4 nucleotides in one or both strands of the interfering RNA or may comprise at least one blunt end. In certain instances, the 3' overhangs in one or both strands of the interfering RNA each independently comprise at least 1, 2, 3, or 4 of any combination of modified and unmodified deoxythymidine (dT) nucleotides, at least 1, 2, 3, or 4 of any combination of modified (e.g., 2'OMe) and unmodified uridine (U) ribonucleotides, or at least 1, 2, 3, or 4 of any combination of modified (e.g., 2'OMe) and unmodified ribonucleotides having complementarity to the target sequence (3' overhang in the antisense strand) or the complementary strand thereof (3' overhang in the sense strand).

In further embodiments, the present invention provides a composition comprising at least one or a cocktail (e.g., at least two, three, four, five, six, seven, eight, nine, ten, or more) of interfering RNAs (e.g., siRNAs) comprising sense and/or antisense sequences set forth in Tables 1-8 and/or interfering RNA (e.g., siRNA) duplexes set forth in Tables 9 and 10. In certain instances, at least about 1, 2, 3, 4, 5, 6, 7, 8, 9, 10, or more (e.g., all) of the interfering RNA sequences present in the composition comprises at least 1, 2, 3, 4, 5, 6, 7, 8, 9, 10, or more modified nucleotides such as 2'OMe nucleotides, e.g., in the double-stranded region.

In some embodiments, the sense strand of each interfering RNA (e.g., siRNA) independently comprises or consists of one of the sense strand sequences set forth in Tables 1-10. In related embodiments, the sense strand of each interfering RNA (e.g., siRNA) independently comprises or consists of at least about 15 contiguous nucleotides (e.g., at least 15, 16, 17, 18, or 19 contiguous nucleotides) of one of the sense strand sequences set forth in Tables 1-10. In one particular embodiment, the sense strand comprises nucleotides 1-19 of one of the sense strand sequences set forth in Tables 1-10. In other embodiments, the sense strand of each interfering RNA (e.g., siRNA) may independently comprise or consist of from about 22 to about 28 nucleotides (e.g., 22, 23, 24, 25, 26, 27, or 28 nucleotides) in length. In certain instances, the sense strand of each interfering RNA has a modified (e.g., 2'OMe) and/or unmodified 3' overhang of 1, 2, 3, or 4 nucleotides, or is blunt ended at the 3' end. One of skill in the art will appreciate that the sense strand sequence may comprise or consist of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more additional nucleotides at the 5' and/or 3' end of one of the 19-mer sense strand sequences set forth in Tables 1-10 (i.e., excluding the 2-nucleotide overhang at the 3'-end of the sequence) that correspond to the contiguous nucleotides 5' and/or 3' of the corresponding 19-mer sequence found in SEQ ID NOS:1-3.

In other embodiments, the antisense strand of each interfering RNA (e.g., siRNA) independently comprises or consists of one of the antisense strand sequences set forth in Tables 1-10. In related embodiments, the antisense strand of each interfering RNA (e.g., siRNA) independently comprises or consists of at least about 15 contiguous nucleotides (e.g., at least 15, 16, 17, 18, or 19 contiguous nucleotides) of one of the antisense strand sequences set forth in Tables 1-10. In one particular embodiment, the antisense strand comprises nucleotides 1-19 of one of the antisense strand sequences set forth in Tables 1-10. In other embodiments, the antisense strand of each interfering RNA (e.g., siRNA) may independently comprise or consist of from about 22 to about 28 nucleotides (e.g., 22, 23, 24, 25, 26, 27, or 28 nucleotides) in length. In certain instances, the antisense strand of each interfering RNA has a modified (e.g., 2'OMe) and/or unmodified 3' overhang of 1, 2, 3, or 4 nucleotides, or is blunt ended at the 3' end. One of skill in the art will appreciate that the antisense strand sequence may comprise or consist of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more additional nucleotides at the 5' and/or 3' end of one of the 19-mer antisense strand sequences set forth in Tables 1-10 (i.e., excluding the 2-nucleotide overhang at the 3'-end of the sequence), wherein the additional nucleotides at the 5' and/or 3' end have complementarity to the contiguous nucleotides 5' and/or 3' of the corresponding 19-mer sequence found in SEQ ID NOS:1-3.

In certain embodiments, the sense strand specifically hybridizes to at least one of the antisense strand sequences set forth in Tables 1-10. In certain other embodiments, the antisense strand specifically hybridizes to at least one of the sense strand sequences set forth in Tables 1-10. In additional embodiments, the antisense strand targets at least one of the sense strand sequences set forth in Tables 1-10. In further embodiments, the sense strand targets at least one of the antisense strand sequences set forth in Tables 1-10.

The present invention also provides a pharmaceutical composition comprising one or a cocktail of interfering RNA (e.g., siRNA) molecules that target TF or LASV (e.g., NP, GP, L, and/or Z) gene expression and a pharmaceutically acceptable carrier.

In another aspect, the present invention provides a nucleic acid-lipid particle that targets TF and/or LASV gene expression. The nucleic acid-lipid particle typically comprises one or more unmodified and/or modified interfering RNA that silence TF and/or LASV (e.g., NP, GP, L, and/or Z) gene expression, a cationic lipid, and a non-cationic lipid. In certain instances, the nucleic acid-lipid particle further comprises a conjugated lipid that inhibits aggregation of particles. In preferred embodiments, the nucleic acid-lipid particle comprises one or more unmodified and/or modified interfering RNA that silence TF and/or LASV (e.g., NP, GP, L, and/or Z) gene expression, a cationic lipid, a non-cationic lipid, and a conjugated lipid that inhibits aggregation of particles.

In some embodiments, the nucleic acid-lipid particle comprises 1, 2, 3, 4, 5, 6, 7, 8, 9, 10, or more interfering RNA molecules, wherein the sense and/or antisense strands of each interfering RNA molecule independently comprises or consists of one of the sense and/or antisense strand sequences as described herein (e.g., at least 15, 16, 17, 18, or 19 contiguous nucleotides of one of the sense and/or antisense strand sequences set forth in Tables 1-10. In preferred embodiments, the nucleic acid-lipid particles (e.g., SNALP) comprise at least one or more of the modified hTF292 and/or LASV NP1284 siRNA duplexes as set forth in Tables 9 and 10. Additional embodiments related to the sense and/or antisense strand siRNA sequences of the invention (e.g., 3' overhangs, blunt ends, length, modified nucleotides, etc.) are described herein.

In other embodiments, the interfering RNA molecules of the invention are fully encapsulated in the nucleic acid-lipid particle (e.g., SNALP). With respect to formulations comprising a cocktail of interfering RNA, the different types of interfering RNA molecules may be co-encapsulated in the same nucleic acid-lipid particle, or each type of interfering RNA species present in the cocktail may be encapsulated in its own particle.

The present invention also provides pharmaceutical compositions comprising a nucleic acid-lipid particle and a pharmaceutically acceptable carrier.

The nucleic acid-lipid particles of the invention are useful for the prophylactic or therapeutic delivery of interfering RNA (e.g., dsRNA) molecules that silence the expression of specific viral genes (e.g., LASV NP, GP, L, and/or Z) or host genes (e.g., TF). In some embodiments, one or more of the interfering RNA molecules described herein are formulated into nucleic acid-lipid particles, and the particles are administered to a mammal (e.g., a rodent such as a mouse or a primate such as a human, chimpanzee, or monkey) requiring such treatment. In certain instances, a therapeutically effective amount of the nucleic acid-lipid particle can be administered to the mammal, e.g., for preventing or treating viral infections caused by one or more species of arenavirus (e.g., LASV) or filovirus (e.g., EBOV, MARV). The nucleic acid-lipid particles of the invention are particularly useful for targeting cells, tissues, or organs infected and/or susceptible of being infected with arenaviruses or filoviruses, such as reticuloendothelial cells (e.g., monocytes, macrophages, etc.), fibroblast cells, endothelial cells, hepatocytes, and/or platelets cells. Administration of the nucleic acid-lipid particle can be by any route known in the art, such as, e.g., oral, intranasal, intravenous, intraperitoneal, intramuscular, intra-articular, intralesional, intratracheal, subcutaneous, or intradermal. In particular embodiments, the nucleic acid-lipid particle is administered systemically, e.g., via enteral or parenteral routes of administration.

In some embodiments, downregulation of LASV (e.g., NP, GP, L, and/or Z) gene expression is determined by detecting LASV RNA or protein levels in a biological sample from a mammal after nucleic acid-lipid particle administration. In other embodiments, downregulation of TF gene expression is determined by detecting TF mRNA or protein levels in a biological sample from a mammal after nucleic acid-lipid particle administration. In further embodiments, downregulation of LASV or TF gene expression may be detected by measuring viral load in a biological sample from a mammal after particle administration. In certain embodiments, downregulation of LASV or TF gene expression may be detected by monitoring symptoms associated with viral infection in a mammal after nucleic acid-lipid particle administration. In other embodiments, downregulation of LASV or TF gene expression is detected by measuring survival of a mammal after particle administration.

In particular embodiments, the mammal has a disease or disorder associated with arenavirus or filovirus infection, e.g., hemorraghic fever. In other embodiments, silencing of viral or host sequences such as LASV or TF that encode genes associated with viral infection and/or survival can conveniently be used in combination with the administration of conventional agents used to treat the viral condition.

In certain embodiments, the present invention provides a method for treating a mammal infected with an arenavirus and/or filovirus (e.g., LASV, EBOV, and/or MARV) comprising administering to a mammal suffering from the viral infection an interfering RNA molecule (e.g., siRNA) that silences TF and/or LASV (e.g., NP, GP, L, and/or Z) gene expression (e.g., encapsulated in a nucleic acid-lipid particle such as SNALP), thereby treating the viral infection in the mammal. In certain other embodiments, the present invention provides a method for treating hemorraghic fever in a mammal comprising administering to a mammal having an arenavirus and/or filovirus infection an interfering RNA (e.g., siRNA) that silences TF and/or LASV gene expression (e.g., encapsulated in a nucleic acid-lipid particle such as SNALP), thereby treating hemorraghic fever in the mammal. In further embodiments, the present invention provides a method for inactivating an arenavirus and/or filovirus and/or inhibiting the replication of an arenavirus and/or filovirus comprising administering to a mammal in need thereof an interfering RNA (e.g., siRNA) that silences TF and/or LASV gene expression (e.g., encapsulated in a nucleic acid-lipid particle such as SNALP), thereby inactivating the arenavirus and/or filovirus and/or inhibiting the replication of the arenavirus and/or filovirus in the mammal.

In additional aspects, the present invention provides a method for preventing or treating a disease or disorder associated with TF expression or overexpression comprising administering to a mammal in need thereof an interfering RNA (e.g., siRNA) that silences TF gene expression (e.g., encapsulated in a nucleic acid-lipid particle such as SNALP). Besides hemorraghic fever, non-limiting examples of other TF indications include pulmonary and bone metastasis, extravascular inflammation such as that involved in rheumatoid arthritis, endotoxemia and sepsis leading to disseminated intravascular coagulation (DIC), colitis, endometriosis, and the like.

In a further aspect, the present invention provides compositions comprising at least one interfering RNA (e.g., siRNA) that silences TF or LASV gene expression and at least one interfering RNA that silences the expression of EBOV, MARV, and/or any other virus that causes hemorraghic fever (e.g., other species of arenaviruses and/or filoviruses). In certain instances, the interfering RNA molecules targeting different genes and/or species of viruses are formulated in the same nucleic acid-lipid particle (e.g., SNALP). As a non-limiting example, the interfering RNA cocktail may be co-encapsulated in the same nucleic acid-lipid particle. In certain other instances, the interfering RNA targeting different genes and/or species of viruses are formulated in separate nucleic acid-lipid particles. In these instances, one formulation may be administered before, during, and/or after the administration of the other formulation to a mammal in need thereof. Exemplary interfering RNA sequences targeting EBOV and MARV are described in, e.g., U.S. Pat. No. 7,838,658, the disclosure of which is herein incorporated by reference in its entirety for all purposes.

Other objects, features, and advantages of the present invention will be apparent to one of skill in the art from the following detailed description and figures.

BRIEF DESCRIPTION OF THE DRAWINGS

FIG. 3 illustrates the relative potency of unmodified and chemically-modified LASV NP siRNAs in a virus-free, plasmid-based system. HepG2 cells were transfected with 1.25 µg/mL plasmid psiCHECK2 (Promega) containing LASV NP gene and 1.25-40 nM siRNA complexed with Lipofectamine 2000 (Invitrogen). Cells were lysed 48 h later for DLR quantitation of *Renilla* Luciferase, normalized against Firefly Luciferase luminescence. Data represents the mean (n=3) of experimental results and ±SD. siRNA targeting *Renilla* Luciferase (rluc-561) and apob-6490 were used as targeting and non-targeting controls respectively.

DETAILED DESCRIPTION OF THE INVENTION

I. Introduction

Figure 1:
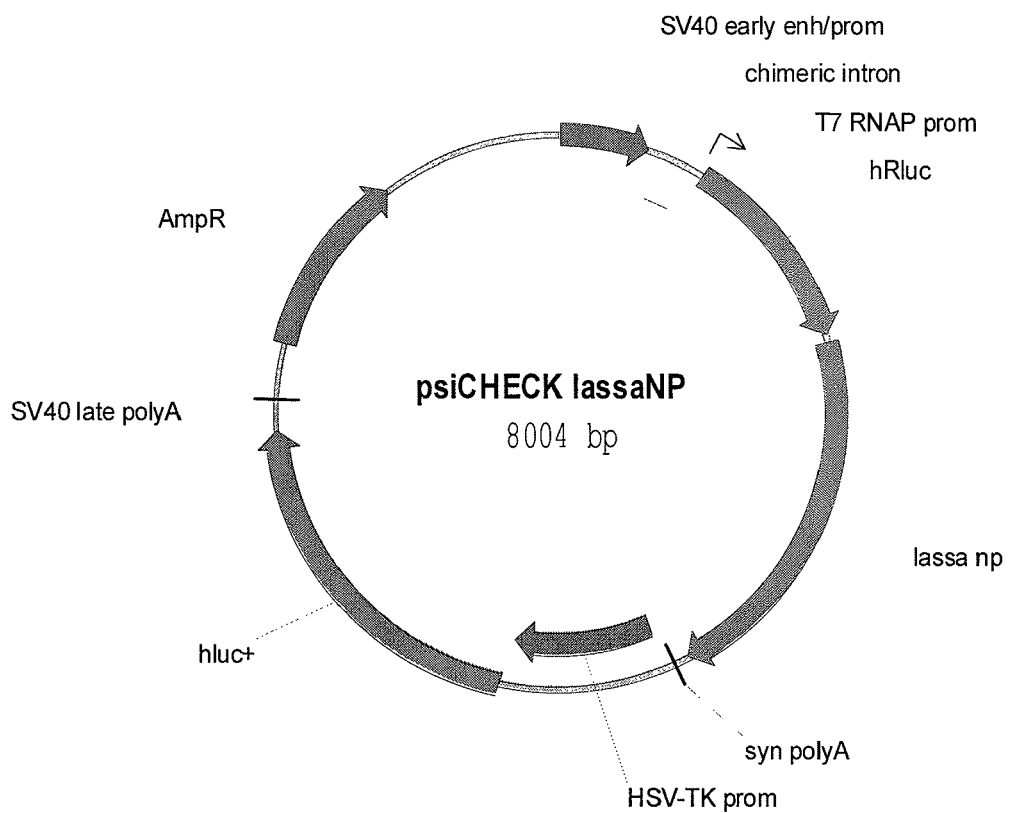
FIG. 1 illustrates LASV-NP in the psiCHECK2 vector backbone.

Though arenavirus infections result in severe cases of hemorrhagic fever, to date, therapies for treatment of LASV are limited. With the appearance of arenavirus epidemics appearing predominantly in the African sub-continent, a large gap in treatment is created with the lack of anti-arenaviral drugs in third-world countries, adding more strain to an already overwhelmed health infrastructure in affected countries. In addition, a concern is the possible weaponization of these viruses and their intended use to spread fear and panic in the general population in the hands of rogue states and individuals. The use of LASV and potentially other arenaviruses as bioweapons and the lack of a readily available therapy make the identification of novel drugs to treat the disease a priority.

The interfering RNA (e.g., siRNA) drug therapy described herein advantageously provides a significant new antiviral strategy that targets the viral genome or host factors that are known to play a direct role in the pathogenesis of hemorrhagic fever viruses including arenavirus and filovirus. In particular, development of a new class of anti-LASV drugs such as siRNAs targeting LASV NP, GP, L, and/or Z as described herein can lead to useful and effective treatments against LASV. In addition, development of a new class of drugs with a broader spectrum of activity against a range of hemorrhagic fever viruses such as siRNAs targeting host factors including Tissue Factor (TF) as described herein can lead to useful and effective treatments against LASV, EBOV, and/or MARV, as well as other arenaviruses and filoviruses. Furthermore, the lipid particles described herein (e.g., SNALP) enable the effective delivery of a nucleic acid drug such as an interfering RNA into target tissues and cells within the body. The presence of the lipid particle confers protection from nuclease degradation in the bloodstream, allows preferential accumulation in target tissue and provides a means of drug entry into the cellular cytoplasm where the siRNAs can perform their intended function of RNA interference, all requisite properties of a successful therapeutic drug.

II. Definitions

As used herein, the following terms have the meanings ascribed to them unless specified otherwise.

The term "Tissue Factor" or "TF" or "coagulation factor III" or "thromboplastin" or "F3" refers to a cell surface glycoprotein that enables cells to initiate the blood coagulation cascades. Tissue Factor functions as the high-affinity receptor for the coagulation factor VII, and the resulting complex provides a catalytic event that is responsible for initiation of the coagulation protease cascades by specific limited proteolysis. Unlike the other cofactors of these protease cascades, which circulate as nonfunctional precursors, Tissue Factor is a potent initiator that is fully functional when expressed on cell surfaces. There are 3 distinct domains of Tissue Factor: extracellular; transmembrane; and cytoplasmic.

The term "Arenavirus" or "Arenaviridae" refers to single-stranded RNA viruses that typically infect primates. The RNA is in two segments, denoted L and S. Both are circular, but the L strand is negative sense and the S strand is ambisense. The S strand encodes the nucleoprotein (NP) and glycoprotein (GP), while the L strand encodes the L polymerase (L) and Z protein (Z). Arenaviruses can be divided into two serogroups, which differ genetically and by geographical distribution: (1) the lymphocytic choriomeningitis virus (LCMV)-Lassa virus (Old World) complex; and (2) the Tacaribe virus (New World) complex. Members of the first group include, but are not limited to, Lassa virus (LASV), LCMV, Ippy virus, Lujo virus, Mobala virus, and Mopeia virus. Members of the second group include, but are not limited to, Amapari virus, Chapare virus, Flexal virus, Guanarito virus, Junin virus, Latino virus, Machupo virus, Oliveros virus, Parana virus, Pichinde virus, Pirital virus, Sabiá virus, Tacaribe virus, Tamiami virus, and Whitewater Arroyo virus.

The term "Filovirus" or "Filoviridae" refers to single-stranded negative sense RNA viruses that typically infect primates. Filoviruses are able to multiply in virtually all cell types. The Filovirus antigens and virions are found primarily in fibroblasts and interstitium of an infected individual. There are two identified genera of Filoviruses: the Ebola virus (EBOV; four species) and the Marburg virus (MARV). The virions (viral particles) are characteristically shaped as long, cylindrical, filamentous particles which may be straight, curved, coiled, or found in a "6" or "U" shaped configuration. They are occasionally branched and the particles vary greatly in length, but the diameter (about 80 nm) is consistent. The filovirus genome comprises seven genes that encode 4 virion structural proteins (VP30, VP35, nucleoprotein (NP), and a polymerase protein (L-pol)) and 3 membrane-associated proteins (VP40, glycoprotein (GP), and VP24).

The term "interfering RNA" or "RNAi" or "interfering RNA sequence" as used herein includes single-stranded RNA (e.g., mature miRNA, ssRNAi oligonucleotides, ssDNAi oligonucleotides), double-stranded RNA (i.e., duplex RNA such as siRNA, Dicer-substrate dsRNA, shRNA, aiRNA, or pre-miRNA), a DNA-RNA hybrid (see, e.g., PCT Publication No. WO 2004/078941), or a DNA-DNA hybrid (see, e.g., PCT Publication No. WO 2004/104199) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. Preferably, the interfering RNA molecules are chemically synthesized. The disclosures of each of the above patent documents are herein incorporated by reference in their entirety for all purposes.

Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 15-30, 15-25, or 19-25 base pairs in length, preferably about 18-22, 19-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule. As used herein, the term "siRNA" includes RNA-RNA duplexes as well as DNA-RNA hybrids (see, e.g., PCT Publication No. WO 2004/078941).

Preferably, siRNA are chemically synthesized. siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *Proc. Natl. Acad. Sci. USA,* 99:9942-9947 (2002); Calegari et al., *Proc. Natl. Acad. Sci. USA,* 99:14236 (2002); Byrom et al., *Ambion TechNotes,* 10(1):4-6 (2003); Kawasaki et al., *Nucleic Acids Res.,* 31:981-987 (2003); Knight et al., *Science,* 293:2269-2271 (2001); and Robertson et al., *J. Biol. Chem.,* 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

As used herein, the term "mismatch motif" or "mismatch region" refers to a portion of an interfering RNA (e.g., siRNA) sequence that does not have 100% complementarity to its target sequence. An interfering RNA may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

The phrase "inhibiting expression of a target gene" refers to the ability of an interfering RNA (e.g., siRNA) of the invention to silence, reduce, or inhibit expression of a target gene (e.g., TF and/or one or more LASV genes such as L, NP, GP, and/or Z). To examine the extent of gene silencing, a test sample (e.g., a sample of cells in culture expressing the target gene) or a test mammal (e.g., a mammal such as a human or an animal model such as a rodent (e.g., mouse) or a non-human primate (e.g., monkey) model) is contacted with an interfering RNA (e.g., siRNA) that silences, reduces, or inhibits expression of the target gene. Expression of the target gene in the test sample or test animal is compared to expression of the target gene in a control sample (e.g., a sample of cells in culture expressing the target gene) or a control mammal (e.g., a mammal such as a human or an animal model such as a rodent (e.g., mouse) or non-human primate (e.g., monkey) model) that is not contacted with or administered the interfering RNA (e.g., siRNA). The expression of the target gene in a control sample or a control mammal may be assigned a value of 100%. In particular embodiments, silencing, inhibition, or reduction of expression of a target gene is achieved when the level of target gene expression in the test sample or the test mammal relative to the level of target gene expression in the control sample or the control mammal is about 95%, 90%, 85%, 80%, 75%, 70%, 65%, 60%, 55%, 50%, 45%, 40%, 35%, 30%, 25%, 20%, 15%, 10%, 5%, or 0%. In other words, the interfering RNAs (e.g., siRNAs) of the present invention are capable of silencing, reducing, or inhibiting the expression of a target gene (e.g., TF and/or one or more LASV genes such as L, NP, GP, and/or Z) by at least about 5%, 10%, 15%, 20%, 25%, 30%, 35%, 40%, 45%, 50%, 55%, 60%, 65%, 70%, 75%, 80%, 85%, 90%, 95%, or 100% in a test sample or a test mammal relative to the level of target gene expression in a control sample or a control mammal not contacted with or administered the interfering RNA. Suitable assays for determining the level of target gene expression include, without limitation, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

An "effective amount" or "therapeutically effective amount" of a therapeutic nucleic acid such as an interfering RNA is an amount sufficient to produce the desired effect, e.g., an inhibition of expression of a target sequence in comparison to the normal expression level detected in the absence of an interfering RNA. Inhibition of expression of a target gene or target sequence is achieved when the value obtained with an interfering RNA relative to the control is about 95%, 90%, 85%, 80%, 75%, 70%, 65%, 60%, 55%, 50%, 45%, 40%, 35%, 30%, 25%, 20%, 15%, 10%, 5%, or 0%. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, as well as phenotypic assays known to those of skill in the art.

By "decrease," "decreasing," "reduce," or "reducing" of an immune response by an interfering RNA is intended to mean a detectable decrease of an immune response to a given interfering RNA (e.g., a modified interfering RNA). The amount of decrease of an immune response by a modified interfering RNA may be determined relative to the level of an immune response in the presence of an unmodified interfering RNA. A detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the presence of the unmodified interfering RNA. A decrease in the immune response to interfering RNA is typically measured by a decrease in cytokine production (e.g., IFNγ, IFNα, TNFα, IL-6, IL-8, or IL-12) by a responder cell in vitro or a decrease in cytokine production in the sera of a mammalian subject after administration of the interfering RNA.

As used herein, the term "responder cell" refers to a cell, preferably a mammalian cell, that produces a detectable immune response when contacted with an immunostimulatory interfering RNA such as an unmodified siRNA. Exemplary responder cells include, e.g., dendritic cells, macrophages, peripheral blood mononuclear cells (PBMCs), splenocytes, and the like. Detectable immune responses include, e.g., production of cytokines or growth factors such as TNF-α, IFN-α, IFN-β, IFN-γ, IL-1, IL-2, IL-3, IL-4, IL-5, IL-6, IL-8, IL-10, IL-12, IL-13, TGF, and combinations thereof. Detectable immune responses also include, e.g., induction of interferon-induced protein with tetratricopeptide repeats 1 (IFIT1) mRNA.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec.-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications*, Academic Press, Inc. N.Y. (1990).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, Ausubel et al., eds.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 55, or 60 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of a number of contiguous positions selected from the group consisting of from about 5 to about 60, usually about 10 to about 45, more usually about 15 to about 30, in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, *Adv. Appl. Math.*, 2:482 (1981), by the homology alignment algorithm of Needleman and Wunsch, *J. Mol. Biol.*, 48:443 (1970), by the search for similarity method of Pearson and Lipman, *Proc. Natl. Acad. Sci. USA*, 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology*, Ausubel et al., eds. (1995 supplement)).

Non-limiting examples of algorithms that are suitable for determining percent sequence identity and sequence similarity are the BLAST and BLAST 2.0 algorithms, which are described in Altschul et al., *Nuc. Acids Res.*, 25:3389-3402 (1977) and Altschul et al., *J. Mol. Biol.*, 215:403-410 (1990), respectively. BLAST and BLAST 2.0 are used, with the parameters described herein, to determine percent sequence identity for the nucleic acids of the invention. Software for performing BLAST analyses is publicly available through the National Center for Biotechnology Information (http://www.ncbi.nlm.nih.gov/). Another example is a global alignment algorithm for determining percent sequence identity such as the Needleman-Wunsch algorithm for aligning protein or nucleotide (e.g., RNA) sequences.

The BLAST algorithm also performs a statistical analysis of the similarity between two sequences (see, e.g., Karlin and Altschul, *Proc. Natl. Acad. Sci. USA*, 90:5873-5787 (1993)). One measure of similarity provided by the BLAST algorithm is the smallest sum probability (P(N)), which provides an indication of the probability by which a match between two nucleotide sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "nucleic acid" as used herein refers to a polymer containing at least two deoxyribonucleotides or ribonucleotides in either single- or double-stranded form and includes DNA, RNA, and hybrids thereof. DNA may be in the form of, e.g., antisense molecules, plasmid DNA, DNA-DNA duplexes, pre-condensed DNA, PCR products, vectors (P1, PAC, BAC, YAC, artificial chromosomes), expression cassettes, chimeric sequences, chromosomal DNA, or derivatives and combinations of these groups. RNA may be in the form of small interfering RNA (siRNA), Dicer-substrate dsRNA, small hairpin RNA (shRNA), asymmetrical interfering RNA (aiRNA), microRNA (miRNA), mRNA, tRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

The term "lipid particle" includes a lipid formulation that can be used to deliver a therapeutic nucleic acid (e.g., interfering RNA) to a target site of interest (e.g., cell, tissue, organ, and the like). In preferred embodiments, the lipid particle of the invention is a nucleic acid-lipid particle, which is typically formed from a cationic lipid, a non-cationic lipid, and optionally a conjugated lipid that prevents aggregation of the particle. In other preferred embodiments, the therapeutic nucleic acid (e.g., interfering RNA) may be encapsulated in the lipid portion of the particle, thereby protecting it from enzymatic degradation.

As used herein, the term "SNALP" refers to a stable nucleic acid-lipid particle. A SNALP represents a particle made from lipids (e.g., a cationic lipid, a non-cationic lipid, and optionally a conjugated lipid that prevents aggregation of the particle), wherein the nucleic acid (e.g., an interfering RNA) is fully encapsulated within the lipid. In certain instances, SNALP are extremely useful for systemic applications, as they can exhibit extended circulation lifetimes following intravenous (i.v.) injection, they can accumulate at distal sites (e.g., sites physically separated from the administration site), and they can mediate silencing of target gene expression at these distal sites. The nucleic acid may be complexed with a condensing agent and encapsulated within a SNALP as set forth in PCT Publication No. WO 00/03683, the disclosure of which is herein incorporated by reference in its entirety for all purposes.

The lipid particles of the invention (e.g., SNALP) typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the present invention, are resistant in aqueous solution to degradation with a nuclease. Nucleic acid-lipid particles and their method of preparation are disclosed in, e.g., U.S. Patent Publication Nos. 20040142025 and 20070042031, the disclosures of which are herein incorporated by reference in their entirety for all purposes.

As used herein, "lipid encapsulated" can refer to a lipid particle that provides a therapeutic nucleic acid, such as an interfering RNA (e.g., siRNA), with full encapsulation, partial encapsulation, or both. In a preferred embodiment, the nucleic acid (e.g., interfering RNA) is fully encapsulated in the lipid particle (e.g., to form a SNALP or other nucleic acid-lipid particle).

The term "lipid conjugate" refers to a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates (e.g., POZ-DAA conjugates; see, e.g., U.S. application Ser. No. 13/006,277, filed Jan. 13, 2011), polyamide oligomers (e.g., ATTA-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain preferred embodiments, non-ester containing linker moieties, such as amides or carbamates, are used. The disclosures of each of the above patent documents are herein incorporated by reference in their entirety for all purposes.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl diacylphosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the $pK_a$ of the cationic lipid and is substantially neutral at a pH above the $pK_a$. The cationic lipids of the invention may also be termed titratable cationic lipids. In some embodiments, the cationic lipids comprise: a protonatable tertiary amine (e.g., pH-titratable) head group; $C_{18}$ alkyl chains, wherein each alkyl chain independently has 0 to 3 (e.g., 0, 1, 2, or 3) double bonds; and ether, ester, or ketal linkages between the head group and alkyl chains.

The term "salts" includes any anionic and cationic complex, such as the complex formed between a cationic lipid and one or more anions. Non-limiting examples of anions include inorganic and organic anions, e.g., hydride, fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof. In particular embodiments, the salts of the cationic lipids disclosed herein are crystalline salts.

The term "fusogenic" refers to the ability of a lipid particle, such as a SNALP, to fuse with the membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles such as SNALP means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of lipid particles that leads to a broad biodistribution of an active agent such as an interfering RNA (e.g., siRNA) within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent such as an interfering RNA (e.g., siRNA) directly to a target site within an organism. For example, an agent can be locally delivered by direct injection into a disease site, other target site, or a target organ such as the liver, heart, pancreas, kidney, and the like.

The term "mammal" refers to any mammalian species such as a human, mouse, rat, dog, cat, hamster, guinea pig, rabbit, livestock, and the like.

The term "reticuloendothelial system" or "RES" refers to the part of the immune system that contains reticuloendothelial cells, including the phagocytic cells located in reticular connective tissue such as monocytes and macrophages. These cells typically accumulate in lymph nodes and the spleen. The Kupffer cells of the liver and tissue histiocytes are also part of the RES. The RES is divided into primary and secondary lymphoid organs. Primary ("central") lymphoid organs are the sites where the cells of the RES are produced. The cells of the RES are produced in the bone marrow. The thymus is also included as it is the required site for T cell maturation. Secondary ("peripheral") lymphoid organs are the sites where the cells of the RES function. This includes the lymph nodes, tonsils, spleen, and "MALT" (mucosa-associated lymphoid tissue). MALT is further divided into "GALT" (gut-associated lymphoid tissue) and "BALT" (bronchus-associated lymphoid tissue). The Kupffer cells of the liver act as part of this system, but are not organized into a tissue; rather, they are dispersed throughout the liver sinusoids. The microglia of the central nervous system (CNS) can be considered a part of the RES. They are scavenger cells that proliferate in response to CNS injury.

III. Description of the Embodiments

The present invention provides therapeutic nucleic acids such as interfering RNA (e.g., dsRNA such as siRNA) that target the expression of viral genes such as Lassa virus (LASV) NP, GP, L, and/or Z genes, or host genes such as tissue factor (TF), lipid particles comprising one or more (e.g., a cocktail) of the therapeutic nucleic acids, methods of making the lipid particles, and methods of delivering and/or administering the lipid particles (e.g., for the prevention or treatment of hemorrhagic fever caused by LASV and/or other arenaviruses and/or filoviruses such as EBOV and MARV).

In one aspect, the present invention provides interfering RNA molecules that target TF gene expression. In another aspect, the present invention provides interfering RNA molecules that target LASV gene expression. Non-limiting examples of interfering RNA molecules include double-stranded RNA capable of mediating RNAi such as siRNA, Dicer-substrate dsRNA, shRNA, aiRNA, pre-miRNA, and mixtures thereof. In certain instances, the present invention provides compositions comprising a combination (e.g., a cocktail, pool, or mixture) of interfering RNAs that target different regions of the LASV genome and/or TF gene. In certain instances, the interfering RNA (e.g., siRNA) molecules of the invention are capable of silencing LASV (e.g., NP, GP, L, and/or Z) gene expression, inactivating LASV, and/or inhibiting the replication of LASV in vitro or in vivo. In certain other instances, the interfering RNA (e.g., siRNA) molecules of the invention are capable of silencing TF gene expression, inactivating hemorraghic fever viruses such as LASV, EBOV, and MARV, and/or inhibiting the replication of hemorraghic fever viruses such as LASV EBOV, and MARV in vitro or in vivo. In further instances, the interfering RNA (e.g., siRNA) of the invention are capable of preventing or treating diseases or disorders associated with TF expression or overexpression.

In particular embodiments, the present invention provides an interfering RNA (e.g., siRNA) that silences TF or LASV (e.g., NP, GP, L, and/or Z) gene expression, wherein the interfering RNA comprises a sense strand and a complementary antisense strand. In certain embodiments, the interfering RNA comprises a double-stranded region of about 15 to about 60 nucleotides in length (e.g., about 15-60, 15-30, 15-25, 19-30, 19-25, 20-60, 20-55, 20-50, 20-45, 20-40, 20-35, 20-30, 20-25, 21-30, 21-29, 22-30, 22-29, 22-28, 23-30, 23-28, 24-30, 24-28, 25-60, 25-55, 25-50, 25-45, 25-40, 25-35, or 25-30 nucleotides in length, or about 15, 16, 17, 18, 19, 20, 21, 22, 23, 24, 25, 26, 27, 28, 29, 30, 31, 32, 33, 34, or 35 nucleotides in length).

In some embodiments, the sense strand comprises or consists of a sequence that is complementary to one of the antisense strand sequences set forth in Tables 1-10 (e.g., Tables 1, 2, 3, 4, 5, 6, 7, 8, 9, and/or 10). In related embodiments, the sense strand comprises or consists of one of the sense strand sequences set forth in Tables 1-10. In further embodiments, the sense strand comprises or consists of at least about 15 contiguous nucleotides (e.g., at least about 15, 16, 17, 18, or 19 contiguous nucleotides) of a sequence that is complementary to one of the antisense strand sequences set forth in Tables 1-10. In related embodiments, the sense strand comprises or consists of at least about 15 contiguous nucleotides (e.g., at least about 15, 16, 17, 18, or 19 contiguous nucleotides) of one of the sense strand sequences set forth in Tables 1-10. In particular embodiments, the sense strand comprises nucleotides 1-19 of one of the sense strand sequences set forth in Tables 1-10. In other embodiments, the sense strand specifically hybridizes to or targets one of the antisense strand sequences set forth in Tables 1-10. In further embodiments, the sense strand comprises or consists of a sequence that is at least about 80%, 85%, 86%, 87%, 88%, 89%, 90%, 91%, 92%, 93%, 94%, 95%, 96%, 97%, 98%, 99%, or 100% identical to one of the sense strand sequences set forth in Tables 1-10. In preferred embodiments, the interfering RNA (e.g., siRNA) comprising such a sense strand sequence is capable of mediating target-specific RNAi.

In other embodiments, the antisense strand comprises or consists of a sequence that is complementary to one of the sense strand sequences set forth in Tables 1-10 (e.g., Tables 1, 2, 3, 4, 5, 6, 7, 8, 9, and/or 10). In related embodiments, the antisense strand comprises or consists of one of the antisense strand sequences set forth in Tables 1-10. In further embodiments, the antisense strand comprises or consists of at least about 15 contiguous nucleotides (e.g., at least about 15, 16, 17, 18, or 19 contiguous nucleotides) of a sequence that is complementary to one of the sense strand sequences set forth in Tables 1-10. In related embodiments, the antisense strand comprises or consists of at least about 15 contiguous nucleotides (e.g., at least about 15, 16, 17, 18, or 19 contiguous nucleotides) of one of the antisense strand sequences set forth in Tables 1-10. In particular embodiments, the antisense strand comprises nucleotides 1-19 of one of the antisense strand sequences set forth in Tables 1-10. In other embodiments, the antisense strand specifically hybridizes to or targets one of the sense strand sequences set forth in Tables 1-10. In further embodiments, the antisense strand comprises or consists of a sequence that is at least about 80%, 85%, 86%, 87%, 88%, 89%, 90%, 91%, 92%, 93%, 94%, 95%, 96%, 97%, 98%, 99%, or 100% identical to one of the antisense strand sequences set forth in Tables 1-10. In preferred embodiments, the interfering RNA (e.g., siRNA) comprising such an antisense strand sequence is capable of mediating target-specific RNAi.

In certain embodiments, the interfering RNA (e.g., siRNA) of the present invention may comprise at least one, two, three, four, five, six, seven, eight, nine, ten, or more modified nucleotides such as 2'OMe nucleotides, e.g., in the sense and/or antisense strand of the double-stranded region of the interfering RNA. Preferably, uridine and/or guanosine nucleotides in the interfering RNA are modified with 2'OMe nucleotides. In certain instances, the interfering RNA contains 2'OMe nucleotides in both the sense and antisense strands and comprises at least one 2'OMe-uridine nucleotide and at least one 2'OMe-guanosine nucleotide in the double-stranded region. In some embodiments, the sense and/or antisense strand of the interfering RNA may further comprise modified (e.g., 2'OMe-modified) adenosine and/or modified (e.g., 2'OMe-modified) cytosine nucleotides, e.g., in the double-stranded region of the interfering RNA.

In particular embodiments, the interfering RNA (e.g., siRNA) molecules of the present invention comprise a 3' overhang of 1, 2, 3, or 4 nucleotides in one or both strands. In certain instances, the interfering RNA may contain at least one blunt end. In particular embodiments, the 3' overhangs in one or both strands of the interfering RNA may each independently comprise 1, 2, 3, or 4 modified and/or unmodified deoxythymidine ("t" or "dT") nucleotides, 1, 2, 3, or 4 modified (e.g., 2'OMe) and/or unmodified uridine ("U") ribonucleotides, or 1, 2, 3, or 4 modified (e.g., 2'OMe) and/or unmodified ribonucleotides or deoxyribonucleotides having complementarity to the target sequence or the complementary strand thereof.

TABLE 1 siRNA sequences that target human Tissue Factor (TF) gene expression.

| siRNA | Target or Sense Strand Sequence (5' → 3') (SEQ ID NO:) | Antisense Strand Sequence (5' → 3') (SEQ ID NO:) |
|---|---|---|
| hTF292 | GUGGCAGCAUAUAAUUUAA (4) | UUAAAUUAUAUGCUGCCAC (5) |
| hTF271 | GCGCUUCAGGCACUACAAA (6) | UUUGUAGUGCCUGAAGCGC (7) |
| hTF1238 | GCAUUAGUCACUUUGAAAU (8) | AUUUCAAAGUGACUAAUGC (9) |
| hTF369 | AGUCUACACUGUUCAAAUA (10) | UAUUUGAACAGUGUAGACU (11) |
| hTF290 | CUGUGGCAGCAUAUAAUUU (12) | AAAUUAUAUGCUGCCACAG (13) |
| hTF288 | UACUGUGGCAGCAUAUAAU (14) | AUUAUAUGCUGCCACAGUA (15) |

TABLE 2 siRNA sequences that target LASV L-pol or NP gene expression.

| siRNA | Target or Sense Strand Sequence (5' → 3') (SEQ ID NO:) | Antisense Strand Sequence (5' → 3') (SEQ ID NO:) |
|---|---|---|
| LS-L-844 | GACAAUAUCGAACACUUAA (16) | UUAAGUGUUCGAUAUUGUC (17) |
| LS-L-1022 | GGAGGAAACUUCUAUUAAU (18) | AUUAAUAGAAGUUUCCUCC (19) |
| LS-L-1778 | CAACAAUAAGCACUAUGAU (20) | AUCAUAGUGCUUAUUGUUG (21) |
| LS-L-3513 | UGCUAUCCUUUCCAUGAAA (22) | UUUCAUGGAAAGGAUAGCA (23) |
| LS-L-6313 | GACCAGGAUCUUGAGAUAU (24) | AUAUCUCAAGAUCCUGGUC (25) |
| LS-NP-548 | CACUGGCAUGUCUGACAAA (26) | UUUGUCAGACAUGCCAGUG (27) |
| LS-NP-672 | AAGUCAUCCCAUCCUAAAU (28) | AUUUAGGAUGGGAUGACUU (29) |
| LS-NP-943 | GAUGGAUGGCCAUAUAUUG (30) | CAAUAUAUGGCCAUCCAUC (31) |
| LS-NP-1222 | GGCUGCUACAUACACUUCU (32) | AGAAGUGUAUGUAGCAGCC (33) |
| LS-NP-1284 | GUACUCACAUGGGAUUGAU (34) | AUCAAUCCCAUGUGAGUAC (35) |

In particular embodiments, one of the sense and/or antisense strand sequences set forth in Tables 1 or 2 (e.g., a sense strand sequence and/or its complementary antisense strand sequence) may comprise at least one, two, three, four, five, six, seven, eight, nine, ten, or more modified nucleotides such as 2'OMe nucleotides (e.g., 2'OMe-guanosine and/or 2'OMe-uridine nucleotides) as described herein. In certain embodiments, the sense and/or antisense strand sequences may each independently comprise or consist of a modified (e.g., 2'OMe) and/or unmodified 3' overhang of 1, 2, 3, or 4 nucleotides, or one or both ends of the double-stranded molecule may be blunt-ended as described herein.

One of skill in the art will understand that the unmodified sequences set forth in Tables 1 and 2 can be modified in accordance with the selective modification patterns described herein (e.g., at selective uridine and/or guanosine nucleotides, and optionally at adenosine and/or cytosine nucleotides, within the RNA duplex), and screened for RNAi activity as well as immune stimulation, such that the degree of chemical modifications introduced into the interfering RNA molecule strikes a balance between reduction or abrogation of the immunostimulatory properties of the interfering RNA and retention of RNAi activity.

In some embodiments, the interfering RNA (e.g., siRNA) that silences Tissue Factor (TF) gene expression comprises one of the following sense and/or antisense strand sequences set forth in Table 3, wherein these sequences correspond to 2'OMe-modified versions of the sense and antisense strand sequences of hTF292 from Table 1 above, and wherein the bolded and underlined nucleotides are 2'OMe nucleotides. In certain instances, the sense strand further comprises a 5'-CU-3' overhang, wherein the bolded and underlined nucleotide is a 2'OMe nucleotide. In certain other instances, the antisense strand further comprises a 5'-AG-3' overhang, wherein the bolded and underlined nucleotide is a 2'OMe nucleotide. In further instances, the sense and/or antisense strand may further comprise at least one, two, three, four, five, six, seven, eight, nine, ten, or more additional modifications such as 2'OMe nucleotides (e.g., additional 2'OMe-guanosine nucleotides and/or 2'OMe-uridine nucleotides, and/or 2'OMe-adenosine and/or 2'OMe-cytosine nucleotides).

TABLE 3

2'OMe-modified sense and antisense strand sequences that target human TF gene expression.

| Name | Sense Strand Sequence (SEQ ID NO:) | Name | Antisense Strand Sequence (SEQ ID NO:) |
|---|---|---|---|
| S-1 | 5'-GUGGCAGCAUAUAAUUUAA-3' (36) | AS-1 | 5'-UUAAAUUAUAUGCUGCCAC-3' (37) |
| S-2 | 5'-GUGGCAGCAUAUAAUUAA-3' (38) | AS-2 | 5'-UUAAAUUAUAUGCUGCCAC-3' (39) |
| S-3 | 5'-GUGGCAGCAUAUAAUUAA-3' (40) | AS-4 | 5'-UUAAAUUAUAUGCUGCCAC-3' (41) |
| | | AS-5b | 5'-UUAAAUUAUAUGCUGCCAC-3' (42) |
| | | AS-6 | 5'-UUAAAUUAUAUGCUGCCAC-3' (43) |

In other embodiments, the interfering RNA (e.g., siRNA) that silences LASV gene expression comprises one of the following sense and/or antisense strand sequences set forth in Table 4, wherein these sequences correspond to 2'OMe-modified versions of the sense and antisense strand sequences of LS-NP-1284 from Table 2 above, and wherein the bolded and underlined nucleotides are 2'OMe nucleotides. In certain instances, the sense strand further comprises a 5'-GU-3' or 5'-GU-3' overhang, wherein the bolded and underlined nucleotides are 2'OMe nucleotides. In certain other instances, the antisense strand further comprises a 5'-UU-3' or 5'-UU-3' overhang, wherein the bolded and underlined nucleotides are 2'OMe nucleotides. In further instances, the sense and/or antisense strand may further comprise at least one, two, three, four, five, six, seven, eight, nine, ten, or more additional modifications such as 2'OMe nucleotides (e.g., additional 2'OMe-guanosine nucleotides and/or 2'OMe-uridine nucleotides, and/or 2'OMe-adenosine and/or 2'OMe-cytosine nucleotides).

TABLE 4

2'OMe-modified sense and antisense strand sequences that target LASV L-pol or NP gene expression.

| Name | Sense Strand Sequence (SEQ ID NO:) | Name | Antisense Strand Sequence (SEQ ID NO:) |
|---|---|---|---|
| S-1 | 5'-GUACUCACAUGGGAUUGAU-3' (44) | AS-1 | 5'-AUCAAUCCCAUGUGAGU**AC-3' (45) |
| S-2 | 5'-GUACUCACAUGGGAUUGAU-3' (46) | AS-2 | 5'-AUCAAUCCCAUGUGAGU**AC-3' (47) |
|  |  | AS-3 | 5'-AUCAAUCCCAUGUGAGUAC-3' (48) |
|  |  | AS-4 | 5'-AUCAAUCCCAUGUGAGUAC-3' (49) |

In another embodiment, the present invention provides a composition comprising a cocktail (e.g., at least 2, 3, 4, 5, 6, 7, 8, 9, 10, 11, 12, 13, 14, 15, 16, 17, 18, 19, 20, or more) of the sequences set forth in Tables 1-10. In particular embodiments, at least 1, 2, 3, 4, 5, 6, 7, 8, 9, 10, 11, 12, 13, 14, 15, 16, 17, 18, 19, 20, or more (e.g., all) of these sequences set forth in Tables 1-10 are chemically modified (e.g., 2'OMe-modified) as described herein.

In preferred embodiments, the present invention provides a composition comprising one or more of the 2'OMe-modified hTF292 and/or LASV NP1284 siRNA duplexes set forth in Tables 9 and 10.

The present invention also provides a pharmaceutical composition comprising one or more (e.g., a cocktail) of the interfering RNAs described herein and a pharmaceutically acceptable carrier.

In another aspect, the present invention provides a nucleic acid-lipid particle (e.g., SNALP) that targets TF and/or LASV gene expression. The nucleic acid-lipid particles (e.g., SNALP) typically comprise one or more (e.g., a cocktail) of the interfering RNAs described herein, a cationic lipid, and a non-cationic lipid. In certain instances, the nucleic acid-lipid particles (e.g., SNALP) further comprise a conjugated lipid that inhibits aggregation of particles. Preferably, the nucleic acid-lipid particles (e.g., SNALP) comprise one or more (e.g., a cocktail) of the interfering RNAs described herein, a cationic lipid, a non-cationic lipid, and a conjugated lipid that inhibits aggregation of particles. In particular embodiments, the nucleic acid-lipid particles (e.g., SNALP) of the invention comprise 1, 2, 3, 4, 5, 6, 7, 8, or more unmodified and/or modified interfering RNAs that silence 1, 2, 3, 4, 5, 6, 7, 8, or more different genes associated with hemorrhagic fever (e.g., TF and/or LASV genes such as NP, GP, L, and/or Z, alone or in combination with one or more genes in the EBOV and/or MARV genomes), a cationic lipid, a non-cationic lipid, and a conjugated lipid that inhibits aggregation of particles.

In some embodiments, the interfering RNAs (e.g., siR-NAs) of the present invention are fully encapsulated in the nucleic acid-lipid particle (e.g., SNALP). With respect to formulations comprising an interfering RNA cocktail, the different types of interfering RNA species present in the cocktail (e.g., interfering RNA compounds with different sequences) may be co-encapsulated in the same particle, or each type of interfering RNA species present in the cocktail may be encapsulated in a separate particle. The interfering RNA cocktail may be formulated in the particles described herein using a mixture of two or more individual interfering RNAs (each having a unique sequence) at identical, similar, or different concentrations or molar ratios. In one embodiment, a cocktail of interfering RNAs (corresponding to a plurality of interfering RNAs with different sequences) is formulated using identical, similar, or different concentrations or molar ratios of each interfering RNA species, and the different types of interfering RNAs are co-encapsulated in the same particle. In another embodiment, each type of interfering RNA species present in the cocktail is encapsulated in different particles at identical, similar, or different interfering RNA concentrations or molar ratios, and the particles thus formed (each containing a different interfering RNA payload) are administered separately (e.g., at different times in accordance with a therapeutic regimen), or are combined and administered together as a single unit dose (e.g., with a pharmaceutically acceptable carrier). The particles described herein are serum-stable, are resistant to nuclease degradation, and are substantially non-toxic to mammals such as humans.

The cationic lipid in the nucleic acid-lipid particles of the invention (e.g., SNALP) may comprise, e.g., one or more cationic lipids of Formula I-XXII described herein or any other cationic lipid species. In one particular embodiment, the cationic lipid is selected from the group consisting of 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), dilinoleylmethyl-3-dimethylaminopropionate (DLin-M-C2-DMA), (6Z,9Z,28Z,31Z)-heptatriaconta-6,9,28,31-tetraen-19-yl-4-(dimethylamino)butanoate (DLin-M-C3-DMA), 3-((6Z,9Z,28Z,31Z)-heptatriaconta-6,9,28,31-tetraen-19-yloxy)-N,N-dimethylpropan-1-amine (MC3 Ether), 4-((6Z, 9Z,28Z,31Z)-heptatriaconta-6,9,28,31-tetraen-19-yloxy)-N, N-dimethylbutan-1-amine (MC4 Ether), salts thereof, and mixtures thereof.

The non-cationic lipid in the nucleic acid-lipid particles of the present invention (e.g., SNALP) may comprise, e.g., one or more anionic lipids and/or neutral lipids. In some embodiments, the non-cationic lipid comprises one of the following neutral lipid components: (1) a mixture of a phospholipid and cholesterol or a derivative thereof; (2) cholesterol or a derivative thereof; or (3) a phospholipid. In certain preferred embodiments, the phospholipid comprises dipalmitoylphosphatidylcholine (DPPC), distearoylphosphatidylcholine (DSPC), or a mixture thereof. In a particularly preferred embodiment, the non-cationic lipid is a mixture of DPPC and cholesterol.

The lipid conjugate in the nucleic acid-lipid particles of the invention (e.g., SNALP) inhibits aggregation of particles and may comprise, e.g., one or more of the lipid conjugates described herein. In one particular embodiment, the lipid conjugate comprises a PEG-lipid conjugate. Examples of PEG-lipid conjugates include, but are not limited to, PEG-DAG conjugates, PEG-DAA conjugates, and mixtures thereof. In certain embodiments, the PEG-DAA conjugate in the lipid particle may comprise a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, or mixtures thereof. In another embodiment, the lipid conjugate comprises a POZ-lipid conjugate such as a POZ-DAA conjugate.

In some embodiments, the present invention provides nucleic acid-lipid particles (e.g., SNALP) comprising: (a) one or more (e.g., a cocktail) interfering RNA molecules that target LASV (e.g., NP, GP, L, and/or Z) and/or TF gene expression; (b) one or more cationic lipids (e.g., cationic lipids of Formula I-XXII) or salts thereof comprising from about 50 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.5 mol % to about 2 mol % of the total lipid present in the particle.

In one aspect of this embodiment, the nucleic acid-lipid particle comprises: (a) one or more (e.g., a cocktail) interfering RNA molecules that target LASV (e.g., NP, GP, L, and/or Z) or TF gene expression; (b) a cationic lipid (e.g., cationic lipid of Formula I-XXII) or a salt thereof comprising from about 52 mol % to about 62 mol % of the total lipid present in the particle; (c) a mixture of a phospholipid and cholesterol or a derivative thereof comprising from about 36 mol % to about 47 mol % of the total lipid present in the particle; and (d) a PEG-lipid conjugate comprising from about 1 mol % to about 2 mol % of the total lipid present in the particle. This embodiment of nucleic acid-lipid particle is generally referred to herein as the "1:57" formulation. In one particular embodiment, the 1:57 formulation is a four-component system comprising about 1.4 mol % PEG-lipid conjugate (e.g., PEG2000-C-DMA), about 57.1 mol % cationic lipid (e.g., cationic lipid of Formula I-XXII) or a salt thereof, about 7.1 mol % DPPC (or DSPC), and about 34.3 mol % cholesterol (or derivative thereof).

In another aspect of this embodiment, the nucleic acid-lipid particle comprises: (a) one or more (e.g., a cocktail) interfering RNA molecules that target LASV (e.g., NP, GP, L, and/or Z) or TF gene expression; (b) a cationic lipid (e.g., cationic lipid of Formula I-XXII) or a salt thereof comprising from about 56.5 mol % to about 66.5 mol % of the total lipid present in the particle; (c) cholesterol or a derivative thereof comprising from about 31.5 mol % to about 42.5 mol % of the total lipid present in the particle; and (d) a PEG-lipid conjugate comprising from about 1 mol % to about 2 mol % of the total lipid present in the particle. This embodiment of nucleic acid-lipid particle is generally referred to herein as the "1:62" formulation. In one particular embodiment, the 1:62 formulation is a three-component system which is phospholipid-free and comprises about 1.5 mol % PEG-lipid conjugate (e.g., PEG2000-C-DMA), about 61.5 mol % cationic lipid (e.g., cationic lipid of Formula I-XXII) or a salt thereof, and about 36.9 mol % cholesterol (or derivative thereof).

Additional embodiments related to the 1:57 and 1:62 formulations are described in PCT Publication No. WO 09/127,060 and U.S. application Ser. No. 12/794,701, filed Jun. 4, 2010, the disclosures of which are herein incorporated by reference in their entirety for all purposes.

In other embodiments, the present invention provides nucleic acid-lipid particles (e.g., SNALP) comprising: (a) one or more (e.g., a cocktail) interfering RNA molecules that target LASV (e.g., NP, GP, L, and/or Z) or TF gene expression; (b) one or more cationic lipids (e.g., cationic lipids of Formula I-XXII) or salts thereof comprising from about 2 mol % to about 50 mol % of the total lipid present in the particle; (c) one or more non-cationic lipids comprising from about 5 mol % to about 90 mol % of the total lipid present in the particle; and (d) one or more conjugated lipids that inhibit aggregation of particles comprising from about 0.5 mol % to about 20 mol % of the total lipid present in the particle.

In one aspect of this embodiment, the nucleic acid-lipid particle comprises: (a) one or more (e.g., a cocktail) interfering RNA molecules that target LASV (e.g., NP, GP, L, and/or Z) or TF gene expression; (b) a cationic lipid (e.g., cationic lipid of Formula I-XXII) or a salt thereof comprising from about 30 mol % to about 50 mol % of the total lipid present in the particle; (c) a mixture of a phospholipid and cholesterol or a derivative thereof comprising from about 47 mol % to about 69 mol % of the total lipid present in the particle; and (d) a PEG-lipid conjugate comprising from about 1 mol % to about 3 mol % of the total lipid present in the particle. This embodiment of nucleic acid-lipid particle is generally referred to herein as the "2:40" formulation. In one particular embodiment, the 2:40 formulation is a four-component system which comprises about 2 mol % PEG-lipid conjugate (e.g., PEG2000-C-DMA), about 40 mol % cationic lipid (e.g., cationic lipid of Formula I-XXII) or a salt thereof, about 10 mol % DPPC (or DSPC), and about 48 mol % cholesterol (or derivative thereof).

In further embodiments, the present invention provides nucleic acid-lipid particles (e.g., SNALP) comprising: (a) one or more (e.g., a cocktail) interfering RNA molecules that target LASV (e.g., NP, GP, L, and/or Z) or TF gene expression; (b) one or more cationic lipids (e.g., cationic lipids of Formula I-XXII) or salts thereof comprising from about 50 mol % to about 65 mol % of the total lipid present in the particle; (c) one or more non-cationic lipids comprising from about 25 mol % to about 45 mol % of the total lipid present in the particle; and (d) one or more conjugated lipids that inhibit aggregation of particles comprising from about 5 mol % to about 10 mol % of the total lipid present in the particle.

In one aspect of this embodiment, the nucleic acid-lipid particle comprises: (a) one or more (e.g., a cocktail) interfering RNA molecules that target LASV (e.g., NP, GP, L, and/or Z) or TF gene expression; (b) a cationic lipid (e.g., cationic lipid of Formula I-XXII) or a salt thereof comprising from about 50 mol % to about 60 mol % of the total lipid present in the particle; (c) a mixture of a phospholipid and cholesterol or a derivative thereof comprising from about 35 mol % to about 45 mol % of the total lipid present in the particle; and (d) a PEG-lipid conjugate comprising from about 5 mol % to about 10 mol % of the total lipid present in the particle. This embodiment of nucleic acid-lipid particle is generally referred to herein as the "7:54" formulation. In certain instances, the non-cationic lipid mixture in the 7:54 formulation comprises: (i) a phospholipid of from about 5 mol % to about 10 mol % of the total lipid present in the particle; and (ii) cholesterol or a derivative thereof of from about 25 mol % to about 35 mol % of the total lipid present in the particle. In one particular embodiment, the 7:54 formulation is a four-component system which comprises about 7 mol % PEG-lipid conjugate (e.g., PEG750-C-DMA), about 54 mol % cationic lipid (e.g., cationic lipid of Formula I-XXII) or a salt thereof, about 7 mol % DPPC (or DSPC), and about 32 mol % cholesterol (or derivative thereof).

In another aspect of this embodiment, the nucleic acid-lipid particle comprises: (a) one or more (e.g., a cocktail) interfering RNA molecules that target LASV (e.g., NP, GP, L, and/or Z) or TF gene expression; (b) a cationic lipid (e.g., cationic lipid of Formula I-XXII) or a salt thereof comprising from about 55 mol % to about 65 mol % of the total lipid present in the particle; (c) cholesterol or a derivative thereof comprising from about 30 mol % to about 40 mol % of the total lipid present in the particle; and (d) a PEG-lipid conjugate comprising from about 5 mol % to about 10 mol % of the total lipid present in the particle. This embodiment of nucleic acid-lipid particle is generally referred to herein as the "7:58" formulation. In one particular embodiment, the 7:58 formulation is a three-component system which is phospholipid-free and comprises about 7 mol % PEG-lipid conjugate (e.g., PEG750-C-DMA), about 58 mol % cationic lipid (e.g., cationic lipid of Formula I-XXII) or a salt thereof, and about 35 mol % cholesterol (or derivative thereof).

Additional embodiments related to the 7:54 and 7:58 formulations are described in U.S. application Ser. No. 12/828,189, filed Jun. 30, 2010, the disclosure of which is herein incorporated by reference in its entirety for all purposes.

The present invention also provides pharmaceutical compositions comprising a nucleic acid-lipid particle such as a SNALP and a pharmaceutically acceptable carrier.

The nucleic acid-lipid particles of the present invention (e.g., SNALP) are useful for the therapeutic delivery of interfering RNAs (e.g., siRNAs) that silence the expression of one or more genes associated with hemorrhagic fever viral pathogenesis (e.g., TF and/or one or more genes in the LASV genome such as NP, GP, L, and/or Z). In some embodiments, a cocktail of interfering RNAs that target one or more LASV genes is formulated into the same or different nucleic acid-lipid particles, and the particles are administered to a mammal (e.g., a human) requiring such treatment. In other embodiments, a cocktail of interfering RNAs that target different regions (e.g., overlapping and/or non-overlapping sequences) of the TF gene is formulated into the same or different nucleic acid-lipid particles, and the particles are administered to a mammal (e.g., a human) requiring such treatment. In certain instances, a therapeutically effective amount of the nucleic acid-lipid particles can be administered to the mammal, e.g., for treating, preventing, reducing the risk of developing, and/or delaying the onset of LASV infections (e.g., in instances where one or more LASV genes are targeted) or hemorrhagic fever (e.g., in instances where one or more LASV genes and/or TF are targeted).

In some embodiments, the interfering RNA (e.g., siRNA) molecules described herein are used in methods for silencing LASV or TF gene expression, e.g., in a cell such as a reticuloendothelial cell (e.g., monocyte or macrophage), an endothelial cell, a liver cell (e.g., hepatocyte), a fibroblast cell, and/or a platelet cell. In particular, it is an object of the present invention to provide methods for treating, preventing, reducing the risk of developing, or delaying the onset of a viral infection in a mammal that causes hemorrhagic fever by downregulating or silencing the transcription and/or translation of TF and LASV genes. In certain embodiments, the present invention provides a method for introducing one or more interfering RNA (e.g., siRNA) molecules described herein into a cell by contacting the cell with a nucleic acid-lipid particle described herein (e.g., a SNALP formulation). In one particular embodiment, the cell is a reticuloendothelial cell (e.g., monocyte or macrophage), an endothelial cell, a liver cell (e.g., hepatocyte), a fibroblast cell, and/or a platelet cell. In another embodiment, the present invention provides a method for the in vivo delivery of one or more interfering RNA (e.g., siRNA) molecules described herein to a cell, tissue, or organ infected and/or susceptible of being infected with an arenavirus (e.g., LASV) and/or filovirus (e.g., EBOV) by administering to a mammal (e.g., human) a lipid particle as described herein (e.g., a SNALP formulation).

In some embodiments, the nucleic acid-lipid particles described herein (e.g., SNALP) are administered by one of the following routes of administration: oral, intranasal, intravenous, intraperitoneal, intramuscular, intra-articular, intralesional, intratracheal, subcutaneous, and intradermal. In particular embodiments, the nucleic acid-lipid particles are administered systemically, e.g., via enteral or parenteral routes of administration.

In certain aspects, the present invention provides methods for silencing LASV gene expression in a mammal (e.g., human) in need thereof, the method comprising administering to the mammal a therapeutically effective amount of a nucleic acid-lipid particle (e.g., a SNALP formulation) comprising one or more interfering RNAs (e.g., siRNAs) described herein (e.g., siRNAs targeting one or more LASV genes). In some embodiments, administration of nucleic acid-lipid particles comprising one or more LASV interfering RNAs reduces LASV viral RNA levels by at least about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% (or any range therein) relative to LASV viral RNA levels detected in the absence of the interfering RNA (e.g., buffer control or irrelevant non-LASV targeting interfering RNA control). In other embodiments, administration of nucleic acid-lipid particles comprising one or more LASV-targeting interfering RNAs reduces LASV viral RNA levels for at least about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days or more (or any range therein) relative to a negative control such as, e.g., a buffer control or an irrelevant non-LASV targeting interfering RNA control. The LASV-targeting interfering RNA molecules may comprise at least one of the sequences set forth in Tables 2, 4-6, and 10 in unmodified and/or modified (e.g., 2'OMe-modified) form.

In other aspects, the present invention provides methods for silencing TF gene expression in a mammal (e.g., human) in need thereof, the method comprising administering to the mammal a therapeutically effective amount of a nucleic acid-lipid particle (e.g., a SNALP formulation) comprising one or more interfering RNAs (e.g., siRNAs) described herein (e.g., siRNAs targeting one or more regions of the TF gene). In some embodiments, administration of nucleic acid-lipid particles comprising one or more TF interfering RNAs reduces TF mRNA levels by at least about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% (or any range therein) relative to TF mRNA levels detected in the absence of the interfering RNA (e.g., buffer control or irrelevant non-TF targeting interfering RNA control). In other embodiments, administration of nucleic acid-lipid particles comprising one or more TF-targeting interfering RNAs reduces TF mRNA levels for at least about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days or more (or any range therein) relative to a negative control such as, e.g., a buffer control or an irrelevant non-TF targeting interfering RNA control. The TF-targeting interfering RNA molecules may comprise at least one of the sequences set forth in Tables 1, 3, and 7-9 in unmodified and/or modified (e.g., 2'OMe-modified) form.

In other aspects, the present invention provides methods for treating, preventing, reducing the risk or likelihood of developing (e.g., reducing the susceptibility to), delaying the onset of, and/or ameliorating one or more symptoms associated with a LASV infection in a mammal (e.g., human) in need thereof, the method comprising administering to the mammal a therapeutically effective amount of a nucleic acid-lipid particle (e.g., a SNALP formulation) comprising one or more interfering RNA molecules (e.g., siRNAs) described herein (e.g., one or more siRNAs targeting LASV gene expression). The LASV-targeting interfering RNA molecules may comprise at least one of the sequences set forth in Tables 2, 4-6, and 10 in unmodified and/or modified (e.g., 2'OMe-modified) form.

In related aspects, the present invention provides methods for treating, preventing, reducing the risk or likelihood of developing (e.g., reducing the susceptibility to), delaying the onset of, and/or ameliorating one or more symptoms associated with an arenavirus and/or filovirus infection in a mammal (e.g., human) in need thereof, the method comprising administering to the mammal a therapeutically effective amount of a nucleic acid-lipid particle (e.g., a SNALP formulation) comprising one or more interfering RNA molecules (e.g., siRNAs) described herein (e.g., one or more siRNAs targeting TF gene expression). The TF-targeting interfering RNA molecules may comprise at least one of the sequences set forth in Tables 1, 3, and 7-9 in unmodified and/or modified (e.g., 2'OMe-modified) form.

In further aspects, the present invention provides methods for treating, preventing, reducing the risk or likelihood of developing (e.g., reducing the susceptibility to), delaying the onset of, and/or ameliorating one or more symptoms associated with hemorrhagic fever, the method comprising administering to the mammal a therapeutically effective amount of a nucleic acid-lipid particle (e.g., a SNALP formulation) comprising one or more interfering RNA molecules (e.g., siRNAs) described herein (e.g., one or more siRNAs targeting LASV and/or TF gene expression). The interfering RNA molecules may comprise at least one of the sequences set forth in Tables 1-10 in unmodified and/or modified (e.g., 2'OMe-modified) form.

In further aspects, the present invention provides a method for inactivating LASV and/or inhibiting the replication of LASV in a mammal (e.g., human) in need thereof (e.g., a mammal with a LASV infection), the method comprising administering to the mammal a therapeutically effective amount of a nucleic acid-lipid particle (e.g., a SNALP formulation) comprising one or more interfering RNAs (e.g., siRNAs) described herein (e.g., one or more siRNAs targeting LASV gene expression). In some embodiments, administration of nucleic acid-lipid particles comprising one or more LASV-targeting interfering RNAs lowers, reduces, or decreases LASV viral load or titer by at least about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% (or any range therein) relative to the LASV viral load or titer detected in the absence of the interfering RNA (e.g., buffer control or irrelevant non-LASV targeting interfering RNA control). The LASV-targeting interfering RNAs may comprise at least one of the sequences set forth in Tables 2, 4-6, and 10 in unmodified and/or modified (e.g., 2'OMe-modified) form.

In related aspects, the present invention provides a method for inactivating an arenavirus or filovirus and/or inhibiting the replication of an arenavirus or filovirus in a mammal (e.g., human) in need thereof (e.g., a mammal with an arenavirus or filovirus infection), the method comprising administering to the mammal a therapeutically effective amount of a nucleic acid-lipid particle (e.g., a SNALP formulation) comprising one or more interfering RNAs (e.g., siRNAs) described herein (e.g., one or more siRNAs targeting TF gene expression). In some embodiments, administration of nucleic acid-lipid particles comprising one or more TF-targeting interfering RNAs lowers, reduces, or decreases arenaviral and/or filoviral load or titer by at least about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% (or any range therein) relative to the arenaviral and/or filoviral load or titer detected in the absence of the interfering RNA (e.g., buffer control or irrelevant non-TF targeting interfering RNA control). The TF-targeting interfering RNAs may comprise at least one of the sequences set forth in Tables 1, 3, and 7-9 in unmodified and/or modified (e.g., 2'OMe-modified) form.

In particular embodiments, the mammal has a disease or disorder associated with arenavirus or filovirus infection, e.g., hemorraghic fever. In other embodiments, silencing of viral or host sequences such as LASV or TF that encode genes associated with viral infection and/or survival can conveniently be used in combination with the administration of one or more conventional agents such as, e.g., anti-viral drugs, used to treat or ameliorate the viral condition or any of the symptoms associated therewith.

Examples of anti-viral drugs include, but are not limited to, abacavir, aciclovir, acyclovir, adefovir, amantadine, amprenavir, arbidol, atazanavir, atripla, cidofovir, combivir, darunavir, delavirdine, didanosine, docosanol, edoxudine, efavirenz, emtricitabine, enfuvirtide, entecavir, entry inhibitors, famciclovir, fixed dose combinations, fomivirsen, fosamprenavir, foscarnet, fosfonet, fusion inhibitors, ganciclovir, ibacitabine, immunovir, idoxuridine, imiquimod, indinavir, inosine, integrase inhibitors, interferon type III (e.g., IFN-λ molecules such as IFN-λ1, IFN-λ2, and IFN-λ3), interferon type II (e.g., IFN-γ), interferon type I (e.g., IFN-α such as PEGylated IFN-α, IFN-β, IFN-κ, IFN-δ, IFN-ε, IFN-τ, IFN-ω, and IFN-α), interferon, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, synergistic enhancers, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, zidovudine, pharmaceutically acceptable salts thereof, stereoisomers thereof, derivatives thereof, analogs thereof, and mixtures thereof.

As non-limiting examples, the dose of one or more nucleic acid-lipid particles can be administered about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, or 24 hours, or about 1, 2, 3, 4, 5, 6, 7, 8, 9, 10, 11, 12, 13, or 14 days, or about 1, 2, 3, 4, 5, 6, 7, 8, 9, or 10 weeks, or about 1, 2, 3, 4, 5, or 6 months, or any interval thereof, after viral (e.g., arenavirus or filovirus) infection. In one particular embodiment, more than one dose of nucleic acid-lipid particles containing one or more siRNAs targeting TF and/or LASV described herein can be administered at different times following viral infection. In certain instances, the infected mammal can be treated with a second, third, fourth, fifth, sixth, seventh, eighth, ninth, tenth, or more dose of the same or different nucleic acid-lipid particles containing one or more siRNAs targeting TF and/or LASV described herein. In another embodiment, the infected mammal can be treated with a daily dose of the same or different particles containing one or more siRNAs targeting TF and/or LASV described herein and assessed for a reduction in viremia and/or severity of clinical symptoms of viral infection. In some embodiments, a mammal susceptible to being infected with a virus such as an arenavirus or filovirus may be pretreated with one or more doses of nucleic acid-lipid particles containing one or more siRNAs targeting TF and/or LASV described herein as a prophylactic measure for preventing a viral infection.

In additional aspects, the present invention provides a method for preventing or treating a disease or disorder associated with TF expression or overexpression comprising administering to a mammal in need thereof an interfering RNA (e.g., siRNA) that silences TF gene expression (e.g., encapsulated in a nucleic acid-lipid particle such as SNALP). Besides hemorrhagic fever, non-limiting examples of other TF indications include pulmonary and bone metastasis, extravascular inflammation such as that involved in rheumatoid arthritis, endotoxemia and sepsis leading to disseminated intravascular coagulation (DIC), colitis, endometriosis, and the like.

In some embodiments, the present invention provides a method for preventing or treating pulmonary and bone metastasis. As described in Politano et al., *Cancer Growth and Metastasis,* 3:21-33 (2010), TF expression on the cell surface of tumor cells results in thrombin generation. This may cause endothelial cell activation, platelet aggregation, and fibrin deposition on the cancer cell surface, which could serve to protect cancer cells from host defense mechanisms such as natural killer (NK) cells. Rak et al., *Semin. Thromb. Hemost.,* 32:054-070 (2006) describes TF as a pivotal element of the tumor-vascular interface and as being involved in many cancer-related processes including hypercoaguability (Trousseau syndrome), tumor growth, angiogenesis, and metastasis, and thus is a promising target for anticancer combination therapies. The disclosures of these documents are herein incorporated by reference in their entirety for all purposes.

In other embodiments, the present invention provides a method for preventing or treating an extravascular inflammation. As described in Busso et al., *Arthritis Res. & Ther.,* 10:R42 (2008), the disclosure of which is herein incorporated by reference in its entirety for all purposes, soluble TF (sTF) can induce inflammatory arthritis when injected into joints, and TF-dependent coagulation was linked to extravascular inflammation as sTF injected into the mouse footpad was an inflammatory stimulus dependent on platelet protease activated receptor 4 (PAR-4) and fibrin. In some instances, the extravascular inflammation is involved in or associated with rheumatoid arthritis (RA).

In yet other embodiments, the present invention provides a method for preventing or treating endotoxemia, which can lead to sepsis or septic shock. As described in Pawlinski et al., *Blood,* 116:806-14 (2010), the disclosure of which is herein incorporated by reference in its entirety for all purposes, TF expression resulted in disseminated intravascular coagulation (DIC) during endotoxemia, but inhibition of TF on either hematopoietic or nonhematopoietic cells reduced plasma thrombin-antithrombin (TAT) levels after administration of bacterial lipopolysaccharide (LPS), thereby reducing activation of the coagulation cascade.

In further embodiments, the present invention provides a method for preventing or treating an inflammatory bowel disease such as colitis. As described in Anthoni et al., *J. Exper. Medicine,* 204:1595-1601 (2007), the disclosure of which is herein incorporated by reference in its entirety for all purposes, TF is a mediator of inflammatory cell recruitment, tissue injury, and thrombus formation in experimental colitis.

In additional embodiments, the present invention provides a method for preventing or treating endometriosis. As described in Krikun et al., *Annals of the New York Academy of Sciences,* 1127:101-105 (2008), the disclosure of which is herein incorporated by reference in its entirety for all purposes, the pattern and level of TF expression was altered in multiple cell types derived from eutopic and ectopic endometrium from women with endometriosis when compared with normal endometrium, implicating TF as a target for therapeutic intervention in endometriosis.

IV. Therapeutic Nucleic Acids

The term "nucleic acid" includes any oligonucleotide or polynucleotide, with fragments containing up to 60 nucleotides generally termed oligonucleotides, and longer fragments termed polynucleotides. In particular embodiments, oligonucleotides of the invention are from about 15 to about 60 nucleotides in length. In some embodiments, nucleic acid is associated with a carrier system such as the lipid particles described herein. In certain embodiments, the nucleic acid is fully encapsulated in the lipid particle. Nucleic acid may be administered alone in the lipid particles of the invention, or in combination (e.g., co-administered) with lipid particles comprising peptides, polypeptides, or small molecules such as conventional drugs.

In the context of this invention, the terms "polynucleotide" and "oligonucleotide" refer to a polymer or oligomer of nucleotide or nucleoside monomers consisting of naturally-occurring bases, sugars and intersugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Oligonucleotides are generally classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose.

The nucleic acid according to this invention includes any form of nucleic acid that is known. The nucleic acids used herein can be single-stranded DNA or RNA, or double-stranded DNA or RNA, or DNA-RNA hybrids. Examples of double-stranded DNA are described herein and include, e.g., structural genes, genes including control and termination regions, and self-replicating systems such as viral or plasmid DNA. Examples of double-stranded RNA are described herein and include, e.g., siRNA and other RNAi agents such as Dicer-substrate dsRNA, shRNA, aiRNA, and pre-miRNA. Single-stranded nucleic acids include, e.g., antisense oligonucleotides, ribozymes, mature miRNA, and triplex-forming oligonucleotides. In further embodiments, the nucleic acids are double-stranded DNA. Examples of double-stranded DNA include, e.g., DNA-DNA hybrids comprising a DNA sense strand and a DNA antisense strand as described in PCT Publication No. WO 2004/104199, the disclosure of which is herein incorporated by reference in its entirety for all purposes.

Nucleic acids of the invention may be of various lengths, generally dependent upon the particular form of nucleic acid. For example, in particular embodiments, plasmids or genes may be from about 1,000 to about 100,000 nucleotide residues in length. In particular embodiments, oligonucleotides may range from about 10 to about 100 nucleotides in length. In various related embodiments, oligonucleotides, both single-stranded, double-stranded, and triple-stranded, may range in length from about 10 to about 60 nucleotides, from about 15 to about 60 nucleotides, from about 20 to about 50 nucleotides, from about 15 to about 30 nucleotides, or from about 20 to about 30 nucleotides in length.

In particular embodiments, an oligonucleotide (or a strand thereof) of the invention specifically hybridizes to or is complementary to a target polynucleotide sequence. The terms "specifically hybridizable" and "complementary" as used herein indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. In preferred embodiments, an oligonucleotide is specifically hybridizable when binding of the oligonucleotide to the target sequence interferes with the normal function of the target sequence to cause a loss of utility or expression therefrom, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, the oligonucleotide may include 1, 2, 3, or more base substitutions as compared to the region of a gene or mRNA sequence that it is targeting or to which it specifically hybridizes.

A. siRNA

The unmodified and modified siRNA molecules of the invention are capable of silencing LASV (e.g., NP, GP, L, and/or Z) or TF gene expression. Each strand of the siRNA duplex is typically about 15 to about 60 nucleotides in length, preferably about 15 to about 30 nucleotides in length. In certain embodiments, the siRNA comprises at least one modified nucleotide. The modified siRNA is generally less immunostimulatory than a corresponding unmodified siRNA sequence and retains RNAi activity against the target gene of interest. In some embodiments, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide. The modified nucleotides can be present in one strand (i.e., sense or antisense) or both strands of the siRNA. In some preferred embodiments, one or more of the uridine and/or guanosine nucleotides are modified (e.g., 2'OMe-modified) in one strand (i.e., sense or antisense) or both strands of the siRNA. In these embodiments, the modified siRNA can further comprise one or more modified (e.g., 2'OMe-modified) adenosine and/or modified (e.g., 2'OMe-modified) cytosine nucleotides. In other preferred embodiments, only uridine and/or guanosine nucleotides are modified (e.g., 2'OMe-modified) in one strand (i.e., sense or antisense) or both strands of the siRNA. In certain embodiments, 2'OMe-modified nucleotides such as 2'OMe-guanosine nucleotides and/or 2'OMe-uridine nucleotides are the only modified nucleotides present in the double-stranded region of the siRNA. The siRNA sequences may have overhangs (e.g., 3' or 5' overhangs as described in Elbashir et al., *Genes Dev.,* 15:188 (2001) or Nykanen et al., *Cell,* 107:309 (2001)), or may lack overhangs (i.e., have blunt ends).

In particular embodiments, the selective incorporation of modified nucleotides such as 2'OMe uridine and/or guanosine nucleotides into the double-stranded region of either or both strands of the siRNA reduces or completely abrogates the immune response to that siRNA molecule. In certain instances, the immunostimulatory properties of specific siRNA sequences and their ability to silence gene expression can be balanced or optimized by the introduction of minimal and selective 2'OMe modifications within the double-stranded region of the siRNA duplex. This can be achieved at therapeutically viable siRNA doses without cytokine induction, toxicity, and off-target effects associated with the use of unmodified siRNA.

The modified siRNA generally comprises from about 1% to about 100% (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%) modified nucleotides in the double-stranded region of the siRNA duplex. In certain embodiments, one, two, three, four, five, six, seven, eight, nine, ten, or more of the nucleotides in the double-stranded region of the siRNA comprise modified nucleotides. In certain other embodiments, some or all of the modified nucleotides in the double-stranded region of the siRNA are 1, 2, 3, 4, 5, 6, 7, 8, 9, 10, or more nucleotides apart from each other. In one preferred embodiment, none of the modified nucleotides in the double-stranded region of the siRNA are adjacent to each other (e.g., there is a gap of at least 1, 2, 3, 4, 5, 6, 7, 8, 9, or 10 unmodified nucleotides between each modified nucleotide).

In some embodiments, less than about 50% (e.g., less than about 49%, 48%, 47%, 46%, 45%, 44%, 43%, 42%, 41%, 40%, 39%, 38%, 37%, or 36%, preferably less than about 35%, 34%, 33%, 32%, 31%, or 30%) of the nucleotides in the double-stranded region of the siRNA comprise modified (e.g., 2'OMe) nucleotides. In one aspect of these embodiments, less than about 50% of the uridine and/or guanosine nucleotides in the double-stranded region of one or both strands of the siRNA are selectively (e.g., only) modified. In another aspect of these embodiments, less than about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein 2'OMe-guanosine nucleotides and 2'OMe-uridine nucleotides are the only 2'OMe nucleotides present in the double-stranded region. In yet another aspect of these embodiments, less than about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the siRNA does not comprise 2'OMe-cytosine nucleotides in the double-stranded region. In a further aspect of these embodiments, less than about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein the siRNA does not comprise 2'OMe-cytosine nucleotides in the double-stranded region. In another aspect of these embodiments, less than about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the 2'OMe nucleotides in the double-stranded region are not adjacent to each other.

In other embodiments, from about 1% to about 50% (e.g., from about 5%-50%, 10%-50%, 15%-50%, 20%-50%, 25%-50%, 30%-50%, 35%-50%, 40%-50%, 45%-50%, 5%-45%, 10%-45%, 15%-45%, 20%-45%, 25%-45%, 30%-45%, 35%-45%, 40%-45%, 5%-40%, 10%-40%, 15%-40%, 20%-40%, 25%-40%, 25%-39%, 25%-38%, 25%-37%, 25%-36%, 26%-39%, 26%-38%, 26%-37%, 26%-36%, 27%-39%, 27%-38%, 27%-37%, 27%-36%, 28%-39%, 28%-38%, 28%-37%, 28%-36%, 29%-39%, 29%-38%, 29%-37%, 29%-36%, 30%-40%, 30%-39%, 30%-38%, 30%-37%, 30%-36%, 31%-39%, 31%-38%, 31%-37%, 31%-36%, 32%-39%, 32%-38%, 32%-37%, 32%-36%, 33%-39%, 33%-38%, 33%-37%, 33%-36%, 34%-39%, 34%-38%, 34%-37%, 34%-36%, 35%-40%, 5%-35%, 10%-35%, 15%-35%, 20%-35%, 21%-35%, 22%-35%, 23%-35%, 24%-35%, 25%-35%, 26%-35%, 27%-35%, 28%-35%, 29%-35%, 30%-35%, 31%-35%, 32%-35%, 33%-35%, 34%-35%, 30%-34%, 31%-34%, 32%-34%, 33%-34%, 30%-33%, 31%-33%, 32%-33%, 30%-32%, 31%-32%, 25%-34%, 25%-33%, 25%-32%, 25%-31%, 26%-34%, 26%-33%, 26%-32%, 26%-31%, 27%-34%, 27%-33%, 27%-32%, 27%-31%, 28%-34%, 28%-33%, 28%-32%, 28%-31%, 29%-34%, 29%-33%, 29%-32%, 29%-31%, 5%-30%, 10%-30%, 15%-30%, 20%-34%, 20%-33%, 20%-32%, 20%-31%, 20%-30%, 21%-30%, 22%-30%, 23%-30%, 24%-30%, 25%-30%, 25%-29%, 25%-28%, 25%-27%, 25%-26%, 26%-30%, 26%-29%, 26%-28%, 26%-27%, 27%-30%, 27%-29%, 27%-28%, 28%-30%, 28%-29%, 29%-30%, 5%-25%, 10%-25%, 15%-25%, 20%-29%, 20%-28%, 20%-27%, 20%-26%, 20%-25%, 5%-20%, 10%-20%, 15%-20%, 5%-15%, 10%-15%, or 5%-10%) of the nucleotides in the double-stranded region of the siRNA comprise modified nucleotides. In one aspect of these embodiments, from about 1% to about 50% of the uridine and/or guanosine nucleotides in the double-stranded region of one or both strands of the siRNA are selectively (e.g., only) modified. In another aspect of these embodiments, from about 1% to about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein 2'OMe-guanosine nucleotides and 2'OMe-uridine nucleotides are the only 2'OMe nucleotides present in the double-stranded region. In yet another aspect of these embodiments, from about 1% to about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the siRNA does not comprise 2'OMe-cytosine nucleotides in the double-stranded region. In a further aspect of these embodiments, from about 1% to about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein the siRNA does not comprise 2'OMe-cytosine nucleotides in the double-stranded region. In another aspect of these embodiments, from about 1% to about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the 2'OMe nucleotides in the double-stranded region are not adjacent to each other.

In certain embodiments, the siRNA molecules of the present invention comprise an asymmetric siRNA duplex as described in PCT Publication No. WO 2004/078941, which comprises a double-stranded region consisting of a DNA sense strand and an RNA antisense strand (e.g., a DNA-RNA hybrid), wherein a blocking agent is located on the siRNA duplex. In some instances, the asymmetric siRNA duplex can be chemically modified as described herein. Other non-limiting examples of asymmetric siRNA duplexes are described in PCT Publication No. WO 2006/074108, which discloses self-protected oligonucleotides comprising a region having a sequence complementary to one, two, three, or more same or different target mRNA sequences (e.g., multivalent siRNAs) and one or more self-complementary regions. Yet other non-limiting examples of asymmetric siRNA duplexes are described in PCT Publication No. WO 2009/076321, which discloses self-forming asymmetric precursor polynucleotides comprising a targeting region comprising a polynucleotide sequence complementary to a region of one, two, three, or more same or different target mRNA sequences (e.g., multivalent siRNAs); a first self-complementary region; and a second self-complementary region, wherein the first and second self-complementary regions are located one at each end of the targeting region and both self-complementary regions form stem-loop structures, wherein the first self-complementary region is capable of being cleaved by a RNase III endoribonuclease that is not a class IV DICER endoribonuclease, and wherein both self-complementary regions comprise a nucleotide sequence that is complementary to a region of the target gene sequence, but wherein a portion of the target sequence present in the targeting region does not have a complementary sequence in either of the self-complementary regions. The disclosures of each of the above patent documents are herein incorporated by reference in their entirety for all purposes.

Additional ranges, percentages, and patterns of modifications that may be introduced into siRNA are described in U.S. Patent Publication No. 20070135372, the disclosure of which is herein incorporated by reference in its entirety for all purposes.

1. Selection of siRNA Sequences

Suitable siRNA sequences can be identified using any means known in the art. Typically, the methods described in Elbashir et al., *Nature*, 411:494-498 (2001) and Elbashir et al., *EMBO J.*, 20:6877-6888 (2001) are combined with rational design rules set forth in Reynolds et al., *Nature Biotech.*, 22(3):326-330 (2004).

As a non-limiting example, the nucleotide sequence 3' of the AUG start codon of a transcript from the target gene of interest may be scanned for dinucleotide sequences (e.g., AA, NA, CC, GG, or UU, wherein N=C, G, or U) (see, e.g., Elbashir et al., *EMBO J.*, 20:6877-6888 (2001)). The nucleotides immediately 3' to the dinucleotide sequences are identified as potential siRNA sequences (i.e., a target sequence or a sense strand sequence). Typically, the 19, 21, 23, 25, 27, 29, 31, 33, 35, or more nucleotides immediately 3' to the dinucleotide sequences are identified as potential siRNA sequences. In some embodiments, the dinucleotide sequence is an AA or NA sequence and the 19 nucleotides immediately 3' to the AA or NA dinucleotide are identified as potential siRNA sequences. siRNA sequences are usually spaced at different positions along the length of the target gene. To further enhance silencing efficiency of the siRNA sequences, potential siRNA sequences may be analyzed to identify sites that do not contain regions of homology to other coding sequences, e.g., in the target cell or organism. For example, a suitable siRNA sequence of about 21 base pairs typically will not have more than 16-17 contiguous base pairs of homology to coding sequences in the target cell or organism. If the siRNA sequences are to be expressed from an RNA Pol III promoter, siRNA sequences lacking more than 4 contiguous A's or T's are selected.

Once a potential siRNA sequence has been identified, a complementary sequence (i.e., an antisense strand sequence) can be designed. A potential siRNA sequence can also be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., http://ihome.ust.hk/~bokcmho/siRNA/siRNA.html. One of skill in the art will appreciate that sequences with one or more of the foregoing characteristics may be selected for further analysis and testing as potential siRNA sequences.

Additionally, potential siRNA sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal fold-back structures. However, one of skill in the art will appreciate that sequences with one or more of the foregoing characteristics may still be selected for further analysis and testing as potential siRNA sequences.

In some embodiments, potential siRNA sequences may be further analyzed based on siRNA duplex asymmetry as described in, e.g., Khvorova et al., *Cell*, 115:209-216 (2003); and Schwarz et al., *Cell*, 115:199-208 (2003). In other embodiments, potential siRNA sequences may be further analyzed based on secondary structure at the target site as described in, e.g., Luo et al., *Biophys. Res. Commun.*, 318:303-310 (2004). For example, secondary structure at the target site can be modeled using the Mfold algorithm (available at http://mfold.burnet.edu.au/rna_form) to select siRNA sequences which favor accessibility at the target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs (e.g., 5'-GU-3',5'-UGU-3',5'-GUGU-3',5'-UGUGU-3', etc.) can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naïve mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-α, IFN-α, IFN-β, IFN-γ, IL-6, IL-8, IL-12, or a combination thereof. An siRNA molecule identified as being immunostimulatory can then be modified to decrease its immunostimulatory properties by replacing at least one of the nucleotides on the sense and/or antisense strand with modified nucleotides. For example, less than about 30% (e.g., less than about 30%, 25%, 20%, 15%, 10%, or 5%) of the nucleotides in the double-stranded region of the siRNA duplex can be replaced with modified nucleotides such as 2'OMe nucleotides. The modified siRNA can then be contacted with a mammalian responder cell as described above to confirm that its immunostimulatory properties have been reduced or abrogated.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., *Radio-immunoassay Methods*, E. and S. Livingstone, Edinburgh (1970)); the "Western blot" method of Gordon et al. (U.S. Pat. No. 4,452,901); immunoprecipitation of labeled ligand (Brown et al., *J. Biol. Chem.*, 255:4980-4983 (1980)); enzyme-linked immunosorbent assays (ELISA) as described, for example, by Raines et al., *J. Biol. Chem.*, 257:5154-5160 (1982); immunocytochemical techniques, including the use of fluorochromes (Brooks et al., *Clin. Exp. Immunol.*, 39:477 (1980)); and neutralization of activity (Bowen-Pope et al., *Proc. Natl. Acad. Sci. USA*, 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876. The disclosures of these references are herein incorporated by reference in their entirety for all purposes.

A non-limiting example of an in vivo model for detecting an immune response includes an in vivo mouse cytokine induction assay as described in, e.g., Judge et al., *Mol. Ther.*, 13:494-505 (2006). In certain embodiments, the assay that can be performed as follows: (1) siRNA can be administered by standard intravenous injection in the lateral tail vein; (2) blood can be collected by cardiac puncture about 6 hours after administration and processed as plasma for cytokine analysis; and (3) cytokines can be quantified using sandwich ELISA kits according to the manufacturer's instructions (e.g., mouse and human IFN-α (PBL Biomedical; Piscataway, N.J.); human IL-6 and TNF-α (eBioscience; San Diego, Calif.); and mouse IL-6, TNF-α, and IFN-γ (BD Biosciences; San Diego, Calif.)).

Monoclonal antibodies that specifically bind cytokines and growth factors are commercially available from multiple sources and can be generated using methods known in the art (see, e.g., Kohler et al., Nature, 256: 495-497 (1975) and Harlow and Lane, ANTIBODIES, A LABORATORY MANUAL, Cold Spring Harbor Publication, New York (1999)). Generation of monoclonal antibodies has been previously described and can be accomplished by any means known in the art (Buhring et al., in Hybridoma, Vol. 10, No. 1, pp. 77-78 (1991)). In some methods, the monoclonal antibody is labeled (e.g., with any composition detectable by spectroscopic, photochemical, biochemical, electrical, optical, or chemical means) to facilitate detection.

2. Generating siRNA Molecules siRNA can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. In some embodiments, siRNA may be produced enzymatically or by partial/total organic synthesis, and modified ribonucleotides can be introduced by in vitro enzymatic or organic synthesis. In certain instances, each strand is prepared chemically. Methods of synthesizing RNA molecules are known in the art, e.g., the chemical synthesis methods as described in Verma and Eckstein (1998) or as described herein.

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by E. coli RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Methods for isolating RNA, synthesizing RNA, hybridizing nucleic acids, making and screening cDNA libraries, and performing PCR are well known in the art (see, e.g., Gubler and Hoffman, Gene, 25:263-269 (1983); Sambrook et al., supra; Ausubel et al., supra), as are PCR methods (see, U.S. Pat. Nos. 4,683,195 and 4,683,202; PCR Protocols: A Guide to Methods and Applications (Innis et al., eds, 1990)). Expression libraries are also well known to those of skill in the art. Additional basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994). The disclosures of these references are herein incorporated by reference in their entirety for all purposes.

Preferably, siRNA are chemically synthesized. The oligonucleotides that comprise the siRNA molecules of the invention can be synthesized using any of a variety of techniques known in the art, such as those described in Usman et al., J. Am. Chem. Soc., 109:7845 (1987); Scaringe et al., Nucl. Acids Res., 18:5433 (1990); Wincott et al., Nucl. Acids Res., 23:2677-2684 (1995); and Wincott et al., Methods Mol. Bio., 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 µmol scale protocol. Alternatively, syntheses at the 0.2 µmol scale can be performed on a 96-well plate synthesizer from Protogene (Palo Alto, Calif.). However, a larger or smaller scale of synthesis is also within the scope of this invention. Suitable reagents for oligonucleotide synthesis, methods for RNA deprotection, and methods for RNA purification are known to those of skill in the art.

siRNA molecules can also be synthesized via a tandem synthesis technique, wherein both strands are synthesized as a single continuous oligonucleotide fragment or strand separated by a cleavable linker that is subsequently cleaved to provide separate fragments or strands that hybridize to form the siRNA duplex. The linker can be a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, siRNA molecules can be synthesized as a single continuous oligonucleotide fragment, where the self-complementary sense and antisense regions hybridize to form an siRNA duplex having hairpin secondary structure.

3. Modifying siRNA Sequences

In certain aspects, siRNA molecules comprise a duplex having two strands and at least one modified nucleotide in the double-stranded region, wherein each strand is about 15 to about 60 nucleotides in length. Advantageously, the modified siRNA is less immunostimulatory than a corresponding unmodified siRNA sequence, but retains the capability of silencing the expression of a target sequence. In preferred embodiments, the degree of chemical modifications introduced into the siRNA molecule strikes a balance between reduction or abrogation of the immunostimulatory properties of the siRNA and retention of RNAi activity. As a non-limiting example, an siRNA molecule that targets a gene of interest can be minimally modified (e.g., less than about 30%, 25%, 20%, 15%, 10%, or 5% modified) at selective uridine and/or guanosine nucleotides within the siRNA duplex to eliminate the immune response generated by the siRNA while retaining its capability to silence target gene expression.

Examples of modified nucleotides suitable for use in the invention include, but are not limited to, ribonucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a Northern conformation such as those described in, e.g., Saenger, Principles of Nucleic Acid Structure, Springer-Verlag Ed. (1984), are also suitable for use in siRNA molecules. Such modified nucleotides include, without limitation, locked nucleic acid (LNA) nucleotides (e.g., 2'-O, 4'-C-methylene-(D-ribofuranosyl)nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2'Cl) nucleotides, and 2'-azido nucleotides. In certain instances, the siRNA molecules described herein include one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., *J. Am. Chem. Soc.*, 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, *Nucl. Acids Res.*, 29:2437-2447 (2001)) can be incorporated into siRNA molecules.

In certain embodiments, siRNA molecules may further comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-(β-D-erythrofuranosyl)nucleotides, 4'-thio nucleotides, carbocyclic nucleotides, 1,5-anhydrohexitol nucleotides, L-nucleotides, α-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., *Tetrahedron* 49:1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., *Nucleic Acid Analogues: Synthesis and Properties*, in *Modern Synthetic Methods*, VCH, 331-417 (1995); Mesmaeker et al., *Novel Backbone Replacements for Oligonucleotides*, in *Carbohydrate Modifications in Antisense Research*, ACS, 24-39 (1994)). Such chemical modifications can occur at the 5'-end and/or 3'-end of the sense strand, antisense strand, or both strands of the siRNA. The disclosures of these references are herein incorporated by reference in their entirety for all purposes.

In some embodiments, the sense and/or antisense strand of the siRNA molecule can further comprise a 3'-terminal overhang having about 1 to about 4 (e.g., 1, 2, 3, or 4) 2'-deoxy ribonucleotides, modified (e.g., 2'OMe) and/or unmodified uridine ribonucleotides, and/or any other combination of modified (e.g., 2'OMe) and unmodified nucleotides.

Additional examples of modified nucleotides and types of chemical modifications that can be introduced into siRNA molecules are described, e.g., in UK Patent No. GB 2,397,818 B and U.S. Patent Publication Nos. 20040192626, 20050282188, and 20070135372, the disclosures of which are herein incorporated by reference in their entirety for all purposes.

The siRNA molecules described herein can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the siRNA molecule. The conjugate can be attached at the 5' and/or 3'-end of the sense and/or antisense strand of the siRNA via a covalent attachment such as, e.g., a biodegradable linker. The conjugate can also be attached to the siRNA, e.g., through a carbamate group or other linking group (see, e.g., U.S. Patent Publication Nos. 20050074771, 20050043219, and 20050158727). In certain instances, the conjugate is a molecule that facilitates the delivery of the siRNA into a cell. Examples of conjugate molecules suitable for attachment to siRNA include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-O-alkoxyalkyl amine, polyamine, CS-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the siRNA molecule can be evaluated for improved pharmacokinetic profiles, bioavailability, and/or stability of the siRNA while retaining RNAi activity. As such, one skilled in the art can screen siRNA molecules having various conjugates attached thereto to identify ones having improved properties and full RNAi activity using any of a variety of well-known in vitro cell culture or in vivo animal models. The disclosures of the above-described patent documents are herein incorporated by reference in their entirety for all purposes.

4. Exemplary siRNA Embodiments

In some embodiments, each strand of the siRNA molecule comprises from about 15 to about 60 nucleotides in length (e.g., about 15-60, 15-50, 15-40, 15-30, 15-25, or 19-25 nucleotides in length, or 15, 16, 17, 18, 19, 20, 21, 22, 23, 24, or 25 nucleotides in length). In one particular embodiment, the siRNA is chemically synthesized. The siRNA molecules of the invention are capable of silencing the expression of a target sequence in vitro and/or in vivo.

In other embodiments, the siRNA comprises at least one modified nucleotide. In certain embodiments, the siRNA comprises one, two, three, four, five, six, seven, eight, nine, ten, or more modified nucleotides in the double-stranded region. In particular embodiments, less than about 50% (e.g., less than about 50%, 45%, 40%, 35%, 30%, 25%, 20%, 15%, 10%, or 5%) of the nucleotides in the double-stranded region of the siRNA comprise modified nucleotides. In preferred embodiments, from about 1% to about 50% (e.g., from about 5%-50%, 10%-50%, 15%-50%, 20%-50%, 25%-50%, 30%-50%, 35%-50%, 40%-50%, 45%-50%, 5%-45%, 10%-45%, 15%-45%, 20%-45%, 25%-45%, 30%-45%, 35%-45%, 40%-45%, 5%-40%, 10%-40%, 15%-40%, 20%-40%, 25%-40%, 30%-40%, 35%-40%, 5%-35%, 10%-35%, 15%-35%, 20%-35%, 25%-35%, 30%-35%, 5%-30%, 10%-30%, 15%-30%, 20%-30%, 25%-30%, 5%-25%, 10%-25%, 15%-25%, 20%-25%, 5%-20%, 10%-20%, 15%-20%, 5%-15%, 10%-15%, or 5%-10%) of the nucleotides in the double-stranded region of the siRNA comprise modified nucleotides.

In further embodiments, the siRNA comprises modified nucleotides including, but not limited to, 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In preferred embodiments, the siRNA comprises 2'OMe nucleotides (e.g., 2'OMe purine and/or pyrimidine nucleotides) such as, e.g., 2'OMe-guanosine nucleotides, 2'OMe-uridine nucleotides, 2'OMe-adenosine nucleotides, 2'OMe-cytosine nucleotides, or mixtures thereof. In one particular embodiment, the siRNA comprises at least one 2'OMe-guanosine nucleotide, 2'OMe-uridine nucleotide, or mixtures thereof. In certain instances, the siRNA does not comprise 2'OMe-cytosine nucleotides. In other embodiments, the siRNA comprises a hairpin loop structure.

In certain embodiments, the siRNA comprises modified nucleotides in one strand (i.e., sense or antisense) or both strands of the double-stranded region of the siRNA molecule. Preferably, uridine and/or guanosine nucleotides are modified at selective positions in the double-stranded region of the siRNA duplex. With regard to uridine nucleotide modifications, at least one, two, three, four, five, six, or more of the uridine nucleotides in the sense and/or antisense strand can be a modified uridine nucleotide such as a 2'OMe-uridine nucleotide. In some embodiments, every uridine nucleotide in the sense and/or antisense strand is a 2'OMe-uridine nucleotide. With regard to guanosine nucleotide modifications, at least one, two, three, four, five, six, or more of the guanosine nucleotides in the sense and/or antisense strand can be a modified guanosine nucleotide such as a 2'OMe-guanosine nucleotide. In some embodiments, every guanosine nucleotide in the sense and/or antisense strand is a 2'OMe-guanosine nucleotide.

In certain embodiments, at least one, two, three, four, five, six, seven, or more 5'-GU-3' motifs in an siRNA sequence may be modified, e.g., by introducing mismatches to eliminate the 5'-GU-3' motifs and/or by introducing modified nucleotides such as 2'OMe nucleotides. The 5'-GU-3' motif can be in the sense strand, the antisense strand, or both strands of the siRNA sequence. The 5'-GU-3' motifs may be adjacent to each other or, alternatively, they may be separated by 1, 2, 3, 4, 5, 6, 7, 8, 9, 10, 11, 12, or more nucleotides.

In some embodiments, a modified siRNA molecule is less immunostimulatory than a corresponding unmodified siRNA sequence. In such embodiments, the modified siRNA molecule with reduced immunostimulatory properties advantageously retains RNAi activity against the target sequence. In another embodiment, the immunostimulatory properties of the modified siRNA molecule and its ability to silence target gene expression can be balanced or optimized by the introduction of minimal and selective 2'OMe modifications within the siRNA sequence such as, e.g., within the double-stranded region of the siRNA duplex. In certain instances, the modified siRNA is at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% less immunostimulatory than the corresponding unmodified siRNA. It will be readily apparent to those of skill in the art that the immunostimulatory properties of the modified siRNA molecule and the corresponding unmodified siRNA molecule can be determined by, for example, measuring INF-α and/or IL-6 levels from about two to about twelve hours after systemic administration in a mammal or transfection of a mammalian responder cell using an appropriate lipid-based delivery system (such as the SNALP delivery system disclosed herein).

In other embodiments, a modified siRNA molecule has an $IC_{50}$ (i.e., half-maximal inhibitory concentration) less than or equal to ten-fold that of the corresponding unmodified siRNA (i.e., the modified siRNA has an $IC_{50}$ that is less than or equal to ten-times the $IC_{50}$ of the corresponding unmodified siRNA). In other embodiments, the modified siRNA has an $IC_{50}$ less than or equal to three-fold that of the corresponding unmodified siRNA sequence. In yet other embodiments, the modified siRNA has an $IC_{50}$ less than or equal to two-fold that of the corresponding unmodified siRNA. It will be readily apparent to those of skill in the art that a dose-response curve can be generated and the $IC_{50}$ values for the modified siRNA and the corresponding unmodified siRNA can be readily determined using methods known to those of skill in the art.

In another embodiment, an unmodified or modified siRNA molecule is capable of silencing at least about 5%, 10%, 15%, 20%, 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the expression of the target sequence relative to a negative control (e.g., buffer only, an siRNA sequence that targets a different gene, a scrambled siRNA sequence, etc.).

In yet another embodiment, a modified siRNA molecule is capable of silencing at least about 5%, 10%, 15%, 20%, 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the expression of the target sequence relative to the corresponding unmodified siRNA sequence.

In some embodiments, the siRNA molecule does not comprise phosphate backbone modifications, e.g., in the sense and/or antisense strand of the double-stranded region. In other embodiments, the siRNA comprises one, two, three, four, or more phosphate backbone modifications, e.g., in the sense and/or antisense strand of the double-stranded region. In preferred embodiments, the siRNA does not comprise phosphate backbone modifications.

In further embodiments, the siRNA does not comprise 2'-deoxy nucleotides, e.g., in the sense and/or antisense strand of the double-stranded region. In yet further embodiments, the siRNA comprises one, two, three, four, or more 2'-deoxy nucleotides, e.g., in the sense and/or antisense strand of the double-stranded region. In preferred embodiments, the siRNA does not comprise 2'-deoxy nucleotides.

In certain instances, the nucleotide at the 3'-end of the double-stranded region in the sense and/or antisense strand is not a modified nucleotide. In certain other instances, the nucleotides near the 3'-end (e.g., within one, two, three, or four nucleotides of the 3'-end) of the double-stranded region in the sense and/or antisense strand are not modified nucleotides.

The siRNA molecules described herein may have 3' overhangs of one, two, three, four, or more nucleotides on one or both sides of the double-stranded region, or may lack overhangs (i.e., have blunt ends) on one or both sides of the double-stranded region. In certain embodiments, the 3' overhang on the sense and/or antisense strand independently comprises one, two, three, four, or more modified nucleotides such as 2'OMe nucleotides and/or any other modified nucleotide described herein or known in the art.

In particular embodiments, siRNAs targeting LASV RNA or TF mRNA are administered using a carrier system such as a nucleic acid-lipid particle. In a preferred embodiment, the nucleic acid-lipid particle comprises: (a) one or more siRNA molecules targeting LASV or TF gene expression; (b) a cationic lipid of Formula I-XXII or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA and/or POZ-DAA).

In addition to its utility in silencing the expression of any of the above-described LASV and TF genes for therapeutic purposes, the siRNA described herein are also useful in research and development applications as well as diagnostic, prophylactic, prognostic, clinical, and other healthcare applications. As a non-limiting example, the siRNA can be used in target validation studies directed at testing whether a gene of interest has the potential to be a therapeutic target. The siRNA can also be used in target identification studies aimed at discovering genes as potential therapeutic targets.

B. Dicer-Substrate dsRNA

As used herein, the term "Dicer-substrate dsRNA" or "precursor RNAi molecule" is intended to include any precursor molecule that is processed in vivo by Dicer to produce an active siRNA which is incorporated into the RISC complex for RNA interference of a target gene.

In one embodiment, the Dicer-substrate dsRNA has a length sufficient such that it is processed by Dicer to produce an siRNA. According to this embodiment, the Dicer-substrate dsRNA comprises (i) a first oligonucleotide sequence (also termed the sense strand) that is between about 25 and about 60 nucleotides in length (e.g., about 25-60, 25-55, 25-50, 25-45, 25-40, 25-35, or 25-30 nucleotides in length), preferably between about 25 and about 30 nucleotides in length (e.g., 25, 26, 27, 28, 29, or 30 nucleotides in length), and (ii) a second oligonucleotide sequence (also termed the antisense strand) that anneals to the first sequence under biological conditions, such as the conditions found in the cytoplasm of a cell. The second oligonucleotide sequence may be between about 25 and about 60 nucleotides in length (e.g., about 25-60, 25-55, 25-50, 25-45, 25-40, 25-35, or 25-30 nucleotides in length), and is preferably between about 25 and about 30 nucleotides in length (e.g., 25, 26, 27, 28, 29, or 30 nucleotides in length). In addition, a region of one of the sequences, particularly of the antisense strand, of the Dicer-substrate dsRNA has a sequence length of at least about 19 nucleotides, for example, from about 19 to about 60 nucleotides (e.g., about 19-60, 19-55, 19-50, 19-45, 19-40, 19-35, 19-30, or 19-25 nucleotides), preferably from about 19 to about 23 nucleotides (e.g., 19, 20, 21, 22, or 23 nucleotides) that are sufficiently complementary to a nucleotide sequence of the RNA produced from the target gene to trigger an RNAi response.

In a second embodiment, the Dicer-substrate dsRNA has several properties which enhance its processing by Dicer. According to this embodiment, the dsRNA has a length sufficient such that it is processed by Dicer to produce an siRNA and has at least one of the following properties: (i) the dsRNA is asymmetric, e.g., has a 3'-overhang on the antisense strand; and/or (ii) the dsRNA has a modified 3'-end on the sense strand to direct orientation of Dicer binding and processing of the dsRNA to an active siRNA. According to this latter embodiment, the sense strand comprises from about 22 to about 28 nucleotides and the antisense strand comprises from about 24 to about 30 nucleotides.

In one embodiment, the Dicer-substrate dsRNA has an overhang on the 3'-end of the antisense strand. In another embodiment, the sense strand is modified for Dicer binding and processing by suitable modifiers located at the 3'-end of the sense strand. Suitable modifiers include nucleotides such as deoxyribonucleotides, acyclonucleotides, and the like, and sterically hindered molecules such as fluorescent molecules and the like. When nucleotide modifiers are used, they replace ribonucleotides in the dsRNA such that the length of the dsRNA does not change. In another embodiment, the Dicer-substrate dsRNA has an overhang on the 3'-end of the antisense strand and the sense strand is modified for Dicer processing. In another embodiment, the 5'-end of the sense strand has a phosphate. In another embodiment, the 5'-end of the antisense strand has a phosphate. In another embodiment, the antisense strand or the sense strand or both strands have one or more 2'-O-methyl (2'OMe) modified nucleotides. In another embodiment, the antisense strand contains 2'OMe modified nucleotides. In another embodiment, the antisense stand contains a 3'-overhang that is comprised of 2'OMe modified nucleotides. The antisense strand could also include additional 2'OMe modified nucleotides. The sense and antisense strands anneal under biological conditions, such as the conditions found in the cytoplasm of a cell. In addition, a region of one of the sequences, particularly of the antisense strand, of the Dicer-substrate dsRNA has a sequence length of at least about 19 nucleotides, wherein these nucleotides are in the 21-nucleotide region adjacent to the 3'-end of the antisense strand and are sufficiently complementary to a nucleotide sequence of the RNA produced from the target gene. Further, in accordance with this embodiment, the Dicer-substrate dsRNA may also have one or more of the following additional properties: (a) the antisense strand has a right shift from the typical 21-mer (i.e., the antisense strand includes nucleotides on the right side of the molecule when compared to the typical 21-mer); (b) the strands may not be completely complementary, i.e., the strands may contain simple mismatch pairings; and (c) base modifications such as locked nucleic acid(s) may be included in the 5'-end of the sense strand.

In a third embodiment, the sense strand comprises from about 25 to about 28 nucleotides (e.g., 25, 26, 27, or 28 nucleotides), wherein the 2 nucleotides on the 3'-end of the sense strand are deoxyribonucleotides. The sense strand contains a phosphate at the 5'-end. The antisense strand comprises from about 26 to about 30 nucleotides (e.g., 26, 27, 28, 29, or 30 nucleotides) and contains a 3'-overhang of 1-4 nucleotides. The nucleotides comprising the 3'-overhang are modified with 2'OMe modified ribonucleotides. The antisense strand contains alternating 2'OMe modified nucleotides beginning at the first monomer of the antisense strand adjacent to the 3'-overhang, and extending 15-19 nucleotides from the first monomer adjacent to the 3'-overhang. For example, for a 27-nucleotide antisense strand and counting the first base at the 5'-end of the antisense strand as position number 1, 2'OMe modifications would be placed at bases 9, 11, 13, 15, 17, 19, 21, 23, 25, 26, and 27. In one embodiment, the Dicer-substrate dsRNA has the following structure:

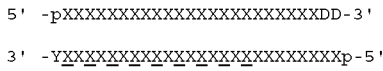

```
5'-pXXXXXXXXXXXXXXXXXXXXXXXXDD-3'

3'-YXXXXXXXXXXXXXXXXXXXXXXXXXXp-5'
``` wherein "X"=RNA, "p"=a phosphate group, "X"=2'OMe RNA, "Y" is an overhang domain comprised of 1, 2, 3, or 4 RNA monomers that are optionally 2'OMe RNA monomers, and "D"=DNA. The top strand is the sense strand, and the bottom strand is the antisense strand.

In a fourth embodiment, the Dicer-substrate dsRNA has several properties which enhance its processing by Dicer. According to this embodiment, the dsRNA has a length sufficient such that it is processed by Dicer to produce an siRNA and at least one of the following properties: (i) the dsRNA is asymmetric, e.g., has a 3'-overhang on the sense strand; and (ii) the dsRNA has a modified 3'-end on the antisense strand to direct orientation of Dicer binding and processing of the dsRNA to an active siRNA. According to this embodiment, the sense strand comprises from about 24 to about 30 nucleotides (e.g., 24, 25, 26, 27, 28, 29, or 30 nucleotides) and the antisense strand comprises from about 22 to about 28 nucleotides (e.g., 22, 23, 24, 25, 26, 27, or 28 nucleotides). In one embodiment, the Dicer-substrate dsRNA has an overhang on the 3'-end of the sense strand. In another embodiment, the antisense strand is modified for Dicer binding and processing by suitable modifiers located at the 3'-end of the antisense strand. Suitable modifiers include nucleotides such as deoxyribonucleotides, acyclonucleotides, and the like, and sterically hindered molecules such as fluorescent molecules and the like. When nucleotide modifiers are used, they replace ribonucleotides in the dsRNA such that the length of the dsRNA does not change. In another embodiment, the dsRNA has an overhang on the 3'-end of the sense strand and the antisense strand is modified for Dicer processing. In one embodiment, the antisense strand has a 5'-phosphate. The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are adjacent to the 3'-end of antisense strand and are sufficiently complementary to a nucleotide sequence of the RNA produced from the target gene. Further, in accordance with this embodiment, the Dicer-substrate dsRNA may also have one or more of the following additional properties: (a) the antisense strand has a left shift from the typical 21-mer (i.e., the antisense strand includes nucleotides on the left side of the molecule when compared to the typical 21-mer); and (b) the strands may not be completely complementary, i.e., the strands may contain simple mismatch pairings.

In a preferred embodiment, the Dicer-substrate dsRNA has an asymmetric structure, with the sense strand having a 25-base pair length, and the antisense strand having a 27-base pair length with a 2 base 3'-overhang. In certain instances, this dsRNA having an asymmetric structure further contains 2 deoxynucleotides at the 3'-end of the sense strand in place of two of the ribonucleotides. In certain other instances, this dsRNA having an asymmetric structure further contains 2'OMe modifications at positions 9, 11, 13, 15, 17, 19, 21, 23, and 25 of the antisense strand (wherein the first base at the 5'-end of the antisense strand is position 1). In certain additional instances, this dsRNA having an asymmetric structure further contains a 3'-overhang on the antisense strand comprising 1, 2, 3, or 4 2'OMe nucleotides (e.g., a 3'-overhang of 2'OMe nucleotides at positions 26 and 27 on the antisense strand).

In another embodiment, Dicer-substrate dsRNAs may be designed by first selecting an antisense strand siRNA sequence having a length of at least 19 nucleotides. In some instances, the antisense siRNA is modified to include about 5 to about 11 ribonucleotides on the 5'-end to provide a length of about 24 to about 30 nucleotides. When the antisense strand has a length of 21 nucleotides, 3-9, preferably 4-7, or more preferably 6 nucleotides may be added on the 5'-end. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has about 22 to about 28 nucleotides. The sense strand is substantially complementary with the antisense strand to anneal to the antisense strand under biological conditions. In one embodiment, the sense strand is synthesized to contain a modified 3'-end to direct Dicer processing of the antisense strand. In another embodiment, the antisense strand of the dsRNA has a 3'-overhang. In a further embodiment, the sense strand is synthesized to contain a modified 3'-end for Dicer binding and processing and the antisense strand of the dsRNA has a 3'-overhang.

In a related embodiment, the antisense siRNA may be modified to include about 1 to about 9 ribonucleotides on the 5'-end to provide a length of about 22 to about 28 nucleotides. When the antisense strand has a length of 21 nucleotides, 1-7, preferably 2-5, or more preferably 4 ribonucleotides may be added on the 3'-end. The added ribonucleotides may have any sequence. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has about 24 to about 30 nucleotides. The sense strand is substantially complementary with the antisense strand to anneal to the antisense strand under biological conditions. In one embodiment, the antisense strand is synthesized to contain a modified 3'-end to direct Dicer processing. In another embodiment, the sense strand of the dsRNA has a 3'-overhang. In a further embodiment, the antisense strand is synthesized to contain a modified 3'-end for Dicer binding and processing and the sense strand of the dsRNA has a 3'-overhang.

Suitable Dicer-substrate dsRNA sequences can be identified, synthesized, and modified using any means known in the art for designing, synthesizing, and modifying siRNA sequences. In certain embodiments, Dicer-substrate dsRNAs of the invention may silence LASV or TF gene expression. In particular embodiments, Dicer-substrate dsRNAs targeting LASV RNA or TF mRNA are administered using a carrier system such as a nucleic acid-lipid particle. In a preferred embodiment, the nucleic acid-lipid particle comprises: (a) one or more Dicer-substrate dsRNA molecules targeting LASV or TF gene expression; (b) a cationic lipid of Formula I-XXII or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA and/or POZ-DAA).

Additional embodiments related to the Dicer-substrate dsRNAs of the invention, as well as methods of designing and synthesizing such dsRNAs, are described in U.S. Patent Publication Nos. 20050244858, 20050277610, and 20070265220, and U.S. application Ser. No. 12/794,701, filed Jun. 4, 2010, the disclosures of which are herein incorporated by reference in their entirety for all purposes.

C. Small Hairpin RNA (shRNA)

A "small hairpin RNA" or "short hairpin RNA" or "shRNA" includes a short RNA sequence that makes a tight hairpin turn that can be used to silence gene expression via RNA interference. The shRNAs of the invention may be chemically synthesized or transcribed from a transcriptional cassette in a DNA plasmid. The shRNA hairpin structure is cleaved by the cellular machinery into siRNA, which is then bound to the RNA-induced silencing complex (RISC).

The shRNAs of the invention are typically about 15-60, 15-50, or 15-40 (duplex) nucleotides in length, more typically about 15-30, 15-25, or 19-25 (duplex) nucleotides in length, and are preferably about 20-24, 21-22, or 21-23 (duplex) nucleotides in length (e.g., each complementary sequence of the double-stranded shRNA is 15-60, 15-50, 15-40, 15-30, 15-25, or 19-25 nucleotides in length, preferably about 20-24, 21-22, or 21-23 nucleotides in length, and the double-stranded shRNA is about 15-60, 15-50, 15-40, 15-30, 15-25, or 19-25 base pairs in length, preferably about 18-22, 19-20, or 19-21 base pairs in length). shRNA duplexes may comprise 3' overhangs of about 1 to about 4 nucleotides or about 2 to about 3 nucleotides on the antisense strand and/or 5'-phosphate termini on the sense strand. In some embodiments, the shRNA comprises a sense strand and/or antisense strand sequence of from about 15 to about 60 nucleotides in length (e.g., about 15-60, 15-55, 15-50, 15-45, 15-40, 15-35, 15-30, or 15-25 nucleotides in length), preferably from about 19 to about 40 nucleotides in length (e.g., about 19-40, 19-35, 19-30, or 19-25 nucleotides in length), more preferably from about 19 to about 23 nucleotides in length (e.g., 19, 20, 21, 22, or 23 nucleotides in length).

Non-limiting examples of shRNA include a double-stranded polynucleotide molecule assembled from a single-stranded molecule, where the sense and antisense regions are linked by a nucleic acid-based or non-nucleic acid-based linker; and a double-stranded polynucleotide molecule with a hairpin secondary structure having self-complementary sense and antisense regions. In preferred embodiments, the sense and antisense strands of the shRNA are linked by a loop structure comprising from about 1 to about 25 nucleotides, from about 2 to about 20 nucleotides, from about 4 to about 15 nucleotides, from about 5 to about 12 nucleotides, or 1, 2, 3, 4, 5, 6, 7, 8, 9, 10, 11, 12, 13, 14, 15, 16, 17, 18, 19, 20, 21, 22, 23, 24, 25, or more nucleotides.

Additional shRNA sequences include, but are not limited to, asymmetric shRNA precursor polynucleotides such as those described in PCT Publication Nos. WO 2006/074108 and WO 2009/076321, the disclosures of which are herein incorporated by reference in their entirety for all purposes. For example, PCT Publication No. WO 2006/074108 discloses self-protected oligonucleotides comprising a region having a sequence complementary to one, two, three, or more same or different target mRNA sequences (e.g., multivalent shRNAs) and one or more self-complementary regions. Similarly, PCT Publication No. WO 2009/076321 discloses self-forming asymmetric precursor polynucleotides comprising a targeting region comprising a polynucleotide sequence complementary to a region of one, two, three, or more same or different target mRNA sequences (e.g., multivalent shRNAs); a first self-complementary region; and a second self-complementary region, wherein the first and second self-complementary regions are located one at each end of the targeting region and both self-complementary regions form stem-loop structures, wherein the first self-complementary region is capable of being cleaved by a RNase III endoribonuclease that is not a class IV DICER endoribonuclease, and wherein both self-complementary regions comprise a nucleotide sequence that is complementary to a region of the target gene sequence, but wherein a portion of the target sequence present in the targeting region does not have a complementary sequence in either of the self-complementary regions.

Suitable shRNA sequences can be identified, synthesized, and modified using any means known in the art for designing, synthesizing, and modifying siRNA sequences. In certain embodiments, shRNAs of the invention may silence LASV or TF gene expression. In particular embodiments, shRNAs targeting LASV RNA or TF mRNA are administered using a carrier system such as a nucleic acid-lipid particle. In a preferred embodiment, the nucleic acid-lipid particle comprises: (a) one or more shRNA molecules targeting LASV or TF gene expression; (b) a cationic lipid of Formula I-XXII or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA and/or POZ-DAA).

Additional embodiments related to the shRNAs of the invention, as well as methods of designing and synthesizing such shRNAs, are described in U.S. patent application Ser. No. 12/794,701, filed Jun. 4, 2010, the disclosure of which is herein incorporated by reference in its entirety for all purposes.

D. aiRNA

Like siRNA, asymmetrical interfering RNA (aiRNA) can recruit the RNA-induced silencing complex (RISC) and lead to effective silencing of a variety of genes in mammalian cells by mediating sequence-specific cleavage of the target sequence between nucleotide 10 and 11 relative to the 5' end of the antisense strand (Sun et al., *Nat. Biotech.,* 26:1379-1382 (2008)). Typically, an aiRNA molecule comprises a short RNA duplex having a sense strand and an antisense strand, wherein the duplex contains overhangs at the 3' and 5' ends of the antisense strand. The aiRNA is generally asymmetric because the sense strand is shorter on both ends when compared to the complementary antisense strand. In some aspects, aiRNA molecules may be designed, synthesized, and annealed under conditions similar to those used for siRNA molecules. As a non-limiting example, aiRNA sequences may be selected and generated using the methods described above for selecting siRNA sequences.

In another embodiment, aiRNA duplexes of various lengths (e.g., about 10-25, 12-20, 12-19, 12-18, 13-17, or 14-17 base pairs, more typically 12, 13, 14, 15, 16, 17, 18, 19, or base pairs) may be designed with overhangs at the 3' and 5' ends of the antisense strand to target an mRNA of interest. In certain instances, the sense strand of the aiRNA molecule is about 10-25, 12-20, 12-19, 12-18, 13-17, or 14-17 nucleotides in length, more typically 12, 13, 14, 15, 16, 17, 18, 19, or 20 nucleotides in length. In certain other instances, the antisense strand of the aiRNA molecule is about 15-60, 15-50, or 15-40 nucleotides in length, more typically about 15-30, 15-25, or 19-25 nucleotides in length, and is preferably about 20-24, 21-22, or 21-23 nucleotides in length.

In some embodiments, the 5' antisense overhang contains one, two, three, four, or more nontargeting nucleotides (e.g., "AA", "UU", "dTdT", etc.). In other embodiments, the 3' antisense overhang contains one, two, three, four, or more nontargeting nucleotides (e.g., "AA", "UU", "dTdT", etc.). In certain aspects, the aiRNA molecules described herein may comprise one or more modified nucleotides, e.g., in the double-stranded (duplex) region and/or in the antisense overhangs. As a non-limiting example, aiRNA sequences may comprise one or more of the modified nucleotides described above for siRNA sequences. In a preferred embodiment, the aiRNA molecule comprises 2'OMe nucleotides such as, for example, 2'OMe-guanosine nucleotides, 2'OMe-uridine nucleotides, or mixtures thereof.

In certain embodiments, aiRNA molecules may comprise an antisense strand which corresponds to the antisense strand of an siRNA molecule, e.g., one of the siRNA molecules described herein. In certain embodiments, aiRNAs of the invention may silence LASV or TF gene expression. In particular embodiments, aiRNAs targeting LASV RNA or TF mRNA are administered using a carrier system such as a nucleic acid-lipid particle. In a preferred embodiment, the nucleic acid-lipid particle comprises: (a) one or more aiRNA molecules targeting LASV or TF gene expression; (b) a cationic lipid of Formula I-XXII or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA and/or POZ-DAA).

Suitable aiRNA sequences can be identified, synthesized, and modified using any means known in the art for designing, synthesizing, and modifying siRNA sequences. Additional embodiments related to the aiRNA molecules of the invention are described in U.S. Patent Publication No. 20090291131 and PCT Publication No. WO 09/127,060, the disclosures of which are herein incorporated by reference in their entirety for all purposes.

E. miRNA

Generally, microRNAs (miRNA) are single-stranded RNA molecules of about 21-23 nucleotides in length which regulate gene expression. miRNAs are encoded by genes from whose DNA they are transcribed, but miRNAs are not translated into protein (non-coding RNA); instead, each primary transcript (a pri-miRNA) is processed into a short stem-loop structure called a pre-miRNA and finally into a functional mature miRNA. Mature miRNA molecules are either partially or completely complementary to one or more messenger RNA (mRNA) molecules, and their main function is to downregulate gene expression. The identification of miRNA molecules is described, e.g., in Lagos-Quintana et al., Science, 294:853-858; Lau et al., Science, 294:858-862; and Lee et al., Science, 294:862-864.

The genes encoding miRNA are much longer than the processed mature miRNA molecule. miRNA are first transcribed as primary transcripts or pri-miRNA with a cap and poly-A tail and processed to short, ~70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha (Denli et al., Nature, 432:231-235 (2004)). These pre-miRNA are then processed to mature miRNA in the cytoplasm by interaction with the endonuclease Dicer, which also initiates the formation of the RNA-induced silencing complex (RISC) (Bernstein et al., Nature, 409:363-366 (2001). Either the sense strand or antisense strand of DNA can function as templates to give rise to miRNA.

When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end (Preall et al., Curr. Biol., 16:530-535 (2006)). The remaining strand, known as the anti-guide or passenger strand, is degraded as a RISC complex substrate (Gregory et al., Cell, 123:631-640 (2005)). After integration into the active RISC complex, miRNAs base pair with their complementary mRNA molecules and induce target mRNA degradation and/or translational silencing.

Mammalian miRNA molecules are usually complementary to a site in the 3' UTR of the target mRNA sequence. In certain instances, the annealing of the miRNA to the target mRNA inhibits protein translation by blocking the protein translation machinery. In certain other instances, the annealing of the miRNA to the target mRNA facilitates the cleavage and degradation of the target mRNA through a process similar to RNA interference (RNAi). miRNA may also target methylation of genomic sites which correspond to targeted mRNA. Generally, miRNA function in association with a complement of proteins collectively termed the miRNP.

In certain aspects, the miRNA molecules described herein are about 15-100, 15-90, 15-80, 15-75, 15-70, 15-60, 15-50, or 15-40 nucleotides in length, more typically about 15-30, 15-25, or 19-25 nucleotides in length, and are preferably about 20-24, 21-22, or 21-23 nucleotides in length. In certain other aspects, miRNA molecules may comprise one or more modified nucleotides. As a non-limiting example, miRNA sequences may comprise one or more of the modified nucleotides described above for siRNA sequences. In a preferred embodiment, the miRNA molecule comprises 2'OMe nucleotides such as, for example, 2'OMe-guanosine nucleotides, 2'OMe-uridine nucleotides, or mixtures thereof.

In some embodiments, miRNA molecules may be used to silence LASV or TF gene expression. In particular embodiments, miRNAs targeting LASV RNA or TF mRNA are administered using a carrier system such as a nucleic acid-lipid particle. In a preferred embodiment, the nucleic acid-lipid particle comprises: (a) one or more miRNA molecules targeting LASV or TF gene expression; (b) a cationic lipid of Formula I-XXII or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA and/or POZ-DAA).

In other embodiments, one or more agents that block the activity of an miRNA targeting LASV RNA or TF mRNA are administered using a lipid particle of the invention (e.g., a nucleic acid-lipid particle). Examples of blocking agents include, but are not limited to, steric blocking oligonucleotides, locked nucleic acid oligonucleotides, and Morpholino oligonucleotides. Such blocking agents may bind directly to the miRNA or to the miRNA binding site on the target RNA.

Additional embodiments related to the miRNA molecules of the invention are described in U.S. Patent Publication No. 20090291131 and PCT Publication No. WO 09/127,060, the disclosures of which are herein incorporated by reference in their entirety for all purposes.

V. Carrier Systems Containing Therapeutic Nucleic Acids

In one aspect, the present invention provides carrier systems containing one or more therapeutic nucleic acids (e.g., interfering RNA such as dsRNA). In some embodiments, the carrier system is a lipid-based carrier system such as a lipid particle (e.g., SNALP), a cationic lipid or liposome nucleic acid complex (i.e., lipoplex), a liposome, a micelle, a virosome, or a mixture thereof. In other embodiments, the carrier system is a polymer-based carrier system such as a cationic polymer-nucleic acid complex (i.e., polyplex). In additional embodiments, the carrier system is a cyclodextrin-based carrier system such as a cyclodextrin polymer-nucleic acid complex. In further embodiments, the carrier system is a protein-based carrier system such as a cationic peptide-nucleic acid complex. Preferably, the carrier system is a lipid particle such as a SNALP. One skilled in the art will appreciate that the therapeutic nucleic acids of the present invention can also be delivered as a naked molecule.

A. Lipid Particles

In certain aspects, the present invention provides lipid particles comprising one or more therapeutic nucleic acids (e.g., interfering RNA such as siRNA) and one or more cationic (amino) lipids or salts thereof. In some embodiments, the lipid particles of the invention further comprise one or more non-cationic lipids. In other embodiments, the lipid particles further comprise one or more conjugated lipids capable of reducing or inhibiting particle aggregation.

Lipid particles include, but are not limited to, lipid vesicles such as liposomes. As used herein, a lipid vesicle includes a structure having lipid-containing membranes enclosing an aqueous interior. In particular embodiments, lipid vesicles comprising one or more of the cationic lipids described herein are used to encapsulate nucleic acids within the lipid vesicles. In other embodiments, lipid vesicles comprising one or more of the cationic lipids described herein are complexed with nucleic acids to form lipoplexes.

The lipid particles of the invention preferably comprise a therapeutic nucleic acid such as an interfering RNA (e.g., siRNA), a cationic lipid, a non-cationic lipid, and a conjugated lipid that inhibits aggregation of particles. In some embodiments, the therapeutic nucleic acid is fully encapsulated within the lipid portion of the lipid particle such that the therapeutic nucleic acid in the lipid particle is resistant in aqueous solution to enzymatic degradation, e.g., by a nuclease. In other embodiments, the lipid particles described herein are substantially non-toxic to mammals such as humans. The lipid particles of the invention typically have a mean diameter of from about 30 nm to about 150 nm, from about 40 nm to about 150 nm, from about 50 nm to about 150 nm, from about 60 nm to about 130 nm, from about 70 nm to about 110 nm, or from about 70 to about 90 nm. The lipid particles of the invention also typically have a lipid:nucleic acid ratio (mass/mass ratio) of from about 1:1 to about 100:1, from about 1:1 to about 50:1, from about 2:1 to about 25:1, from about 3:1 to about 20:1, from about 5:1 to about 15:1, or from about 5:1 to about 10:1.

In preferred embodiments, the lipid particles of the invention are serum-stable nucleic acid-lipid particles (SNALP) which comprise an interfering RNA (e.g., dsRNA such as siRNA, Dicer-substrate dsRNA, shRNA, aiRNA, and/or miRNA), a cationic lipid (e.g., one or more cationic lipids of Formula I-XXII or salts thereof as set forth herein), a non-cationic lipid (e.g., mixtures of one or more phospholipids and cholesterol), and a conjugated lipid that inhibits aggregation of the particles (e.g., one or more PEG-lipid conjugates). The SNALP may comprise at least 1, 2, 3, 4, 5, 6, 7, 8, 9, 10, or more unmodified and/or modified interfering RNA molecules (e.g., siRNA) that target one or more of the genes described herein and optionally target additional genes associated with viral infection and survival. Nucleic acid-lipid particles and their method of preparation are described in, e.g., U.S. Pat. Nos. 5,753,613; 5,785,992; 5,705,385; 5,976,567; 5,981,501; 6,110,745; and 6,320,017; and PCT Publication No. WO 96/40964, the disclosures of which are each herein incorporated by reference in their entirety for all purposes.

In the nucleic acid-lipid particles of the invention, the nucleic acid may be fully encapsulated within the lipid portion of the particle, thereby protecting the nucleic acid from nuclease degradation. In preferred embodiments, a SNALP comprising a nucleic acid such as an interfering RNA is fully encapsulated within the lipid portion of the particle, thereby protecting the nucleic acid from nuclease degradation. In certain instances, the nucleic acid in the SNALP is not substantially degraded after exposure of the particle to a nuclease at 37° C. for at least about 20, 30, 45, or 60 minutes. In certain other instances, the nucleic acid in the SNALP is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours. In other embodiments, the nucleic acid is complexed with the lipid portion of the particle. One of the benefits of the formulations of the present invention is that the nucleic acid-lipid particle compositions are substantially non-toxic to mammals such as humans.

The term "fully encapsulated" indicates that the nucleic acid in the nucleic acid-lipid particle is not significantly degraded after exposure to serum or a nuclease assay that would significantly degrade free DNA or RNA. In a fully encapsulated system, preferably less than about 25% of the nucleic acid in the particle is degraded in a treatment that would normally degrade 100% of free nucleic acid, more preferably less than about 10%, and most preferably less than about 5% of the nucleic acid in the particle is degraded. "Fully encapsulated" also indicates that the nucleic acid-lipid particles are serum-stable, that is, that they do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Specific dyes such as OliGreen® and RiboGreen® (Invitrogen Corp.; Carlsbad, Calif.) are available for the quantitative determination of plasmid DNA, single-stranded deoxyribonucleotides, and/or single- or double-stranded ribonucleotides. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_o-I)/I_o$, where I and $I_o$ refer to the fluorescence intensities before and after the addition of detergent (see, Wheeler et al., Gene Ther., 6:271-281 (1999)).

In other embodiments, the present invention provides a nucleic acid-lipid particle (e.g., SNALP) composition comprising a plurality of nucleic acid-lipid particles.

In some instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the nucleic acid encapsulated therein.

In other instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the input nucleic acid is encapsulated in the particles.

Depending on the intended use of the lipid particles of the invention, the proportions of the components can be varied and the delivery efficiency of a particular formulation can be measured using, e.g., an endosomal release parameter (ERP) assay.

In particular embodiments, the present invention provides a lipid particle (e.g., SNALP) composition comprising a plurality of lipid particles described herein and an antioxidant. In certain instances, the antioxidant in the lipid particle composition reduces, prevents, and/or inhibits the degradation of a cationic lipid (e.g., a polyunsaturated cationic lipid) present in the lipid particle. In instances wherein the active agent is a therapeutic nucleic acid such as an interfering RNA (e.g., siRNA), the antioxidant in the lipid particle composition reduces, prevents, and/or inhibits the degradation of the nucleic acid payload, e.g., by reducing, preventing, and/or inhibiting the oxidation of the cationic lipid, by reducing, preventing, and/or inhibiting the degradation of the nucleic acid payload, by reducing, preventing, and/or inhibiting the desulfurization of a phosphorothioate (PS)-modified nucleic acid payload, and/or by stabilizing both the lipid and nucleic acid components.

Examples of antioxidants include, but are not limited to, metal chelators (e.g., ethylenediaminetetraacetic acid (EDTA), citrate, and the like), primary antioxidants (e.g., vitamin E isomers such as α-tocopherol or a salt thereof, butylated hydroxyanisole (BHA), butylhydroxytoluene (BHT), tert-butylhydroquinone (TBHQ), and the like), secondary antioxidants (e.g., ascorbic acid, ascorbyl palmitate, cysteine, glutathione, α-lipoic acid, and the like), salts thereof, and mixtures thereof. If needed, the antioxidant is typically present in an amount sufficient to prevent, inhibit, and/or reduce the degradation of the cationic lipid and/or active agent present in the lipid particle. In particular embodiments, the antioxidant comprises EDTA or a salt thereof (e.g., from about 20 mM to about 100 mM), alone or in combination with a primary antioxidant such as α-tocopherol or a salt thereof (e.g., from about 0.02 mol % to about 0.5 mol %) and/or secondary antioxidant such as ascorbyl palmitate or a salt thereof (e.g., from about 0.02 mol % to about 5.0 mol %). An antioxidant such as EDTA may be included at any step or at multiple steps in the lipid particle formation process described in Section VI (e.g., prior to, during, and/or after lipid particle formation).

Additional embodiments related to methods of preventing the degradation of cationic lipids and/or active agents (e.g., therapeutic nucleic acids) present in lipid particles, compositions comprising lipid particles stabilized by these methods, methods of making these lipid particles, and methods of delivering and/or administering these lipid particles are described in PCT Application No. PCT/CA2010/001919, filed Dec. 1, 2010, the disclosure of which is herein incorporated by reference in its entirety for all purposes.

In one aspect, the lipid particles of the invention may include a targeting lipid. In some embodiments, the targeting lipid comprises a GalNAc moiety (i.e., an N-galactosamine moiety). As a non-limiting example, a targeting lipid comprising a GalNAc moiety can include those described in U.S. application Ser. No. 12/328,669, filed Dec. 4, 2008, the disclosure of which is herein incorporated by reference in its entirety for all purposes. A targeting lipid can also include any other lipid (e.g., targeting lipid) known in the art, for example, as described in U.S. application Ser. No. 12/328,669 or PCT Publication No. WO 2008/042973, the contents of each of which are incorporated herein by reference in their entirety for all purposes. In some embodiments, the targeting lipid includes a plurality of GalNAc moieties, e.g., two or three GalNAc moieties. In some embodiments, the targeting lipid contains a plurality, e.g., two or three N-acetylgalactosamine (GalNAc) moieties. In some embodiments, the lipid in the targeting lipid is 1,2-Di-O-hexadecyl-sn-glyceride (i.e., DSG). In some embodiments, the targeting lipid includes a PEG moiety (e.g., a PEG moiety having a molecular weight of at least about 500 Da, such as about 1000 Da, 1500 Da, 2000 Da or greater), for example, the targeting moiety is connected to the lipid via a PEG moiety. Examples of GalNAc targeting lipids include, but are not limited to, (GalNAc)$_3$-PEG-DSG, (GalNAc)$_3$-PEG-LCO, and mixtures thereof.

In some embodiments, the targeting lipid includes a folate moiety. For example, a targeting lipid comprising a folate moiety can include those described in U.S. application Ser. No. 12/328,669, the disclosure of which is herein incorporated by reference in its entirety for all purposes. Examples of folate targeting lipids include, but are not limited to, 1,2-distearoyl-sn-glycero-3-phosphoethanolamine-N-[folate (polyethylene glycol)-2000] (ammonium salt) (Folate-PEG-DSPE), Folate-PEG2000-DSG, Folate-PEG3400-DSG, and mixtures thereof.

In another aspect, the lipid particles of the invention may further comprise one or more apolipoproteins. As used herein, the term "apolipoprotein" or "lipoprotein" refers to apolipoproteins known to those of skill in the art and variants and fragments thereof and to apolipoprotein agonists, analogues, or fragments thereof described in, e.g., PCT Publication No. WO 2010/0088537, the disclosure of which is herein incorporated by reference in its entirety for all purposes. Suitable apolipoproteins include, but are not limited to, ApoA-I, ApoA-II, ApoA-IV, ApoA-V, and ApoE (e.g., ApoE2, ApoE3, etc.), and active polymorphic forms, isoforms, variants, and mutants as well as fragments or truncated forms thereof. Isolated ApoE and/or active fragments and polypeptide analogues thereof, including recombinantly produced forms thereof, are described in U.S. Pat. Nos. 5,672,685; 5,525,472; 5,473,039; 5,182,364; 5,177,189; 5,168,045; and 5,116,739, the disclosures of which are herein incorporated by reference in their entirety for all purposes.

1. Cationic Lipids

Any of a variety of cationic lipids or salts thereof may be used in the lipid particles of the present invention (e.g., SNALP), either alone or in combination with one or more other cationic lipid species or non-cationic lipid species. In particular embodiments, one or more of the cationic lipids of Formula I-XXII or salts thereof as set forth herein may be used in the lipid particles of the present invention (e.g., SNALP), either alone or in combination with one or more other cationic lipid species or non-cationic lipid species. The cationic lipids include the (R) and/or (S) enantiomers thereof.

In some embodiments, the cationic lipid comprises a racemic mixture. In other embodiments, the cationic lipid comprises a mixture of one or more diastereomers. In certain embodiments, the cationic lipid is enriched in one enantiomer, such that the cationic lipid comprises at least about 55%, 60%, 65%, 70%, 75%, 80%, 85%, 90%, or 95% enantiomeric excess. In certain other embodiments, the cationic lipid is enriched in one diastereomer, such that the cationic lipid comprises at least about 55%, 60%, 65%, 70%, 75%, 80%, 85%, 90%, or 95% diastereomeric excess. In certain additional embodiments, the cationic lipid is chirally pure (e.g., comprises a single optical isomer). In further embodiments, the cationic lipid is enriched in one optical isomer (e.g., an optically active isomer), such that the cationic lipid comprises at least about 55%, 60%, 65%, 70%, 75%, 80%, 85%, 90%, or 95% isomeric excess. The present invention provides the synthesis of the cationic lipids of Formulas I-XXII as a racemic mixture or in optically pure form.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, the $C_{3-8}$ cycloalkyls described herein, while unsaturated cyclic alkyls include, without limitation, the $C_{3-8}$ cycloalkenyls described herein.

The term "heteroalkyl," includes a straight chain or branched, noncyclic or cyclic, saturated aliphatic hydrocarbon as defined above having from about 1 to about 5 heteroatoms (i.e., 1, 2, 3, 4, or 5 heteroatoms) such as, for example, O, N, Si, and/or S, wherein the nitrogen and sulfur atoms may optionally be oxidized and the nitrogen heteroatom may optionally be quaternized. The heteroalkyl group can be attached to the remainder of the molecule through a carbon atom or a heteroatom.

The term "cyclic alkyl" includes any of the substituted or unsubstituted cycloalkyl, heterocycloalkyl, cycloalkenyl, and heterocycloalkenyl groups described below.

The term "cycloalkyl" includes a substituted or unsubstituted cyclic alkyl group having from about 3 to about 8 carbon atoms (i.e., 3, 4, 5, 6, 7, or 8 carbon atoms) as ring vertices. Preferred cycloalkyl groups include those having from about 3 to about 6 carbon atoms as ring vertices. Examples of $C_{3-8}$ cycloalkyl groups include, but are not limited to, cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl, and cyclooctyl, as well as other substituted $C_{3-8}$ cycloalkyl groups.

The term "heterocycloalkyl" includes a substituted or unsubstituted cyclic alkyl group as defined above having from about 1 to about 3 heteroatoms as ring members selected from the group consisting of O, N, Si and S, wherein the nitrogen and sulfur atoms may optionally be oxidized and the nitrogen heteroatom may optionally be quaternized. The heterocycloalkyl group can be attached to the remainder of the molecule through a carbon atom or a heteroatom.

The term "cycloalkenyl" includes a substituted or unsubstituted cyclic alkenyl group having from about 3 to about 8 carbon atoms (i.e., 3, 4, 5, 6, 7, or 8 carbon atoms) as ring vertices. Preferred cycloalkenyl groups are those having from about 3 to about 6 carbon atoms as ring vertices. Examples of $C_{3-8}$ cycloalkenyl groups include, but are not limited to, cyclopropenyl, methyl-cyclopropenyl, dimethyl-cyclopropenyl, cyclobutenyl, cyclopentenyl, cyclohexenyl, cycloheptenyl, and cyclooctenyl, as well as other substituted $C_{3-8}$ cycloalkenyl groups.

The term "heterocycloalkenyl" includes a substituted or unsubstituted cyclic alkenyl group as defined above having from about 1 to about 3 heteroatoms as ring members selected from the group consisting of O, N, Si and S, wherein the nitrogen and sulfur atoms may optionally be oxidized and the nitrogen heteroatom may optionally be quaternized. The heterocycloalkenyl group can be attached to the remainder of the molecule through a carbon atom or a heteroatom.

The term "alkoxy" includes a group of the formula alkyl-O—, wherein "alkyl" has the previously given definition. Non-limiting examples of alkoxy groups include methoxy, ethoxy, n-propoxy, iso-propoxy, n-butoxy, iso-butoxy, sec-butoxy and tert-butoxy.

The term "alkenyl" includes an alkyl, as defined above, containing at least one double bond between adjacent carbon atoms. Alkenyls include both cis and trans isomers. Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like. Representative cyclic alkenyls are described above.

The term "alkynyl" includes any alkyl or alkenyl, as defined above, which additionally contains at least one triple bond between adjacent carbons. Representative straight chain and branched alkynyls include, without limitation, acetylenyl, propynyl, 1-butynyl, 2-butynyl, 1-pentynyl, 2-pentynyl, 3-methyl-1 butynyl, and the like.

The term "aryl" includes a polyunsaturated, typically aromatic, hydrocarbon group which can be a single ring or multiple rings (up to three rings) which are fused together or linked covalently, and which optionally carries one or more substituents, such as, for example, halogen, trifluoromethyl, amino, alkyl, alkoxy, alkylcarbonyl, cyano, carbamoyl, alkoxycarbamoyl, methylenedioxy, carboxy, alkoxycarbonyl, aminocarbonyl, alkylaminocarbonyl, dialkylaminocarbonyl, hydroxy, nitro, and the like. Non-limiting examples of unsubstituted aryl groups include phenyl, naphthyl, and biphenyl. Examples of substituted aryl groups include, but are not limited to, phenyl, chlorophenyl, trifluoromethylphenyl, chlorofluorophenyl, and aminophenyl.

The terms "alkylthio," "alkylsulfonyl," "alkylsulfinyl," and "arylsulfonyl" include groups having the formula —S—$R^i$, —S(O)$_2$—$R^i$, —S(O)—$R^i$ and —S(O)$_2R^j$, respectively, wherein $R^i$ is an alkyl group as previously defined and $R^j$ is an aryl group as previously defined.

The terms "alkenyloxy" and "alkynyloxy" include groups having the formula —O—$R^i$, wherein $R^i$ is an alkenyl or alkynyl group, respectively.

The terms "alkenylthio" and "alkynylthio" include groups having the formula —S—$R^k$, wherein $R^k$ is an alkenyl or alkynyl group, respectively.

The term "alkoxycarbonyl" includes a group having the formula —C(O)O—$R^i$, wherein $R^i$ is an alkyl group as defined above and wherein the total number of carbon atoms refers to the combined alkyl and carbonyl moieties.

The term "acyl" includes any alkyl, alkenyl, or alkynyl wherein the carbon at the point of attachment is substituted with an oxo group, as defined below. The following are non-limiting examples of acyl groups: —C(=O)alkyl, —C(=O)alkenyl, and —C(=O)alkynyl.

The term "heterocycle" includes a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include, but are not limited to, heteroaryls as defined below, as well as morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "heteroaryl" includes an aromatic 5- to 10-membered heterocycle which contains one, two, or more heteroatoms selected from nitrogen (N), oxygen (O), and sulfur (S). The heteroaryl can be substituted on one or more carbon atoms with substituents such as, for example, halogen, alkyl, alkoxy, cyano, haloalkyl (e.g., trifluoromethyl), heterocyclyl (e.g., morpholinyl or pyrrolidinyl), and the like. Non-limiting examples of heteroaryls include pyridinyl and furanyl.

The term "halogen" includes fluoro, chloro, bromo, and iodo.

The terms "optionally substituted alkyl," "optionally substituted cyclic alkyl," "optionally substituted alkenyl," "optionally substituted alkynyl," "optionally substituted acyl," and "optionally substituted heterocycle" mean that, when substituted, at least one hydrogen atom is replaced with a substituent. In the case of an "oxo" substituent (=O), two hydrogen atoms are replaced. Non-limiting examples of substituents include oxo, halogen, heterocycle, —CN, —$OR^x$, —$NR^xR^y$, —$NR^xC(=O)R^y$, —$NR^xSO_2R^y$, —$C(=O)R^x$, —$C(=O)OR^x$, —$C(=O)NR^xR^y$, —$SO_nR^x$, and —$SO_n$-$NR^xR^y$, wherein n is 0, 1, or 2, $R^x$ and $R^y$ are the same or different and are independently hydrogen, alkyl, or heterocycle, and each of the alkyl and heterocycle substituents may be further substituted with one or more of oxo, halogen, —OH, —CN, alkyl, —$OR^x$, heterocycle, —$NR^xR^y$, —$NR^xC(=O)R^y$, —$NR^xSO_2R^y$, —$C(=O)R^x$, —$C(=O)OR^x$, —$C(=O)NR^xR^y$, —$SO_nR^x$, and —$SO_nNR^xR^y$. The term "optionally substituted," when used before a list of substituents, means that each of the substituents in the list may be optionally substituted as described herein.

In one aspect, cationic lipids of Formula I having the following structure (or salts thereof) are useful in the present invention:

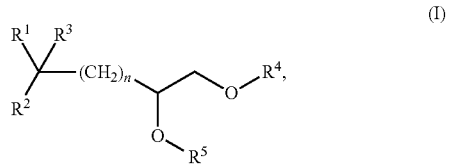

wherein $R^1$ and $R^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof;

$R^3$ is either absent or is hydrogen (H) or a $C_1$-$C_6$ alkyl to provide a quaternary amine;

$R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of $R^4$ and $R^5$ comprises at least two sites of unsaturation; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In one preferred embodiment, $R^1$ and $R^2$ are both methyl groups. In other preferred embodiments, n is 1 or 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group). In certain embodiments, at least one or both $R^4$ and $R^5$ independently comprises at least 2, 3, 4, 5, or 6 sites of unsaturation (e.g., 2, 3, 4, 5, 6, 2-3, 2-4, 2-5, or 2-6 sites of unsaturation).

In certain instances, $R^4$ and $R^5$ may independently comprise a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In particular embodiments, $R^4$ and $R^5$ are both linoleyl moieties. In other instances, the octadecatrienyl moiety is a linolenyl moiety or a γ-linolenyl moiety. In particular embodiments, $R^4$ and $R^5$ are both linolenyl moieties or γ-linolenyl moieties. In certain instances, $R^4$ and $R^5$ are different, e.g., $R^4$ is a tetradectrienyl ($C_{14}$) and $R^5$ is linoleyl ($C_{18}$). In a preferred embodiment, the cationic lipid of Formula I is symmetrical, i.e., $R^4$ and $R^5$ are both the same. In further embodiments, the double bonds present in one or both $R^4$ and $R^5$ may be in the cis and/or trans configuration.

In some groups of embodiments to the cationic lipids of Formula I, $R^4$ and $R^5$ are either the same or different and are independently selected from the group consisting of:

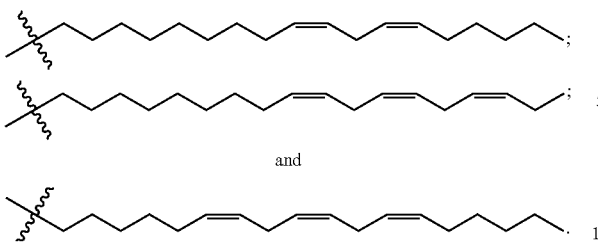

In particular embodiments, the cationic lipid of Formula I comprises 1,2-dilinoleyloxy-N,N-dimethylaminopropane (DLinDMA), 1,2-dilinolenyloxy-N,N-dimethylaminopropane (DLenDMA), or mixtures thereof.

In some embodiments, the cationic lipid of Formula I forms a salt (preferably a crystalline salt) with one or more anions. In one particular embodiment, the cationic lipid of Formula I is the oxalate (e.g., hemioxalate) salt thereof, which is preferably a crystalline salt.

In another aspect, cationic lipids of Formula II having the following structure (or salts thereof) are useful in the present invention:

(II)

wherein $R^1$ and $R^2$ are independently selected and are H or $C_1$-$C_3$ alkyls, $R^3$ and $R^4$ are independently selected and are alkyl groups having from about 10 to about 20 carbon atoms, and at least one of $R^3$ and $R^4$ comprises at least two sites of unsaturation. In certain instances, $R^3$ and $R^4$ are both the same, i.e., $R^3$ and $R^4$ are both linoleyl ($C_{18}$), etc. In certain other instances, $R^3$ and $R^4$ are different, i.e., $R^3$ is tetradectrienyl ($C_{14}$) and $R^4$ is linoleyl ($C_{18}$). In a preferred embodiment, the cationic lipid of Formula II is symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from the group consisting of dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl.

In some embodiments, the cationic lipid of Formula II forms a salt (preferably a crystalline salt) with one or more anions. In one particular embodiment, the cationic lipid of Formula II is the oxalate (e.g., hemioxalate) salt thereof, which is preferably a crystalline salt.

The synthesis of cationic lipids such as DLinDMA and DLenDMA, as well as additional cationic lipids falling within the scope of Formulas I and II, is described in U.S. Patent Publication No. 20060083780, the disclosure of which is herein incorporated by reference in its entirety for all purposes.

In yet another aspect, cationic lipids of Formula III having the following structure (or salts thereof) are useful in the present invention:

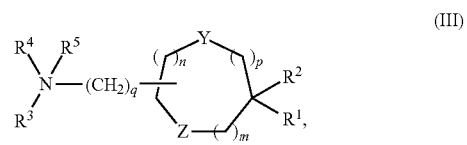

(III)

wherein $R^1$ and $R^2$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; $R^3$ and $R^4$ are either the same or different and are independently an optionally substituted $C_1$-$C_6$ alkyl, $C_2$-$C_6$ alkenyl, or $C_2$-$C_6$ alkynyl, or $R^3$ and $R^4$ may join to form an optionally substituted heterocyclic ring of 4 to 6 carbon atoms and 1 or 2 heteroatoms chosen from nitrogen and oxygen; $R^5$ is either absent or is hydrogen (H) or a $C_1$-$C_6$ alkyl to provide a quaternary amine; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH.

In some embodiments, $R^3$ and $R^4$ are independently an optionally substituted $C_1$-$C_4$ alkyl, $C_2$-$C_4$ alkenyl, or $C_2$-$C_4$ alkynyl. In a preferred embodiment, $R^3$ and $R^4$ are both methyl groups. In one embodiment, q is 1 or 2. In another embodiment, q is 1-2, 1-3, 1-4, 2-3, or 2-4. In further embodiments, $R^5$ is absent when the pH is above the $pK_a$ of the cationic lipid and $R^5$ is hydrogen when the pH is below the $pK_a$ of the cationic lipid such that the amino head group is protonated. In an alternative embodiment, $R^5$ is an optionally substituted $C_1$-$C_4$ alkyl to provide a quaternary amine. In additional embodiments, Y and Z are both O.

In other embodiments, $R^1$ and $R^2$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group). In certain embodiments, at least one or both $R^1$ and $R^2$ independently comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group. In certain instances, the unsaturated side-chain may comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In particular embodiments, $R^1$ and $R^2$ are both linoleyl moieties. In other instances, the octadecatrienyl moiety is a linolenyl moiety or a γ-linolenyl moiety. In particular embodiments, $R^1$ and $R^2$ are both linolenyl moieties or γ-linolenyl moieties.

In embodiments where one or both $R^1$ and $R^2$ independently comprises at least 1, 2, 3, 4, 5, or 6 sites of unsaturation, the double bonds present in one or both $R^1$ and $R^2$ may be in the cis and/or trans configuration. In certain instances, $R^1$ and $R^2$ are both the same, e.g., $R^1$ and $R^2$ are both linoleyl ($C_{18}$) moieties, etc. In certain other instances, $R^1$ and $R^2$ are different, e.g., $R^1$ is a tetradectrienyl ($C_{14}$) moiety and $R^2$ is a linoleyl ($C_{18}$) moiety. In a preferred embodiment, the cationic lipid of Formula III is symmetrical, i.e., $R^1$ and $R^2$ are both the same. In another preferred embodiment, at least one or both $R^1$ and $R^2$ comprises at least two sites of unsaturation (e.g., 2, 3, 4, 5, 6, 2-3, 2-4, 2-5, or 2-6 sites of unsaturation).

In embodiments where one or both $R^1$ and $R^2$ independently comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl (3,7,11,15-tetramethyl-hexadecanyl) moiety and the branched acyl group comprises a phytanoyl (3,7,11,15-tetramethyl-hexadecanoyl) moiety. In particular embodiments, $R^1$ and $R^2$ are both phytanyl moieties.

In some groups of embodiments to the cationic lipids of Formula III, $R^1$ and $R^2$ are either the same or different and are independently selected from the group consisting of:

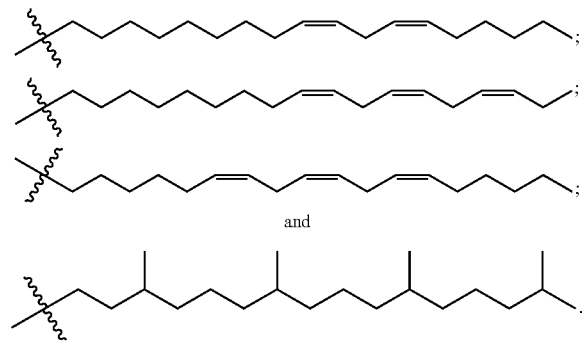

and

In certain embodiments, cationic lipids falling within the scope of Formula III include, but are not limited to, the following: 2,2-dilinoleyl-4-(2-dimethylaminoethyl)-[1,3]-dioxolane (DLin-K-C2-DMA; "XTC2" or "C2K"), 2,2-dilinoleyl-4-dimethylaminomethyl-[1,3]-dioxolane (DLin-K-DMA), 2,2-dilinoleyl-4-(3-dimethylaminopropyl)-[1,3]-dioxolane (DLin-K-C3-DMA; "C3K"), 2,2-dilinoleyl-4-(4-dimethylaminobutyl)[1,3]-dioxolane (DLin-K-C4-DMA; "C4K"), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dioleoyl-4-dimethylaminomethyl-[1,3]-dioxolane (DO-K-DMA), 2,2-distearoyl-4-dimethylaminomethyl-[1,3]-dioxolane (DS-K-DMA), 2,2-dilinoleyl-4-N-morpholino-[1,3]-dioxolane (DLin-K-MA), 2,2-Dilinoleyl-4-trimethylamino-[1,3]-dioxolane chloride (DLin-K-TMA.Cl), 2,2-dilinoleyl-4,5-bis(dimethylaminomethyl)-[1,3]-dioxolane (DLin-K²-DMA), 2,2-dilinoleyl-4-methylpiperzine-[1,3]-dioxolane (D-Lin-K-N-methylpiperzine), DLen-C2K-DMA, γ-DLen-C2K-DMA, DPan-C2K-DMA, DPan-C3K-DMA, or mixtures thereof. In preferred embodiments, the cationic lipid of Formula III comprises DLin-K-C2-DMA and/or DLin-K-DMA.

In some embodiments, the cationic lipids of Formula III form a salt (preferably a crystalline salt) with one or more anions. In one particular embodiment, the cationic lipid of Formula III is the oxalate (e.g., hemioxalate) salt thereof, which is preferably a crystalline salt.

The synthesis of cationic lipids such as DLin-K-C2-DMA, DLin-K-C3-DMA, DLin-K-C4-DMA, DLin-K6-DMA, DLin-K-MPZ, DO-K-DMA, DS-K-DMA, DLin-K-MA, DLin-K-TMA.Cl, DLin-K²-DMA, D-Lin-K-N-methylpiperzine, as well as additional cationic lipids, is described in PCT Publication No. WO 2010/042877, the disclosure of which is incorporated herein by reference in its entirety for all purposes.

The synthesis of cationic lipids such as DLin-K-DMA, as well as additional cationic lipids, is described in PCT Publication No. WO 09/086,558, the disclosure of which is herein incorporated by reference in its entirety for all purposes.

In particular embodiments, cationic lipids of Formula IV having the following structure (or salts thereof) are useful in the present invention:

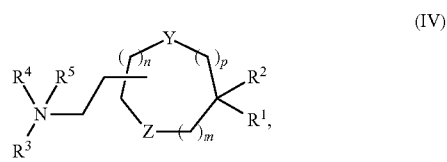

(IV)

wherein $R^1$ and $R^2$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; $R^3$ and $R^4$ are either the same or different and are independently an optionally substituted $C_1$-$C_6$ alkyl, $C_2$-$C_6$ alkenyl, or $C_2$-$C_6$ alkynyl, or $R^3$ and $R^4$ may join to form an optionally substituted heterocyclic ring of 4 to 6 carbon atoms and 1 or 2 heteroatoms chosen from nitrogen and oxygen; $R^5$ is either absent or is hydrogen (H) or a $C_1$-$C_6$ alkyl to provide a quaternary amine; m, n, and p are either the same or different and are independently either 0, 1, or 2, with the proviso that m, n, and p are not simultaneously 0; and Y and Z are either the same or different and are independently O, S, or NH.

In some embodiments, $R^3$ and $R^4$ are independently an optionally substituted $C_1$-$C_4$ alkyl, $C_2$-$C_4$ alkenyl, or $C_2$-$C_4$ alkynyl. In a preferred embodiment, $R^3$ and $R^4$ are both methyl groups. In further embodiments, $R^5$ is absent when the pH is above the $pK_a$ of the cationic lipid and $R^5$ is hydrogen when the pH is below the $pK_a$ of the cationic lipid such that the amino head group is protonated. In an alternative embodiment, $R^5$ is an optionally substituted $C_1$-$C_4$ alkyl to provide a quaternary amine. In additional embodiments, Y and Z are both O.

In other embodiments, $R^1$ and $R^2$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group). In certain embodiments, at least one or both $R^1$ and $R^2$ independently comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group. In certain instances, the unsaturated side-chain may comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In particular embodiments, $R^1$ and $R^2$ are both linoleyl moieties. In other instances, the octadecatrienyl moiety is a linolenyl moiety or a γ-linolenyl moiety. In particular embodiments, $R^1$ and $R^2$ are both linolenyl moieties or γ-linolenyl moieties.

In embodiments where one or both $R^1$ and $R^2$ independently comprises at least 1, 2, 3, 4, 5, or 6 sites of unsaturation, the double bonds present in one or both $R^1$ and $R^2$ may be in the cis and/or trans configuration. In certain instances, $R^1$ and $R^2$ are both the same, e.g., $R^1$ and $R^2$ are both linoleyl ($C_{18}$) moieties, etc. In certain other instances, $R^1$ and $R^2$ are different, e.g., $R^1$ is a tetradectrienyl ($C_{14}$) moiety and $R^2$ is a linoleyl ($C_{18}$) moiety. In a preferred embodiment, the cationic lipid of Formula IV is symmetrical, i.e., $R^1$ and $R^2$ are both the same. In another preferred embodiment, at least one or both $R^1$ and $R^2$ comprises at least two sites of unsaturation (e.g., 2, 3, 4, 5, 6, 2-3, 2-4, 2-5, or 2-6 sites of unsaturation).

In embodiments where one or both $R^1$ and $R^2$ independently comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl (3,7,11,15-tetramethyl-hexadecanyl) moiety and the branched acyl group comprises a phytanoyl (3,7,11,15-tetramethyl-hexadecanoyl) moiety. In particular embodiments, $R^1$ and $R^2$ are both phytanyl moieties.

In some groups of embodiments to the cationic lipids of Formula IV, $R^1$ and $R^2$ are either the same or different and are independently selected from the group consisting of:

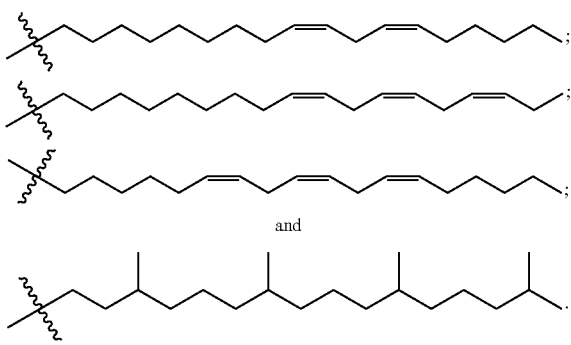

In certain embodiments, cationic lipids falling within the scope of Formula IV include, but are not limited to, the following: 2,2-dilinoleyl-4-(2-dimethylaminoethyl)-[1,3]-dioxolane (DLin-K-C2-DMA; "XTC2" or "C2K"), DLen-C2K-DMA, γ-DLen-C2K-DMA, DPan-C2K-DMA, or mixtures thereof. In preferred embodiments, the cationic lipid of Formula IV comprises DLin-K-C2-DMA.

In some embodiments, the cationic lipids of Formula IV form a salt (preferably a crystalline salt) with one or more anions. In one particular embodiment, the cationic lipid of Formula IV is the oxalate (e.g., hemioxalate) salt thereof, which is preferably a crystalline salt.

The synthesis of DLin-K-C2-DMA (C2K) is described in PCT Publication No. WO 2010/042877, the disclosure of which is incorporated herein by reference in its entirety for all purposes.

In a further aspect, cationic lipids of Formula V having the following structure are useful in the present invention:

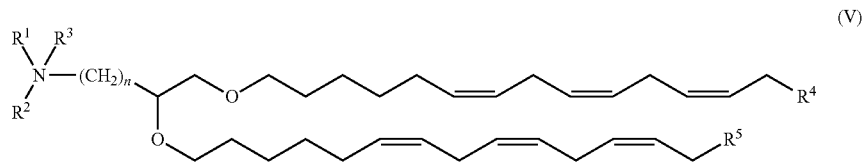

(V)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either absent or present and when present are either the same or different and are independently an optionally substituted $C_1$-$C_{10}$ alkyl or $C_2$-$C_{10}$ alkenyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, $R^4$ and $R^5$ are both butyl groups. In yet another preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_2$-$C_6$ or $C_2$-$C_4$ alkyl or $C_2$-$C_6$ or $C_2$-$C_4$ alkenyl.

In an alternative embodiment, the cationic lipid of Formula V comprises ester linkages between the amino head group and one or both of the alkyl chains. In some embodiments, the cationic lipid of Formula V forms a salt (preferably a crystalline salt) with one or more anions. In one particular embodiment, the cationic lipid of Formula V is the oxalate (e.g., hemioxalate) salt thereof, which is preferably a crystalline salt.

Although each of the alkyl chains in Formula V contains cis double bonds at positions 6, 9, and 12 (i.e., cis,cis,cis-$\Delta^6$,$\Delta^9$, $\Delta^{12}$), in an alternative embodiment, one, two, or three of these double bonds in one or both alkyl chains may be in the trans configuration.

In a particularly preferred embodiment, the cationic lipid of Formula V has the structure:

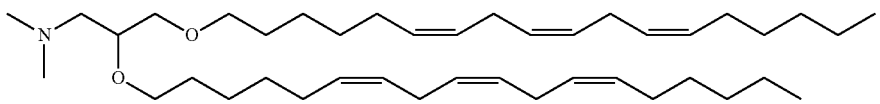

γ-DLenDMA.

In another aspect, cationic lipids of Formula VI having the following structure are useful in the present invention:

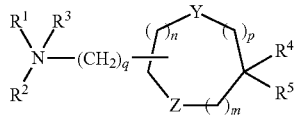

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, wherein at least one of $R^4$ and $R^5$ comprises at least three sites of unsaturation or a substituted $C_{12}$-$C_{24}$ alkyl; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, q is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In embodiments where at least one of $R^4$ and $R^5$ comprises a branched alkyl group (e.g., a substituted $C_{12}$-$C_{24}$ alkyl group), the branched alkyl group may comprise a $C_{12}$-$C_{24}$ alkyl having at least 1-6 (e.g., 1, 2, 3, 4, 5, 6, or more) $C_1$-$C_6$ alkyl substituents. In particular embodiments, the branched alkyl group comprises a $C_{12}$-$C_{20}$ or $C_{14}$-$C_{22}$ alkyl with 1-6 (e.g., 1, 2, 3, 4, 5, 6) $C_1$-$C_4$ alkyl (e.g., methyl, ethyl, propyl, or butyl) substituents. Preferably, the branched alkyl group comprises a phytanyl (3,7,11,15-tetramethyl-hexadecanyl) moiety. In other preferred embodiments, $R^4$ and $R^5$ are both phytanyl moieties.

In alternative embodiments, at least one of $R^4$ and $R^5$ comprises a branched acyl group (e.g., a substituted $C_{12}$-$C_{24}$ acyl group). In certain instances, the branched acyl group may comprise a $C_{12}$-$C_{24}$ acyl having at least 1-6 (e.g., 1, 2, 3, 4, 5, 6, or more) $C_1$-$C_6$ alkyl substituents. In particular embodiments, the branched acyl group comprises a $C_{12}$-$C_{20}$ or $C_{14}$-$C_{22}$ acyl with 1-6 (e.g., 1, 2, 3, 4, 5, 6) $C_1$-$C_4$ alkyl (e.g., methyl, ethyl, propyl, or butyl) substituents. Preferably, the branched acyl group comprises a phytanoyl (3,7,11,15-tetramethyl-hexadecanoyl) moiety.

In embodiments where at least one of $R^4$ and $R^5$ comprises at least three sites of unsaturation, the double bonds present in one or both alkyl chains may be in the cis and/or trans configuration. In some embodiments, $R^4$ and $R^5$ are independently selected from the group consisting of a dodecatrienyl moiety, a tetradectrienyl moiety, a hexadecatrienyl moiety, an octadecatrienyl moiety, an icosatrienyl moiety, and a phytanyl moiety, as well as acyl derivatives thereof (e.g., linolenoyl, γ-linolenoyl, phytanoyl, etc.). In certain instances, the octadecatrienyl moiety is a linolenyl moiety or a γ-linolenyl moiety. In preferred embodiments, $R^4$ and $R^5$ are both linolenyl moieties or γ-linolenyl moieties. In particular embodiments, $R^4$ and $R^5$ independently comprise a backbone of from about 16 to about 22 carbon atoms, and one or both of $R^4$ and $R^5$ independently comprise at least three, four, five, or six sites of unsaturation.

In some embodiments, the cationic lipid of Formula VI forms a salt (preferably a crystalline salt) with one or more anions. In one particular embodiment, the cationic lipid of Formula VI is the oxalate (e.g., hemioxalate) salt thereof, which is preferably a crystalline salt.

In a particularly preferred embodiment, the cationic lipid of Formula VI has a structure selected from the group consisting of:

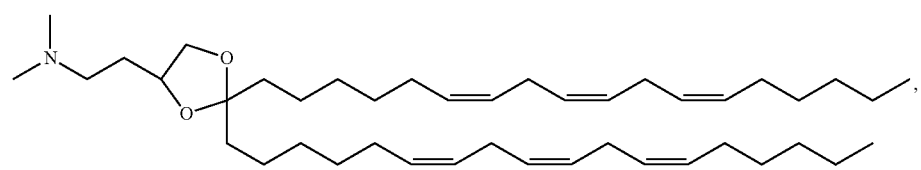

γ-DLen-C2K-DMA

-continued

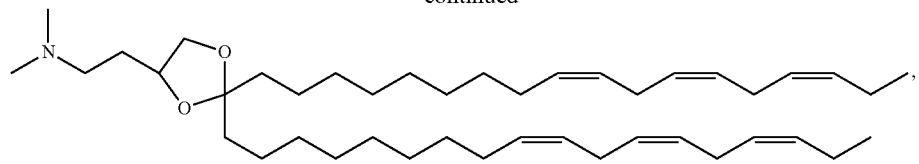

DLen-C2K-DMA

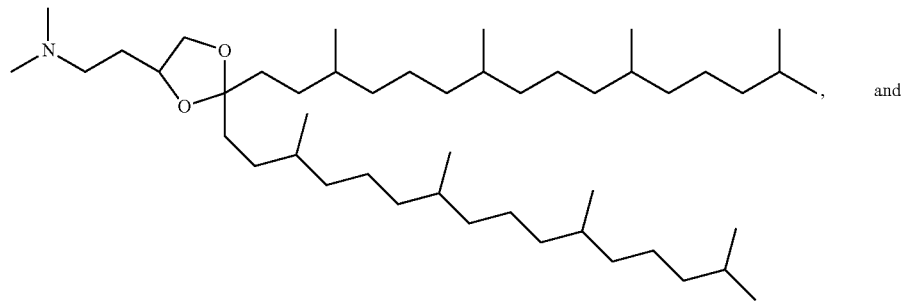

DPan-C2K-DMA

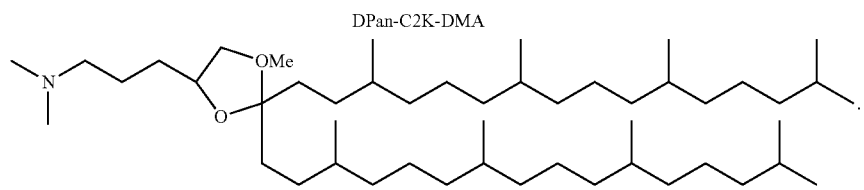

DPan-C3K-DMA

In yet another aspect, cationic lipids of Formula VII having the following structure are useful in the present invention:

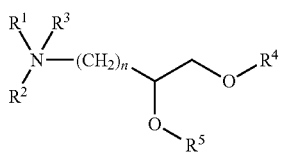

(VII)

or salts thereof, wherein: $R^1$ and $R^2$ are joined to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; and n is 0, 1, 2, 3, or 4.

In some embodiments, $R^1$ and $R^2$ are joined to form a heterocyclic ring of 5 carbon atoms and 1 nitrogen atom. In certain instances, the heterocyclic ring is substituted with a substituent such as a hydroxyl group at the ortho, meta, and/or para positions. In a preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

In some embodiments, the cationic lipid of Formula VII forms a salt (preferably a crystalline salt) with one or more anions. In one particular embodiment, the cationic lipid of Formula VII is the oxalate (e.g., hemioxalate) salt thereof, which is preferably a crystalline salt.

In a particularly preferred embodiment, the cationic lipid of Formula VII has a structure selected from the group consisting of:

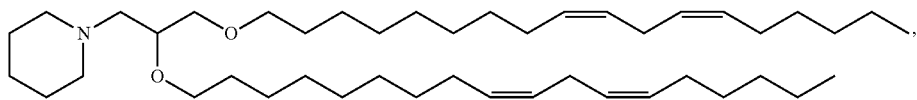

DLinPip

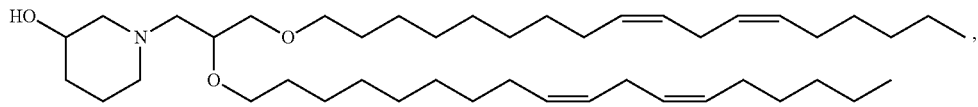

DLinPip (3-OH)

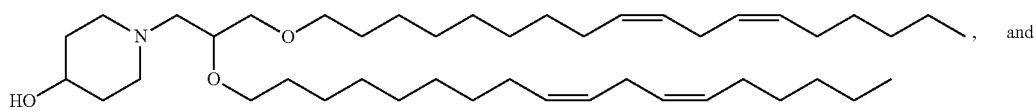

DLinPip (4-OH)

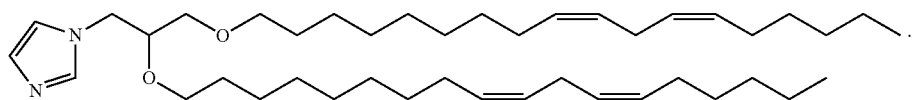

DLinIm

In still yet another aspect, cationic lipids of Formula VIII having the following structure are useful in the present invention:

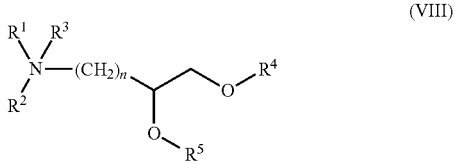

(VIII)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; and n is 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, n is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

In some embodiments, the cationic lipid of Formula VIII forms a salt (preferably a crystalline salt) with one or more anions. In one particular embodiment, the cationic lipid of Formula VIII is the oxalate (e.g., hemioxalate) salt thereof, which is preferably a crystalline salt.

In a particularly preferred embodiment, the cationic lipid of Formula VIII has a structure selected from the group consisting of:

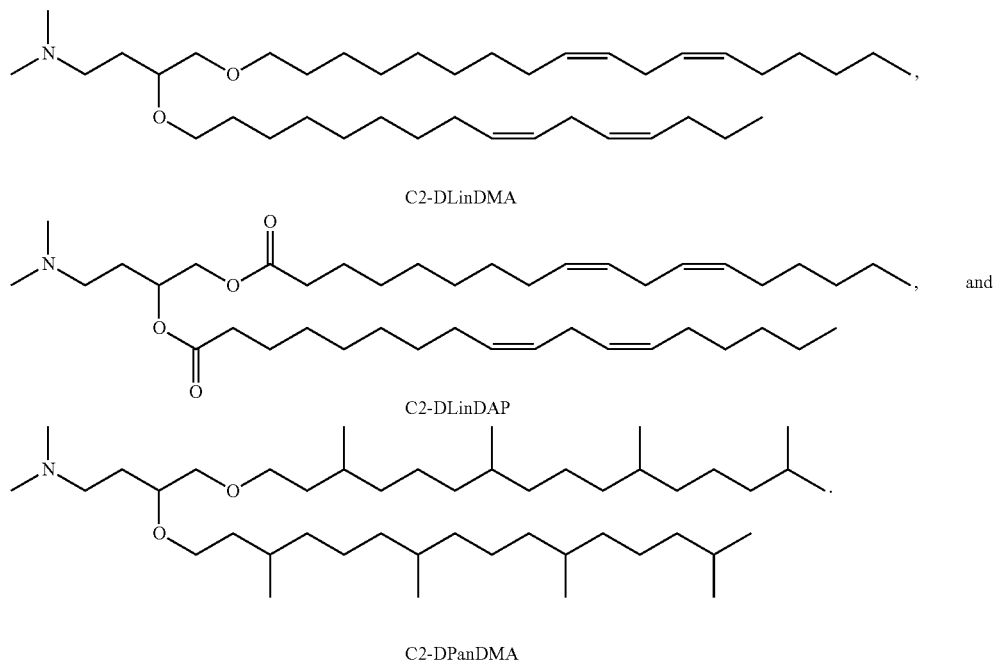

C2-DLinDMA

C2-DLinDAP , and

C2-DPanDMA

In another aspect, cationic lipids of Formula IX having the following structure are useful in the present invention:

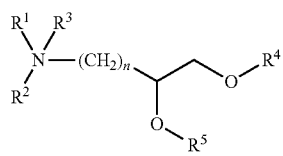

(IX)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are different and are independently an optionally substituted $C_1$-$C_{24}$ alkyl, $C_2$-$C_{24}$ alkenyl, $C_2$-$C_{24}$ alkynyl, or $C_1$-$C_{24}$ acyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are different and are independently an optionally substituted $C_4$-$C_{20}$ alkyl, $C_4$-$C_{20}$ alkenyl, $C_4$-$C_{20}$ alkynyl, or $C_4$-$C_{20}$ acyl.

In some embodiments, $R^4$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, and $R^5$ is an optionally substituted $C_4$-$C_{10}$ alkyl, $C_4$-$C_{10}$ alkenyl, $C_4$-$C_{10}$ alkynyl, or $C_4$-$C_{10}$ acyl. In certain instances, $R^4$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, and $R^5$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl.

In other embodiments, $R^4$ is an optionally substituted $C_4$-$C_{10}$ alkyl, $C_4$-$C_{10}$ alkenyl, $C_4$-$C_{10}$ alkynyl, or $C_4$-$C_{10}$ acyl, and $R^5$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl. In certain instances, $R^4$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl, and $R^5$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In particular embodiments, $R^4$ is a linoleyl moiety, and $R^5$ is a $C_6$ alkyl moiety, a $C_6$ alkenyl moiety, an octadecyl moiety, an oleyl moiety, a linolenyl moiety, a γ-linolenyl moiety, or a phytanyl moiety. In other embodiments, one of $R^4$ or $R^5$ is a phytanyl moiety.

In some embodiments, the cationic lipid of Formula IX forms a salt (preferably a crystalline salt) with one or more anions. In one particular embodiment, the cationic lipid of Formula IX is the oxalate (e.g., hemioxalate) salt thereof, which is preferably a crystalline salt.

In a particularly preferred embodiment, the cationic lipid of Formula IX is an asymmetric lipid having a structure selected from the group consisting of:

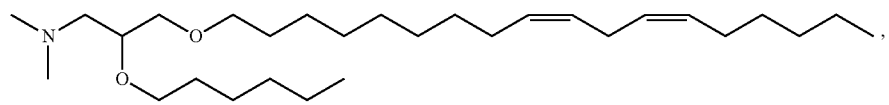

Linoleyl/C$_6$:0 DMA

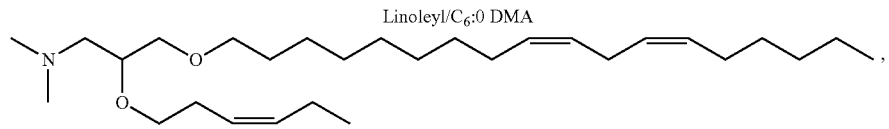

Linoleyl/C$_6$:1 DMA

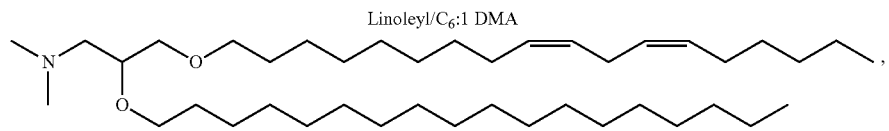

Linoleyl/Stearyl DMA

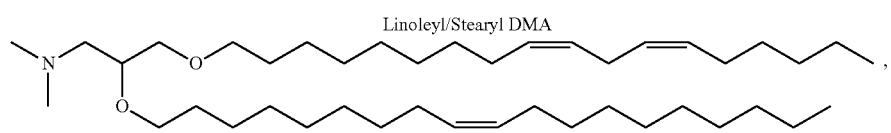

Linoleyl/Oleyl DMA, and

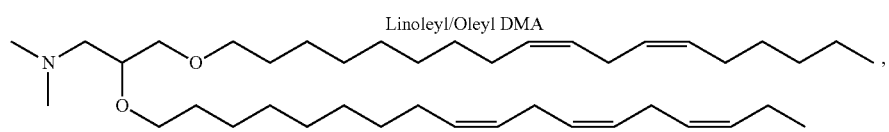

Linoleyl/Linolenyl DMA

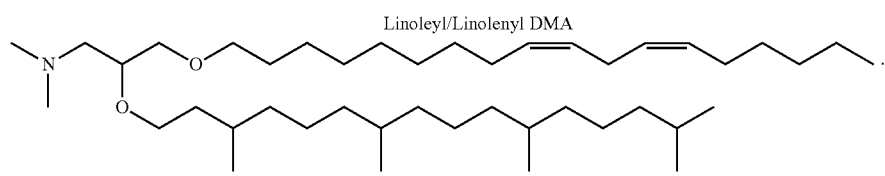

Linoleyl/Phytanyl DMA

In yet another aspect, cationic lipids of Formula X having the following structure are useful in the present invention:

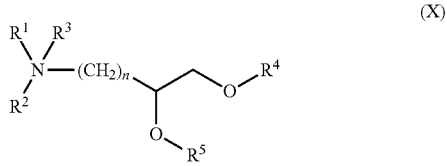

(X)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, wherein at least one of $R^4$ and $R^5$ comprises at least four sites of unsaturation or a substituted $C_{12}$-$C_{24}$ alkyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, n is 1. In other embodiments, $R^3$ is absent when the pH is above the pK$_a$ of the cationic lipid and $R^3$ is hydrogen when the pH is below the pK$_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In embodiments where at least one of $R^4$ and $R^5$ comprises a branched alkyl group (e.g., a substituted $C_{12}$-$C_{24}$ alkyl group), the branched alkyl group may comprise a $C_{12}$-$C_{24}$ alkyl having at least 1-6 (e.g., 1, 2, 3, 4, 5, 6, or more) $C_1$-$C_6$ alkyl substituents. In particular embodiments, the branched alkyl group comprises a $C_{12}$-$C_{20}$ or $C_{14}$-$C_{22}$ alkyl with 1-6 (e.g., 1, 2, 3, 4, 5, 6) $C_1$-$C_4$ alkyl (e.g., methyl, ethyl, propyl, or butyl) substituents. Preferably, the branched alkyl group comprises a phytanyl (3,7,11,15-tetramethyl-hexadecanyl) moiety.

In alternative embodiments, at least one of $R^4$ and $R^5$ comprises a branched acyl group (e.g., a substituted $C_{12}$-$C_{24}$ acyl group). In certain instances, the branched acyl group may comprise a $C_{12}$-$C_{24}$ acyl having at least 1-6 (e.g., 1, 2, 3, 4, 5, 6, or more) $C_1$-$C_6$ alkyl substituents. In particular embodiments, the branched acyl group comprises a $C_{12}$-$C_{20}$ or $C_{14}$-$C_{22}$ acyl with 1-6 (e.g., 1, 2, 3, 4, 5, 6) $C_1$-$C_4$ alkyl (e.g., methyl, ethyl, propyl, or butyl) substituents. Preferably, the branched acyl group comprises a phytanoyl (3,7,11,15-tetramethyl-hexadecanoyl) moiety.

In embodiments where at least one of $R^4$ and $R^5$ comprises at least four sites of unsaturation, the double bonds present in one or both alkyl chains may be in the cis and/or trans configuration. In a particular embodiment, $R^4$ and $R^5$ independently comprise four, five, or six sites of unsaturation. In some instances, $R^4$ comprises four, five, or six sites of unsaturation and $R^5$ comprises zero, one, two, three, four, five, or six sites of unsaturation. In other instances, $R^4$ comprises zero, one, two, three, four, five, or six sites of unsaturation and $R^5$ comprises four, five, or six sites of unsaturation. In a preferred embodiment, both $R^4$ and $R^5$ comprise four, five, or six sites of unsaturation. In particular embodiments, $R^4$ and $R^5$ independently comprise a backbone of from about 18 to about 24 carbon atoms, and one or both of $R^4$ and $R^5$ independently comprise at least four, five, or six sites of unsaturation.

In some embodiments, the cationic lipid of Formula X forms a salt (preferably a crystalline salt) with one or more anions. In one particular embodiment, the cationic lipid of Formula X is the oxalate (e.g., hemioxalate) salt thereof, which is preferably a crystalline salt.

In a particularly preferred embodiment, the cationic lipid of Formula X has a structure selected from the group consisting of:

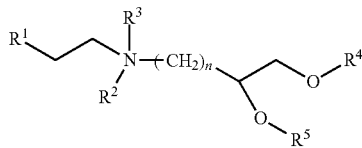

(XI)

or salts thereof, wherein: $R^1$ is hydrogen (H) or —$(CH_2)_q$—$NR^6R^7R^8$, wherein: $R^6$ and $R^7$ are either the same or different and are independently an optionally substituted $C_1$-$C_6$ alkyl, $C_2$-$C_6$ alkenyl, or $C_2$-$C_6$ alkynyl, or $R^6$ and $R^7$ may join to form an optionally substituted heterocyclic ring of 4 to 6 carbon atoms and 1 or 2 heteroatoms selected from the group consisting of nitrogen (N), oxygen (O), and mixtures thereof; $R^8$ is either absent or is hydrogen (H) or a $C_1$-$C_6$ alkyl to provide a quaternary amine; and q is 0, 1, 2, 3, or 4; $R^2$ is an optionally substituted $C_1$-$C_6$ alkyl, $C_2$-$C_6$ alkenyl, or $C_2$-$C_6$ alkynyl; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; and n is 0, 1, 2, 3, or 4.

In some embodiments, $R^2$ is an optionally substituted $C_1$-$C_4$ alkyl, $C_2$-$C_4$ alkenyl, or $C_2$-$C_4$ alkynyl. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In certain embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

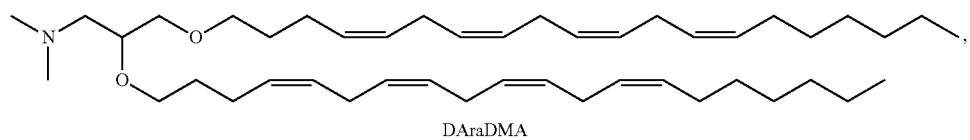

DAraDMA

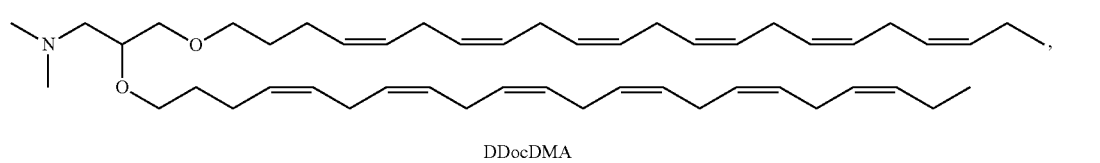

DDocDMA, and

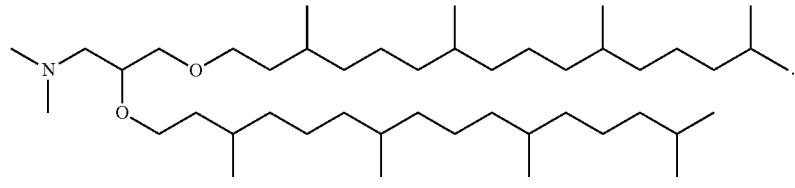

DPanDMA

In still yet another aspect, cationic lipids of Formula XI having the following structure are useful in the present invention:

In further embodiments, $R^6$ and $R^7$ are independently an optionally substituted $C_1$-$C_4$ alkyl, $C_2$-$C_4$ alkenyl, or $C_2$-$C_4$ alkynyl. In other embodiments, $R^8$ is absent when the pH is above the pK$_a$ of the cationic lipid and R$^8$ is hydrogen when the pH is below the pK$_a$ of the cationic lipid such that the amino head group is protonated. In an alternative embodiment, R$^8$ is an optionally substituted C$_1$-C$_4$ alkyl to provide a quaternary amine.

In a preferred embodiment, R$^1$ is hydrogen and R$^2$ is an ethyl group. In another preferred embodiment, R$^6$ and R$^7$ are both methyl groups. In certain instances, n is 1. In certain other instances, q is 1.

In certain embodiments, R$^4$ and R$^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, R$^4$ and R$^5$ are both linoleyl moieties, linolenyl moieties, γ-linolenyl moieties, or phytanyl moieties.

In some embodiments, the cationic lipid of Formula XI forms a salt (preferably a crystalline salt) with one or more anions. In one particular embodiment, the cationic lipid of Formula XI is the oxalate (e.g., hemioxalate) salt thereof, which is preferably a crystalline salt.

In a particularly preferred embodiment, the cationic lipid of Formula XI has a structure selected from the group consisting of:

or salts thereof, wherein: R$^1$ and R$^2$ are either the same or different and are independently an optionally substituted C$_1$-C$_6$ alkyl, C$_2$-C$_6$ alkenyl, or C$_2$-C$_6$ alkynyl, or R$^1$ and R$^2$ may join to form an optionally substituted heterocyclic ring of 4 to 6 carbon atoms and 1 or 2 heteroatoms selected from the group consisting of nitrogen (N), oxygen (O), and mixtures thereof; R$^3$ is either absent or is hydrogen (H) or a C$_1$-C$_6$ alkyl to provide a quaternary amine; R$^4$, R$^5$, and R$^6$ are either the same or different and are independently an optionally substituted C$_{12}$-C$_{24}$ alkyl, C$_{12}$-C$_{24}$ alkenyl, C$_{12}$-C$_{24}$ alkynyl, or C$_{12}$-C$_{24}$ acyl; and n is 0, 1, 2, 3, or 4.

In some embodiments, R$^1$ and R$^2$ are independently an optionally substituted C$_1$-C$_4$ alkyl, C$_2$-C$_4$ alkenyl, or C$_2$-C$_4$ alkynyl. In a preferred embodiment, R$^1$ and R$^2$ are both methyl groups. In another preferred embodiment, n is 1. In other embodiments, R$^3$ is absent when the pH is above the pK$_a$ of the cationic lipid and R$^3$ is hydrogen when the pH is below the pK$_a$ of the cationic lipid such that the amino head group is protonated. In an alternative embodiment, R$^3$ is an optionally substituted C$_1$-C$_4$ alkyl to provide a quaternary amine. In further embodiments, R$^4$, R$^5$, and R$^6$ are independently an optionally substituted C$_{12}$-C$_{20}$ or C$_{14}$-C$_{22}$ alkyl, C$_{12}$-C$_{20}$ or C$_{14}$-C$_{22}$ alkenyl, C$_{12}$-C$_{20}$ or C$_{14}$-C$_{22}$ alkynyl, or C$_{12}$-C$_{20}$ or C$_{14}$-C$_{22}$ acyl.

In certain embodiments, R$^4$, R$^5$, and R$^6$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl

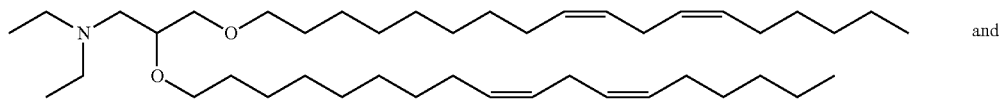

DLinDEA

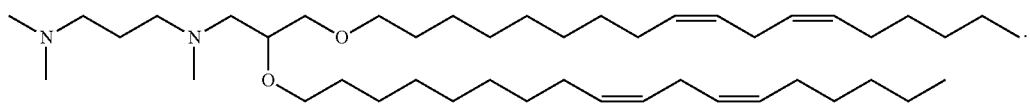

2N-DLinDMA

In another aspect, cationic lipids of Formula XII having the following structure are useful in the present invention:

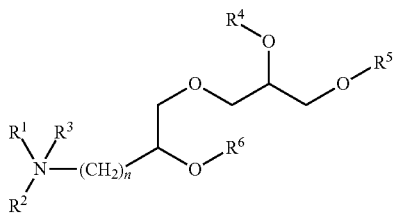

(XII)

moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, R$^4$, R$^5$, and R$^6$ are all linoleyl moieties, linolenyl moieties, γ-linolenyl moieties, or phytanyl moieties.

In some embodiments, the cationic lipid of Formula XII forms a salt (preferably a crystalline salt) with one or more anions. In one particular embodiment, the cationic lipid of Formula XII is the oxalate (e.g., hemioxalate) salt thereof, which is preferably a crystalline salt.

In a particularly preferred embodiment, the cationic lipid of Formula XII has a structure selected from the group consisting of:

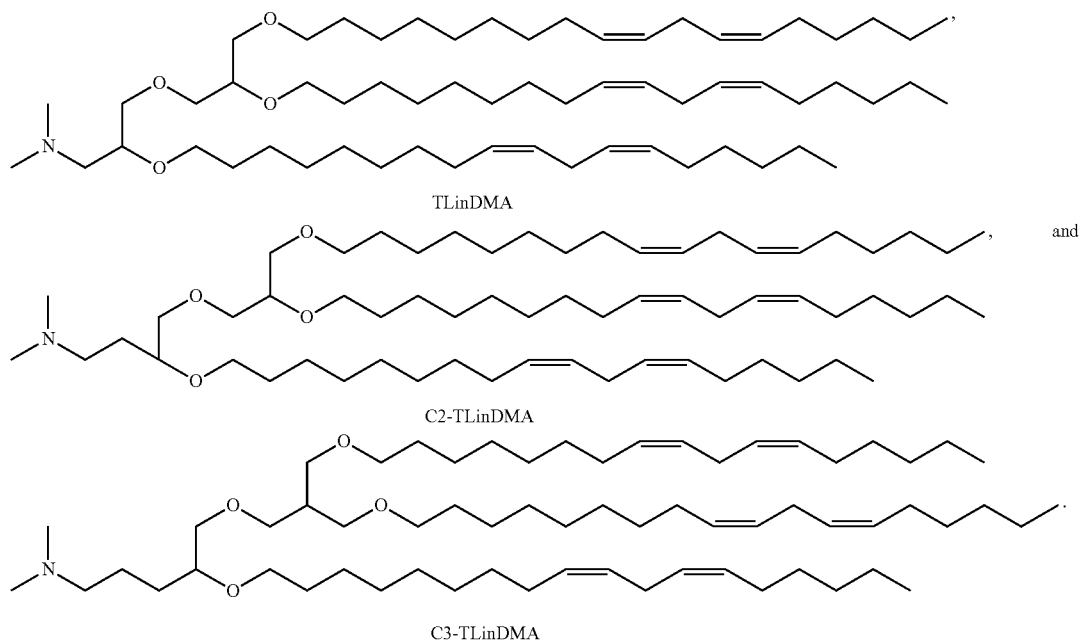

TLinDMA

C2-TLinDMA

C3-TLinDMA

In yet another aspect, cationic lipids of Formula XIII having the following structure are useful in the present invention:

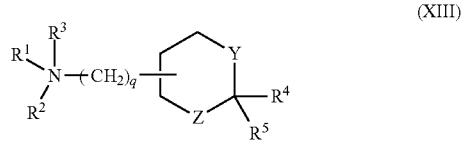

(XIII)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; q is 0, 1, 2, 3, or 4; and Y and Z are either the same or different and are independently O, S, or NH, wherein if q is 1, $R^1$ and $R^2$ are both methyl groups, $R^4$ and $R^5$ are both linoleyl moieties, and Y and Z are both O, then the alkylamino group is attached to one of the two carbons adjacent to Y or Z (i.e., at the '4' or '6' position of the 6-membered ring).

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, q is 2. In a particular embodiments, Y and Z are both oxygen (O). In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In other embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

The alkylamino head group of Formula XIII may be attached to the '4' or '5' position of the 6-membered ring as shown below in an exemplary embodiment wherein $R^1$ and $R^2$ are both methyl groups:

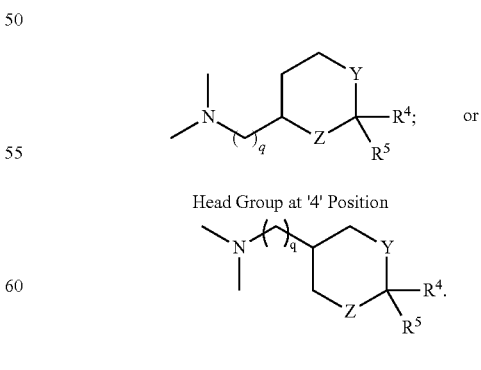

Head Group at '4' Position

Head Group at '5' Position

In further embodiments, the 6-membered ring of Formula XIII may be substituted with 1, 2, 3, 4, or 5 independently selected $C_1$-$C_6$ alkyl, $C_2$-$C_6$ alkenyl, $C_2$-$C_6$ alkynyl, $C_1$-$C_6$ alkoxyl, or hydroxyl substituents. In one particular embodiment, the 6-membered ring is substituted with 1, 2, 3, 4, or 5 independently selected $C_1$-$C_4$ alkyl (e.g., methyl, ethyl, propyl, or butyl) substituents. An exemplary embodiment of a cationic lipid of Formula XIII having a substituted 6-membered ring (methyl group attached to the '4' position) and wherein $R^1$ and $R^2$ are both methyl groups is shown below:

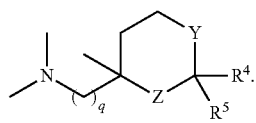

In particular embodiments, the cationic lipids of Formula XIII may be synthesized using 2-hydroxymethyl-1,4-butanediol and 1,3,5-pentanetriol (or 3-methyl-1,3,5-pentanetriol) as starting materials.

In some embodiments, the cationic lipid of Formula XIII forms a salt (preferably a crystalline salt) with one or more anions. In one particular embodiment, the cationic lipid of Formula XIII is the oxalate (e.g., hemioxalate) salt thereof, which is preferably a crystalline salt.

In a particularly preferred embodiment, the cationic lipid of Formula XIII has the structure:

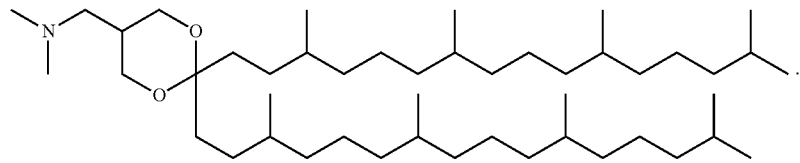

DPan-C1K6-DMA

In still yet another aspect, the present invention provides a cationic lipid of Formula XIV having the following structure:

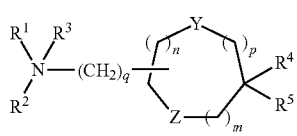

(XIV)

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, wherein at least one of $R^4$ and $R^5$ comprises at least one site of unsaturation in the trans (E) configuration; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, q is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, at least one of $R^4$ and $R^5$ further comprises one, two, three, four, five, six, or more sites of unsaturation in the cis and/or trans configuration. In some instances, $R^4$ and $R^5$ are independently selected from any of the substituted or unsubstituted alkyl or acyl groups described herein, wherein at least one or both of $R^4$ and $R^5$ comprises at least one, two, three, four, five, or six sites of unsaturation in the trans configuration. In one particular embodiment, $R^4$ and $R^5$ independently comprise a backbone of from about 12 to about 22 carbon atoms (e.g., 12, 13, 14, 15, 16, 17, 18, 19, 20, 21, or 22 carbon atoms), and one or both of $R^4$ and $R^5$ independently comprise at least one, two, three, four, five, or six sites of unsaturation in the trans configuration. In some preferred embodiments, at least one of $R^4$ and $R^5$ comprises an (E)-heptadeceyl moiety. In other preferred embodiments, $R^4$ and $R^5$ are both (E)-8-heptadeceyl moieties.

In some embodiments, the cationic lipid of Formula XIV forms a salt (preferably a crystalline salt) with one or more anions. In one particular embodiment, the cationic lipid of Formula XIV is the oxalate (e.g., hemioxalate) salt thereof, which is preferably a crystalline salt.

In a particularly preferred embodiment, the cationic lipid of Formula XIV has the structure:

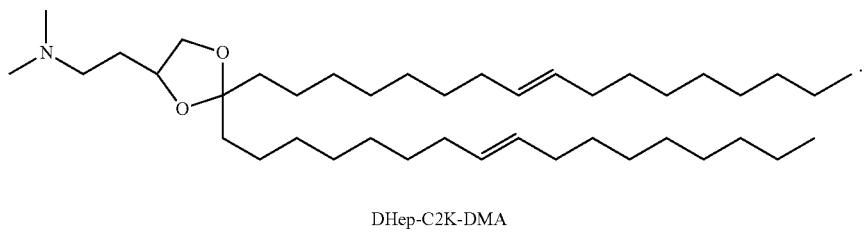 [SMILES: CCCCCCCC/C=C/CCCCCCCC1(CCCCCCC/C=C/CCCCCCCC)OCC(CCN(C)C)O1]

DHep-C2K-DMA

In another aspect, the present invention provides a cationic lipid of Formula XV having the following structure:

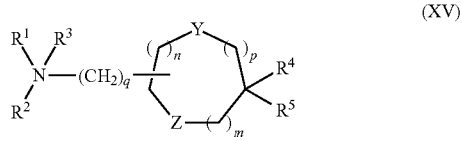

(XV)

or salts thereof, wherein: $R^1$ and $R^2$ are joined to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH.

In some embodiments, $R^1$ and $R^2$ are joined to form a heterocyclic ring of 5 carbon atoms and 1 nitrogen atom. In certain instances, the heterocyclic ring is substituted with a substituent such as a hydroxyl group at the ortho, meta, and/or para positions. In a preferred embodiment, q is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, and a branched alkyl group as described above (e.g., a phytanyl moiety), as well as acyl derivatives thereof (e.g., linoleoyl, linolenoyl, γ-linolenoyl, phytanoyl, etc.). In some instances, the octadecadienyl moiety is a linoleyl moiety. In other instances, the octadecatrienyl moiety is a linolenyl moiety or a γ-linolenyl moiety. In particular embodiments, $R^4$ and $R^5$ are both linoleyl moieties, linolenyl moieties, γ-linolenyl moieties, or phytanyl moieties.

In some embodiments, the cationic lipid of Formula XV forms a salt (preferably a crystalline salt) with one or more anions. In one particular embodiment, the cationic lipid of Formula XV is the oxalate (e.g., hemioxalate) salt thereof, which is preferably a crystalline salt.

In a particularly preferred embodiment, the cationic lipid of Formula XV has the

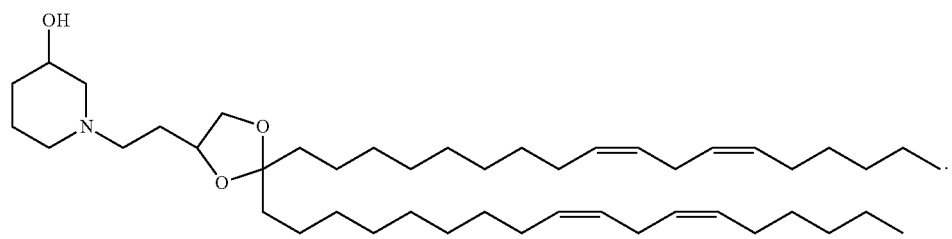

DLin-C2K-Pip-3OH

In yet another aspect, the present invention provides a cationic lipid of Formula XVI having the following structure:

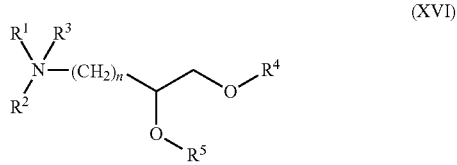

(XVI)

or salts thereof, wherein:
$R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof;

$R^3$ is either absent or is hydrogen (H) or a $C_1$-$C_6$ alkyl to provide a quaternary amine;

$R^4$ and $R^5$ are either the same or different and are independently a substituted $C_{12}$-$C_{24}$ alkyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In one particular embodiment, n is 1. In another particular embodiment, n is 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine.

In embodiments where at least one of $R^4$ and $R^5$ comprises a branched alkyl group (e.g., a substituted $C_{12}$-$C_{24}$ alkyl group), the branched alkyl group may comprise a $C_{12}$-$C_{24}$ alkyl having at least 1-6 (e.g., 1, 2, 3, 4, 5, 6, or more) $C_1$-$C_6$ alkyl substituents. In particular embodiments, the branched alkyl group comprises a $C_{12}$-$C_{20}$ or $C_{14}$-$C_{22}$ alkyl with 1-6 (e.g., 1, 2, 3, 4, 5, 6) $C_1$-$C_4$ alkyl (e.g., methyl, ethyl, propyl, or butyl) substituents. Preferably, the branched alkyl group comprises a phytanyl (3,7,11,15-tetramethyl-hexadecanyl) moiety. In particular embodiments, $R^4$ and $R^5$ are both phytanyl moieties.

In alternative embodiments, at least one of $R^4$ and $R^5$ comprises a branched acyl group (e.g., a substituted $C_{12}$-$C_{24}$ acyl group). In certain instances, the branched acyl group may comprise a $C_{12}$-$C_{24}$ acyl having at least 1-6 (e.g., 1, 2, 3, 4, 5, 6, or more) $C_1$-$C_6$ alkyl substituents. In particular embodiments, the branched acyl group comprises a $C_{12}$-$C_{20}$ or $C_{14}$-$C_{22}$ acyl with 1-6 (e.g., 1, 2, 3, 4, 5, 6) $C_1$-$C_4$ alkyl (e.g., methyl, ethyl, propyl, or butyl) substituents. Preferably, the branched acyl group comprises a phytanoyl (3,7,11,15-tetramethyl-hexadecanoyl) moiety. In particular embodiments, $R^4$ and $R^5$ are both phytanoyl moieties.

In some embodiments, the cationic lipid of Formula XVI forms a salt (preferably a crystalline salt) with one or more anions. In one particular embodiment, the cationic lipid of Formula XVI is the oxalate (e.g., hemioxalate) salt thereof, which is preferably a crystalline salt.

In a particularly preferred embodiment, the cationic lipid of Formula XVI has a structure selected from the group consisting of:

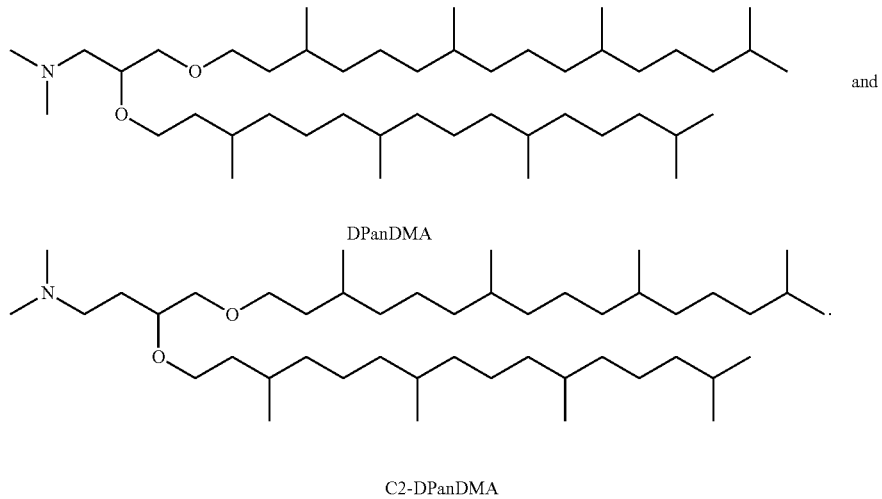

DPanDMA and

C2-DPanDMA

The synthesis of cationic lipids of Formulas V-XVI is described in PCT Application No. PCT/CA2010/001029, filed Jun. 30, 2010, the disclosure of which is herein incorporated by reference in its entirety for all purposes.

In a further aspect, cationic lipids of Formula XVII having the following structure are useful in the present invention:

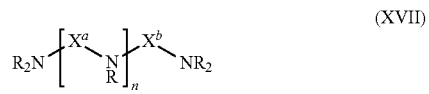

(XVII)

or salts thereof, wherein:

each $X^a$ and $X^b$, for each occurrence, is independently a $C_{1-6}$ alkylene;

n is 0, 1, 2, 3, 4, or 5;

each R is independently H,

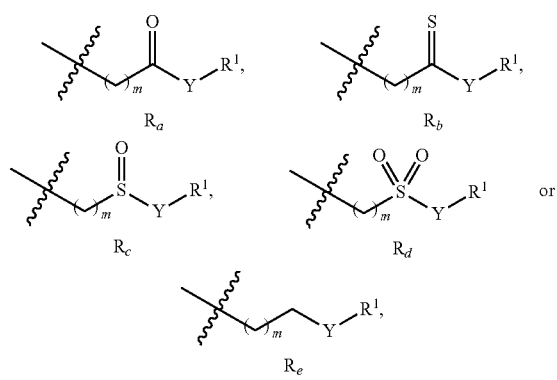

wherein:
at least n+2 of the R moieties in at least about 80% of the molecules of the compound of Formula (XVII) in the preparation are not H;
m is 1, 2, 3 or 4; Y is O, $NR^2$, or S;
$R^1$ is H, alkyl, alkenyl or alkynyl, each of which is optionally substituted with one or more substituents; and
$R^2$ is H, alkyl alkenyl or alkynyl, each of which is optionally substituted with one or more substituents;
provided that at least one of $R^1$ or $R^2$ is an alkenyl group comprising at least two sites of unsaturation, and
provided that if n=0, then at least n+3 of the R moieties are not H.

The synthesis of cationic lipids of Formula XVII, as well as additional cationic lipids, is described in U.S. Patent Publication No. 20090023673, the disclosure of which is herein incorporated by reference in its entirety for all purposes.

In another aspect, cationic lipids of Formula XVIII having the following structure are useful in the present invention:

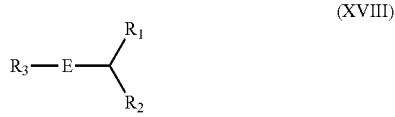

(XVIII)

wherein:
$R_1$ and $R_2$ are each independently for each occurrence optionally substituted $C_{10}$-$C_{30}$ alkyl, optionally substituted $C_{10}$-$C_{30}$ alkenyl, optionally substituted $C_{10}$-$C_{30}$ alkynyl, optionally substituted $C_{10}$-$C_{30}$ acyl, or -linker-ligand; $R_3$ is H, optionally substituted $C_1$-$C_{10}$ alkyl, optionally substituted $C_2$-$C_{10}$ alkenyl, optionally substituted $C_2$-$C_{10}$ alkynyl, alkylheterocycle, alkylphosphate, alkylphosphorothioate, alkylphosphorodithioate, alkylphosphonates, alkylamines, hydroxyalkyls, ω-aminoalkyls, ω-(substituted)aminoalkyls, ω-phosphoalkyls, ω-thiophosphoalkyls, optionally substituted polyethylene glycol (PEG, mw 100-40K), optionally substituted mPEG (mw 120-40K), heteroaryl, heterocycle, or linker-ligand; E is O, S, N(Q), C(O), C(O)O, OC(O), N(Q)C(O), C(O)N(Q), (Q)N(CO)O, O(CO)N(Q), S(O), NS(O)$_2$N(Q), S(O)$_2$, N(Q)S(O)$_2$, SS, O=N, aryl, heteroaryl, cyclic or heterocycle; and Q is H, alkyl, ω-aminoalkyl, ω-(substituted)aminoalkyl, ω-phosphoalkyl, or ω-thiophosphoalkyl; or a salt or isomer thereof.

In one embodiment, $R_1$ and $R_2$ are each independently for each occurrence optionally substituted $C_{10}$-$C_{30}$ alkyl, optionally substituted $C_{10}$-$C_{30}$ alkoxy, optionally substituted $C_{10}$-$C_{30}$ alkenyl, optionally substituted $C_{10}$-$C_{30}$ alkenyloxy, optionally substituted $C_{10}$-$C_{30}$ alkynyl, optionally substituted $C_{10}$-$C_{30}$ alkynyloxy, or optionally substituted $C_{10}$-$C_{30}$ acyl.

In another embodiment, $R_3$ is H, optionally substituted $C_1$-$C_{10}$ alkyl, optionally substituted $C_2$-$C_{10}$ alkenyl, optionally substituted $C_2$-$C_{10}$ alkynyl, optionally substituted alkylheterocycle, optionally substituted heterocycloalkyl, optionally substituted alkylphosphate, optionally substituted phosphoalkyl, optionally substituted alkylphosphorothioate, optionally substituted phosphorothioalkyl, optionally substituted alkylphosphorodithioate, optionally substituted phosphorodithioalkyl, optionally substituted alkylphosphonate, optionally substituted phosphonoalkyl, optionally substituted amino, optionally substituted alkylamino, optionally substituted di(alkyl)amino, optionally substituted aminoalkyl, optionally substituted alkylaminoalkyl, optionally substituted di(alkyl)aminoalkyl, optionally substituted hydroxyalkyl, optionally substituted polyethylene glycol (PEG, mw 100-40K), optionally substituted mPEG (mw 120-40K), optionally substituted heteroaryl, optionally substituted heterocycle, or linker-ligand.

In yet another embodiment, E is —O—, —S—, —N(Q)-, —C(O)—, —C(O)O—, —OC(O)—, —N(Q)C(O)—, —C(O)N(Q)-, —N(Q)C(O)O—, —OC(O)N(Q)-, S(O), —N(Q)S(O)$_2$N(Q)-, —S(O)$_2$—, —N(Q)S(O)$_2$—, —SS—, —O—N=, =N—O—, —C(O)—N(Q)-N=, —N(Q)-N=, —N(Q)-O—, —C(O)S—, arylene, heteroarylene, cyclalkylene, or heterocyclylene; and Q is H, alkyl, ω-aminoalkyl, ω-(substituted)aminoalkyl, ω-phosphoalkyl or ω-thiophosphoalkyl.

In another embodiment, the lipid is a compound of Formula XVIII, wherein E is O, S, N(Q), C(O), C(O)O, OC(O), N(Q)C(O), C(O)N(Q), (Q)N(CO)O, O(CO)N(Q), S(O), NS(O)$_2$N(Q), S(O)$_2$, N(Q)S(O)$_2$, SS, O=N, aryl, heteroaryl, cyclic or heterocycle.

In one embodiment, the lipid is a compound of Formula XVIII, wherein $R_3$ is H, optionally substituted $C_2$-$C_{10}$ alkenyl, optionally substituted $C_2$-$C_{10}$ alkynyl, alkylheterocycle, alkylphosphate, alkylphosphorothioate, alkylphosphorodithioate, alkylphosphonates, alkylamines, hydroxyalkyls, ω-aminoalkyls, ω-(substituted)aminoalkyls, ω-phosphoalkyls, ω-thiophosphoalkyls, optionally substituted polyethylene glycol (PEG, mw 100-40K), optionally substituted mPEG (mw 120-40K), heteroaryl, heterocycle, or linker-ligand.

In yet another embodiment, the lipid is a compound of Formula XVIII, wherein $R_1$ and $R_2$ are each independently for each occurrence optionally substituted $C_{10}$-$C_{30}$ alkyl, optionally substituted $C_{10}$-$C_{30}$ alkynyl, optionally substituted $C_{10}$-$C_{30}$ acyl, or -linker-ligand.

In yet another aspect, cationic lipids of Formula XIX having the following structure are useful in the present invention:

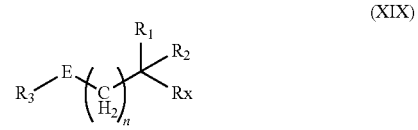

(XIX)

wherein:
E is O, S, N(Q), C(O), C(O)O, OC(O), N(Q)C(O), C(O)N(Q), (Q)N(CO)O, O(CO)N(Q), S(O), NS(O)$_2$N(Q), S(O)$_2$, N(Q)S(O)$_2$, SS, O=N, aryl, heteroaryl, cyclic or heterocycle; Q is H, alkyl, ω-aminoalkyl, ω-(substituted)aminoalkyl, ω-phosphoalkyl, or ω-thiophosphoalkyl; $R_1$ and $R_2$ and $R_x$ are each independently for each occurrence H, optionally substituted $C_1$-$C_{10}$ alkyl, optionally substituted $C_{10}$-$C_{30}$ alkyl, optionally substituted $C_{10}$-$C_{30}$ alkenyl, optionally substituted $C_{10}$-$C_{30}$ alkynyl, optionally substituted $C_{10}$-$C_{30}$ acyl, or linker-ligand, provided that at least one of $R_1$, $R_2$ and $R_x$ is not H; $R_3$ is H, optionally substituted $C_1$-$C_{10}$ alkyl, optionally substituted $C_2$-$C_{10}$ alkenyl, optionally substituted $C_2$-$C_{10}$ alkynyl, alkylheterocycle, alkylphosphate, alkylphosphorothioate, alkylphosphorodithioate, alkylphosphonates, alkylamines, hydroxyalkyls, ω-aminoalkyls, ω-(substituted)aminoalkyls, ω-phosphoalkyls, ω-thiophosphoalkyls, optionally substituted polyethylene glycol (PEG, mw 100-40K), optionally substituted mPEG (mw 20-40K), heteroaryl, heterocycle, or linker-ligand; and n is 0, 1, 2, or 3; or a salt or isomer thereof.

In some embodiments, each of $R_1$ and $R_2$ is independently for each occurrence optionally substituted $C_{10}$-$C_{30}$ alkyl, optionally substituted $C_{10}$-$C_{30}$ alkenyl, optionally substituted $C_{10}$-$C_{30}$ alkynyl, optionally substituted $C_{10}$-$C_{30}$ acyl, or linker-ligand. In some embodiments, $R_x$ is H or optionally substituted $C_1$-$C_{10}$ alkyl. In some embodiments, $R_x$ is optionally substituted $C_{10}$-$C_{30}$ alkyl, optionally substituted $C_{10}$-$C_{30}$ alkenyl, optionally substituted $C_{10}$-$C_{30}$ alkynyl, optionally substituted $C_{10}$-$C_{30}$ acyl, or linker-ligand.

In one embodiment, $R_1$ and $R_2$ are each independently for each occurrence optionally substituted $C_{10}$-$C_{30}$ alkyl, optionally substituted $C_{10}$-$C_{30}$ alkoxy, optionally substituted $C_{10}$-$C_{30}$ alkenyl, optionally substituted $C_{10}$-$C_{30}$ alkenyloxy, optionally substituted $C_{10}$-$C_{30}$ alkynyl, optionally substituted $C_{10}$-$C_{30}$ alkynyloxy, or optionally substituted $C_{10}$-$C_{30}$ acyl, or -linker-ligand.

In one embodiment, $R_3$ is independently for each occurrence H, optionally substituted $C_1$-$C_{10}$ alkyl, optionally substituted $C_2$-$C_{10}$ alkenyl, optionally substituted $C_2$-$C_{10}$ alkynyl, optionally substituted alkylheterocycle, optionally substituted heterocycloalkyl, optionally substituted alkylphosphate, optionally substituted phosphoalkyl, optionally substituted alkylphosphorothioate, optionally substituted phosphorothioalkyl, optionally substituted alkylphosphorodithioate, optionally substituted phosphorodithioalkyl, optionally substituted alkylphosphonate, optionally substituted phosphonoalkyl, optionally substituted amino, optionally substituted alkylamino, optionally substituted di(alkyl) amino, optionally substituted aminoalkyl, optionally substituted alkylaminoalkyl, optionally substituted di(alkyl) aminoalkyl, optionally substituted hydroxyalkyl, optionally substituted polyethylene glycol (PEG, mw 100-40K), optionally substituted mPEG (mw 120-40K), optionally substituted heteroaryl, or optionally substituted heterocycle, or linker-ligand.

Non-limiting examples of cationic lipids of Formula XVIII which may be included in the lipid particles of the present invention include cationic lipids such as (6Z,9Z,28Z,31Z)-heptatriaconta-6,9,28,31-tetraen-19-yl 4-(dimethylamino) butanoate (DLin-M-C3-DMA or "MC3"; also called dilinoleylmethyl 4-(dimethylamino)butanoate) and certain analogs thereof. The synthesis of cationic lipids of Formula XVIII, as well as additional cationic lipids such as cationic lipids of Formula XIX, are described in U.S. Provisional Patent Application No. 61/384,050, entitled "Novel Cationic Lipids and Methods of Use Thereof," filed Sep. 17, 2010, U.S. Provisional Application No. 61/185,800, entitled "Novel Lipids and Compositions for the Delivery of Therapeutics," filed Jun. 10, 2009, U.S. Provisional Application No. 61/287,995, entitled "Methods and Compositions for Delivery of Nucleic Acids," filed Dec. 18, 2009, and PCT Publication Nos. WO 2010/054401, WO 2010/054405, WO 2010/054406, and WO 2010/054384, the disclosures of which are herein incorporated by reference in their entirety for all purposes.

In another aspect, cationic lipids of Formula XX having the following structure are useful in the present invention:

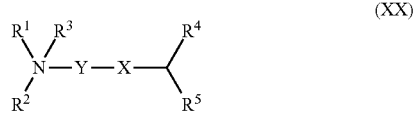

(XX)

or salts thereof, wherein:

$R^1$ and $R^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof;

$R^3$ is either absent or is hydrogen (H) or a $C_1$-$C_6$ alkyl to provide a quaternary amine;

$R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl;

X is O, S, N($R^6$), C(O), C(O)O, OC(O), C(O)N($R^6$), N($R^6$)C(O), OC(O)N($R^6$), N($R^6$)C(O)O, C(O)S, C(S)O, S(O), S(O)(O), or C(S), wherein $R^6$ is hydrogen (H) or an optionally substituted $C_1$-$C_6$ alkyl, $C_2$-$C_6$ alkenyl, or $C_2$-$C_6$ alkynyl; and Y is either absent or is an optionally substituted $C_1$-$C_6$ alkyl, $C_2$-$C_6$ alkenyl, or $C_2$-$C_6$ alkynyl.

In some embodiments, $R^1$, $R^2$, and $R^6$ are each independently hydrogen (H) or an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In other embodiments, $R^1$ and $R^2$ are joined to form a heterocyclic ring of 5 carbon atoms and 1 nitrogen atom, wherein the heterocyclic ring can be substituted with a substituent such as a hydroxyl (—OH) group at the ortho, meta, and/or para positions. In particular embodiments, $R^1$ and $R^2$ are both methyl groups. In certain instances, $R^3$ is absent when the pH is above the $pK_a$ of the cationic lipid and $R^3$ is hydrogen (H) when the pH is below the $pK_a$ of the cationic lipid such that the amino head group is protonated. In certain other instances, $R^3$ is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, or $C_5$-$C_6$ alkyl to provide a quaternary amine. In one particular embodiment, X is C(O)O. In another particular embodiment, X is O. In certain other embodiments, X is C(O)N($R^6$), N($R^6$)C(O)O, or C(O)S. In one particular embodiment, X is N($R^6$)C(O)O and $R^6$ is hydrogen (H) or a methyl group. In other instances, $R^1$ and $R^2$ are not both methyl groups when X is C(O)O, Y is $(CH_2)_2$ or $(CH_2)_3$, and $R^4$ and $R^5$ are both linoleyl moieties.

In certain embodiments, at least one or both $R^4$ and $R^5$ independently comprises an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl or acyl group (i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl or acyl group). In other embodiments, at least one or both $R^4$ and $R^5$ independently comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group. In certain instances, the unsaturated side-chain may comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In particular embodiments, $R^4$ and $R^5$ are both linoleyl moieties. In other instances, the octadecatrienyl moiety is a linolenyl moiety or a γ-linolenyl moiety. In particular embodiments, $R^4$ and $R^5$ are both linolenyl moieties or γ-linolenyl moieties. In embodiments where one or both $R^4$ and $R^5$ independently comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl (3,7,11,15-tetramethyl-hexadecanyl) moiety and the branched acyl group comprises a phytanoyl (3,7,11,15-tetramethyl-hexadecanoyl) moiety. In particular embodiments, $R^4$ and $R^5$ are both phytanyl moieties.

In other embodiments, at least one or both $R^4$ and $R^5$ independently comprises at least 1, 2, 3, 4, 5, 6, or more optionally substituted cyclic alkyl groups (e.g., 1-2, 1-3, 1-4, 1-5, 1-6, 2-3, 2-4, 2-5, or 2-6 optionally substituted cyclic alkyl groups). In certain instances, at least one or both $R^4$ and $R^5$ independently comprises an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group), wherein at least one of $R^4$ and $R^5$ comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups).

In particular embodiments, one or more of the optionally substituted cyclic alkyl groups present in $R^4$ and/or $R^5$ are independently selected from the group consisting of an optionally substituted saturated cyclic alkyl group, an optionally substituted unsaturated cyclic alkyl group, and combinations thereof. In certain instances, the optionally substituted saturated cyclic alkyl group comprises an optionally substituted $C_{3-8}$ cycloalkyl group (e.g., cyclopropyl, cyclobutyl, cyclopentyl, cyclohexyl, cycloheptyl, cyclooctyl, etc.). In preferred embodiments, the optionally substituted saturated cyclic alkyl group comprises a cyclopropyl group, optionally containing one or more substituents and/or heteroatoms. In other instances, the optionally substituted unsaturated cyclic alkyl group comprises an optionally substituted $C_{3-8}$ cycloalkenyl group (e.g., cyclopropenyl, cyclobutenyl, cyclopentenyl, cyclohexenyl, cycloheptenyl, cyclooctenyl, etc.).

In some embodiments, one of $R^4$ or $R^5$ comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group, and the other side-chain comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In embodiments where one of $R^4$ or $R^5$ comprises at least 1, 2, 3, 4, 5, or 6 sites of unsaturation, the unsaturated side-chain may comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In other instances, the octadecatrienyl moiety is a linolenyl moiety or a γ-linolenyl moiety. In embodiments where one of $R^4$ or $R^5$ comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl moiety and the branched acyl group comprises a phytanoyl moiety.

In particular embodiments, $R^4$ and $R^5$ are both independently selected $C_{12}$-$C_{20}$ alkyl groups (i.e., $C_{12}$, $C_{13}$, $C_{14}$, $C_{15}$, $C_{16}$, $C_{17}$, $C_{18}$, $C_{19}$, or $C_{20}$ alkyl groups) having at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In preferred embodiments, $R^4$ and $R^5$ are both $C_{18}$ alkyl groups having at least one, two, three, or more optionally substituted cyclic alkyl groups such as, for example, an optionally substituted $C_{3-8}$ cycloalkyl group (e.g., a cyclopropyl group, optionally containing one or more substituents and/or heteroatoms). In certain embodiments, each of the optionally substituted cyclic alkyl groups is independently selected and can be the same cyclic alkyl group (e.g., all cyclopropyl groups) or different cyclic alkyl groups (e.g., cyclopropyl and other cycloalkyl, heterocycloalkyl, cycloalkenyl, and/or heterocycloalkenyl groups).

In preferred embodiments, the optionally substituted cyclic alkyl groups present in $R^4$ and/or $R^5$ are located at the site(s) of unsaturation in the corresponding unsaturated side-chain. As a non-limiting example, one or both of $R^4$ and $R^5$ are $C_{18}$ alkyl groups having 1, 2, or 3 optionally substituted cyclic alkyl groups, wherein the optionally substituted cyclic alkyl groups (e.g., independently selected cyclopropyl groups) are located at one or more (e.g., all) of the sites of unsaturation present in a corresponding linoleyl moiety, linolenyl moiety, or γ-linolenyl moiety.

In alternative embodiments to the cationic lipid of Formula XX, $R^4$ and $R^5$ are different and are independently an optionally substituted $C_1$-$C_{24}$ alkyl, $C_2$-$C_{24}$ alkenyl, $C_2$-$C_{24}$ alkynyl, or $C_1$-$C_{24}$ acyl. In particular embodiments, at least one or both $R^4$ and $R^5$ comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In certain embodiments, $R^4$ and $R^5$ are different and are independently an optionally substituted $C_4$-$C_{20}$ alkyl, $C_4$-$C_{20}$ alkenyl, $C_4$-$C_{20}$ alkynyl, or $C_4$-$C_{20}$ acyl. In some instances, $R^4$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, and $R^5$ is an optionally substituted $C_4$-$C_{10}$ alkyl, $C_4$-$C_{10}$ alkenyl, $C_4$-$C_{10}$ alkynyl, or $C_4$-$C_{10}$ acyl. In other instances, $R^4$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, and $R^5$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl. In certain instances, $R^4$ is an optionally substituted $C_4$-$C_{10}$ alkyl, $C_4$-$C_{10}$ alkenyl, $C_4$-$C_{10}$ alkynyl, or $C_4$-$C_{10}$ acyl, and $R^5$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl. In certain other instances, $R^4$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl, and $R^5$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl. In particular embodiments, one or more of the optionally substituted cyclic alkyl groups, when present in $R^4$ and/or $R^5$, are as described above.

In some groups of embodiments to the cationic lipid of Formula XX, $R^4$ and $R^5$ are either the same or different and are independently selected from the group consisting of:

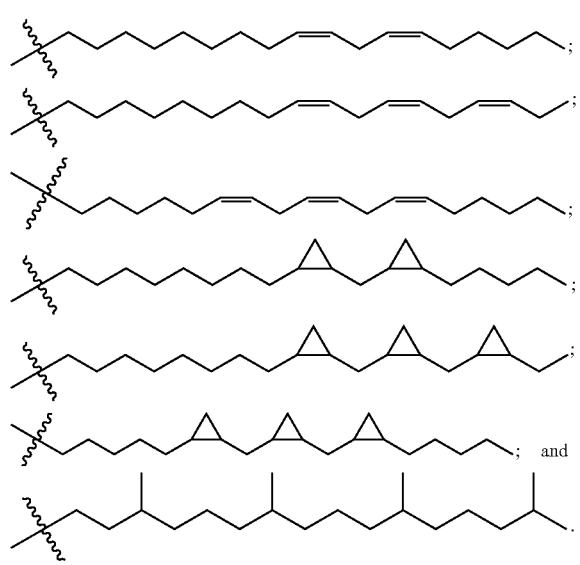

In certain embodiments, Y is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In one particular embodiment, Y is $(CH_2)_n$ and n is 0, 1, 2, 3, 4, 5, or 6 (e.g., 1-2, 1-3, 1-4, 1-5, 1-6, 2-3, 2-4, 2-5, or 2-6). In a preferred embodiment, n is 2, 3, or 4.

In particular embodiments, the cationic lipid of Formula XX has the following structure:

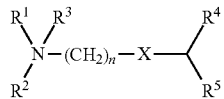

or salts thereof, wherein $R^1$, $R^2$, $R^3$, $R^4$, $R^5$, X, and n are the same as described above.

In some embodiments, the cationic lipid of Formula XX forms a salt (preferably a crystalline salt) with one or more anions. In one particular embodiment, the cationic lipid of Formula XX is the oxalate (e.g., hemioxalate) salt thereof, which is preferably a crystalline salt.

In particularly preferred embodiments, the cationic lipid of Formula XX has one of the following structures:

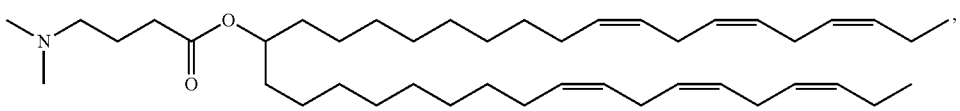

LenMC3

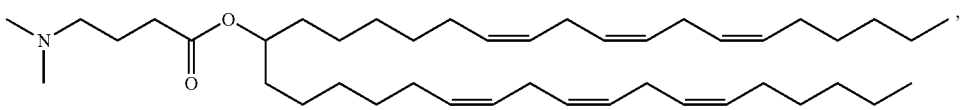

γ-LenMC3

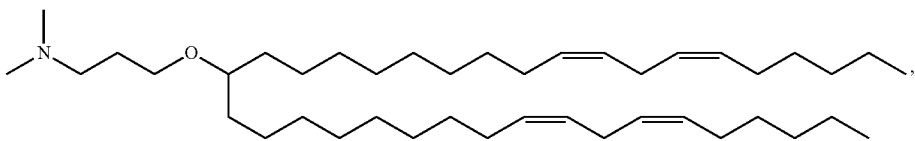

MC3 Ether

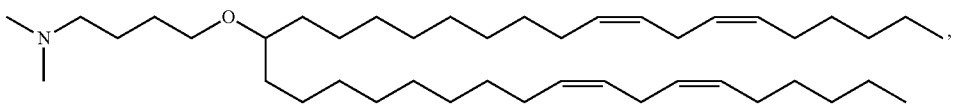

MC4 Ether

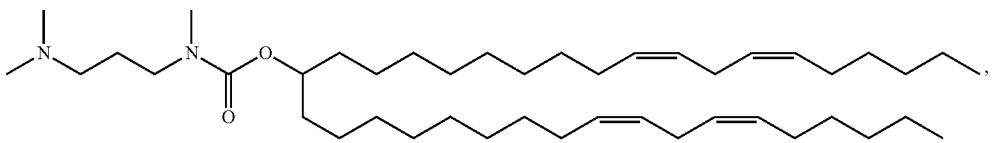

MC3MC

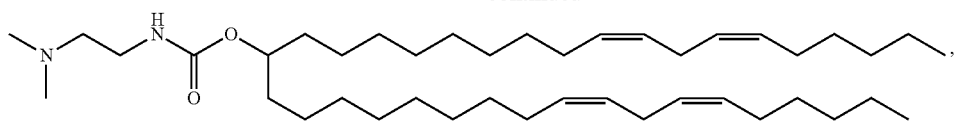
MC2C
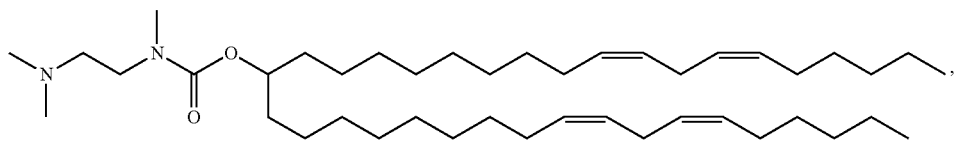
MC2MC
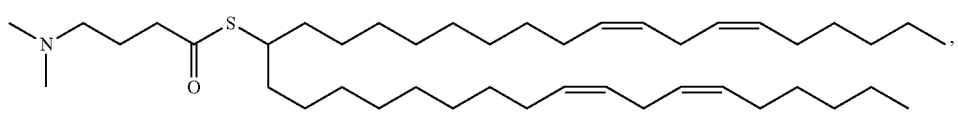
MC3 Thioester
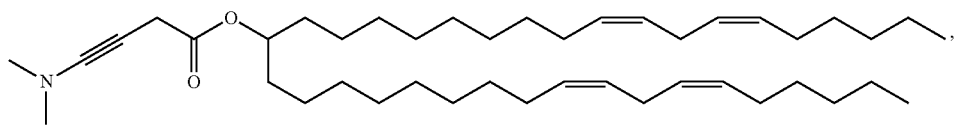
MC3 Alkyne
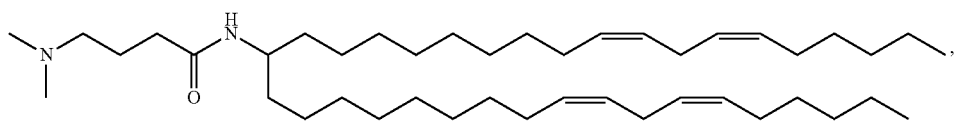
MC3 Amide
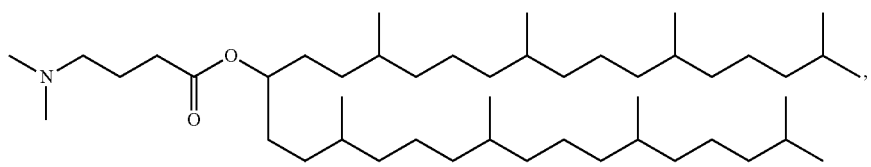
Pan-MC3
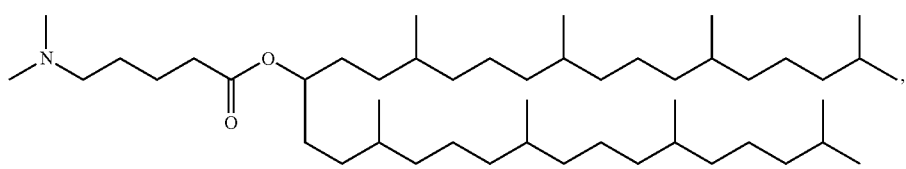
Pan-MC4
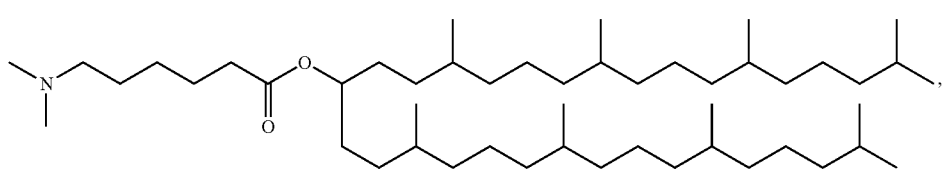
Pan-MC5

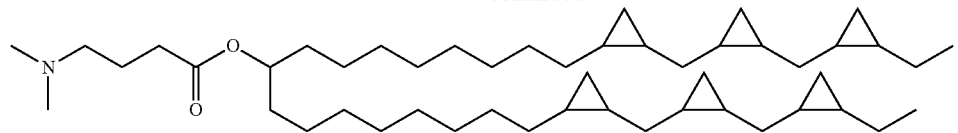

CP-LenMC3

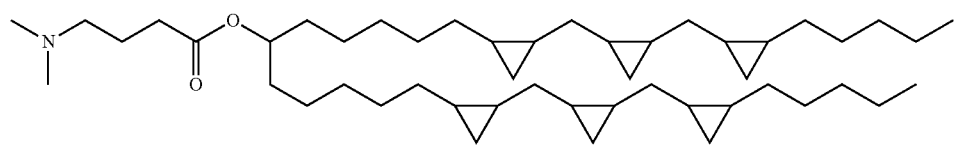

CP-γ-LenMC3

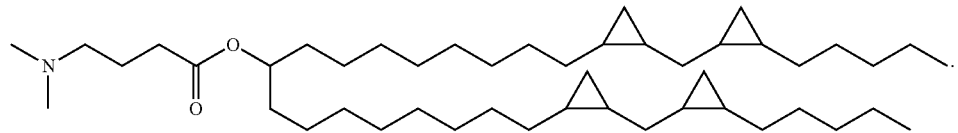

CP-MC3

The synthesis of cationic lipids of Formula XX, including, but not limited to, MC3 Ether (3-((6Z,9Z,28Z,31Z)-heptatriaconta-6,9,28,31-tetraen-19-yloxy)-N,N-dimethylpropan-1-amine; also called dilinoleylmethyl 4-(dimethylamino)propyl ether) and MC4 Ether (4-((6Z,9Z,28Z,31Z)-heptatriaconta-6,9,28,31-tetraen-19-yloxy)-N,N-dimethylbutan-1-amine; also called dilinoleylmethyl 4-(dimethylamino)butyl ether), is described in U.S. Provisional Patent Application No. 61/384,050, entitled "Novel Cationic Lipids and Methods of Use Thereof," filed Sep. 17, 2010, the disclosure of which is herein incorporated by reference in its entirety for all purposes.

In yet another aspect, cationic lipids of Formula XXI having the following structure are useful in the present invention:

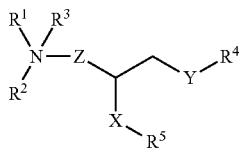

(XXI)

or salts thereof, wherein:

$R^1$ and $R^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof;

$R^3$ is either absent or is hydrogen (H) or a $C_1$-$C_6$ alkyl to provide a quaternary amine;

$R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of $R^4$ and $R^5$ comprises at least 1, 2, 3, 4, 5, 6, or more optionally substituted cyclic alkyl groups (e.g., 1-2, 1-3, 1-4, 1-5, 1-6, 2-3, 2-4, 2-5, or 2-6 optionally substituted cyclic alkyl groups);

X and Y are either the same or different and are independently O, S, N($R^6$), C(O), C(O)O, OC(O), C(O)N($R^6$), N($R^6$)C(O), OC(O)N($R^6$), N($R^6$)C(O)O, C(O)S, C(S)O, S(O), S(O)(O), or C(S), wherein $R^6$ is hydrogen (H) or an optionally substituted $C_1$-$C_6$ alkyl, $C_2$-$C_6$ alkenyl, or $C_2$-$C_6$ alkynyl; and Z is either absent or is an optionally substituted $C_1$-$C_6$ alkyl, $C_2$-$C_6$ alkenyl, or $C_2$-$C_6$ alkynyl.

In some embodiments, $R^1$, $R^2$, and $R^6$ are each independently hydrogen (H) or an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In other embodiments, $R^1$ and $R^2$ are joined to form a heterocyclic ring of 5 carbon atoms and 1 nitrogen atom, wherein the heterocyclic ring can be substituted with a substituent such as a hydroxyl (—OH) group at the ortho, meta, and/or para positions. In particular embodiments, $R^1$ and $R^2$ are both methyl groups. In certain instances, $R^3$ is absent when the pH is above the $pK_a$ of the cationic lipid and $R^3$ is hydrogen (H) when the pH is below the $pK_a$ of the cationic lipid such that the amino head group is protonated. In certain other instances, $R^3$ is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, or $C_5$-$C_6$ alkyl to provide a quaternary amine. In one particular embodiment, X and Y are both oxygen (O).

In other embodiments, $R^4$ and $R^5$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group), wherein at least one of $R^4$ and $R^5$ comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In particular embodiments, one or more of the optionally substituted cyclic alkyl groups present in $R^4$ and/or $R^5$ are independently selected from the group consisting of an optionally substituted saturated cyclic alkyl group, an optionally substituted unsaturated cyclic alkyl group, and combinations thereof. In certain instances, the optionally substituted saturated cyclic alkyl group comprises an optionally substituted $C_{3-8}$ cycloalkyl group (e.g., cyclopropyl, cyclobutyl, cyclopentyl, cyclohexyl, cycloheptyl, cyclooctyl, etc.). In preferred embodiments, the optionally substituted saturated cyclic alkyl group comprises a cyclopropyl group, optionally containing one or more substituents and/or heteroatoms. In other instances, the optionally substituted unsaturated cyclic alkyl group comprises an optionally substituted $C_{3-8}$ cycloalkenyl group (e.g., cyclopropenyl, cyclobutenyl, cyclopentenyl, cyclohexenyl, cycloheptenyl, cyclooctenyl, etc.).

In certain embodiments, one of $R^4$ or $R^5$ comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group, and the other side-chain comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In embodiments where one of $R^4$ or $R^5$ comprises at least 1, 2, 3, 4, 5, or 6 sites of unsaturation, the unsaturated side-chain may comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In other instances, the octadecatrienyl moiety is a linolenyl moiety or a γ-linolenyl moiety. In embodiments where one of $R^4$ or $R^5$ comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl (3,7,11,15-tetramethyl-hexadecanyl) moiety and the branched acyl group comprises a phytanoyl (3,7,11,15-tetramethyl-hexadecanoyl) moiety.

In particular embodiments, $R^4$ and $R^5$ are both independently selected $C_{12}$-$C_{20}$ alkyl groups (i.e., $C_{12}$, $C_{13}$, $C_{14}$, $C_{15}$, $C_{16}$, $C_{17}$, $C_{18}$, $C_{19}$, or $C_{20}$ alkyl groups) having at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In preferred embodiments, $R^4$ and $R^5$ are both $C_{18}$ alkyl groups having at least one, two, three, or more optionally substituted cyclic alkyl groups such as, for example, an optionally substituted $C_{3-8}$ cycloalkyl group (e.g., a cyclopropyl group, optionally containing one or more substituents and/or heteroatoms). In certain embodiments, each of the optionally substituted cyclic alkyl groups is independently selected and can be the same cyclic alkyl group (e.g., all cyclopropyl groups) or different cyclic alkyl groups (e.g., cyclopropyl and other cycloalkyl, heterocycloalkyl, cycloalkenyl, and/or heterocycloalkenyl groups).

In preferred embodiments, the optionally substituted cyclic alkyl groups present in $R^4$ and/or $R^5$ are located at the site(s) of unsaturation in the corresponding unsaturated side-chain. As a non-limiting example, one or both of $R^4$ and $R^5$ are $C_{18}$ alkyl groups having 1, 2, or 3 optionally substituted cyclic alkyl groups, wherein the optionally substituted cyclic alkyl groups (e.g., independently selected cyclopropyl groups) are located at one or more (e.g., all) of the sites of unsaturation present in a corresponding linoleyl moiety, linolenyl moiety, or γ-linolenyl moiety.

In alternative embodiments to the cationic lipid of Formula XXI, $R^4$ and $R^5$ are different and are independently an optionally substituted $C_1$-$C_{24}$ alkyl, $C_2$-$C_{24}$ alkenyl, $C_2$-$C_{24}$ alkynyl, or $C_1$-$C_{24}$ acyl, wherein at least one of $R^4$ and $R^5$ comprises at least one optionally substituted cyclic alkyl group. In certain embodiments, $R^4$ and $R^5$ are different and are independently an optionally substituted $C_4$-$C_{20}$ alkyl, $C_4$-$C_{20}$ alkenyl, $C_4$-$C_{20}$ alkynyl, or $C_4$-$C_{20}$ acyl. In some instances, $R^4$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, and $R^5$ is an optionally substituted $C_4$-$C_{10}$ alkyl, $C_4$-$C_{10}$ alkenyl, $C_4$-$C_{10}$ alkynyl, or $C_4$-$C_{10}$ acyl. In other instances, $R^4$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, and $R^5$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl. In certain instances, $R^4$ is an optionally substituted $C_4$-$C_{10}$ alkyl, $C_4$-$C_{10}$ alkenyl, $C_4$-$C_{10}$ alkynyl, or $C_4$-$C_{10}$ acyl, and $R^5$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl. In certain other instances, $R^4$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl, and $R^5$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl. In particular embodiments, one or more of the optionally substituted cyclic alkyl groups present in $R^4$ and/or $R^5$ are as described above.

In some groups of embodiments to the cationic lipid of Formula XXI, $R^4$ and $R^5$ are either the same or different and are independently selected from the group consisting of:

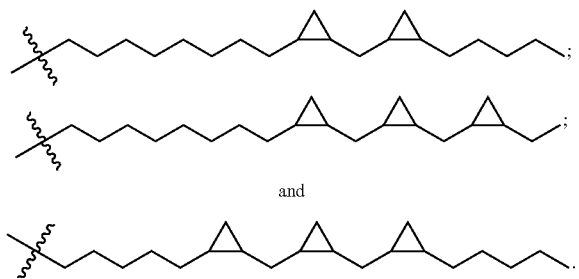

and

In other groups of embodiments to the cationic lipid of Formula XXI, one of $R^4$ or $R^5$ is selected from the group consisting of:

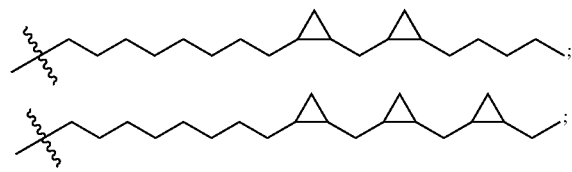

-continued

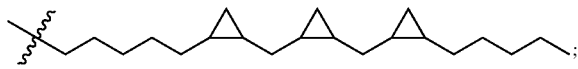

and and the other of R⁴ or R⁵ is selected from the group consisting of:

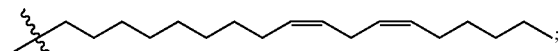

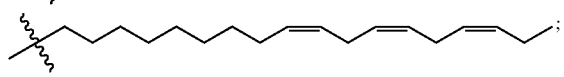

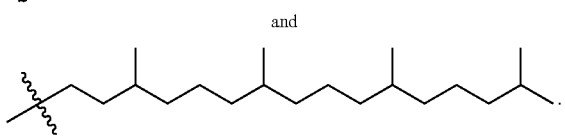

In certain embodiments, Z is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In one particular embodiment, Z is $(CH_2)_n$ and n is 0, 1, 2, 3, 4, 5, or 6 (e.g., 1-2, 1-3, 1-4, 1-5, 1-6, 2-3, 2-4, 2-5, or 2-6). In a preferred embodiment, n is 1. In certain other embodiments, n is 2 or 3.

In particular embodiments, the cationic lipid of Formula XXI has the following structure:

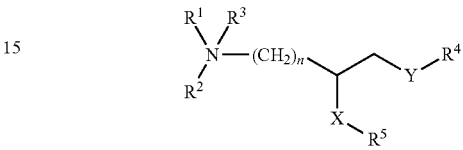

or salts thereof, wherein $R^1$, $R^2$, $R^3$, $R^4$, $R^5$, X, Y, and n are the same as described above.

In some embodiments, the cationic lipid of Formula XXI forms a salt (preferably a crystalline salt) with one or more anions. In one particular embodiment, the cationic lipid of Formula XXI is the oxalate (e.g., hemioxalate) salt thereof, which is preferably a crystalline salt.

In particularly preferred embodiments, the cationic lipid of Formula XXI has one of the following structures:

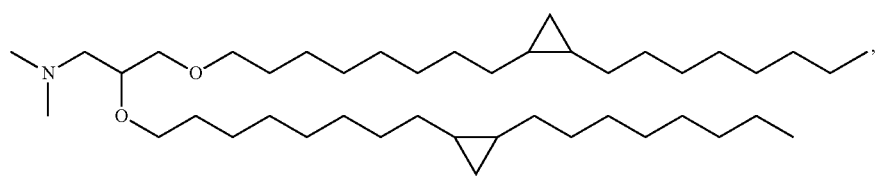

CP-DODMA

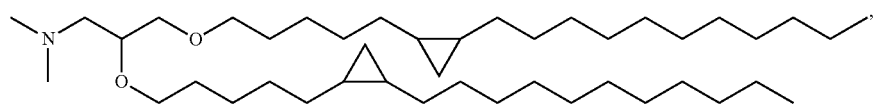

CP-DPetroDMA

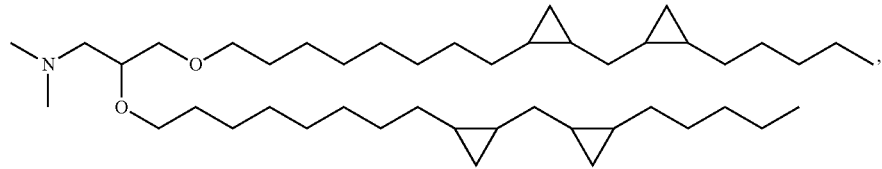

CP-DLinDMA

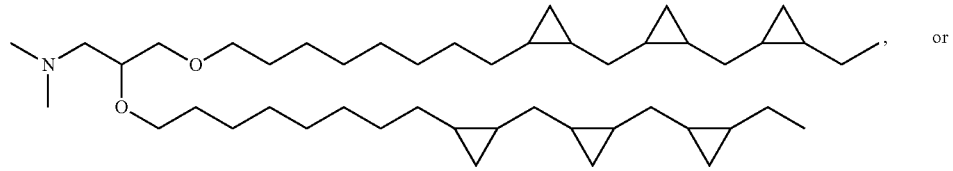

CP-DLenDMA

CP-γDLenDMA

In still yet another aspect, cationic lipids of Formula XXII having the following structure are useful in the present invention:

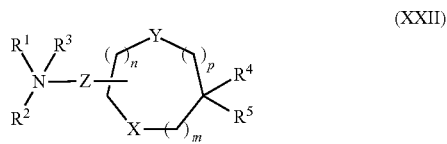

(XXII)

or salts thereof, wherein:
  $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof;
  $R^3$ is either absent or is hydrogen (H) or a $C_1$-$C_6$ alkyl to provide a quaternary amine;
  $R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of $R^4$ and $R^5$ comprises at least 1, 2, 3, 4, 5, 6, or more optionally substituted cyclic alkyl groups (e.g., 1-2, 1-3, 1-4, 1-5, 1-6, 2-3, 2-4, 2-5, or 2-6 optionally substituted cyclic alkyl groups);
  m, n, and p are either the same or different and are independently either 0, 1, or 2, with the proviso that m, n, and p are not simultaneously 0;
  X and Y are either the same or different and are independently O, S, N($R^6$), C(O), C(O)O, OC(O), C(O)N($R^6$), N($R^6$)C(O), OC(O)N($R^6$), N($R^6$)C(O)O, C(O)S, C(S) O, S(O), S(O)(O), or C(S), wherein $R^6$ is hydrogen (H) or an optionally substituted $C_1$-$C_6$ alkyl, $C_2$-$C_6$ alkenyl, or $C_2$-$C_6$ alkynyl; and
  Z is either absent or is an optionally substituted $C_1$-$C_6$ alkyl, $C_2$-$C_6$ alkenyl, or $C_2$-$C_6$ alkynyl.

In some embodiments, $R^1$, $R^2$, and $R^6$ are each independently hydrogen (H) or an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In other embodiments, $R^1$ and $R^2$ are joined to form a heterocyclic ring of 5 carbon atoms and 1 nitrogen atom, wherein the heterocyclic ring can be substituted with a substituent such as a hydroxyl (—OH) group at the ortho, meta, and/or para positions. In particular embodiments, $R^1$ and $R^2$ are both methyl groups. In certain instances, $R^3$ is absent when the pH is above the $pK_a$ of the cationic lipid and $R^3$ is hydrogen (H) when the pH is below the $pK_a$ of the cationic lipid such that the amino head group is protonated. In certain other instances, $R^3$ is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, or $C_5$-$C_6$ alkyl to provide a quaternary amine. In one particular embodiment, X and Y are both oxygen (O).

In other embodiments, $R^4$ and $R^5$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group), wherein at least one of $R^4$ and $R^5$ comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In particular embodiments, one or more of the optionally substituted cyclic alkyl groups present in $R^4$ and/or $R^5$ are independently selected from the group consisting of an optionally substituted saturated cyclic alkyl group, an optionally substituted unsaturated cyclic alkyl group, and combinations thereof. In certain instances, the optionally substituted saturated cyclic alkyl group comprises an optionally substituted $C_{3-8}$ cycloalkyl group (e.g., cyclopropyl, cyclobutyl, cyclopentyl, cyclohexyl, cycloheptyl, cyclooctyl, etc.). In preferred embodiments, the optionally substituted saturated cyclic alkyl group comprises a cyclopropyl group, optionally containing one or more substituents and/or heteroatoms. In other instances, the optionally substituted unsaturated cyclic alkyl group comprises an optionally substituted $C_{3-8}$ cycloalkenyl group (e.g., cyclopropenyl, cyclobutenyl, cyclopentenyl, cyclohexenyl, cycloheptenyl, cyclooctenyl, etc.).

In certain embodiments, one of $R^4$ or $R^5$ comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group, and the other side-chain comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In embodiments where one of $R^4$ or $R^5$ comprises at least 1, 2, 3, 4, 5, or 6 sites of unsaturation, the unsaturated side-chain may comprise a myristoleyl moiety, a palmitoleyl moiety, an oleyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., linoleoyl, linolenoyl, γ-linolenoyl, etc.). In some instances, the octadecadienyl moiety is a linoleyl moiety. In other instances, the octadecatrienyl moiety is a linolenyl moiety or a γ-linolenyl moiety. In embodiments where one of $R^4$ or $R^5$ comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl (3,7,11,15-tetramethyl-hexadecanyl) moiety and the branched acyl group comprises a phytanoyl (3,7,11,15-tetramethyl-hexadecanoyl) moiety.

In particular embodiments, $R^4$ and $R^5$ are both independently selected $C_{12}$-$C_{20}$ alkyl groups (i.e., $C_{12}$, $C_{13}$, $C_{14}$, $C_{15}$, $C_{16}$, $C_{17}$, $C_{18}$, $C_{19}$, or $C_{20}$ alkyl groups) having at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In preferred embodiments, $R^4$ and $R^5$ are both $C_{18}$ alkyl groups having at least one, two, three, or more optionally substituted cyclic alkyl groups such as, for example, an optionally substituted $C_{3-8}$ cycloalkyl group (e.g., a cyclopropyl group, optionally containing one or more substituents and/or heteroatoms). In certain embodiments, each of the optionally substituted cyclic alkyl groups is independently selected and can be the same cyclic alkyl group (e.g., all cyclopropyl groups) or different cyclic alkyl groups (e.g., cyclopropyl and other cycloalkyl, heterocycloalkyl, cycloalkenyl, and/or heterocycloalkenyl groups).

In preferred embodiments, the optionally substituted cyclic alkyl groups present in $R^4$ and/or $R^5$ are located at the site(s) of unsaturation in the corresponding unsaturated sidechain. As a non-limiting example, one or both of $R^4$ and $R^5$ are $C_{18}$ alkyl groups having 1, 2, or 3 optionally substituted cyclic alkyl groups, wherein the optionally substituted cyclic alkyl groups (e.g., independently selected cyclopropyl groups) are located at one or more (e.g., all) of the sites of unsaturation present in a corresponding linoleyl moiety, linolenyl moiety, or γ-linolenyl moiety.

In alternative embodiments to the cationic lipid of Formula XXII, $R^4$ and $R^5$ are different and are independently an optionally substituted $C_1$-$C_{24}$ alkyl, $C_2$-$C_{24}$ alkenyl, $C_2$-$C_{24}$ alkynyl, or $C_1$-$C_{24}$ acyl, wherein at least one of $R^4$ and $R^5$ comprises at least one optionally substituted cyclic alkyl group. In certain embodiments, $R^4$ and $R^5$ are different and are independently an optionally substituted $C_4$-$C_{20}$ alkyl, $C_4$-$C_{20}$ alkenyl, $C_4$-$C_{20}$ alkynyl, or $C_4$-$C_{20}$ acyl. In some instances, $R^4$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, and $R^5$ is an optionally substituted $C_4$-$C_{10}$ alkyl, $C_4$-$C_{10}$ alkenyl, $C_4$-$C_{10}$ alkynyl, or $C_4$-$C_{10}$ acyl. In other instances, $R^4$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, and $R^5$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl. In certain instances, $R^4$ is an optionally substituted $C_4$-$C_{10}$ alkyl, $C_4$-$C_{10}$ alkenyl, $C_4$-$C_{10}$ alkynyl, or $C_4$-$C_{10}$ acyl, and $R^5$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl. In certain other instances, $R^4$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl, and $R^5$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl. In particular embodiments, one or more of the optionally substituted cyclic alkyl groups present in $R^4$ and/or $R^5$ are as described above.

In some groups of embodiments to the cationic lipid of Formula XXII, $R^4$ and $R^5$ are either the same or different and are independently selected from the group consisting of:

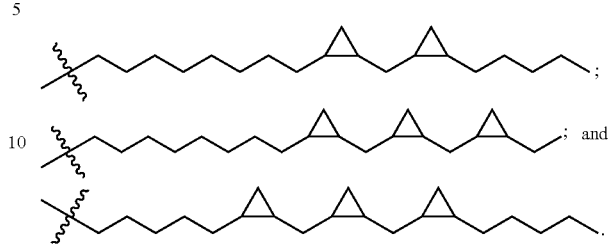

In other groups of embodiments to the cationic lipid of Formula XXII, one of $R^4$ or $R^5$ is selected from the group consisting of:

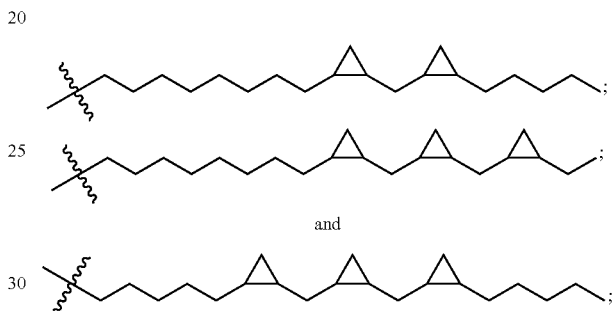

and the other of $R^4$ or $R^5$ is selected from the group consisting of:

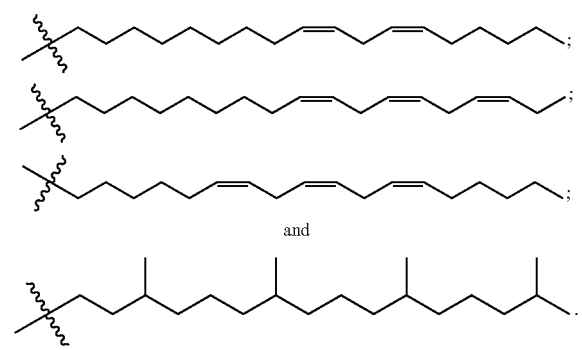

In certain embodiments, Z is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In one particular embodiment, Z is $(CH_2)_q$ and q is 0, 1, 2, 3, 4, 5, or 6 (e.g., 1-2, 1-3, 1-4, 1-5, 1-6, 2-3, 2-4, 2-5, or 2-6). In a preferred embodiment, q is 2. In certain other embodiments, q is 1 or 3.

In particular embodiments, the cationic lipid of Formula XXII has the following structure:

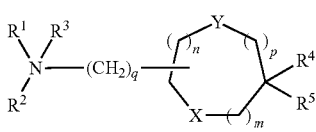

or salts thereof, wherein $R^1$, $R^2$, $R^3$, $R^4$, $R^5$, X, Y, m, n, p, and q are the same as described above.

In some embodiments, the cationic lipid of Formula XXII forms a salt (preferably a crystalline salt) with one or more anions. In one particular embodiment, the cationic lipid of Formula XXII is the oxalate (e.g., hemioxalate) salt thereof, which is preferably a crystalline salt.

In particularly preferred embodiments, the cationic lipid of Formula XXII has one of the following structures:

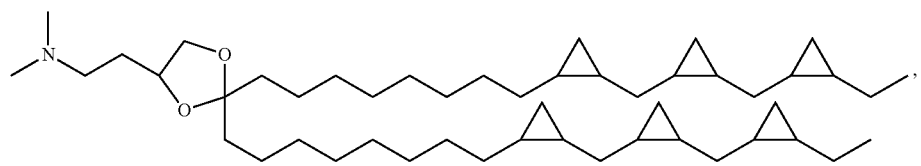

CP-DLen-C2K-DMA

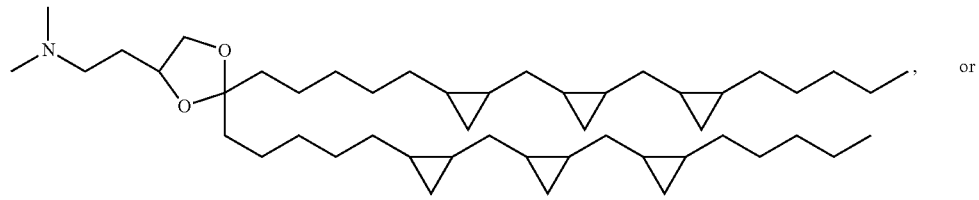

CP-γDLen-C2K-DMA

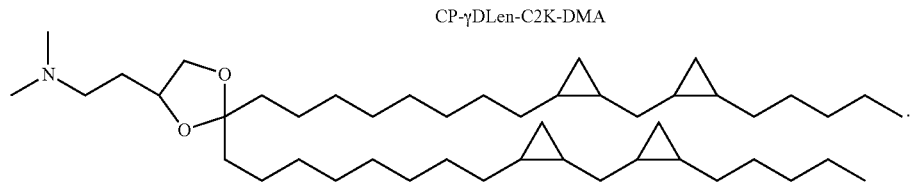

CP-C2K-DMA

The synthesis of cationic lipids of Formula XXI and XXII, as well as additional cyclic cationic lipids, is described in U.S. Provisional Patent Application No. 61/334,096, entitled "Novel Cyclic Cationic Lipids and Methods of Use Thereof," filed May 12, 2010, the disclosure of which is herein incorporated by reference in its entirety for all purposes.

In preferred embodiments, the cationic lipid component of the nucleic acid-lipid particles (e.g., SNALP) described herein comprises one or a mixture of two, three, four, or more cationic lipids of Formulas I-XXII. Examples of preferred cationic lipids include, but are not limited to, DLinDMA, DLenDMA, γ-DLenDMA, DLin-K-C2-DMA, DLin-K-DMA, DLin-M-C3-DMA, MC3 Ether, MC4 Ether, and a mixture thereof.

In certain instances, other cationic lipids (e.g., saturated, monounsaturated, and/or polyunsaturated cationic lipids) or salts thereof may be included in the lipid particles of the present invention. Such cationic lipids include, but are not limited to, 1,2-dioeylcarbamoyloxy-3-dimethylaminopropane (DO-C-DAP), 1,2-dimyristoleoyl-3-dimethylaminopropane (DMDAP), 1,2-dioleoyl-3-trimethylaminopropane chloride (DOTAP.Cl), dilinoleylmethyl-3-dimethylaminopropionate (DLin-M-K-DMA; also known as DLin-M-DMA, DLin-M-C2-DMA, or MC2), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethyl-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin- TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), and mixtures thereof.

The synthesis of cationic lipids such as DO-C-DAP, DMDAP, DOTAP.Cl, DLin-M-K-DMA, as well as additional cationic lipids, is described in PCT Publication No. WO 2010/042877, the disclosure of which is incorporated herein by reference in its entirety for all purposes.

The synthesis of cationic lipids such as DLin-C-DAP, DLinDAC, DLinMA, DLinDAP, DLin-S-DMA, DLin-2-DMAP, DLinTMA.Cl, DLinTAP.Cl, DLinMPZ, DLinAP, DOAP, and DLin-EG-DMA, as well as additional cationic lipids, is described in PCT Publication No. WO 09/086,558, the disclosure of which is herein incorporated by reference in its entirety for all purposes.

The synthesis of cationic lipids such as CLinDMA, as well as additional cationic lipids, is described in U.S. Patent Publication No. 20060240554, the disclosure of which is herein incorporated by reference in its entirety for all purposes.

The synthesis of a number of other cationic lipids and related analogs has been described in U.S. Pat. Nos. 5,208,036; 5,264,618; 5,279,833; 5,283,185; 5,753,613; and 5,785,992; and PCT Publication No. WO 96/10390, the disclosures of which are each herein incorporated by reference in their entirety for all purposes. Additionally, a number of commercial preparations of cationic lipids can be used, such as, e.g., LIPOFECTIN® (including DOTMA and DOPE, available from GIBCO/BRL); LIPOFECTAMINE® (including DOSPA and DOPE, available from GIBCO/BRL); and TRANSFECTAM® (including DOGS, available from Promega Corp.).

In some embodiments, the cationic lipid comprises from about 45 mol % to about 90 mol %, from about 45 mol % to about 85 mol %, from about 45 mol % to about 80 mol %, from about 45 mol % to about 75 mol %, from about 45 mol % to about 70 mol %, from about 45 mol % to about 65 mol %, from about 45 mol % to about 60 mol %, from about 45 mol % to about 55 mol %, from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, from about 50 mol % to about 60 mol %, from about 55 mol % to about 65 mol % or from about 55 mol % to about 70 mol % (or any fraction thereof or range therein) of the total lipid present in the particle.

In certain preferred embodiments, the cationic lipid comprises from about 50 mol % to about 58 mol %, from about 51 mol % to about 59 mol %, from about 51 mol % to about 58 mol %, from about 51 mol % to about 57 mol %, from about 52 mol % to about 58 mol %, from about 52 mol % to about 57 mol %, from about 52 mol % to about 56 mol %, or from about 53 mol % to about 55 mol % (or any fraction thereof or range therein) of the total lipid present in the particle. In particular embodiments, the cationic lipid comprises about 50 mol %, 51 mol %, 52 mol %, 53 mol %, 54 mol %, 55 mol %, 56 mol %, 57 mol %, 58 mol %, 59 mol %, 60 mol %, 61 mol %, 62 mol %, 63 mol %, 64 mol %, or 65 mol % (or any fraction thereof or range therein) of the total lipid present in the particle. In certain other embodiments, the cationic lipid comprises (at least) about 66, 67, 68, 69, 70, 71, 72, 73, 74, 75, 76, 77, 78, 79, 80, 81, 82, 83, 84, 85, 86, 87, 88, 89, or 90 mol % (or any fraction thereof or range therein) of the total lipid present in the particle.

In additional embodiments, the cationic lipid comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % (or any fraction thereof or range therein) of the total lipid present in the particle.

Additional percentages and ranges of cationic lipids suitable for use in the lipid particles of the present invention are described in PCT Publication No. WO 09/127,060, U.S. application Ser. No. 12/794,701, filed Jun. 4, 2010, and U.S. application Ser. No. 12/828,189, filed Jun. 30, 2010, the disclosures of which are herein incorporated by reference in their entirety for all purposes.

It should be understood that the percentage of cationic lipid present in the lipid particles of the invention is a target amount, and that the actual amount of cationic lipid present in the formulation may vary, for example, by ±5 mol %. For example, in the 1:57 lipid particle (e.g., SNALP) formulation, the target amount of cationic lipid is 57.1 mol %, but the actual amount of cationic lipid may be ±5 mol %, ±4 mol %, ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle). Similarly, in the 7:54 lipid particle (e.g., SNALP) formulation, the target amount of cationic lipid is 54.06 mol %, but the actual amount of cationic lipid may be ±5 mol %, ±4 mol %, ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

2. Non-Cationic Lipids

The non-cationic lipids used in the lipid particles of the invention (e.g., SNALP) can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5α-cholestanol, 5β-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5β-cholestanone, and cholesteryl decanoate; and mixtures thereof. In preferred embodiments, the cholesterol derivative is a polar analogue such as cholesteryl-(4'-hydroxy)-butyl ether. The synthesis of cholesteryl-(2'-hydroxy)-ethyl ether is described in PCT Publication No. WO 09/127,060, the disclosure of which is herein incorporated by reference in its entirety for all purposes.

In some embodiments, the non-cationic lipid present in the lipid particles (e.g., SNALP) comprises or consists of a mixture of one or more phospholipids and cholesterol or a derivative thereof. In other embodiments, the non-cationic lipid present in the lipid particles (e.g., SNALP) comprises or consists of one or more phospholipids, e.g., a cholesterol-free lipid particle formulation. In yet other embodiments, the non-cationic lipid present in the lipid particles (e.g., SNALP) comprises or consists of cholesterol or a derivative thereof, e.g., a phospholipid-free lipid particle formulation.

Other examples of non-cationic lipids suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

In some embodiments, the non-cationic lipid comprises from about 10 mol % to about 60 mol %, from about 20 mol % to about 55 mol %, from about 20 mol % to about 45 mol %, from about 20 mol % to about 40 mol %, from about 25 mol % to about 50 mol %, from about 25 mol % to about 45 mol %, from about 30 mol % to about 50 mol %, from about 30 mol % to about 45 mol %, from about 30 mol % to about 40 mol %, from about 35 mol % to about 45 mol %, from about 37 mol % to about 42 mol %, or about 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to about 40 mol %, 45 mol %, 50 mol %, 55 mol %, or 60 mol % of the total lipid present in the particle.

In some embodiments, the phospholipid component in the mixture may comprise from about 2 mol % to about 20 mol %, from about 2 mol % to about 15 mol %, from about 2 mol % to about 12 mol %, from about 4 mol % to about 15 mol %, or from about 4 mol % to about 10 mol % (or any fraction thereof or range therein) of the total lipid present in the particle. In certain preferred embodiments, the phospholipid component in the mixture comprises from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. As a non-limiting example, a 1:57 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 34 mol % (or any fraction thereof) of the total lipid present in the particle. As another non-limiting example, a 7:54 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 32 mol % (or any fraction thereof) of the total lipid present in the particle.

In other embodiments, the cholesterol component in the mixture may comprise from about 25 mol % to about 45 mol %, from about 25 mol % to about 40 mol %, from about 30 mol % to about 45 mol %, from about 30 mol % to about 40 mol %, from about 27 mol % to about 37 mol %, from about 25 mol % to about 30 mol %, or from about 35 mol % to about 40 mol % (or any fraction thereof or range therein) of the total lipid present in the particle. In certain preferred embodiments, the cholesterol component in the mixture comprises from about 25 mol % to about 35 mol %, from about 27 mol % to about 35 mol %, from about 29 mol % to about 35 mol %, from about 30 mol % to about 35 mol %, from about 30 mol % to about 34 mol %, from about 31 mol % to about 33 mol %, or about 30 mol %, 31 mol %, 32 mol %, 33 mol %, 34 mol %, or 35 mol % (or any fraction thereof or range therein) of the total lipid present in the particle. In other embodiments, the cholesterol component in the mixture comprises about 36, 37, 38, 39, 40, 41, 42, 43, 44, or 45 mol % (or any fraction thereof or range therein) of the total lipid present in the particle. Typically, a 1:57 lipid particle formulation comprising a mixture of phospholipid and cholesterol may comprise cholesterol or a cholesterol derivative at about 34 mol % (or any fraction thereof), e.g., in a mixture with a phospholipid such as DPPC or DSPC at about 7 mol % (or any fraction thereof) of the total lipid present in the particle. Typically, a 7:54 lipid particle formulation comprising a mixture of phospholipid and cholesterol may comprise cholesterol or a cholesterol derivative at about 32 mol % (or any fraction thereof), e.g., in a mixture with a phospholipid such as DPPC or DSPC at about 7 mol % (or any fraction thereof) of the total lipid present in the particle.

In embodiments where the lipid particles are phospholipid-free, the cholesterol or derivative thereof may comprise up to about 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle formulation may comprise from about 25 mol % to about 45 mol %, from about 25 mol % to about 40 mol %, from about 30 mol % to about 45 mol %, from about 30 mol % to about 40 mol %, from about 31 mol % to about 39 mol %, from about 32 mol % to about 38 mol %, from about 33 mol % to about 37 mol %, from about 35 mol % to about 45 mol %, from about 30 mol % to about 35 mol %, from about 35 mol % to about 40 mol %, or about 30 mol %, 31 mol %, 32 mol %, 33 mol %, 34 mol %, 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle. As a non-limiting example, a 1:62 lipid particle formulation may comprise cholesterol at about 37 mol % (or any fraction thereof) of the total lipid present in the particle. As another non-limiting example, a 7:58 lipid particle formulation may comprise cholesterol at about 35 mol % (or any fraction thereof) of the total lipid present in the particle.

In other embodiments, the non-cationic lipid comprises from about 5 mol % to about 90 mol %, from about 10 mol % to about 85 mol %, from about 20 mol % to about 80 mol %, about 10 mol % (e.g., phospholipid only), or about 60 mol %

(e.g., phospholipid and cholesterol or derivative thereof) (or any fraction thereof or range therein) of the total lipid present in the particle.

Additional percentages and ranges of non-cationic lipids suitable for use in the lipid particles of the present invention are described in PCT Publication No. WO 09/127,060, U.S. application Ser. No. 12/794,701, filed Jun. 4, 2010, and U.S. application Ser. No. 12/828,189, filed Jun. 30, 2010, the disclosures of which are herein incorporated by reference in their entirety for all purposes.

It should be understood that the percentage of non-cationic lipid present in the lipid particles of the invention is a target amount, and that the actual amount of non-cationic lipid present in the formulation may vary, for example, by ±5 mol %. For example, in the 1:57 lipid particle (e.g., SNALP) formulation, the target amount of phospholipid is 7.1 mol % and the target amount of cholesterol is 34.3 mol %, but the actual amount of phospholipid may be ±2 mol %, ±1.5 mol %, ±1 mol %, ±0.75 mol %, ±0.5 mol %, ±0.25 mol %, or ±0.1 mol % of that target amount, and the actual amount of cholesterol may be ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle). Similarly, in the 7:54 lipid particle (e.g., SNALP) formulation, the target amount of phospholipid is 6.75 mol % and the target amount of cholesterol is 32.43 mol %, but the actual amount of phospholipid may be ±2 mol %, ±1.5 mol %, ±1 mol %, ±0.75 mol %, ±0.5 mol %, ±0.25 mol %, or ±0.1 mol % of that target amount, and the actual amount of cholesterol may be ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

3. Lipid Conjugates

In addition to cationic and non-cationic lipids, the lipid particles of the invention (e.g., SNALP) may further comprise a lipid conjugate. The conjugated lipid is useful in that it prevents the aggregation of particles. Suitable conjugated lipids include, but are not limited to, PEG-lipid conjugates, POZ-lipid conjugates, ATTA-lipid conjugates, cationic-polymer-lipid conjugates (CPLs), and mixtures thereof. In certain embodiments, the lipid particles comprise either a PEG-lipid conjugate or an ATTA-lipid conjugate together with a CPL. The term "ATTR" or "polyamide" includes, without limitation, compounds described in U.S. Pat. Nos. 6,320,017 and 6,586,559, the disclosures of which are herein incorporated by reference in their entirety for all purposes.

In a preferred embodiment, the lipid conjugate is a PEG-lipid. Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof. The disclosures of these patent documents are herein incorporated by reference in their entirety for all purposes.

Additional PEG-lipids suitable for use in the invention include, without limitation, mPEG2000-1,2-di-O-alkyl-sn3-carbomoylglyceride (PEG-C-DOMG). The synthesis of PEG-C-DOMG is described in PCT Publication No. WO 09/086,558, the disclosure of which is herein incorporated by reference in its entirety for all purposes. Yet additional suitable PEG-lipid conjugates include, without limitation, 1-[8'-(1,2-dimyristoyl-3-propanoxy)-carboxamido-3',6'-dioxaoctanyl]carbamoyl-w-methyl-poly(ethylene glycol) (2 KPEG-DMG). The synthesis of 2 KPEG-DMG is described in U.S. Pat. No. 7,404,969, the disclosure of which is herein incorporated by reference in its entirety for all purposes.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, but are not limited to, the following: monomethoxypolyethylene glycol (MePEG-OH), monomethoxypolyethylene glycol-succinate (MePEG-S), monomethoxypolyethylene glycol-succinimidyl succinate (MePEG-S—NHS), monomethoxypolyethylene glycol-amine (MePEG-NH$_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S—NHS, HO-PEG-NH$_2$, etc.). Other PEGs such as those described in U.S. Pat. Nos. 6,774,180 and 7,053,150 (e.g., mPEG (20 KDa) amine) are also useful for preparing the PEG-lipid conjugates of the present invention. The disclosures of these patents are herein incorporated by reference in their entirety for all purposes. In addition, monomethoxypolyethyleneglycol-acetic acid (Me-PEG-CH$_2$COOH) is particularly useful for preparing PEG-lipid conjugates including, e.g., PEG-DAA conjugates.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In other instances, the PEG moiety has an average molecular weight of from about 550 daltons to about 1000 daltons, from about 250 daltons to about 1000 daltons, from about 400 daltons to about 1000 daltons, from about 600 daltons to about 900 daltons, from about 700 daltons to about 800 daltons, or about 200, 250, 300, 350, 400, 450, 500, 550, 600, 650, 700, 750, 800, 850, 900, 950, or 1000 daltons. In preferred embodiments, the PEG moiety has an average molecular weight of about 2,000 daltons or about 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skilled in the art. Phosphatidyl-ethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

The term "diacylglycerol" or "DAG" includes a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl ($C_{12}$), myristoyl ($C_{14}$), palmitoyl ($C_{16}$), stearoyl ($C_{18}$), and icosoyl ($C_{20}$). In preferred embodiments, $R^1$ and $R^2$ are the same, i.e., $R^1$ and $R^2$ are both myristoyl (i.e., dimyristoyl), $R^1$ and $R^2$ are both stearoyl (i.e., distearoyl), etc. Diacylglycerols have the following general formula:

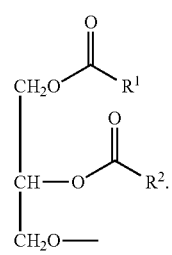

(XXIII)

The term "dialkyloxypropyl" or "DAA" includes a compound having 2 alkyl chains, $R^1$ and $R^2$, both of which have independently between 2 and 30 carbons. The alkyl groups can be saturated or have varying degrees of unsaturation. Dialkyloxypropyls have the following general formula:

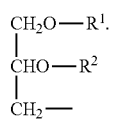

(XXIV)

In a preferred embodiment, the PEG-lipid is a PEG-DAA conjugate having the following formula:

(XXV)

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, decyl ($C_{10}$), lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula XXV above, the PEG has an average molecular weight ranging from about 550 daltons to about 10,000 daltons. In certain instances, the PEG has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In other instances, the PEG moiety has an average molecular weight of from about 550 daltons to about 1000 daltons, from about 250 daltons to about 1000 daltons, from about 400 daltons to about 1000 daltons, from about 600 daltons to about 900 daltons, from about 700 daltons to about 800 daltons, or about 200, 250, 300, 350, 400, 450, 500, 550, 600, 650, 700, 750, 800, 850, 900, 950, or 1000 daltons. In preferred embodiments, the PEG has an average molecular weight of about 2,000 daltons or about 750 daltons. The PEG can be optionally substituted with alkyl, alkoxy, acyl, or aryl groups. In certain embodiments, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

In particular embodiments, the PEG-lipid conjugate is selected from:

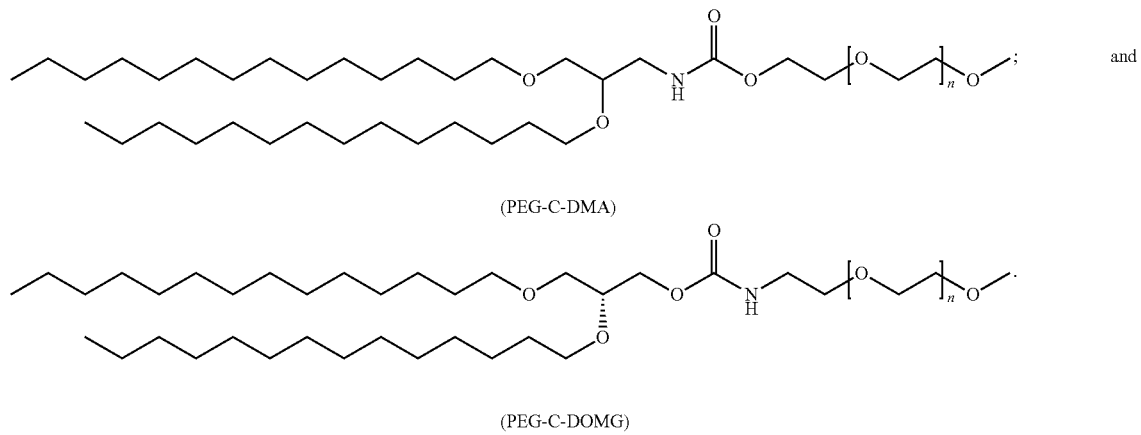

(PEG-C-DMA)

(PEG-C-DOMG)

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992); Larock, COMPREHENSIVE ORGANIC TRANSFORMATIONS (VCH 1989); and Furniss, VOGEL'S TEXTBOOK OF PRACTICAL ORGANIC CHEMISTRY, 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of about 750 or about 2,000 daltons. In one particularly preferred embodiment, the PEG-lipid conjugate comprises PEG2000-C-DMA, wherein the "2000" denotes the average molecular weight of the PEG, the "C" denotes a carbamate linker moiety, and the "DMA" denotes dimyristyloxypropyl. In another particularly preferred embodiment, the PEG-lipid conjugate comprises PEG750-C-DMA, wherein the "750" denotes the average molecular weight of the PEG, the "C" denotes a carbamate linker moiety, and the "DMA" denotes dimyristyloxypropyl. In particular embodiments, the terminal hydroxyl group of the PEG is substituted with a methyl group. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In addition to the foregoing components, the lipid particles (e.g., SNALP) of the present invention can further comprise cationic poly(ethylene glycol) (PEG) lipids or CPLs (see, e.g., Chen et al., Bioconj. Chem., 11:433-437 (2000); U.S. Pat. No. 6,852,334; PCT Publication No. WO 00/62813, the disclosures of which are herein incorporated by reference in their entirety for all purposes).

In some embodiments, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle.

In other embodiments, the lipid conjugate (e.g., PEG-lipid) comprises from about 0 mol % to about 20 mol %, from about 0.5 mol % to about 20 mol %, from about 2 mol % to about 20 mol %, from about 1.5 mol % to about 18 mol %, from about 2 mol % to about 15 mol %, from about 4 mol % to about 15 mol %, from about 2 mol % to about 12 mol %, from about 5 mol % to about 12 mol %, or about 2 mol % (or any fraction thereof or range therein) of the total lipid present in the particle.

In further embodiments, the lipid conjugate (e.g., PEG-lipid) comprises from about 4 mol % to about 10 mol %, from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle.

Additional examples, percentages, and/or ranges of lipid conjugates suitable for use in the lipid particles of the invention are described in PCT Publication No. WO 09/127,060, U.S. application Ser. No. 12/794,701, filed Jun. 4, 2010, U.S. application Ser. No. 12/828,189, filed Jun. 30, 2010, U.S. Provisional Application No. 61/294,828, filed Jan. 13, 2010, U.S. Provisional Application No. 61/295, 140, filed Jan. 14, 2010, and PCT Publication No. WO 2010/006282, the disclosures of which are herein incorporated by reference in their entirety for all purposes.

It should be understood that the percentage of lipid conjugate (e.g., PEG-lipid) present in the lipid particles of the invention is a target amount, and that the actual amount of lipid conjugate present in the formulation may vary, for example, by ±2 mol %. For example, in the 1:57 lipid particle (e.g., SNALP) formulation, the target amount of lipid conjugate is 1.4 mol %, but the actual amount of lipid conjugate may be ±0.5 mol %, ±0.4 mol %, ±0.3 mol %, ±0.2 mol %, ±0.1 mol %, or ±0.05 mol % of that target amount, with the balance of the formulation being made up of other lipid components (adding up to 100 mol % of total lipids present in the particle). Similarly, in the 7:54 lipid particle (e.g., SNALP) formulation, the target amount of lipid conjugate is 6.76 mol %, but the actual amount of lipid conjugate may be ±2 mol %, ±1.5 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. For instance, when a PEG-DAA conjugate is used as the lipid conjugate, the rate at which the lipid particle becomes fusogenic can be varied, for example, by varying the concentration of the lipid conjugate, by varying the molecular weight of the PEG, or by varying the chain length and degree of saturation of the alkyl groups on the PEG-DAA conjugate. In addition, other variables including, for example, pH, temperature, ionic strength, etc. can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle (e.g., SNALP) size.

B. Additional Carrier Systems

Non-limiting examples of additional lipid-based carrier systems suitable for use in the present invention include lipoplexes (see, e.g., U.S. Patent Publication No. 20030203865; and Zhang et al., *J. Control Release*, 100:165-180 (2004)), pH-sensitive lipoplexes (see, e.g., U.S. Patent Publication No. 20020192275), reversibly masked lipoplexes (see, e.g., U.S. Patent Publication Nos. 20030180950), cationic lipid-based compositions (see, e.g., U.S. Pat. No. 6,756,054; and U.S. Patent Publication No. 20050234232), cationic liposomes (see, e.g., U.S. Patent Publication Nos. 20030229040, 20020160038, and 20020012998; U.S. Pat. No. 5,908,635; and PCT Publication No. WO 01/72283), anionic liposomes (see, e.g., U.S. Patent Publication No. 20030026831), pH-sensitive liposomes (see, e.g., U.S. Patent Publication No. 20020192274; and AU 2003210303), antibody-coated liposomes (see, e.g., U.S. Patent Publication No. 20030108597; and PCT Publication No. WO 00/50008), cell-type specific liposomes (see, e.g., U.S. Patent Publication No. 20030198664), liposomes containing nucleic acid and peptides (see, e.g., U.S. Pat. No. 6,207,456), liposomes containing lipids derivatized with releasable hydrophilic polymers (see, e.g., U.S. Patent Publication No. 20030031704), lipid-entrapped nucleic acid (see, e.g., PCT Publication Nos. WO 03/057190 and WO 03/059322), lipid-encapsulated nucleic acid (see, e.g., U.S. Patent Publication No. 20030129221; and U.S. Pat. No. 5,756,122), other liposomal compositions (see, e.g., U.S. Patent Publication Nos. 20030035829 and 20030072794; and U.S. Pat. No. 6,200,599), stabilized mixtures of liposomes and emulsions (see, e.g., EP1304160), emulsion compositions (see, e.g., U.S. Pat. No. 6,747,014), and nucleic acid micro-emulsions (see, e.g., U.S. Patent Publication No. 20050037086).

Examples of polymer-based carrier systems suitable for use in the present invention include, but are not limited to, cationic polymer-nucleic acid complexes (i.e., polyplexes). To form a polyplex, a nucleic acid (e.g., interfering RNA) is typically complexed with a cationic polymer having a linear, branched, star, or dendritic polymeric structure that condenses the nucleic acid into positively charged particles capable of interacting with anionic proteoglycans at the cell surface and entering cells by endocytosis. In some embodiments, the polyplex comprises nucleic acid (e.g., interfering RNA) complexed with a cationic polymer such as polyethylenimine (PEI) (see, e.g., U.S. Pat. No. 6,013,240; commercially available from Qbiogene, Inc. (Carlsbad, Calif.) as In vivo jetPEI™, a linear form of PEI), polypropylenimine (PPI), polyvinylpyrrolidone (PVP), poly-L-lysine (PLL), diethylaminoethyl (DEAE)-dextran, poly(β-amino ester) (PAE) polymers (see, e.g., Lynn et al., *J. Am. Chem. Soc.*, 123:8155-8156 (2001)), chitosan, polyamidoamine (PAMAM) dendrimers (see, e.g., Kukowska-Latallo et al., *Proc. Natl. Acad. Sci. USA*, 93:4897-4902 (1996)), porphyrin (see, e.g., U.S. Pat. No. 6,620,805), polyvinylether (see, e.g., U.S. Patent Publication No. 20040156909), polycyclic amidinium (see, e.g., U.S. Patent Publication No. 20030220289), other polymers comprising primary amine, imine, guanidine, and/or imidazole groups (see, e.g., U.S. Pat. No. 6,013,240; PCT Publication No. WO/9602655; PCT Publication No. WO95/21931; Zhang et al., *J. Control Release*, 100:165-180 (2004); and Tiera et al., *Curr. Gene Ther.*, 6:59-71 (2006)), and a mixture thereof. In other embodiments, the polyplex comprises cationic polymer-nucleic acid complexes as described in U.S. Patent Publication Nos. 20060211643, 20050222064, 20030125281, and 20030185890, and PCT Publication No. WO 03/066069; biodegradable poly(β-amino ester) polymer-nucleic acid complexes as described in U.S. Patent Publication No. 20040071654; microparticles containing polymeric matrices as described in U.S. Patent Publication No. 20040142475; other microparticle compositions as described in U.S. Patent Publication No. 20030157030; condensed nucleic acid complexes as described in U.S. Patent Publication No. 20050123600; and nanocapsule and microcapsule compositions as described in AU 2002358514 and PCT Publication No. WO 02/096551.

In certain instances, the interfering RNA may be complexed with cyclodextrin or a polymer thereof. Non-limiting examples of cyclodextrin-based carrier systems include the cyclodextrin-modified polymer-nucleic acid complexes described in U.S. Patent Publication No. 20040087024; the linear cyclodextrin copolymer-nucleic acid complexes described in U.S. Pat. Nos. 6,509,323, 6,884,789, and 7,091,192; and the cyclodextrin polymer-complexing agent-nucleic acid complexes described in U.S. Pat. No. 7,018,609. In certain other instances, the interfering RNA may be complexed with a peptide or polypeptide. An example of a protein-based carrier system includes, but is not limited to, the cationic oligopeptide-nucleic acid complex described in PCT Publication No. WO95/21931.

VI. Preparation of Lipid Particles

The lipid particles of the present invention, e.g., SNALP, in which a nucleic acid such as an interfering RNA (e.g., siRNA)

is entrapped within the lipid portion of the particle and is protected from degradation, can be formed by any method known in the art including, but not limited to, a continuous mixing method, a direct dilution process, and an in-line dilution process. In certain embodiments, one or more antioxidants such as metal chelators (e.g., EDTA), primary antioxidants, and/or secondary antioxidants may be included at any step or at multiple steps in the process (e.g., prior to, during, and/or after lipid particle formation) as described in PCT Application No. PCT/CA2010/001919, the disclosure of which is herein incorporated by reference in its entirety for all purposes.

In particular embodiments, the cationic lipids may comprise at least one, two, three, four, five, or more cationic lipids such as those set forth in Formulas I-XXII or salts thereof, alone or in combination with other cationic lipid species. In other embodiments, the non-cationic lipids may comprise one, two, or more lipids including egg sphingomyelin (ESM), distearoylphosphatidylcholine (DSPC), dioleoylphosphatidylcholine (DOPC), 1-palmitoyl-2-oleoyl-phosphatidylcholine (POPC), dipalmitoyl-phosphatidylcholine (DPPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1 PE (1-stearoyl-2-oleoyl-phosphatidylethanolamine (SOPE)), 16:0-18:1 PE (1-palmitoyl-2-oleoyl-phosphatidylethanolamine (POPE)), polyethylene glycol-based polymers (e.g., PEG 2000, PEG 5000, PEG-modified diacylglycerols, or PEG-modified dialkyloxypropyls), cholesterol, derivatives thereof, or combinations thereof.

In certain embodiments, the present invention provides nucleic acid-lipid particles (e.g., SNALP) produced via a continuous mixing method, e.g., a process that includes providing an aqueous solution comprising a nucleic acid (e.g., interfering RNA) in a first reservoir, providing an organic lipid solution in a second reservoir (wherein the lipids present in the organic lipid solution are solubilized in an organic solvent, e.g., a lower alkanol such as ethanol), and mixing the aqueous solution with the organic lipid solution such that the organic lipid solution mixes with the aqueous solution so as to substantially instantaneously produce a lipid vesicle (e.g., liposome) encapsulating the nucleic acid within the lipid vesicle. This process and the apparatus for carrying out this process are described in detail in U.S. Patent Publication No. 20040142025, the disclosure of which is herein incorporated by reference in its entirety for all purposes.

The action of continuously introducing lipid and buffer solutions into a mixing environment, such as in a mixing chamber, causes a continuous dilution of the lipid solution with the buffer solution, thereby producing a lipid vesicle substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The nucleic acid-lipid particles formed using the continuous mixing method typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

In another embodiment, the present invention provides nucleic acid-lipid particles (e.g., SNALP) produced via a direct dilution process that includes forming a lipid vesicle (e.g., liposome) solution and immediately and directly introducing the lipid vesicle solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of lipid vesicle solution introduced thereto. As a non-limiting example, a lipid vesicle solution in 45% ethanol when introduced into the collection vessel containing an equal volume of dilution buffer will advantageously yield smaller particles.

In yet another embodiment, the present invention provides nucleic acid-lipid particles (e.g., SNALP) produced via an in-line dilution process in which a third reservoir containing dilution buffer is fluidly coupled to a second mixing region. In this embodiment, the lipid vesicle (e.g., liposome) solution formed in a first mixing region is immediately and directly mixed with dilution buffer in the second mixing region. In preferred aspects, the second mixing region includes a T-connector arranged so that the lipid vesicle solution and the dilution buffer flows meet as opposing 180° flows; however, connectors providing shallower angles can be used, e.g., from about 27° to about 180° (e.g., about 90°). A pump mechanism delivers a controllable flow of buffer to the second mixing region. In one aspect, the flow rate of dilution buffer provided to the second mixing region is controlled to be substantially equal to the flow rate of lipid vesicle solution introduced thereto from the first mixing region. This embodiment advantageously allows for more control of the flow of dilution buffer mixing with the lipid vesicle solution in the second mixing region, and therefore also the concentration of lipid vesicle solution in buffer throughout the second mixing process. Such control of the dilution buffer flow rate advantageously allows for small particle size formation at reduced concentrations.

These processes and the apparatuses for carrying out these direct dilution and in-line dilution processes are described in detail in U.S. Patent Publication No. 20070042031, the disclosure of which is herein incorporated by reference in its entirety for all purposes.

The nucleic acid-lipid particles formed using the direct dilution and in-line dilution processes typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

If needed, the lipid particles of the invention (e.g., SNALP) can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323, the disclosure of which is herein incorporated by reference in its entirety for all purposes. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In some embodiments, the nucleic acids present in the particles are precondensed as described in, e.g., U.S. patent application Ser. No. 09/744,103, the disclosure of which is herein incorporated by reference in its entirety for all purposes.

In other embodiments, the methods may further comprise adding non-lipid polycations which are useful to effect the lipofection of cells using the present compositions. Examples of suitable non-lipid polycations include, hexadimethrine bromide (sold under the brand name POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In some embodiments, the nucleic acid to lipid ratios (mass/mass ratios) in a formed nucleic acid-lipid particle (e.g., SNALP) will range from about 0.01 to about 0.2, from about 0.05 to about 0.2, from about 0.02 to about 0.1, from about 0.03 to about 0.1, or from about 0.01 to about 0.08. The ratio of the starting materials (input) also falls within this range. In other embodiments, the particle preparation uses about 400 μg nucleic acid per 10 mg total lipid or a nucleic acid to lipid mass ratio of about 0.01 to about 0.08 and, more preferably, about 0.04, which corresponds to 1.25 mg of total lipid per 50 μg of nucleic acid. In other preferred embodiments, the particle has a nucleic acid:lipid mass ratio of about 0.08.

In other embodiments, the lipid to nucleic acid ratios (mass/mass ratios) in a formed nucleic acid-lipid particle (e.g., SNALP) will range from about 1 (1:1) to about 100 (100:1), from about 5 (5:1) to about 100 (100:1), from about 1 (1:1) to about 50 (50:1), from about 2 (2:1) to about 50 (50:1), from about 3 (3:1) to about 50 (50:1), from about 4 (4:1) to about 50 (50:1), from about 5 (5:1) to about 50 (50:1), from about 1 (1:1) to about 25 (25:1), from about 2 (2:1) to about 25 (25:1), from about 3 (3:1) to about 25 (25:1), from about 4 (4:1) to about 25 (25:1), from about 5 (5:1) to about 25 (25:1), from about 5 (5:1) to about 20 (20:1), from about 5 (5:1) to about 15 (15:1), from about 5 (5:1) to about 10 (10:1), or about 5 (5:1), 6 (6:1), 7 (7:1), 8 (8:1), 9 (9:1), 10 (10:1), 11 (11:1), 12 (12:1), 13 (13:1), 14 (14:1), 15 (15:1), 16 (16:1), 17 (17:1), 18 (18:1), 19 (19:1), 20 (20:1), 21 (21:1), 22 (22:1), 23 (23:1), 24 (24:1), or 25 (25:1), or any fraction thereof or range therein. The ratio of the starting materials (input) also falls within this range.

As previously discussed, the conjugated lipid may further include a CPL. A variety of general methods for making SNALP-CPLs (CPL-containing SNALP) are discussed herein. Two general techniques include the "post-insertion" technique, that is, insertion of a CPL into, for example, a pre-formed SNALP, and the "standard" technique, wherein the CPL is included in the lipid mixture during, for example, the SNALP formation steps. The post-insertion technique results in SNALP having CPLs mainly in the external face of the SNALP bilayer membrane, whereas standard techniques provide SNALP having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPLs are taught, for example, in U.S. Pat. Nos. 5,705,385; 6,586,410; 5,981, 501; 6,534,484; and 6,852,334; U.S. Patent Publication No. 20020072121; and PCT Publication No. WO 00/62813, the disclosures of which are herein incorporated by reference in their entirety for all purposes.

VII. Kits

The present invention also provides lipid particles (e.g., SNALP) in kit form. In some embodiments, the kit comprises a container which is compartmentalized for holding the various elements of the lipid particles (e.g., the nucleic acid component and the individual lipid components of the particles). Preferably, the kit comprises a container (e.g., a vial or ampoule) which holds the lipid particles of the invention (e.g., SNALP), wherein the particles are produced by one of the processes set forth herein. In some embodiments, the kit may further comprise one or more antioxidants such as metal chelators (e.g., EDTA), primary antioxidants, and/or secondary antioxidants. In other embodiments, the kit may further comprise an endosomal membrane destabilizer (e.g., calcium ions). The kit typically contains the particle compositions of the present invention, either as a suspension in a pharmaceutically acceptable carrier or in dehydrated form, with instructions for their rehydration (if lyophilized) and administration.

The SNALP formulations of the present invention can be tailored to preferentially target particular cells, tissues, or organs of interest. Preferential targeting of SNALP may be carried out by controlling the composition of the SNALP itself. In particular embodiments, the kits of the invention comprise these lipid particles, wherein the particles are present in a container as a suspension or in dehydrated form. Such kits are particularly advantageous for use in providing effective postexposure treatment strategies for combating arenavirus (e.g., LASV) and/or filovirus (e.g., EBOV, MARV) infections.

In certain instances, it may be desirable to have a targeting moiety attached to the surface of the lipid particle to further enhance the targeting of the particle. Methods of attaching targeting moieties (e.g., antibodies, proteins, etc.) to lipids (such as those used in the present particles) are known to those of skill in the art.

VIII. Administration of Lipid Particles

Once formed, the lipid particles of the invention (e.g., SNALP) are particularly useful for the introduction of nucleic acids (e.g., interfering RNA such as dsRNA) into cells. Accordingly, the present invention also provides methods for introducing a nucleic acid (e.g., interfering RNA) into a cell. In particular embodiments, the nucleic acid (e.g., interfering RNA) is introduced into an infected cell (or a cell capable of being infected in prophylactic or preventive measures or care) such as reticuloendothelial cells (e.g., macrophages, monocytes, etc.) as well as other cell types, including endothelial cells (such as those lining the interior surface of blood vessels), liver cells (e.g., hepatocytes), fibroblasts, and/or platelet cells. The methods may be carried out in vitro or in vivo by first forming the particles as described above and then contacting the particles with the cells for a period of time sufficient for delivery of the interfering RNA to the cells to occur.

The lipid particles of the invention (e.g., SNALP) can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid (e.g., interfering RNA) portion of the particle can take place via any one of these pathways. In particular, when fusion takes place, the particle membrane is integrated into the cell membrane and the contents of the particle combine with the intracellular fluid.

The lipid particles of the invention (e.g., SNALP) can be administered either alone or in a mixture with a pharmaceutically acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically acceptable" refers to molecular entities and compositions that do not produce an allergic or similar untoward reaction when administered to a human.

The pharmaceutically acceptable carrier is generally added following lipid particle formation. Thus, after the lipid particle (e.g., SNALP) is formed, the particle can be diluted into pharmaceutically acceptable carriers such as normal buffered saline.

The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol, and water-soluble iron-specific chelators, such as ferrioxamine, are suitable.

In some embodiments, the lipid particles of the invention (e.g., SNALP) are particularly useful in methods for the therapeutic delivery of one or more nucleic acids comprising an interfering RNA sequence (e.g., siRNA). In particular, it is an object of this invention to provide in vitro and in vivo methods for treatment of arenavirus (e.g., LASV) and/or filovirus (e.g., EBOV, MARV) infections in a mammal (e.g., a rodent such as a mouse or a primate such as a human, chimpanzee, or monkey) by downregulating or silencing the transcription and/or translation of one or more target nucleic acid sequences or genes of interest (such as TF and/or LASV NP, GP, L, Z, or combinations thereof). As a non-limiting example, the methods of the invention are useful for the in vivo delivery of interfering RNA (e.g., siRNA) to infected cells of a mammalian subject for the treatment of an arenavirus (e.g., LASV) and/or filovirus (e.g., EBOV, MARV) infection. In certain embodiments, the infection is associated with expression and/or overexpression of an viral or host gene and expression or overexpression of the gene is reduced by the interfering RNA (e.g., siRNA). In certain other embodiments, a therapeutically effective amount of the lipid particle may be administered to the mammal. In some instances, one, two, three, or more interfering RNA molecules (e.g., siRNA) are formulated into a SNALP, and the particles are administered to patients requiring such treatment. In other instances, cells are removed from a patient, the interfering RNA is delivered in vitro (e.g., using a SNALP described herein), and the cells are reinjected into the patient.

A. In Vivo Administration

Systemic delivery for in vivo therapy, e.g., delivery of a therapeutic nucleic acid to a distal target cell via body systems such as the circulation, has been achieved using nucleic acid-lipid particles such as those described in PCT Publication Nos. WO 05/007196, WO 05/121348, WO 05/120152, and WO 04/002453, the disclosures of which are herein incorporated by reference in their entirety for all purposes. The present invention also provides fully encapsulated lipid particles that protect the nucleic acid from nuclease degradation in serum, are non-immunogenic, are small in size, and are suitable for repeat dosing.

For in vivo administration, administration can be in any manner known in the art, e.g., by injection, oral administration, inhalation (e.g., intransal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.*, 101:512 (1983); Mannino et al., *Biotechniques*, 6:682 (1988); Nicolau et al., *Crit. Rev. Ther. Drug Carrier Syst.*, 6:239 (1989); and Behr, *Acc. Chem. Res.*, 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)). The disclosures of the above-described references are herein incorporated by reference in their entirety for all purposes.

In embodiments where the lipid particles of the present invention (e.g., SNALP) are administered intravenously, at least about 5%, 10%, 15%, 20%, or 25% of the total injected dose of the particles is present in plasma about 8, 12, 24, 36, or 48 hours after injection. In other embodiments, more than about 20%, 30%, 40% and as much as about 60%, 70% or 80% of the total injected dose of the lipid particles is present in plasma about 8, 12, 24, 36, or 48 hours after injection. In certain instances, more than about 10% of a plurality of the particles is present in the plasma of a mammal about 1 hour after administration. In certain other instances, the presence of the lipid particles is detectable at least about 1 hour after administration of the particle. In some embodiments, the presence of a therapeutic nucleic acid such as an interfering RNA molecule is detectable in cells at about 8, 12, 24, 36, 48, 60, 72 or 96 hours after administration. In other embodiments, downregulation of expression of a target sequence, such as a viral or host sequence, by an interfering RNA (e.g., siRNA) is detectable at about 8, 12, 24, 36, 48, 60, 72 or 96 hours after administration. In yet other embodiments, downregulation of expression of a target sequence, such as a viral or host sequence, by an interfering RNA (e.g., siRNA) occurs preferentially in infected cells and/or cells capable of being infected. In further embodiments, the presence or effect of an interfering RNA (e.g., siRNA) in cells at a site proximal or distal to the site of administration is detectable at about 12, 24, 48, 72, or 96 hours, or at about 6, 8, 10, 12, 14, 16, 18, 19, 20, 22, 24, 26, or 28 days after administration. In additional embodiments, the lipid particles (e.g., SNALP) of the invention are administered parenterally or intraperitoneally.

The compositions of the present invention, either alone or in combination with other suitable components, can be made into aerosol formulations (i.e., they can be "nebulized") to be administered via inhalation (e.g., intranasally or intratracheally) (see, Brigham et al., *Am. J. Sci.*, 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Similarly, transmucosal drug delivery in the form of a polytetrafluoroethylene support matrix is described in U.S. Pat. No. 5,780,045. The disclosures of the above-described patents are herein incorporated by reference in their entirety for all purposes.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the lipid particle formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

In certain applications, the lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451, the disclosures of which are herein incorporated by reference in their entirety for all purposes). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of a packaged therapeutic nucleic acid (e.g., interfering RNA) suspended in diluents such as water, saline, or PEG 400; (b) capsules, sachets, or tablets, each containing a predetermined amount of a therapeutic nucleic acid (e.g., interfering RNA), as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a therapeutic nucleic acid (e.g., interfering RNA) in a flavor, e.g., sucrose, as well as pastilles comprising the therapeutic nucleic acid in an inert base, such as gelatin and glycerin or sucrose and acacia emulsions, gels, and the like containing, in addition to the therapeutic nucleic acid, carriers known in the art.

In another example of their use, lipid particles can be incorporated into a broad range of topical dosage forms. For instance, a suspension containing nucleic acid-lipid particles such as SNALP can be formulated and administered as gels, oils, emulsions, topical creams, pastes, ointments, lotions, foams, mousses, and the like.

When preparing pharmaceutical preparations of the lipid particles of the invention, it is preferable to use quantities of the particles which have been purified to reduce or eliminate empty particles or particles with therapeutic agents such as nucleic acid associated with the external surface.

The methods of the present invention may be practiced in a variety of hosts. Preferred hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of therapeutic nucleic acid (e.g., interfering RNA) to lipid, the particular therapeutic nucleic acid used, the disease or disorder being treated, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

B. In Vitro Administration

For in vitro applications, the delivery of therapeutic nucleic acids (e.g., interfering RNA) can be to any cell grown in culture, whether of plant or animal origin, vertebrate or invertebrate, and of any tissue or type. In preferred embodiments, the cells are animal cells, more preferably mammalian cells, and most preferably human cells.

Contact between the cells and the lipid particles, when carried out in vitro, takes place in a biologically compatible medium. The concentration of particles varies widely depending on the particular application, but is generally between about 1 μmol and about 10 mmol. Treatment of the cells with the lipid particles is generally carried out at physiological temperatures (about 37° C.) for periods of time of from about 1 to 48 hours, preferably of from about 2 to 4 hours.

In one group of preferred embodiments, a lipid particle suspension is added to 60-80% confluent plated cells having a cell density of from about $10^3$ to about $10^5$ cells/ml, more preferably about $2 \times 10^4$ cells/ml. The concentration of the suspension added to the cells is preferably of from about 0.01 to 0.2 μg/ml, more preferably about 0.1 μg/ml.

To the extent that tissue culture of cells may be required, it is well-known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

Using an Endosomal Release Parameter (ERP) assay, the delivery efficiency of the SNALP or other lipid particle of the invention can be optimized. An ERP assay is described in detail in U.S. Patent Publication No. 20030077829, the disclosure of which is herein incorporated by reference in its entirety for all purposes. More particularly, the purpose of an ERP assay is to distinguish the effect of various cationic lipids and helper lipid components of SNALP or other lipid particle based on their relative effect on binding/uptake or fusion with/destabilization of the endosomal membrane. This assay allows one to determine quantitatively how each component of the SNALP or other lipid particle affects delivery efficiency, thereby optimizing the SNALP or other lipid particle. Usually, an ERP assay measures expression of a reporter protein (e.g., luciferase, β-galactosidase, green fluorescent protein (GFP), etc.), and in some instances, a SNALP formulation optimized for an expression plasmid will also be appropriate for encapsulating an interfering RNA. In other instances, an ERP assay can be adapted to measure downregulation of transcription or translation of a target sequence in the presence or absence of an interfering RNA (e.g., siRNA). By comparing the ERPs for each of the various SNALP or other lipid particles, one can readily determine the optimized system, e.g., the SNALP or other lipid particle that has the greatest uptake in the cell.

C. Cells for Delivery of Lipid Particles

The compositions and methods of the present invention are particularly well suited for treating arenavirus and/or filovirus infections by targeting, e.g., LASV and/or TF gene expression in vivo. The present invention can be practiced on a wide variety of cell types from any vertebrate species, including mammals, such as, e.g, canines, felines, equines, bovines, ovines, caprines, rodents (e.g., mice, rats, and guinea pigs), lagomorphs, swine, and primates (e.g. monkeys, chimpanzees, and humans). Suitable cells include, but are not limited to, any cell infected with a hemorrhagic fever virus or capable of becoming infected with a hemorrhagic fever virus, such as, e.g., endothelial cells including reticuloendothelial cells (e.g., monocytes, macrophages, Kupffer cells, tissue histiocytes, etc.), liver cells such as hepatocytes, fibroblast cells, and/or platelet cells. Other cell types include, but are not limited to, epithelial cells, hematopoietic precursor (stem) cells, keratinocytes, skeletal and smooth muscle cells, osteoblasts, neurons, quiescent lymphocytes, terminally differentiated cells, slow or noncycling primary cells, parenchymal cells, lymphoid cells, bone cells, and the like.

D. Detection of Lipid Particles

In some embodiments, the lipid particles of the present invention (e.g., SNALP) are detectable in the subject at about 1, 2, 3, 4, 5, 6, 7, 8 or more hours. In other embodiments, the lipid particles of the present invention (e.g., SNALP) are detectable in the subject at about 8, 12, 24, 48, 60, 72, or 96 hours, or about 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, detection of a therapeutic nucleic acid such as an interfering RNA (e.g., siRNA) sequence, detection of the target sequence of interest (i.e., by detecting expression or reduced expression of the sequence of interest), detection of a compound modulated by an viral protein (e.g., interferon), detection of viral load in the subject, or a combination thereof.

1. Detection of Particles

Lipid particles of the invention such as SNALP can be detected using any method known in the art. For example, a label can be coupled directly or indirectly to a component of the lipid particle using methods well-known in the art. A wide variety of labels can be used, with the choice of label depending on sensitivity required, ease of conjugation with the lipid particle component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^3$H, $^{125}$I, $^{35}$S, $^{14}$C, $^{32}$P, $^{33}$P, etc.; enzymes such as horse radish peroxidase, alkaline phosphatase, etc.; spectral colorimetric labels such as colloidal gold or colored glass or plastic beads such as polystyrene, polypropylene, latex, etc. The label can be detected using any means known in the art.

2. Detection of Nucleic Acids

Nucleic acids (e.g., interfering RNA) are detected and quantified herein by any of a number of means well-known to those of skill in the art. The detection of nucleic acids may proceed by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through the use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification, and other RNA polymerase mediated techniques (e.g., NASBA™) are found in Sambrook et al., In *Molecular Cloning: A Laboratory Manual*, Cold Spring Harbor Laboratory Press (2000); and Ausubel et al., SHORT PROTOCOLS IN MOLECULAR BIOLOGY, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif. (1990); Arnheim & Levinson (Oct. 1, 1990), *C&EN* 36; *The Journal Of NIH Research*, 3:81 (1991); Kwoh et al., *Proc. Natl. Acad. Sci. USA*, 86:1173 (1989); Guatelli et al., *Proc. Natl. Acad. Sci. USA*, 87:1874 (1990); Lomell et al., *J. Clin. Chem.*, 35:1826 (1989); Landegren et al., *Science*, 241:1077 (1988); Van Brunt, *Biotechnology*, 8:291 (1990); Wu and Wallace, *Gene*, 4:560 (1989); Barringer et al., *Gene*, 89:117 (1990); and Sooknanan and Malek, *Biotechnology*, 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation. The disclosures of the above-described references are herein incorporated by reference in their entirety for all purposes.

Nucleic acids for use as probes, e.g., in in vitro amplification methods, for use as gene probes, or as inhibitor components are typically synthesized chemically according to the solid phase phosphoramidite triester method described by Beaucage et al., *Tetrahedron Letts.*, 22:1859 1862 (1981), e.g., using an automated synthesizer, as described in Needham VanDevanter et al., *Nucleic Acids Res.*, 12:6159 (1984). Purification of polynucleotides, where necessary, is typically performed by either native acrylamide gel electrophoresis or by anion exchange HPLC as described in Pearson et al., *J. Chrom.*, 255:137 149 (1983). The sequence of the synthetic polynucleotides can be verified using the chemical degradation method of Maxam and Gilbert (1980) in Grossman and Moldave (eds.) Academic Press, New York, *Methods in Enzymology*, 65:499.

An alternative means for determining the level of transcription is in situ hybridization. In situ hybridization assays are well-known and are generally described in Angerer et al., *Methods Enzymol.*, 152:649 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

3. Detection of Virus Load

Viral load can be detected using any means known in the art. Typically, viral load is detected in a biological sample from the subject. For example, viral load in the subject's blood can be detected by measuring viral antigens using an immunoassay such as an ELISA (see, e.g., Meissner et al., *Virology*, 300:236-43 (2002); and Ksiazek et al., *J. Clin. Microbiol.*, 30:947-950 (1992)). Viral load can also be detected by amplifying viral nucleic acids (see, e.g., Drosten et al., *J. Clin. Microbiol.*, 40: 2323-2330 (2002)) or by conventional plaque assay using monolayers of Vero or Vero E6 cells (see, e.g., Jahrling, Filoviruses and Arenaviruses, In *Manual of Clinical Microbiology*, Eds. Baron, Pfaller, Tenover, and Yolken, ASM Press, Washington, D.C. (1999)).

IX. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Stable Nucleic Acid Lipid Particle (SNALP)-Enabled siRNA-Based Therapy for Hemorrhagic Fever Viral Infection

I. Introduction

This example demonstrates the feasibility and anti-viral efficacy of broad-spectrum small-interfering RNA (siRNA)-based therapies targeting genes of Lassa Virus (LASV), a CDC Category A arenavirus. The candidate siRNAs and control sequences were designed and delivered using stable nucleic acid-lipid particles (SNALP). Properly designed siRNA can potently suppress the expression of target genes by harnessing the power of RNA interference (RNAi). Previous approaches to the treatment of arenaviruses have been limited and unsuccessful due to numerous technical and biological barriers. SNALP have been designed specifically to encapsulate and stabilize nucleic acids such as siRNA, and address the inability of current delivery systems to overcome the barriers to systemic delivery (e.g., effective delivery to the disease site and the target cell). The safety, efficacy and broad utility of the SNALP technology has previously been applied to the inhibition of virus systems such as Ebola Virus (EBOV) (1) and Hepatitis B virus (2). SNALP was instrumental in the first demonstration of RNAi in non-human primates following systemic administration of siRNA in vivo (3), validating its potential as an effective drug delivery system. To target the LASV genome, siRNA directed against LASV and control sequences were designed and formulated in SNALP in quantities suitable for systemic administration. Non-immunostimulatory analogs of the siRNAs directed against the LASV gene targets were also designed and synthesized.

II. Development of siRNA Targeting Lassa Virus

The initial objective of this study was to design siRNA targeting Lassa virus (LASV) mRNA and to assess the gene silencing activity of these constructs in vitro. Active siRNA sequences were chemically modified to inhibit their capacity to activate the mammalian innate immune response, then tested using in vitro assays to assess anti-viral activity against LASV. Selected LASV siRNA are tested in appropriate in vivo models of LASV infection to assess their therapeutic potential. The application of siRNA as a systemic therapeutic agent against hemorrhagic fever viruses is enabled by their encapsulation into stable nucleic acid-lipid particles (SNALP).

LASV siRNA Design

LASV (strain Josiah) genes L-polymerase (Lpol) and the nucleoprotein (NP) were selected as targets for siRNA-mediated inhibition due to their importance in viral pathogenesis (4-6). GenBank accession numbers were identified for the viral gene targets, NC_004296 and NC_004297, respectively. An initial list of siRNA candidates targeting LASV Josiah Lpol and NP genes were designed using an internet-based software tool (http://jura.wi.mit.edu/bioc/siRNAext/home.php) using the following parameters against the Lpol or NP mRNA coding sequence: (i) NAN21 search; (ii) eliminate sequences with thermodynamics <-2.0 and % GC content <53%; and the following parameters against the Lpol coding sequence: (i) AAN19TT with thermodynamics <-1.0 and % GC content <50%, NAN21 with thermodynamics <-4.0 and % GC<50%. Using the BLAST program, siRNA candidates were eliminated with high homology to mouse and/or human genomic sequences (alignment to positions 4 to 17 on the antisense strand of the siRNA). Furthermore, using the Mfold program, theoretical secondary structures were generated for each of the target transcripts (http://frontend.bioinfo.rpi.edu/applications/mfold/cgi-bin/rna-form1.cgi). For the NP target, folding analysis was performed on the entire S-segment of the genome, for Lpol, analysis was conducted on the 3' 6,000 bases of the Lpol gene only. Lastly, the most energetically favorable siRNA candidates were selected, in particular: i) those targeting mRNA loop structures on the periphery of the structure with the least degree of intra-molecular base pairing and steric hindrance (7), and ii) those thermodynamically biased towards entry of 5' antisense end (versus 5' sense end) into Dicer machinery (8).

TABLE 5

List of siRNAs Designed to Target LASV-Lpol and -NP Genes

| siRNA ID No.[a] | Sense Strand (5'-3')[b] (SEQ ID NO:) | Antisense Strand (5'-3')[b] (SEQ ID NO:) |
|---|---|---|
| LS-L-844 | GACAAUAUCGAACACUUAA*dTdT* (50) | UUAAGUGUUCGAUAUUGUC*dTdT* (51) |
| LS-L-1022 | GGAGGAAACUUCUAUUAAU*dTdT* (52) | AUUAAUAGAAGUUUCCUCC*dTdT* (53) |
| LS-L-1778 | CAACAAUAAGCACUAUGAU*dTdT* (54) | AUCAUAGUGCUUAUUGUUG*dTdT* (55) |
| LS-L-3513 | UGCUAUCCUUUCCAUGAAA*dTdT* (56) | UUUCAUGGAAAGGAUAGCA*dTdT* (57) |
| LS-L-6313 | GACCAGGAUCUUGAGAUAU*dTdT* (58) | AUAUCUCAAGAUCCUGGUC*dTdT* (59) |
| LS-NP-548 | CACUGGCAUGUCUGACAAA*dTdT* (60) | UUUGUCAGACAUGCCAGUG*dTdT* (61) |
| LS-NP-672 | AAGUCAUCCCAUCCUAAAU*dTdT* (62) | AUUUAGGAUGGGAUGACUU*dTdT* (63) |
| LS-NP-943 | GAUGGAUGGCCAUAUAUUG*dTdT* (64) | CAAUAUAUGGCCAUCCAUC*dTdT* (65) |

TABLE 5-continued

List of siRNAs Designed to Target LASV-Lpol and -NP Genes

| siRNA ID No.[a] | Sense Strand (5'-3')[b] (SEQ ID NO:) | Antisense Strand (5'-3')[b] (SEQ ID NO:) |
|---|---|---|
| LS-NP-1222 | GGCUGCUACAUACACUUCU*dTdT* (66) | AGAAGUGUAUGUAGCAGCC*dTdT* (67) |
| LS-NP-1284 | GUACUCACAUGGGAUUGAU*dTdT* (68) | AUCAAUCCCAUGUGAGUAC*dTdT* (69) |

[a] siRNA ID Legend: LS = Lassavirus, L = L-polymerase, NP = nucleoprotein, the number in the ID refers to the position of the 5' nucleotide of the siRNA sense strand with regards to the coding sequence of the gene.
[b] 3'-overhangs are indicated in bold and italicized. The 3'-overhangs on one or both strands of the siRNA molecule may alternatively comprise 1-4 deoxythymidine (dT) nucleotides, 1-4 modified and/or unmodified uridine (U) ribonucleotides, or 1-4 ribonucleotides having complementarity to the target sequence or the complementary strand thereof.

In Table 5 above, the last 2 nucleotides at the 3' ends of the sense and antisense strands correspond to the 3' overhang sequence. In other words, nucleotides 1-19 of each sense and antisense strand sequence depicted in Table 5 correspond to that portion of the sense or antisense strand that is present in the double-stranded region of the siRNA duplex. In alternative embodiments, the 3' overhang on one or both strands of the siRNA molecule may comprise 1-4 (e.g., 1, 2, 3, or 4) modified and/or unmodified deoxythymidine (t or dT) nucleotides, 1-4 (e.g., 1, 2, 3, or 4) modified (e.g., 2'OMe) and/or unmodified uridine (U) ribonucleotides, and/or 1-4 (e.g., 1, 2, 3, or 4) modified (e.g., 2'OMe) and/or unmodified ribonucleotides or deoxyribonucleotides having complementarity to the target sequence or the complementary strand thereof. In certain instances, the sense and/or antisense strand of the siRNA molecule lacks 3' overhangs (i.e., does not contain the last 2 nucleotides at the 3' ends of the sense and/or antisense strand). In some embodiments, the sense and/or antisense strand comprises modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides. In particular embodiments, the sense and/or antisense strand comprises 2'OMe nucleotides in accordance with at least one or more of the selective modification patterns described herein.

Design of Control siRNAs

For the purpose of research and development of siRNA-based therapy, it is important to demonstrate that observed efficacy is a result of the intended RNAi mechanism, and not due to off-target effects. Based upon our prior experience (9), we selected appropriate, non-LASV targeting control siRNA sequences (both immunostimulatory and non-stimulatory). These controls are a means of determining whether immunostimulation alone will cause a detectable anti-viral effect and survival advantage in animal efficacy studies. Through a number of studies we have confirmed that the chemically modified, non-stimulatory control siRNAs do not induce measurable cytokine induction in mice (10).

Assessment of siRNA-Mediated Knockdown of LASV NP Gene Expression In Vitro

Evaluation of the anti-viral efficacy of candidate therapies is best performed in animal models that support viral infection and have sequelae similar to those observed in humans, due to the multi-factorial nature of the disease and treatment. However, large-scale screening of potential siRNAs in animal models is prohibitively expensive and would require the use of limited resources such as BSL-4 laboratory space and trained personnel. RNA interference activity of LASV siRNAs was assessed therefore in virus-free in vitro plasmid-based gene expression assays in vitro.

The LASV-NP gene was sub-cloned from the pCGAGS vector expressing LASV-NP. For QG analysis, the NP gene was subcloned into the pCI-neo mammalian expression vector (GenBank Accession No. U47120, the disclosure of which is herein incorporated by reference in its entirety for all purposes; Promega Corp.). For DLR analyses, the LASV-NP gene was subcloned into the Promega Corp. psiCHECK2 expression vector (FIG. 1) using the appropriate restriction/cloning sites.

The virus-free methods rely on the use of mammalian expression plasmids to produce small portions of viral mRNA in cultured mammalian cells. The selected viral mRNA portion encodes all or part of a chosen gene target, such as LASV NP. siRNAs introduced into these mammalian cells can then bind to and cause the destruction of the plasmid-expressed mRNA via the RNAi mechanism. The degree of mRNA silencing can be measured in a number of ways, including via reverse transcriptase quantitative polymerase chain reaction (RT-QPCR). Models were established utilizing methods that were faster, less labor-intensive and more amenable to scale-up than RT-QPCR: i) QuantiGene (QG) branched DNA assay (Panomics) and ii) Dual Luciferase Reporter (DLR) Assay (Promega). The QG assay directly measures the amount of intact mRNA remaining in the cell sample using an mRNA capture technique analogous to ELISA for protein quantitation. The DLR assay indirectly measures the amount of intact

List of Control siRNAs Used in LASV Studies

| siRNA ID | Sense Strand (5'-3')[a] (SEQ ID NO:) | Antisense Strand (5'-3')[a] (SEQ ID NO:) |
|---|---|---|
| anti-Luc | GAUUAUGUCCGGUUAUGUAUU (70) | UACAUAACCGGACAUAAUCUU (71) |
| Luc U/U v2 | GAmUmUAmUGmUCCGGmUmUAmUGmUAdTdT (72) | UACAmUAACCGGACAmUAAmUCdTdT (73) |
| Luc U/U v3 | GAmUmUAmUGmUCCGGmUmUAmUGmUAAA (74) | UACAmUAACCGGACAmUAAmUCAU (75) |

[a] 'm' denotes the presence of 2' O-Me modification at that nucleotide.

mRNA remaining by quantifying the amount of luciferase protein activity in a cell sample wherein the luciferase protein is produced from a fusion mRNA composed of the luciferase gene together with the target gene sequence. Both methods were found to be comparable in their assessment of siRNA-mediated inhibition.

Methodology:

Briefly, approximately 50,000-75,000 HepG2 cells were transfected with 0.75-1.25 μg of the appropriate plasmid containing the LASV NP gene using LipoFectamine 2000 (Invitrogen, Burlington, Canada) in a 96-well plate. siRNAs to be tested experimentally were also complexed with Lipo-Fectamine 2000 (Invitrogen) and added to wells in triplicate. Media was replaced 24 hours post-transfection and siRNA-mediated knockdown activity was assayed by either Panomic's QG assay or Promega's DLR assay 48 hours post-transfection. Minimal modifications were made to the manufacturer's supplied assay protocols.

Figure 2:
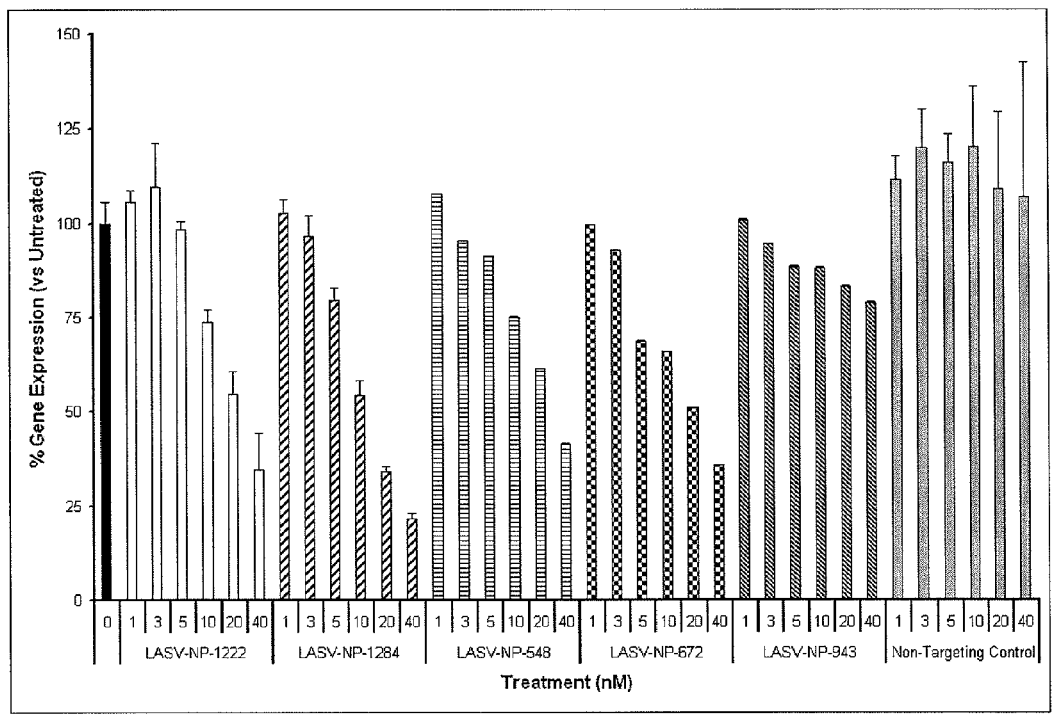
FIG. 2 illustrates the relative potency of siRNA targeting LASV-NP in vitro in a virus-free, plasmid-based system. HepG2 cells were reverse-transfected with 0.75 µg/mL plasmid pCGAGS containing LASV NP gene and 1.25-40 nM siRNA complexed with Lipofectamine 2000 (Invitrogen). Cells were lysed 48 h later for QG quantitation of NP mRNA, normalized against GAPD mRNA. Data represents the mean (n=3) of experimental results and ±SD. KD50 values are indicated above the data sets for the individual siRNAs tested.

Experimental Results:

Gene silencing activity was observed in the QG assay from all five siRNA designed against LASV-NP (FIG. 2). Furthermore, the dose response range was used to interpolate a $KD_{50}$ value (the siRNA dose at which target is reduced by 50 percent) for each siRNA candidate. This approach generated the following siRNA potency ranking (most potent to least potent): LS-NP-1284>LS-NP-1222>LS-NP-672>LS-NP-943~LS-NP-548.

From these studies, LS-NP-1284 and LS-NP-1222 were picked as lead siRNA sequences targeting LASV NP gene expression.

Development of Chemically-Modified LASV siRNA

In order to minimize any immunostimulatory properties found inherently in native siRNA sequences, lead LASV siRNAs were designed and synthesized with the addition of 2' O-methyl chemical modifications (Table 6). This 'minimal modification' strategy involves the selective incorporation of 2'-OMe nucleotides into siRNA molecules. This approach has been demonstrated to abrogate the induction of the immune response and associated toxicities in primary human cell cultures, mice and non-human primates, indicating the preservation of the inhibitory mechanism across species (3,11).

the siRNA molecule may comprise 1-4 (e.g., 1, 2, 3, or 4) modified and/or unmodified deoxythymidine (t or dT) nucleotides, 1-4 (e.g., 1, 2, 3, or 4) modified (e.g., 2'OMe) and/or unmodified uridine (U) ribonucleotides, and/or 1-4 (e.g., 1, 2, 3, or 4) modified (e.g., 2'OMe) and/or unmodified ribonucleotides or deoxyribonucleotides having complementarity to the target sequence or the complementary strand thereof. In certain instances, the sense and/or antisense strand of the siRNA molecule lacks 3' overhangs (i.e., does not contain the last 2 nucleotides at the 3' ends of the sense and/or antisense strand). In some embodiments, the sense and/or antisense strand comprises additional modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides.

Figure 3:
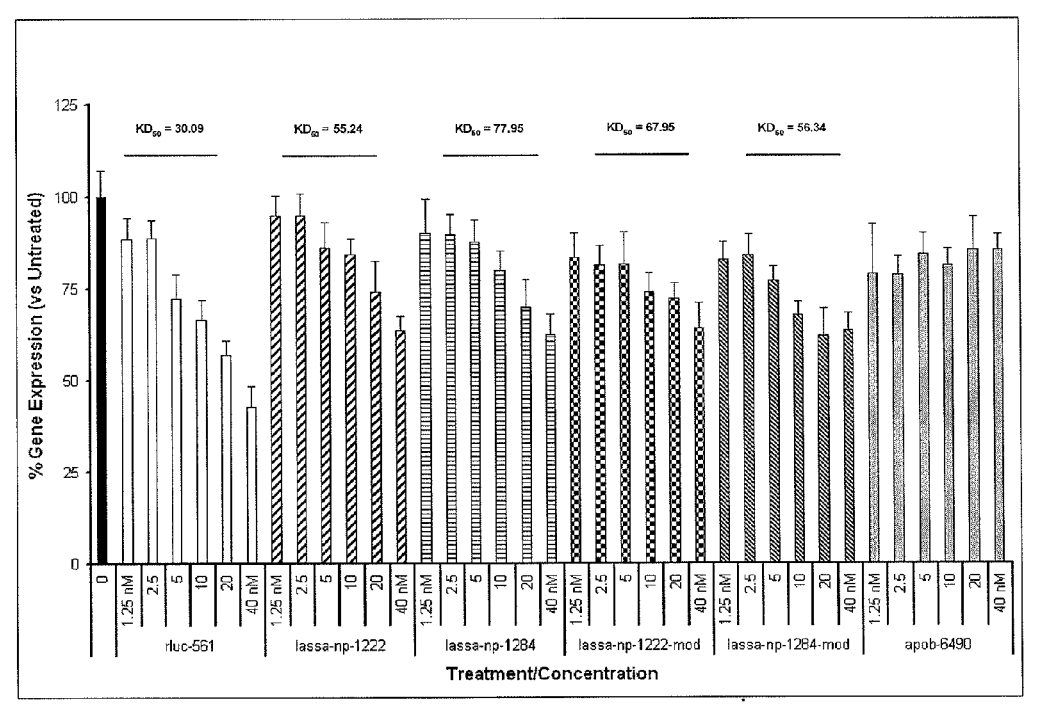

Using the DLR-based approach, the activity of both unmodified and modified LASV-NP targeting siRNAs was ascertained (FIG. 3). Activity of siRNA was not significantly altered by chemical modification, validating this strategy to minimize unwanted immune responses without compromising efficacy in vivo.

Figure 4:
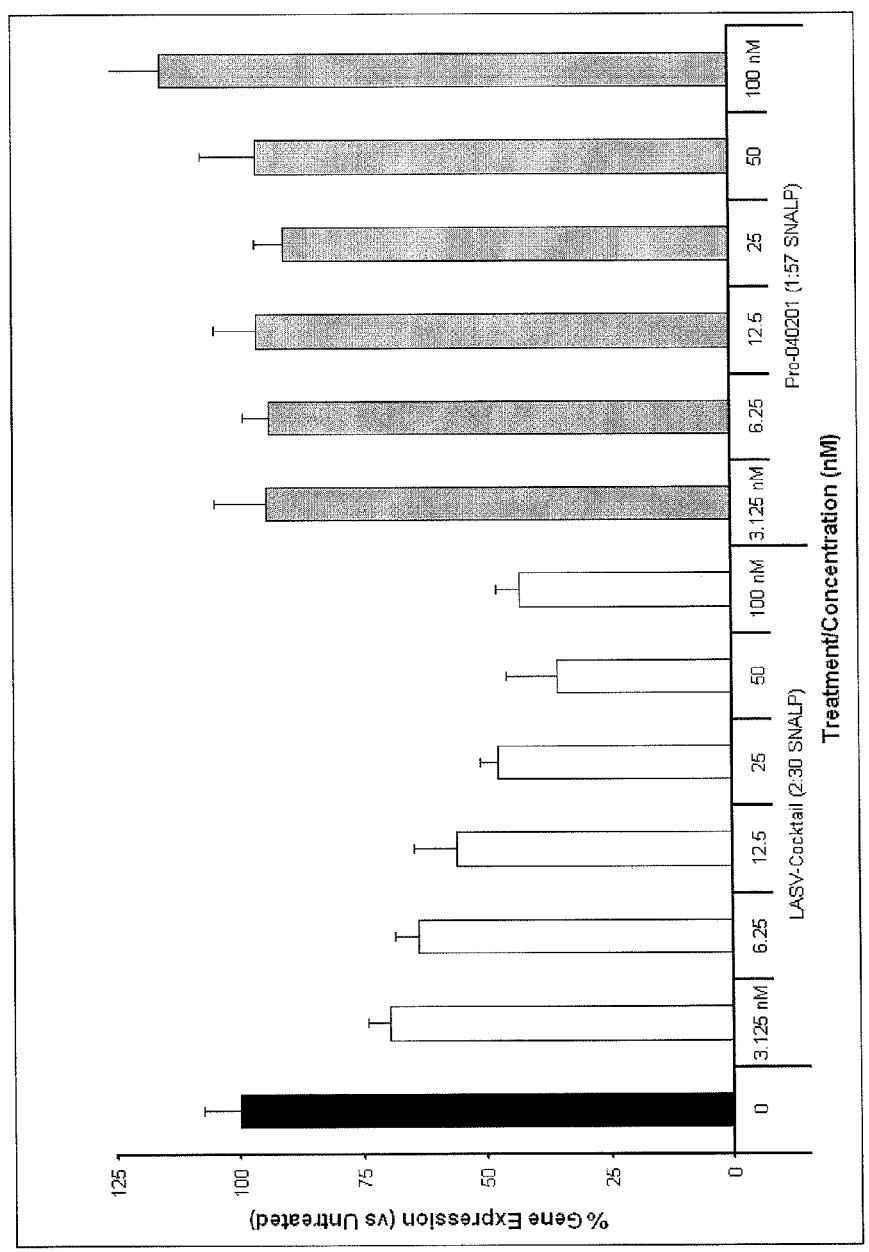
FIG. 4 illustrates the relative potency of a SNALP-encapsulated siRNA-cocktail targeting LASV in vitro in a virus-free, plasmid-based system. HepG2 cells were transfected with 1.25 µg/mL plasmid psiCHECK2 (Promega) containing Lassavirus NP gene and 3.1-100 nM siRNA formulated in SNALP. Cells were lysed 48 h later for DLR quantitation of *Renilla* Luciferase, normalized against Firefly Luciferase luminescence. Data represents the mean (n=3) of experimental results and ±SD. LASV-Cocktail KD50 value was 51.82. Pro-040201 was used as a non-targeting control.

To assess the potential of combining LASV siRNA to make a cocktail of active siRNA in a single drug product, we selected the 2 lead NP siRNA plus 2 Lpol siRNA and formulated these at 1:1:1:1 mass ratio in a SNALP formulation (termed '2:30'). The efficacy of the 2:30 LASV-targeting SNALP cocktail (composition: LASV-Lpol3513mod; LASV-Lpol6313-mod; LASV-NP1222-mod; and LASV-NP1284-mod siRNA) was assayed in the virus-free plasmid expression system and demonstrated a significant inhibition of the LASV NP gene transcript in vitro (FIG. 4). This result indicates that the NP siRNA component of this cocktail remains fully active when combined with potential Lpol siRNA candidates.

Development of an Infectious Cell Culture Model to Screen siRNA SNALP for Activity Against Hemorrhagic Fever Viruses A SNALP system for transfection of Vero E6 cells with siRNA has been developed that can be used for screening anti-viral activity against hemorrhagic fever viruses includ-

TABLE 6

Chemically Modified LASV siRNAs Targeting L-pol and NP Genes

| siRNA ID No.[a] | Sense Strand (5'-3')[b] (SEQ ID NO:) | Antisense Strand (5'-3')[b] (SEQ ID NO:) |
|---|---|---|
| LASV-Lpo13513-mod | UmGCUAmUCCUUUCCAmUGAAAUU (76) | UUmUCAUmGGAAAGmGAUAGCAUU (77) |
| LASV-Lpo16313-mod | GACCAmGGAUCUmUGAGAmUAUUU (78) | AUAUCmUCAAGAUCCUmGGmUCUU (79) |
| LASV-NP1222-mod | mGGCmUGCUACAUACACmUUCUUC (80) | AGAAGmUGmUAUGUAmGCAGCCUG (81) |
| LASV-NP1284-mod | GmUACUCACAUGmGGAmUUmGAUGU (82) | AUCAAUCCCAUGmUGAGmUACUU (83) |

[a]LASV = Lassavirus, Lpol = L-polymerase, NP = nucleoprotein, the number in the ID refers to the position of the 5' nucleotide of the siRNA sense strand with regards to the coding sequence of the gene.
[b]'m' denotes 2' O—Me nucleotides. 3'-overhangs are indicated in bold and italicized. The 3'-overhangs on one or both strands of the siRNA molecule may alternatively comprise 1-4 deoxythymidine (dT) nucleotides, 1-4 modified and/or unmodified uridine (U) ribonucleotides, or 1-4 ribonucleotides having complementarity to the target sequence or the omplementary strand thereof.

In Table 6 above, the last 2 nucleotides at the 3' ends of the sense and antisense strands correspond to the 3' overhang sequence. In other words, nucleotides 1-19 of each sense and antisense strand sequence depicted in Table 6 correspond to that portion of the sense or antisense strand that is present in the double-stranded region of the siRNA duplex. In alternative embodiments, the 3' overhang on one or both strands of ing LASV, ZEBOV and MARV. The advantage of these live virus models is that it not only assays for the relative activity of viral mRNA silencing, but also assesses the relative antiviral effect of silencing that particular gene. See, for example, PCT Publication No. WO 2011/011447, the disclosure of which is herein incorporated by reference in its entirety for all purposes.

III. Design of Broad Spectrum Antiviral siRNAs for Hemorrhagic Fevers

As an alternative approach to developing siRNA that specifically target viral RNA transcripts, the targeting of host genes that are known to play a direct role in the pathogenisis of hemorrhagic fever viruses including arenavirus and filovirus was investigated. Such an approach has the advantage of developing an siRNA therapeutic with a broader spectrum of activity against a range of hemorrhagic fever viruses, compared to the relative specificity of siRNA targeting gene transcripts from particular viral species or strains. Tissue factor (TF) has been identified as one such host factor that regulates a cellular pathway common in hemorrhagic fever viral pathogenesis.

Figure 5:
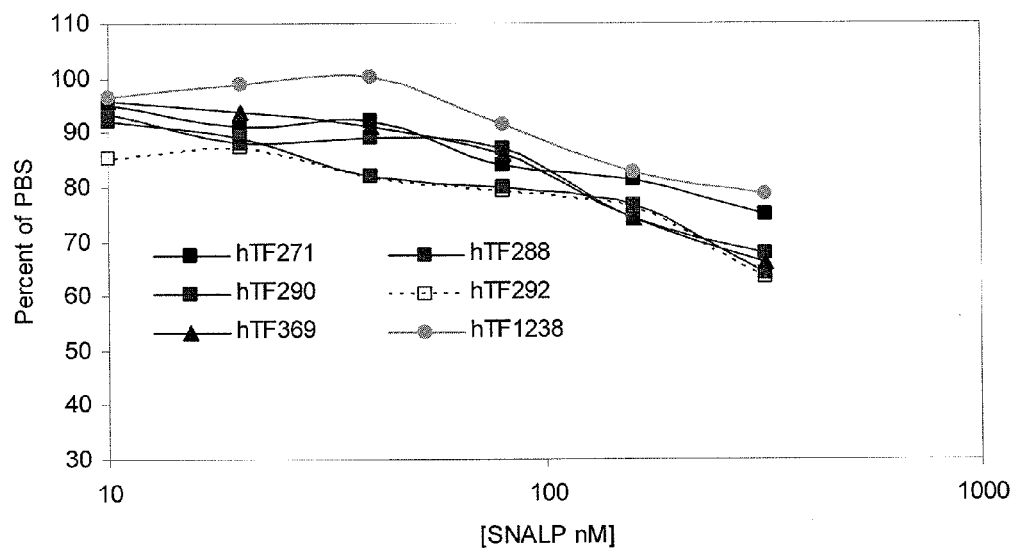
FIG. 5 illustrates the silencing of TF mRNA with SNALP in human immune cells, U937 cell line. Human tissue factor (TF) mRNA expression in U937 cells after transfection with SNALP identifies lead siRNAs. U937 cells were plated at 250,000 cells/well in 96 well plates and immediately transfected with SNALP at 0, 10, 20, 40, 80, 160 or 320 nM of hTF271, hTF288, hTF290, hTF292, hTF369 or hTF1238 or PBS control and cells harvested 16 h after SNALP transfection by lysis for Quantigene analysis. Quantigene 2.0 for human TF mRNA was performed for triplicate wells. Relative mRNA levels to PBS control are shown.
Figure 6:
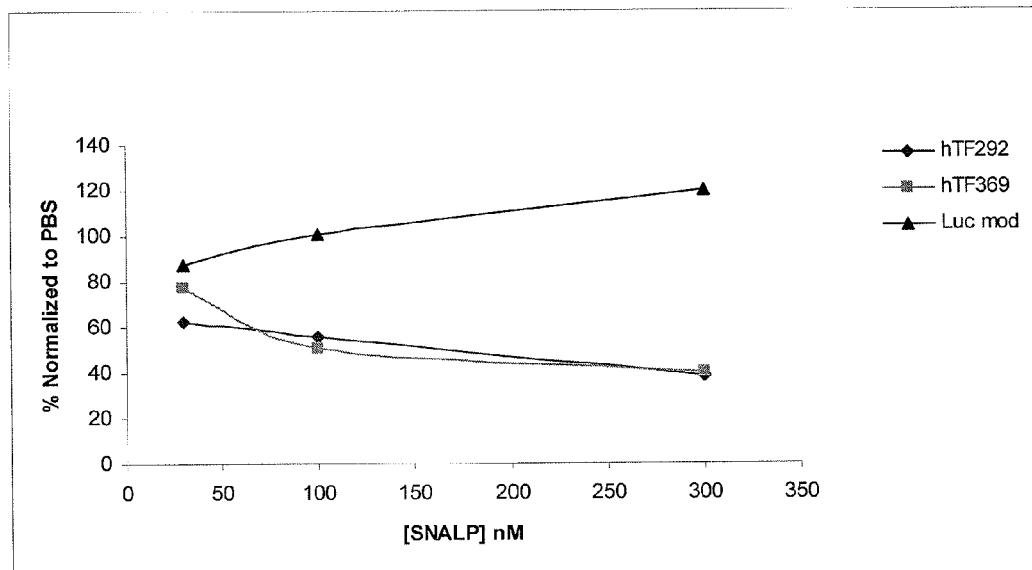
FIG. 6 illustrates the silencing of TF mRNA with SNALP in Human CD34+ cord blood derived macrophage cells. Human tissue factor (TF) mRNA expression in CD34+ cord blood cell derived macrophages after transfection with SNALP confirms lead modified siRNA activity. After 21 days of culture and differentiation, CD34+ cord blood cell derived macrophage cells were plated at 100,000 cells/well in 96 well plates and immediately transfected with SNALP at 0, 30, 100 and 300 nM of hTF292-mod, hTF369-mod or Luc mod SNALP or PBS control and cells harvested 24 h after SNALP transfection by lysis for Quantigene analysis. Quantigene 2.0 for human TF mRNA was performed for triplicate wells. Relative mRNA levels to PBS control are shown.

Previously, it was reported that EBOV induces overexpression of TF in primate monocytes and macrophages (12-13). Similar findings have also been observed for Marburg virus (MARV). TF expression is observed only in infected cells, suggesting a direct correlation with the virus and a role in viral pathogenesis. Recently, it was found that treatment of NHP with recombinant nematode anticoagulant protein c2 (rNAPc2), which targets TF activation of the extrinsic pathway, could protect ~33% of NHP from ZEBOV infection and result in a statistically significant increase in the mean time to death. These studies not only demonstrated the potential for rNAPc2, but also the potential benefit of targeting the clinical manifestation of the disease itself rather than direct viral replication. To this end, a panel of siRNAs that are cross-reactive to NHP and human TF was designed and tested against ZEBOV (as well as LASV, MARV and other HF viruses) in human monocyte culture (Table 7). siRNAs were initially screened for TF knockdown in the human U937 monocyte cell line (FIG. 5), and the most active (hTF292 and hTF369) were modified using the 2'OMe modification strategy described herein to inhibit immune activation (Table 8). These active and non-immunostimulatory anti-TF siRNA were tested on human CD34+ cord blood derived monocyte and macrophage cultures, and found to significantly reduce TF mRNA levels (FIG. 6). These same SNALP can be screened against ZEBOV infection in vitro in human monocyte culture. siRNAs that show promising activity against ZEBOV in human monocytes can be evaluated in NHP for antiviral efficacy. This same siRNA design and testing strategy can be applied to other endogenous targets (host factors) that are known to have a role in hemorrhagic fever (HF) virus pathogenesis.

TABLE 7

Novel siRNA Sequences Targeting Human/NHP Tissue Factor

| Sequence Name | Sequence 5' to 3' (SEC) ID NO:) |
|---|---|
| hTF292-5' antisense | rUrUrA rArArU rUrArU rArUrG rCrUrG rCrCrA rCrArG (84) |
| hTF292-5' sense | rGrUrG rGrCrA rGrCrA rUrArU rArArU rUrUrA rArCrU (85) |
| hTF271-5' antisense | rUrUrU rGrUrA rGrUrG rCrCrU rGrArA rGrCrG rCrCrG (86) |
| hTF271-5' sense | rGrCrG rCrUrU rCrArG rGrCrA rCrUrA rCrArA rArUrA (87) |
| hTF1238-5' antisense | rArUrU rUrCrA rArArG rUrGrA rCrUrA rArUrG rCrUrG (88) |
| hTF1238-5' sense | rGrCrA rUrUrA rGrUrC rArCrU rUrUrG rArArA rUrGrU (89) |
| hTF369-5' antisense | rUrArU rUrUrG rArArC rArGrU rGrUrA rGrArC rUrUrG (90) |
| hTF369-5' sense | rArGrU rCrUrA rCrArC rUrGrU rUrCrA rArArU rArArG (91) |
| hTF290-5' antisense | rArArA rUrUrA rUrArU rGrCrU rGrCrC rArCrA rGrUrA (92) |
| hTF290-5' sense | rCrUrG rUrGrG rCrArG rCrArU rArUrA rArUrU rUrArA (93) |
| hTF288-5' sense | rUrArC rUrGrU rGrGrC rArGrC rArUrA rUrArA rUrUrU (94) |
| hTF288-5' antisense | rArUrU rArUrA rUrGrC rUrGrC rCrArC rArGrU rArUrU (95) | r = ribonucleotide base. 3'-overhangs are indicated in bold and italicized. The 3'-overhangs on one or both strands of the siRNA molecule may alternatively comprise 1-4 deoxythymidine (dT) nucleotides, 1-4 modified and/or unmodified uridine (U) ribonucleotides, or 1-4 ribonucleotides having complementarity to the target sequence or the complementary strand thereof.

In Table 7 above, the last 2 nucleotides at the 3' ends of the sense and antisense strands correspond to the 3' overhang sequence. In other words, nucleotides 1-19 of each sense and antisense strand sequence depicted in Table 7 correspond to that portion of the sense or antisense strand that is present in the double-stranded region of the siRNA duplex. In alternative embodiments, the 3' overhang on one or both strands of the siRNA molecule may comprise 1-4 (e.g., 1, 2, 3, or 4) modified and/or unmodified deoxythymidine (t or dT) nucleotides, 1-4 (e.g., 1, 2, 3, or 4) modified (e.g., 2'OMe) and/or unmodified uridine (U) ribonucleotides, and/or 1-4 (e.g., 1, 2, 3, or 4) modified (e.g., 2'OMe) and/or unmodified ribonucleotides or deoxyribonucleotides having complementarity to the target sequence or the complementary strand thereof. In certain instances, the sense and/or antisense strand of the siRNA molecule lacks 3' overhangs (i.e., does not contain the last 2 nucleotides at the 3' ends of the sense and/or antisense strand). In some embodiments, the sense and/or antisense strand comprises modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides. In particular embodiments, the sense and/or antisense strand comprises 2'OMe nucleotides in accordance with one or more of the selective modification patterns described herein.

TABLE 8

2'O-Methyl Modification of Lead Human/NHP Tissue Factor siRNA

| Sequence Name | Sequence 5' to 3' (SEC) ID NO:) |
|---|---|
| hTF292-S1 | rGmUrG rGrCrA rGrCrA rUrArU rArArU mUrUrA r*ArCmU* (96) |
| hTF292-AS1 | rUrUrA rArArU rUrArU rArUmG rCrUrG rCrCrA r*CrAmG* (97) |
| hTF369-S1 | rAmGrU rCrUrA rCrArC rUrGmU rUrCrA rArArU r*ArAmG* (98) |
| hTF369-ASI | rUrArU rUrUrG rArArC rArGmU rGrUrA rGrArC r*UmUrG* (99) | m = 2'O methyl modified base; r = ribonucleotide base. 3'-overhangs are indicated in bold and italicized. The 3'-overhangs on one or both strands of the siRNA molecule may alternatively comprise 1-4 deoxythymidine (dT) nucleotides, 1-4 modified and/or unmodified uridine (U) ribonucleotides, or 1-4 ribonucleotides having complementarity to the target sequence or the complementary strand thereof.

In Table 8 above, the last 2 nucleotides at the 3' ends of the sense and antisense strands correspond to the 3' overhang sequence. In other words, nucleotides 1-19 of each sense and antisense strand sequence depicted in Table 8 correspond to that portion of the sense or antisense strand that is present in the double-stranded region of the siRNA duplex. In alternative embodiments, the 3' overhang on one or both strands of the siRNA molecule may comprise 1-4 (e.g., 1, 2, 3, or 4) modified and/or unmodified deoxythymidine (t or dT) nucleotides, 1-4 (e.g., 1, 2, 3, or 4) modified (e.g., 2'OMe) and/or unmodified uridine (U) ribonucleotides, and/or 1-4 (e.g., 1, 2, 3, or 4) modified (e.g., 2'OMe) and/or unmodified ribonucleotides or deoxyribonucleotides having complementarity to the target sequence or the complementary strand thereof. In certain instances, the sense and/or antisense strand of the siRNA molecule lacks 3' overhangs (i.e., does not contain the last 2 nucleotides at the 3' ends of the sense and/or antisense strand). In some embodiments, the sense and/or antisense strand comprises additional modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides.

IV. Conclusions

This study addresses the threats of unanticipated diseases and their consequences through the development of a non-antibiotic small molecule therapeutic. The objective of the study was to develop broad-spectrum siRNA-nanoparticle drug products for the prevention and treatment of hemorrhagic fever caused by CDC classified Category A arenaviruses. The final products envisioned from this effort were stable siRNA cocktails that are administered intravenously, in the form of stable nucleic acid-lipid particles (SNALP), following exposure to a Category A hemorrhagic fever arenavirus. The resulting broad spectrum therapeutic can be manufactured, stockpiled, and made available to infected patients in the event of an outbreak or laboratory accident.

To this end, panels of siRNA molecules targeting arenaviral genes necessary for viral replication and/or infection have been designed, as well as the appropriate control siRNA molecules required to confirm that anti-viral activity of candidate drug products arises from the intended drug mechanism rather than non-specific effects. siRNAs targeting the endogenous mRNA for tissue factor (TF) have also been designed as a potential broad spectrum antiviral therapeutic for LASV and other HF viruses. Such siRNA design contributions included chemistry modifications to ameliorate native immunostimulatory properties of siRNA, thus creating safer drug products with improved toxicity profiles. Suitable quantities of siRNA were manufactured, formulated into stable nucleic acid-lipid particles (SNALP), and manufactured in sufficient quantify to support preclinical murine efficacy studies.

V. References

1. Geisbert T W, Hensley L E, Kagan E, Yu E Z, Geisbert J B, Daddario-DiCaprio K, et al. Postexposure protection of guinea pigs against a lethal ebola virus challenge is conferred by RNA interference. J Infect Dis. 2006 Jun. 15; 193(12):1650-7.
2. Morrissey D V, Blanchard K, Shaw L, Jensen K, Lockridge J A, Dickinson B, et al. Activity of stabilized short interfering RNA in a mouse model of hepatitis B virus infection. Hepatology. 2005; 41(6):1349-56.
3. Zimmermann T S, Lee A C, Akinc A, Bramlage B, Bumcrot D, Fedoruk M N, et al. RNAi-mediated gene silencing in non-human primates. Nature. 2006 May 4; 441(7089):111-4.
4. Muller S, Gunther S. Broad-spectrum antiviral activity of small interfering RNA targeting the conserved RNA termini of Lassa virus. Antimicrob Agents Chemother. 2007 June; 51(6):2215-8.
5. Urata S, Noda T, Kawaoka Y, Yokosawa H, Yasuda J. Cellular factors required for Lassa virus budding. J Virol. 2006 April; 80(8):4191-5.
6. Sanchez A B, Perez M, Cornu T, de la Tone J C. RNA interference-mediated virus clearance from cells both acutely and chronically infected with the prototypic arenavirus lymphocytic choriomeningitis virus. J Virol. 2005 September; 79(17):11071-81.
7. Westerhout E M B, B. A Systemic analysis of the effect of target RNA structure on RNA interference. Nucl Acids Res. 2007; 35(13):4322-30.
8. Schwarz D S, Hutvagner G, Du T, Xu Z, Aronin N, Zamore P D. Asymmetry in the assembly of the RNAi enzyme complex. Cell. 2003 Oct. 17; 115(2):199-208.
9. Robbins M, Judge A, Ambegia E, Choi C, Yaworski E, Palmer L, et al. Misinterpreting the therapeutic effects of siRNA caused by immune stimulation. Hum Gene Ther. 2008 Aug. 19.
10. Judge A D, Robbins M, Tavakoli I, Levi J, Hu L, Fronda A, et al. Confirming the RNAi-mediated mechanism of action of siRNA-based cancer therapeutics in mice. J Clin Invest. 2009 March; 119(3):661-73.
11. Judge A, MacLachlan I. Overcoming the innate immune response to small interfering RNA. Hum Gene Ther. 2008 February; 19(2):111-24.
12. Geisbert T W, Hensley L E, Jahrling P B, Larsen T, Geisbert J B, Paragas J, et al. Treatment of Ebola virus infection with a recombinant inhibitor of factor VIIa/tissue factor: a study in rhesus monkeys. Lancet. 2003 Dec. 13; 362(9400):1953-8.

13. Geisbert T W, Young H A, Jahrling P B, Davis K J, Kagan E, Hensley L E. Mechanisms underlying coagulation abnormalities in ebola hemorrhagic fever: overexpression of tissue factor in primate monocytes/macrophages is a key event. J Infect Dis. 2003 Dec. 1; 188(11):1618-29.

Example 2

In Vitro and In Vivo Activity Screen of Modified LASV and TF siRNAs

Human Tissue Factor (hTF or hF3) siRNAs of the same nucleotide sequence were modified to incorporate an increasing number and alternate patterns of 2'OMe nucleotides. 3 different sense strands (S-1 to S-3) and 7 different antisense strands (AS-1, AS-2, AS-3, AS-4, AS-5, AS-5b, and AS-6) were designed. hTF double-stranded siRNAs were generated by mix and match annealing of all possible combinations of sense strands and antisense strands. The number of modifications for double-stranded hTF siRNAs ranged from 3 to 10 2'OMe nucleotides in the double-stranded region. In some embodiments, the pattern of modification included 2'OMe-modified nucleotides in the 3' overhang of one or both strands of the siRNA, such that the number of modifications was further increased in the entire siRNA molecule. Table 9 shows exemplary modified double-stranded hTF siRNAs that resulted from the mix and match annealing of sense strands S-1, S-2, or S-3 with antisense strands AS-1, AS-2, AS-3, AS-4, AS-5, AS-5b, or AS-6.

TABLE 9

| siRNA | hTF siRNA Sequence | SEQ ID NO: | % 2'OMe-Modified | % Modified in DS Region |
|---|---|---|---|---|
| hF3 292 1/1 | 5'-GUGGCAGCAUAUAAUUUAACU-3'<br>3'-GACACCGUCGUAUAUUAAAUU-3' | 100<br>101 | 5/42 = 11.9% | 3/38 = 7.9% |
| hF3 292 1/2 | 5'-GUGGCAGCAUAUAAUUUAACU-3'<br>3'-GACTCCGUCGUAUAUUAAAUU-5' | 100<br>102 | 6/42 = 14.3% | 4/38 = 10.5% |
| hF3 292 1/3 | 5'-GUGGCAGCAUAUAAUUUAACU-3'<br>3'-GACACCGUCGUAUAUUAAAUU-5' | 100<br>103 | 7/42 = 16.7% | 5/38 = 13.2% |
| hF3 292 1/4 | 5'-GUGGCAGCAUAUAAUUUAACU-3'<br>3'-GACACCGUCGUAUAUUAAAUU-5' | 100<br>104 | 6/42 = 14.3% | 4/38 = 10.5% |
| hF3 292 1/5 | 5'-GUGGCAGCAUAUAAUUUAACU-3'<br>3'-GACACCGUCGUAUAUUAAAUU-5' | 100<br>105 | 8/42 = 19% | 6/38 = 15.8% |
| hF3 292 1/5b | 5'-GUGGCAGCAUAUAAUUUAACU-3'<br>3'-GACACCGUCGUAUAUUAAAUU-5' | 100<br>106 | 7/42 = 16.7% | 5/38 = 13.2% |
| hF3 292 1/6 | 5'-GUGGCAGCAUAUAAUUUAACU-3'<br>3'-GACACCGUCGUAUAUUAAAUU-5' | 100<br>107 | 8/42 = 19% | 6/38 = 15.8% |
| hF3 292 2/1 | 5'-GUGGCAGCAUAUAAUUUAACU-3'<br>3'-GACACCGUCGUAUAUUAAAUU-5' | 108<br>101 | 9/42 = 21.4% | 7/38 = 18.4% |
| hF3 292 2/2 | 5'-GUGGCAGCAUAUAAUUUAACU-3'<br>3'-GACACCGUCGUAUAUUAAAUU-5' | 108<br>102 | 10/42 = 23.8% | 8/38 = 21.1% |
| hF3 292 2/3 | 5'-GUGGCAGCAUAUAAUUUAACU-3'<br>3'-GACACCGUCGUAUAUUAAAUU-5' | 108<br>103 | 11/42 = 26.2% | 9/38 = 23.7% |
| hF3 292 2/4 | 5'-GUGGCAGCAUAUAAUUUAACU-3'<br>3'-GACACCGUCGUAUAUUAAAUU-5' | 108<br>104 | 10/42 = 23.8% | 8/38 = 21.1% |
| hF3 292 2/5 | 5'-GUGGCAGCAUAUAAUUUAACU-3'<br>3'-GACACCGUCGUAUAUUAAAUU-5' | 108<br>105 | 12/42 = 28.6% | 10/38 = 26.3% |
| hF3 292 2/5b | 5'-GUGGCAGCAUAUAAUUUAACU-3'<br>3'-GACACCGUCGUAUAUUAAAUU-5' | 108<br>106 | 11/42 = 26.2% | 9/38 = 23.7% |
| hF3 292 2/6 | 5'-GUGGCAGCAUAUAAUUUAACU-3'<br>3'-GACACCGUCGUAUAUUAAAUU-5' | 108<br>107 | 12/42 = 28.6% | 10/38 = 26.3% |
| hF3 292 3/1 | 5'-GUGGCAGCAUAUAAUUUAACU-3'<br>3'-GACACCGUCGUAUAUUAAAUU-5' | 109<br>101 | 7/42 = 16.7% | 5/38 = 13.2% |
| hF3 292 3/2 | 5'-GUGGCAGCAUAUAAUUUAACU-3'<br>3'-GACACCGUCGUAUAUUAAAUU-5' | 109<br>102 | 8/42 = 19% | 6/38 = 15.8% |
| hF3 292 3/3 | 5'-GUGGCAGCAUAUAAUUUAACU-3'<br>3'-GACACCGUCGUAUAUUAAAUU-5' | 109<br>103 | 9/42 = 21.4% | 7/38 = 18.4% |
| hF3 292 3/4 | 5'-GUGGCAGCAUAUAAUUUAACU-3'<br>3'-GACACCGUCGUAUAUUAAAUU-5' | 109<br>104 | 8/42 = 19% | 6/38 = 15.8% |
| hF3 292 3/5 | 5'-GUGGCAGCAUAUAAUUUAACU-3'<br>3'-GACACCGUCGUAUAUUAAAUU-5' | 109<br>105 | 10/42 = 23.8% | 8/38 = 21.1% |

TABLE 9-continued

| siRNA | hTF siRNA Sequence | SEQ ID NO: | % 2'OMe-Modified | % Modified in DS Region |
|---|---|---|---|---|
| hF3 292 3/5b | 5'-GUGGCAGCAUAUAAUUUAACU-3'<br>3'-GACACCGUCGUAUAUUAAAUU-5' | 109<br>106 | 9/42 = 21.4% | 7/38 = 18.4% |
| hF3 292 3/6 | 5'-GUGGCAGCAUAUAAUUUAACU-3'<br>3'-GACACCGUCGUAUAUUAAAUU-5' | 109<br>107 | 10/42 = 23.8% | 8/38 = 21.1% |

2'OMe nucleotides are bolded and underlined.

LASV NP siRNAs of the same nucleotide sequence were modified to incorporate an increasing number and alternate patterns of 2'OMe nucleotides. 2 different sense strands (S-1 to S-2) and 4 different antisense strands (AS-1 to AS-4) were designed. LASV NP double-stranded siRNAs were generated by mix and match annealing of all possible combinations of sense strands and antisense strands. The number of modifications for double-stranded LASV NP siRNAs ranged from 6 to 8 2'OMe nucleotides in the double-stranded region. In certain embodiments, the pattern of modification can include 2'OMe-modified nucleotides in the 3' overhang of one or both strands of the siRNA, such that the number of modifications is further increased in the entire siRNA molecule. Table 10 shows exemplary modified double-stranded LASV NP siRNAs that resulted from the mix and match annealing of sense strands S-1 to S-2 with antisense strands AS-1 to AS-4.

TABLE 10

| siRNA | LASV NP siRNA Sequence | SEP ID NO: | % 2'OMe-Modified | % Modified in DS Region |
|---|---|---|---|---|
| LASV NP1284 1/1 | 5'-GUACUCACAUGGGAUUGAUGU-3'<br>3'-UUCAUGAGUGUACCCUAACUA-5' | 110<br>111 | 6/42 = 14.3% | 6/38 = 15.8% |
| LASV NP1284 1/2 | 5'-GUACUCACAUGGGAUUGAUGU-3'<br>3'-UUCAUGAGUGUACCCUAACUA-5' | 110<br>112 | 8/42 = 19% | 6/38 = 15.8% |
| LASV NP1284 1/3 | 5'-GUACUCACAUGGGAUUGAUGU-3'<br>3'-UUCAUGAGUGUACCCUAACUA-5' | 110<br>113 | 9/42 = 21.4% | 7/38 = 18.4% |
| LASV NP1284 1/4 | 5'-GUACUCACAUGGGAUUGAUGU-3'<br>3'-UUCAUGAGUGUACCCUAACUA-5' | 110<br>114 | 9/42 = 21.4% | 7/38 = 18.4% |
| LASV NP1284 2/1 | 5'-GUACUCACAUGGGAUUGAUGU-3'<br>3'-UUCAUGAGUGUACCCUAACUA-5' | 115<br>111 | 9/42 = 21.4% | 7/38 = 18.4% |
| LASV NP1284 2/2 | 5'-GUACUCACAUGGGAUUGAUGU-3'<br>3'-UUCAUGAGUGUACCCUAACUA-5' | 115<br>112 | 11/42 = 26.2% | 7/38 = 18.4% |
| LASV NP1284 2/3 | 5'-GUACUCACAUGGGAUUGAUGU-3'<br>3'-UUCAUGAGUGUACCCUAACUA-5' | 115<br>113 | 12/42 = 28.6% | 8/38 = 21.1% |
| LASV NP1284 2/4 | 5'-GUACUCACAUGGGAUUGAUGU-3'<br>3'-UUCAUGAGUGUACCCUAACUA-5' | 115<br>114 | 12/42 = 28.6% | 8/38 = 21.1% |

2'OMe nucleotides are bolded and underlined.

In certain embodiments, TF AND LASV NP siRNA duplexes can be prepared and tested in vitro and in vivo as follows: (1) siRNA sense strand (e.g., at 2×1 µmol scale) and antisense strand (e.g., at 1×1 µmol scale) sequences are synthesized; (2) the sense and antisense sequences are hydrated in RNA buffer to, e.g., 5 mg/ml, and quantitated at OD260 using a nanodrop; (3) the sense and antisense sequences (e.g., 600 µg of each) are annealed and formulated into SNALP as described herein (e.g., as a 1:57 SNALP using a syringe press method) at, e.g., a 250 µg scale, and tested on human whole blood for immunostimulation as described, for example, in Example 2 from PCT Publication No. WO 2011/011447; (4) non-immunostimulatory siRNAs are formulated into SNALP (e.g., as a 1:57 SNALP formulation using a pH loading method) and tested on cells such as Vero E6 cells against, e.g., ZEBOV as described, e.g., in Example 1 from PCT Publication No. WO 2011/011447, or tested on cells such as Human Umbilical Vein Endotheilal Cells as described in Example 3 below, e.g., for examination of TF mRNA knockdown via RNAi in vitro; and (5) lead modified siRNAs are scaled up (e.g., at a 500 mg scale) and tested in vivo in an animal model such as monkeys for assessment of non-human primate (NHP) efficacy as described, e.g., in Example 1 from PCT Publication No. WO 2011/011447. The disclosure of PCT Publication No. WO 2011/011447 is herein incorporated by reference in its entirety for all purposes.

In particular embodiments, increasing the number of selective 2'OMe modifications to the siRNA sequence (e.g., 2'OMe modifications at G's and/or U's in the double-stranded and/or 3' overhang regions of the siRNA sequence) does not decrease activity, and in some cases increases silencing activity.

Example 3

Potent Silencing of Tissue Factor (TF) Gene Expression with Modified TF siRNAs

This example demonstrates the relative activity of the hTF292 mod siRNA shown in Tables 8 and 9 (hTF292 S1/AS1; also known as hF3 292 1/1) and the hTF369 mod siRNA shown in Table 8 (hTF369 S1/AS1) targeting Tissue Factor (TF or F3) mRNA. The Human Umbilical Vein Endotheilal Cell (HUVEC) system, when activated by IL-1μ, is a sensitive system for examination of TF mRNA induction and resultant knockdown via RNAi in vitro. Example 1 illustrates that the hTF292 S1/AS1 siRNA was more active than hTF369 S1/AS1 siRNA in U937 and CD34 cell derived monocytes/macrophages. The HUVEC system was used in this study to further evaluate the knockdown of TF mRNA via the hTF292 S1/AS1 and hTF369 S1/AS1 siRNAs in a 1:57 SNALP formulation containing either DLin-C2K-DMA ("C2K"), MC4 Ether ("1-B17"), DLinDMA, or MC3 Ether ("1-B11") as the cationic lipid component. The HUVEC system was also used in this study to evaluate and compare the knockdown of TF mRNA via many of the modified hTF292 siRNAs set forth in Table 9.

Method of HUVEC Transfection and Cell Priming with IL-1β:

HUVEC cells of human origin were purchased from Lonza and cultured in HUVEC Medium as recommended by the manufacturer. Cells at passage 9 (for data shown in FIGS. 7 and 8), passage 15 (for data shown in FIG. 9), and passage 14 (for data shown in FIG. 10) were seeded in 96 well plates at a density of 50,000 cells/ml in a 100 μl volume/well. 24 h after seeding cells, media was changed to fresh and diluted SNALP (in PBS) was added. 24 h after SNALP transfection, IL-10 (1 ng/ml) was added and cells lysed for the measurement of hTF mRNA and the PPIB normalization gene by QG 2.0 analysis after 6 h of IL-1β stimulation.

Figure 7:
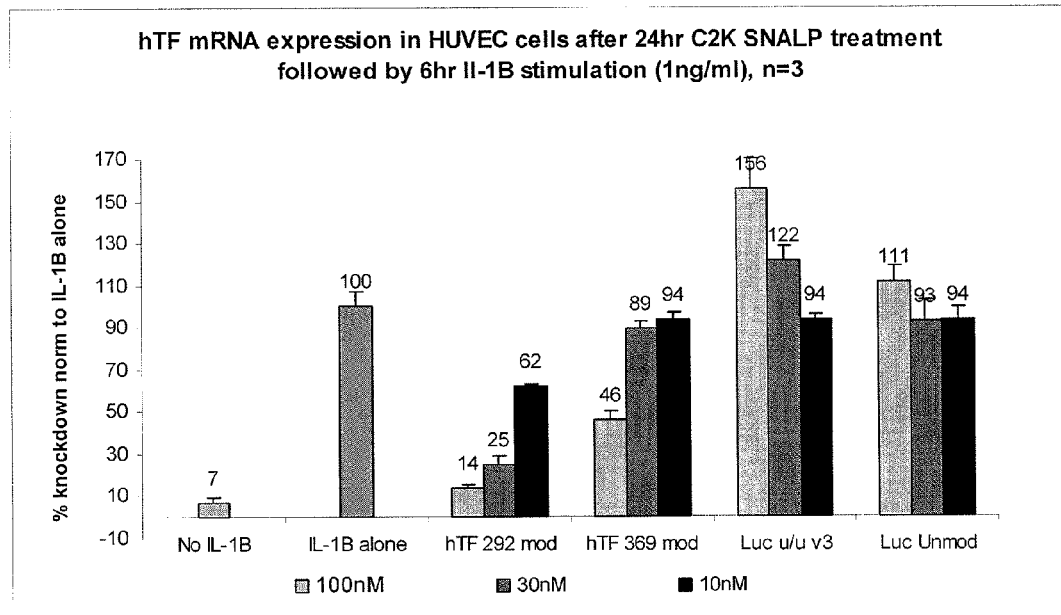
FIG. 7 illustrates that hTF292 mod (hTF292 S1/AS1) siRNA in a 1:57 C2K SNALP formulation exhibited the best knockdown of TF mRNA in endothelial cells.

TF mRNA Knockdown with 1:57 C2K SNALP Formulation:

FIG. 7 shows that the hTF292 S1/AS1 siRNA in a 1:57 C2K SNALP formulation exhibited significant knockdown of TF mRNA compared to cells expressing TF (e.g., IL-1β-stimulated HUVEC cells) that were either not treated with any siRNA ("IL-1B alone") or treated with a luciferase (Luc) control siRNA ("Luc u/u v3", "Luc Unmod"). In particular, hTF292 S1/AS1 1:57 C2K (6:1) SNALP at 100 nM showed 85% knockdown of TF mRNA in a 6 h TF induction model. Significant knockdown (75%) also occurred with hTF292 S1/AS1 siRNA treatment at 30 nM. hTF292 S1/AS1 siRNA showed significantly better knockdown of induced TF mRNA than hTF369 S1/AS1 in the HUVEC cell culture system. These data demonstrate that human endothelial cells can be transfected by SNALP to mediate specific knockdown of mRNA targets in this cell type.

Figure 8:
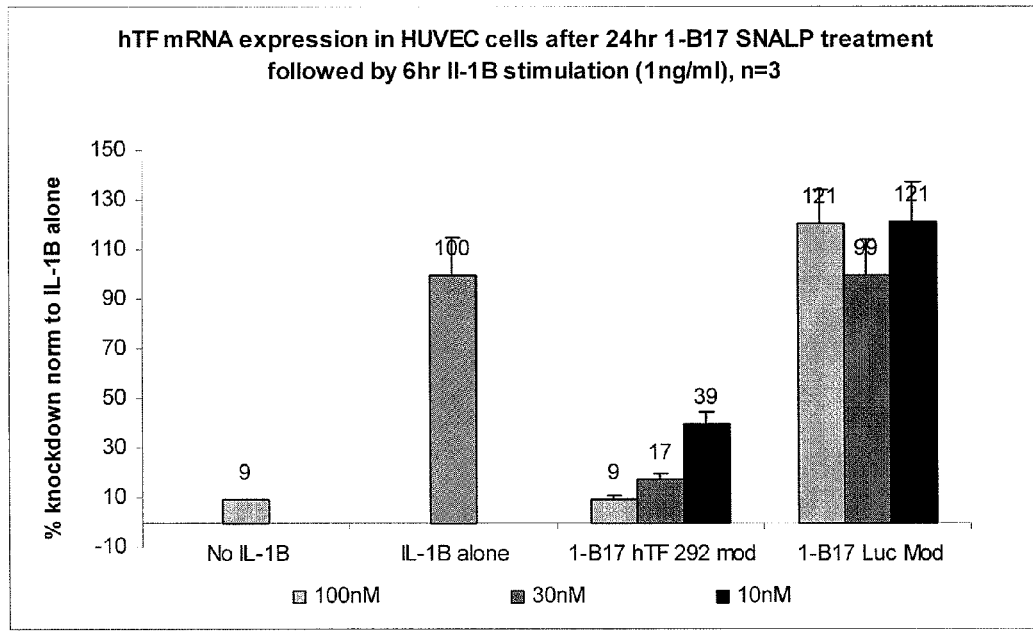
FIG. 8 illustrates that hTF292 S1/AS1 siRNA in a 1:57 1-B17 SNALP formulation exhibited significant knockdown of TF mRNA in endothelial cells.

TF mRNA Knockdown with 1:57 1-B17 SNALP Formulation:

FIG. 8 shows that hTF292 S1/AS1 siRNA in a 1:57 1-B17 SNALP formulation exhibited significant knockdown of TF mRNA in HUVEC cells compared to HUVEC cells expressing TF (e.g., IL-1β-stimulated HUVEC cells) that were either not treated with any siRNA ("IL-1B alone") or treated with a luciferase (Luc) control siRNA ("1-B17 Luc Mod"). In particular, hTF292 S1/AS1 1:57 1-B17 SNALP at 100 nM showed 91% knockdown of TF mRNA in a 6 h TF induction model. Significant knockdown (83%) also occurred with hTF292 S1/AS1 siRNA treatment at 30 nM and 10 nM (61%).

Figure 9:
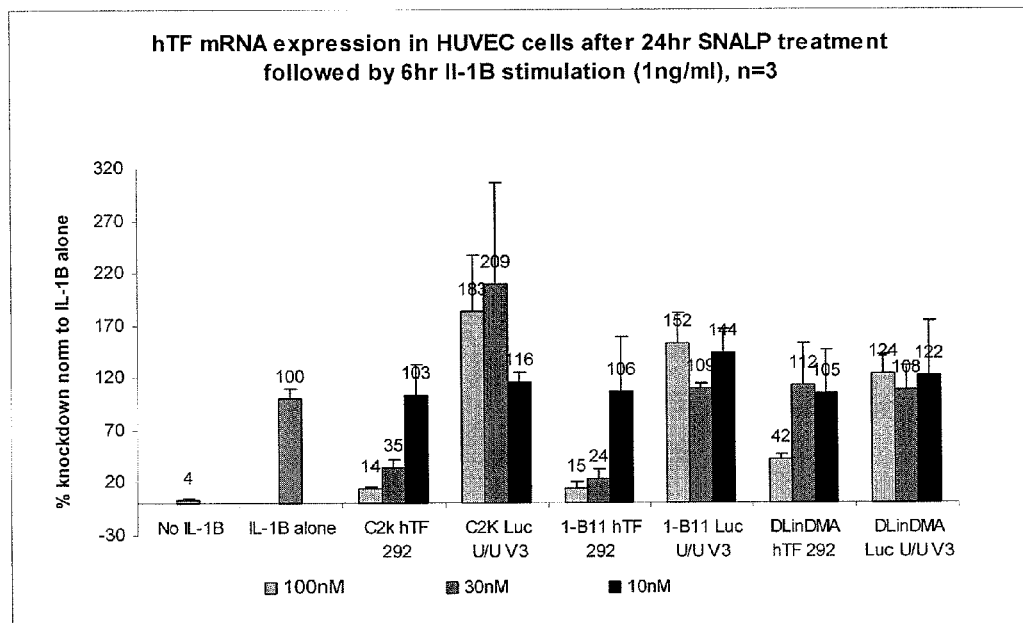
FIG. 9 illustrates that 1:57 SNALP formulations containing hTF292 S1/AS1 siRNA and various cationic lipids such as, e.g., 1-B11, DLinDMA, and C2K exhibited significant knockdown of TF mRNA in endothelial cells.

TF mRNA Knockdown with 1:57 1-B11, DLinDMA, and C2K SNALP Formulations:

FIG. 9 shows that 1:57 SNALP formulations containing hTF292 S1/AS1 siRNA and various cationic lipids such as, e.g., 1-B11, DLinDMA, and C2K exhibited significant knockdown of TF mRNA in HUVEC cells compared to HUVEC cells expressing TF (e.g., IL-1β-stimulated HUVEC cells) that were either not treated with any siRNA ("IL-1B alone") or treated with a luciferase (Luc) control siRNA ("C2K Luc U/U v3", "1-B11 Luc U/U v3", "DLinDMA Luc U/U v3"). In particular, the hTF292 S1/AS1 1:57 1-B11 SNALP at 100 nM showed 85% knockdown of TF mRNA in a 6 h TF induction model. Significant knockdown (76%) also occurred with hTF292 S1/AS1 siRNA treatment at 30 nM.

Figure 10:
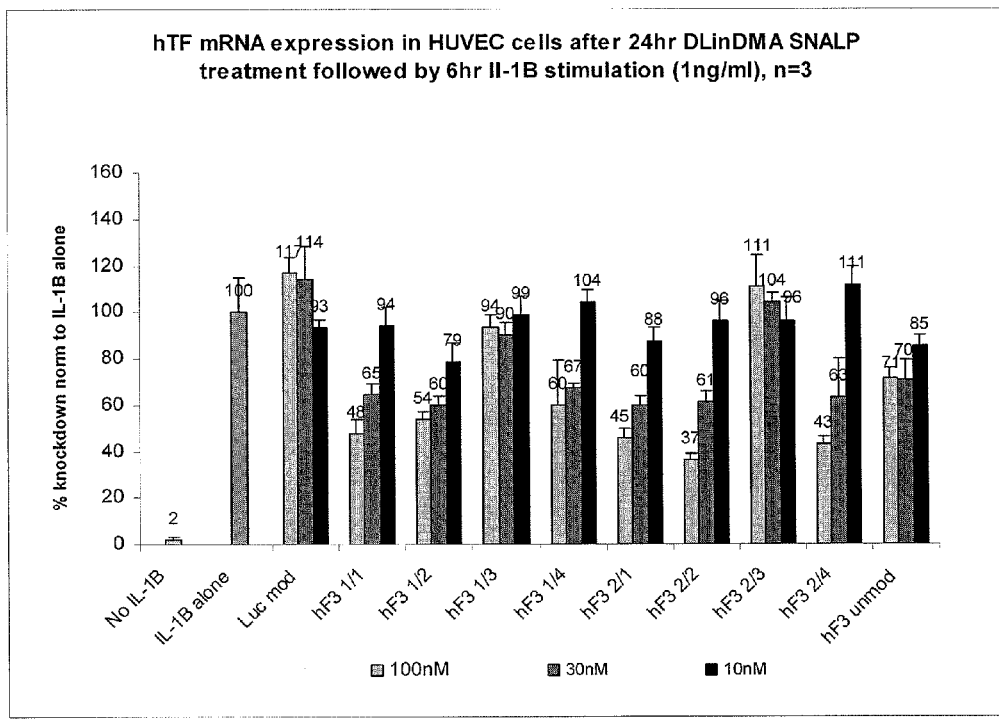
FIG. 10 illustrates that 1:57 SNALP formulations containing hTF292 S1/AS1 siRNA (also known as hF3 292 1/1) as well as other 2'OMe-modified siRNA such as, e.g., hF3 292 1/2, hF3 292 1/4, hF3 292 2/1, hF3 292 2/2, and hF3 292 2/4 exhibited significant knockdown of TF mRNA in endothelial cells.

TF mRNA Knockdown with 1:57 SNALP Formulations Containing Various Modified siRNAs:

FIG. 10 shows that 1:57 DLinDMA SNALP formulations containing hTF292 S1/AS1 siRNA (also known as hF3 292 1/1) as well as other 2'OMe-modified siRNA set forth in Table 9 such as, e.g., hF3 292 1/2, hF3 292 1/4, hF3 292 2/1, hF3 292 2/2, and hF3 292 2/4, exhibited significant knockdown of TF mRNA in HUVEC cells compared to HUVEC cells expressing TF (e.g., IL-1β-stimulated HUVEC cells) that were either not treated with any siRNA ("IL-1B alone") or treated with a luciferase (Luc) control siRNA ("Luc Mod"). In particular, hTF 292 1/1 1:57 DLinDMA SNALP at 100 nM and 30 nM showed approximately 50% and 35% knockdown of TF mRNA, respectively, in a 6 h TF induction model, which was in the range of the unmodified version. Similar TF mRNA knockdown also occurred with all of the other hF3 292 modified variants, except for those siRNAs with AS3 (i.e., hF3 292 1/3 and hF3 292 2/3), which exhibited a loss of activity.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

What is claimed is:

1. A composition comprising an interfering RNA that silences Lassa virus (LASV) gene expression, wherein the interfering RNA comprises a sense strand and a complementary antisense strand, and wherein the antisense strand comprises one of the antisense strand sequences set forth in SEQ ID NOS:17, 19, 21, 23, 25, 27, 29, 31, 33, and 35.

2. The composition of claim 1, wherein the interfering RNA comprises an siRNA.

3. The composition of claim 1, wherein the antisense strand comprises the following sequence: 5'-AUCAAUCCCAUGUGAGUAC-3' (SEQ ID NO:35).

4. The composition of claim 3, wherein the sense strand comprises the following sequence: 5'-GUACUCACAUGGGAUUGAU-3' (SEQ ID NO: 34).

5. The composition of claim 1, wherein the antisense strand comprises one of the antisense strand sequences set forth in SEQ ID NOS:45, 47, 48, and 49.

6. The composition of claim 5, wherein the sense strand comprises one of the sense strand sequences set forth in SEQ ID NOS:44 and 46.

7. The composition of claim 2, wherein the siRNA comprises one of the duplexes set forth in SEQ ID NOS:110 and 111, 110 and 112, 110 and 113, 110 and 114, 115 and 111, 115 and 112, 115 and 113, and 115 and 114.

8. A nucleic acid-lipid particle comprising:
   (a) a composition of claim 1;
   (b) a cationic lipid; and
   (c) a non-cationic lipid.

9. A method for introducing an interfering RNA that silences LASV gene expression into a cell, the method comprising:
   contacting the cell with a nucleic acid-lipid particle of claim 8.

10. A method for silencing LASV gene expression in a mammal in need thereof, the method comprising:
    administering to the mammal a nucleic acid-lipid particle of claim 8.

11. A method for the in vivo delivery of an interfering RNA that silences LASV gene expression, the method comprising:
    administering to a mammal a nucleic acid-lipid particle of claim 8.

12. A method for treating and/or ameliorating one or more symptoms associated with an infection by a virus that causes hemorrhagic fever in a mammal in need thereof, the method comprising:
    administering to the mammal a therapeutically effective amount of a nucleic acid-lipid particle of claim 8.

13. A method for inactivating and/or inhibiting the replication of a virus that causes hemorrhagic fever in a mammal in need thereof, the method comprising:
    administering to the mammal a therapeutically effective amount of a nucleic acid-lipid particle of claim 8.

14. A method for preventing and/or treating hemorrhagic fever in a mammal in need thereof, the method comprising:
    administering to the mammal a therapeutically effective amount of a nucleic acid-lipid particle of claim 8.

15. The composition of claim 2, wherein the siRNA is chemically synthesized.

16. The composition of claim 2, wherein the siRNA comprises a double-stranded region of about 19 to about 25 nucleotides in length.

17. The composition of claim 16, wherein one or more of the nucleotides in the double-stranded region of the siRNA comprise modified nucleotides.

18. The composition of claim 17, wherein the modified nucleotides comprise 2'-O-methyl (2'OMe) nucleotides.

19. The composition of claim 18, wherein the 2'OMe nucleotides comprise at least one, two, three, four, five, six, seven, eight, nine, ten, or eleven 2'OMe-guanosine nucleotides, 2'OMe-uridine nucleotides, or mixtures thereof.

20. The composition of claim 2, wherein the siRNA comprises a 3' overhang in one or both strands of the siRNA.

21. The composition of claim 20, wherein one or more of the nucleotides in the 3' overhang of one or both strands comprise modified nucleotides.

22. The composition of claim 21, wherein the modified nucleotides comprise 2'-O-methyl (2'OMe) nucleotides.

23. The composition of claim 22, wherein the 2'OMe nucleotides comprise at least one, two, three, or four 2'OMe-guanosine nucleotides, 2'OMe-uridine nucleotides, or mixtures thereof.

24. The composition of claim 6, wherein the sense strand comprises a 5'-GU-3' or 5'-GU-3' overhang and the antisense strand comprises a 5'-UU-3' or 5'-UU-3' overhang, wherein the bolded and underlined nucleotides are 2'OMe nucleotides.

25. The composition of claim 1, further comprising one or more interfering RNA that silence the expression of one or more host factor genes.

26. The composition of claim 1, further comprising a pharmaceutically acceptable carrier.

27. The nucleic acid-lipid particle of claim 8, wherein the non-cationic lipid is selected from the group consisting of a phospholipid, cholesterol or a derivative thereof, and a mixture of a phospholipid and cholesterol or a derivative thereof.

28. The nucleic acid-lipid particle of claim 8, further comprising a conjugated lipid that inhibits aggregation of particles.

29. The nucleic acid-lipid particle of claim 28, wherein the conjugated lipid that inhibits aggregation of particles comprises a polyethyleneglycol (PEG)-lipid conjugate.

30. A pharmaceutical composition comprising a nucleic acid-lipid particle of claim 8 and a pharmaceutically acceptable carrier.

\* \* \* \* \*